(12) United States Patent
Adusumilli

(10) Patent No.: US 11,738,048 B2
(45) Date of Patent: Aug. 29, 2023

(54) IMMUNE CELL COMPOSITIONS AND METHODS OF USE FOR TREATING VIRAL AND OTHER INFECTIONS

(71) Applicant: Memorial Sloan Kettering Cancer Center, New York, NY (US)

(72) Inventor: Prasad S. Adusumilli, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 836 days.

(21) Appl. No.: 16/329,142

(22) PCT Filed: Aug. 29, 2017

(86) PCT No.: PCT/US2017/049085
§ 371 (c)(1),
(2) Date: Feb. 27, 2019

(87) PCT Pub. No.: WO2018/044866
PCT Pub. Date: Mar. 8, 2018

(65) Prior Publication Data
US 2021/0275584 A1     Sep. 9, 2021

Related U.S. Application Data

(60) Provisional application No. 62/381,219, filed on Aug. 30, 2016, provisional application No. 62/468,881, filed on Mar. 8, 2017.

(51) Int. Cl.
*A61K 35/17* (2015.01)
*C07K 14/705* (2006.01)
*C07K 14/71* (2006.01)
*C12N 9/22* (2006.01)

(52) U.S. Cl.
CPC ........ *A61K 35/17* (2013.01); *C07K 14/70521* (2013.01); *C07K 14/71* (2013.01); *C12N 9/22* (2013.01); *C07K 2319/02* (2013.01); *C07K 2319/03* (2013.01); *C07K 2319/70* (2013.01)

(58) Field of Classification Search
CPC ..... C07K 2319/03; A61K 35/17; A61P 21/12; C12N 2510/00; C12N 5/0638
See application file for complete search history.

(56) References Cited

U.S. PATENT DOCUMENTS

| | | | |
|---|---|---|---|
| 4,956,778 A | 9/1990 | Naito | |
| 5,091,513 A | 2/1992 | Huston et al. | |
| 5,132,405 A | 7/1992 | Huston et al. | |
| 5,399,346 A | 3/1995 | Anderson et al. | |
| 7,446,190 B2 | 11/2008 | Sadelain et al. | |
| 8,802,374 B2 | 8/2014 | Jensen | |
| 11,242,375 B2 | 2/2022 | Adusumilli et al. | |
| 2003/0105000 A1 | 6/2003 | Pero et al. | |
| 2005/0196754 A1 | 9/2005 | Drmanac et al. | |
| 2010/0135974 A1 | 6/2010 | Eshhar et al. | |
| 2013/0071414 A1 | 3/2013 | Dotti et al. | |
| 2015/0031624 A1 | 1/2015 | Feldman et al. | |
| 2015/0376296 A1 | 12/2015 | Fedorov et al. | |
| 2016/0256488 A1 | 9/2016 | Wu | |
| 2016/0348073 A1* | 12/2016 | Meissner ............. | C12N 15/102 |
| 2017/0158749 A1 | 6/2017 | Cooper et al. | |
| 2017/0159025 A1 | 6/2017 | Li et al. | |
| 2017/0258835 A1 | 9/2017 | Zhao et al. | |
| 2018/0273601 A1 | 9/2018 | Adusumilli et al. | |
| 2018/0291080 A1 | 10/2018 | Sentman et al. | |
| 2018/0360884 A1 | 12/2018 | Adusumilli | |
| 2020/0010803 A1 | 1/2020 | Adusumilli | |
| 2022/0112263 A1 | 4/2022 | Adusumilli et al. | |

FOREIGN PATENT DOCUMENTS

| | | |
|---|---|---|
| JP | 2016-520302 A | 7/2016 |
| WO | WO 2013/019615 A2 | 7/2013 |
| WO | WO 2014055668 A1 | 4/2014 |
| WO | WO 2014107171 A1 | 7/2014 |
| WO | WO 2014/172584 A1 | 10/2014 |
| WO | WO 2014/184744 A1 | 11/2014 |
| WO | WO 2015/188141 A2 | 12/2015 |

(Continued)

OTHER PUBLICATIONS

Luo et al. 2015; Oncogenic viruses and cancer. Virologica Sinica. 30(2): 83-84.*
Gargett et al. 2014; The inducible caspase-9 suicide gene system as a "safety switch" to limit on-target, off-tumor toxicities of chimeric antigen receptor T cells. Frontiers in Pharmacology. vol. 5, article 235, pp. 1-7.*
Ramirez-Garcia et al. 2016, published online Jun. 20, 2014; Candida albicans and cancer: Can this yeast induce cancer development or progression? Critical Reviews in Microbiology. 42(2): 181-193.*
Benamrouz et al. 2012; Parasites and malignancies, a review, with emphasis on digestive cancer induced by cryptosporidium parvum (Alveolata: Apicomplexa). Parasite.19: 101-115.*

(Continued)

*Primary Examiner* — Karen Cochrane Carlson
(74) *Attorney, Agent, or Firm* — Jones Day

(57) ABSTRACT

Disclosed herein are cells that are immune cells, which cells recombinantly express a dominant negative form of an inhibitor of a cell-mediated immune response of the immune cell, and optionally recombinantly express a chimeric antigen receptor (CAR), wherein the CAR binds to a viral antigen. In certain embodiments, the immune cell is an immunostimulatory cell, such as a T cell. In certain embodiments, the immune cell is an immunoinhibitory cell, such as a regulatory T cell. Also disclosed herein are immune cells that recognize and are sensitized to a viral antigen, which immune cells recombinantly express a dominant negative form of an inhibitor of a cell-mediated immune response of the immune cell. The cells can be sensitized to an antigen that is a viral antigen. Additionally provided are methods of using such cells to treat a viral infection in a subject in need thereof.

43 Claims, 41 Drawing Sheets

Figure 1A:
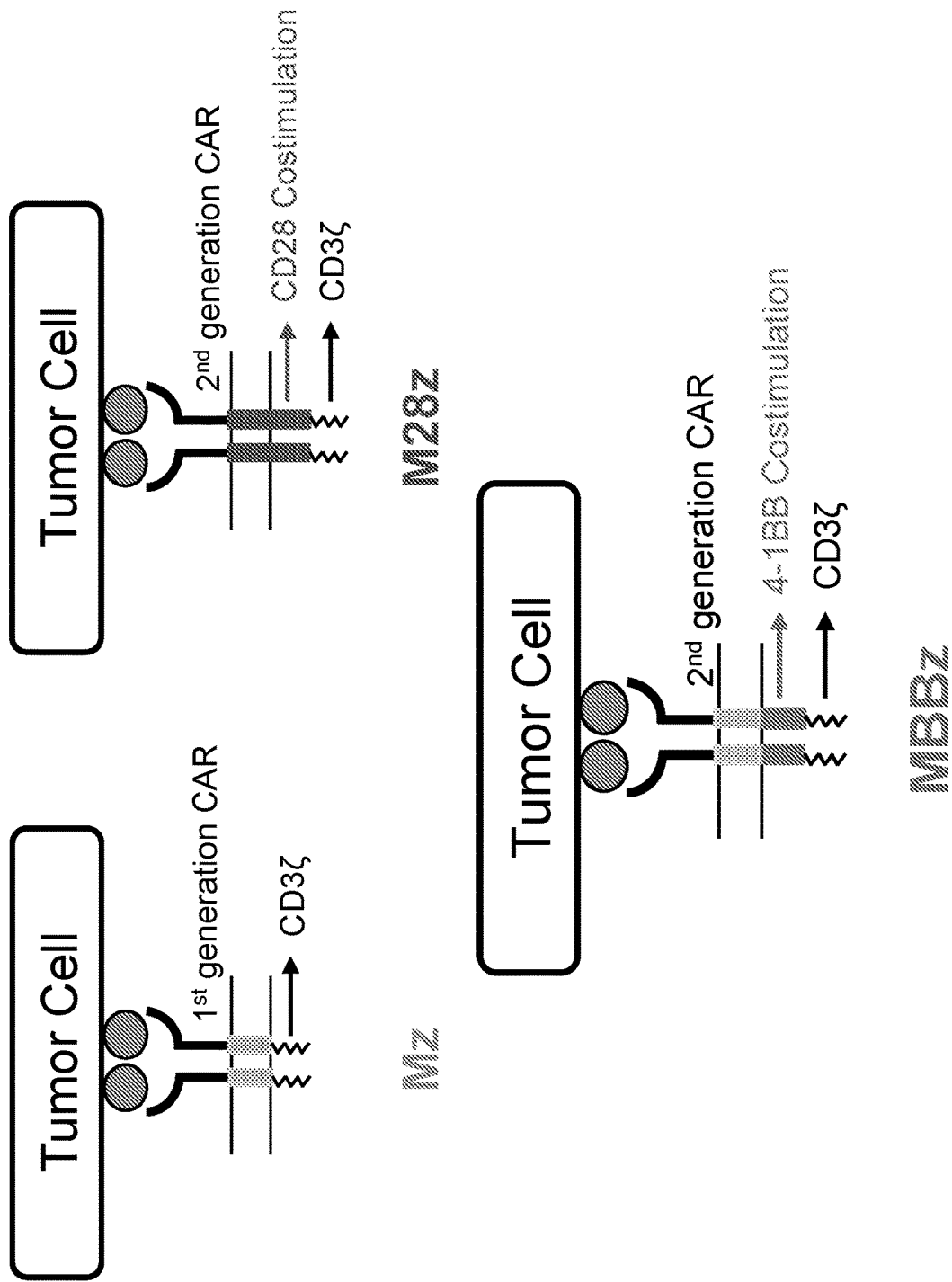

Specification includes a Sequence Listing.

(56) References Cited

FOREIGN PATENT DOCUMENTS

| WO | WO 2016/113203 A1 | 7/2016 |
|----|-------------------|--------|
| WO | WO 2016/138846 A1 | 9/2016 |
| WO | WO 2017/040945 A1 | 3/2017 |
| WO | WO 2017/100428 A1 | 6/2017 |
| WO | WO 2018/044866 A1 | 3/2018 |
| WO | WO 2018/165228 A1 | 9/2018 |

OTHER PUBLICATIONS

Adusumilli et al., "Regional delivery of mesothelin-targeted CAR T cell therapy generates potent and long-lasting CD4-dependent tumor immunity," *Sci. Transl. Med.*, 6(261):261ra151 (2014).
Ahmad et al., "scFv antibody: principles and clinical application," *Clin. Dev. Immunol.*, 2012: ID980250 (2012).
Ali et al., "HIV-1-Specific Chimeric Antigen Receptors Based on Broadly Neutralizing Antibodies," *J. Virol.*, 90(15):6999-7006 (2016).
Assenmacher et al., "Cytometric Cytokine Secretion Assay," *Analyzing T Cell Responses: How to Analyze Cellular Immune Responses Against Tumor Associated Antigens*, Nagorsen et al., eds., Springer, The Netherlands, Ch. 10, pp. 183-195 (2005).
Ataca et al., "Chimeric Antigen Receptor T Cell Therapy in Hematology," *Turk. J. Hematol.*, 32:285-294 (2015).
Bacher et al., "Antigen-specific expansion of human regulatory T cells as a major tolerance mechanism against mucosal fungi," *Mucosal. Immunol.*, 7(4):916-928 (2014).
Barber et al., "Restoring function in exhausted CD8 T cells during chronic viral infection," *Nature*, 439(7077):682-687 (2006).
Bluestone et al., "T cells in the control of organ-specific autoimmunity," *J. Clin. Invest.*, 125(6):2250-2260 (2015).
Bluestone et al., "Type 1 diabetes immunotherapy using polyclonal regulatory T cells," *Sci. Transl. Med.*, 7(315):315ra189 (2015).
Bollard et al., "Adapting a transforming growth factor beta-related tumor protection strategy to enhance antitumor immunity," *Blood*, 99:3179-3187 (2002).
Bottinger et al., "Expression of a dominant-negative mutant TGF-beta type II receptor in transgenic mice reveals essential roles for TGF-beta in regulation of growth and differentiation in the exocrine pancreas," *EMBO J.*, 16:2621-2633 (1997).
Brentjens et al., "Genetically targeted T cells eradicate systemic acute lymphoblastic leukemia xenografts," *Clin. Cancer Res.*, 13:5426-5435 (2007).
Brusko et al., "Human antigen-specific regulatory T cells generated by T cell receptor gene transfer," *PLoS One*, 5(7):e11726 (2010).
Bunos et al., "Automated isolation of primary antigen-specific T cells from donor lymphocyte concentrates: results of a feasibility exercise," *Vox Sanguinis*, 109:387-393 (2015).
Carter et al., "PD-1:PD-L inhibitory pathway affects both CD4(+) and CD8(+) T cells and is overcome by IL-2," *Eur. J Immunol.*, 32(3):634-643 (2002).
Chen et al., "CAR T-cell intrinsic PD-1 checkpoint blockade: A two-in-one approach for solid tumor immunotherapy," *Oncoimmunology*, 6(2):e1273302 (2017).
Chen et al., "Direct expansion of human allospecific FoxP3+CD4+ regulatory T cells with allogeneic B cells for therapeutic application.," *J. Immunol.*, 183:4094-4102 (2009).
Chen et al., "Molecular mechanisms of T cell co-stimulation and co-inhibition," *Nat. Rev. Immunol.*, 13(4):227-242 (2013).
Chen, "Co-inhibitory molecules of the B7-CD28 family in the control of T-cell immunity," *Nat. Rev. Immunol.*, 4:336-347 (2004).
Cherkassky et al., "Genetic-Engineering Strategies to Enhance CAR T-Cell Therapy Efficacy against PD-L1 Expressing Lung Adenocarcinoma and Mesothelioma," *J. Thorac. Oncol.*, 10:S794, presented at the World Conference on Lung Cancer, Sep. 6-9, 2015.
Cherkassky et al., "Human CAR T cells with cell-intrinsic PD-1 checkpoint blockade resist tumor-mediated inhibition," *J Clin. Invest.*, 126(8):3130-3144 (2016).
Chmielewski et al., "TRUCKs: the fourth generation of CARs," *Exp. Opin. Biolog. Ther.*, 15(8):1145-1154 (2015).
Chuang et al., "The CD28 and CTLA-4 receptors associate with the serine/threonine phosphatase PP2A," *Immunity*, 13(3):313-322 (2000).
Day et al., "PD-1 expression on HIV-specific T cells is associated with T-cell exhaustion and disease progression," *Nature*, 224:350-354 (2006).
Dotti et al., "Design and development of therapies using chimeric antigen receptor-expressing T cells," *Immunol. Reviews*, 257(1):107-126 (2013).
Dupont et al., "Artificial antigen-presenting cells transduced with telomerase efficiently expand epitope-specific, human leukocyte antigen-restricted cytotoxic T cells," *Cancer Res.*, 65:5417-5427 (2005).
Fedorov et al., "PD-1- and CTLA-4-based inhibitory chimeric antigen receptors (iCARs) divert off-target immunotherapy responses," *Sci. Transl. Med.*, 5(215):215ra172 (2013).
Feng et al., "A novel human monoclonal antibody that binds with high affinity to mesothelin-expressing cells and kills them by antibody-dependent cell-mediated cytotoxicity," *Mol. Cancer Ther.*, 8:1113-1118 (2009).
Finney et al., "Chimeric receptors providing both primary and costimulatory signaling in T cells from a single gene product," *J. Immunol.*, 161:2791-2797 (1998).
Foster et al., "Antitumor activity of EBV-specific T lymphocytes transduced with a dominant negative TGF-beta receptor," *J. Immunother.*, 31:500-505 (2008).
Fransson et al., "CAR/FoxP3-engineered T regulatory cells target the CNS and suppress EAE upon intranasal delivery," *J. Neuroinflammation*, 9:112 (2012).
Freeman et al., "Engagement of the PD-1 immunoinhibitory receptor by a novel B7 family member leads to negative regulation of lymphocyte activation," *J Exp. Med.*, 192(7): 1027-1034 (2000).
Gade et al., "Targeted elimination of prostate cancer by genetically directed human T lymphocytes," *Cancer Res.*, 65:9080-9088 (2005).
GenBank Accession No. AAH69566.1, "Cytotoxic T-lymphocyte-associated protein 4 [*Homo sapiens*]," (Jul. 15, 2006).
GenBank Accession No. AAP44003.1, "B and T lymphocyte attenuator [*Homo sapiens*]," (Jun. 18, 2003).
GenBank Accession No. CAA36243.3, "LAG-3 protein precursor [*Homo sapiens*]," (Sep. 12, 2001).
GenBank Accession No. NP_000607.1, "T-cell surface glycoprotein CD4 isoform 1 precursor [*Homo sapiens*]," (Apr. 23, 2016).
GenBank Accession No. NP_001020018.1, "TGF-beta receptor type-2 isoform A precursor [*Homo sapiens*]," (Apr. 30, 2016).
GenBank Accession No. NP_001139345.1, "T-cell surface glycoprotein CD8 alpha chain isoform 1 precursor [*Homo sapiens*]," (Mar. 15, 2015).
GenBank Accession No. NP_001160135.1, "natural killer cell receptor 2B4 isoform 2 precursor [*Homo sapiens*]," (Jan. 8, 2016).
GenBank Accession No. NP_001181943.1, "T-cell surface glycoprotein CD4 isoform 2 [*Homo sapiens*]," (Mar. 15, 2015).
GenBank Accession No. NP_001181944.1, "T-cell surface glycoprotein CD4 isoform 3 [*Homo sapiens*]," (Mar. 15, 2015).
GenBank Accession No. NP_001181945.1, "T-cell surface glycoprotein CD4 isoform 3 [*Homo sapiens*]," (Mar. 15, 2015).
GenBank Accession No. NP_001181946.1, "T-cell surface glycoprotein CD4 isoform 3 [*Homo sapiens*]," (Mar. 15, 2015).
GenBank Accession No. NP_001275952.2, "leukocyte-associated immunoglobulin-like receptor 1 isoform c precursor [*Homo sapiens*]," (Aug. 28, 2016).
GenBank Accession No. NP_001275954.2, "leukocyte-associated immunoglobulin-like receptor 1 isoform e precursor [*Homo sapiens*]," (Aug. 28, 2016).
GenBank Accession No. NP_001275955.2, "leukocyte-associated immunoglobulin-like receptor 1 isoform f [*Homo sapiens*]," (Aug. 28, 2016).
GenBank Accession No. NP_001275956.2, "leukocyte-associated immunoglobulin-like receptor 1 isoform g [*Homo sapiens*]," (Aug. 28, 2016).
GenBank Accession No. NP_001552.2, "tumor necrosis factor receptor superfamily member 9 precursor [*Homo sapiens*]," (Sep. 1, 2016).
GenBank Accession No. NP_002277.4, "lymphocyte activation gene 3 protein precursor [*Homo sapiens*]," (Jan. 23, 2016).

(56) References Cited

OTHER PUBLICATIONS

GenBank Accession No. NP_002278.2, "leukocyte-associated immunoglobulin-like receptor 1 isoform a precursor [*Homo sapiens*]," (Aug. 28, 2016).
GenBank Accession No. NP_003318.1, "tumor necrosis factor receptor superfamily member 4 precursor [*Homo sapiens*]," (Sep. 1, 2016).
GenBank Accession No. NP_005009.2, "programmed cell death protein 1 precursor [*Homo sapiens*]," (Mar. 15, 2015).
GenBank Accession No. NP_005205.2, "cytotoxic T-lymphocyte protein 4 isoform CTLA4-TM precursor [*Homo sapiens*]," (Aug. 28, 2016).
GenBank Accession No. NP_006130.1, "T-cell-specific surface glycoprotein CD28 isoform 1 precursor [*Homo sapiens*]," (Mar. 15, 2015).
GenBank Accession No. NP_008984.1, "160 antigen precursor [*Homo sapiens*]," (Mar. 15, 2015).
GenBank Accession No. NP_036224.1, "inducible T-cell costimulator precursor [*Homo sapiens*]," (May 30, 2016).
GenBank Accession No. NP_055081.1, "hematopoietic cell signal transducer isoform 1 precursor [*Homo sapiens*]," (Mar. 15, 2015).
GenBank Accession No. NP_068352.2, "leukocyte-associated immunoglobulin-like receptor 1 isoform b precursor [*Homo sapiens*]," (Aug. 28, 2016).
GenBank Accession No. NP_116171.3, "hepatitis A virus cellular receptor 2 precursor [*Homo sapiens*]," (Sep. 1, 2016).
GenBank Accession No. NP_776160.2, "T-cell immunoreceptor with Ig and ITIM domains precursor [*Homo sapiens*]," (Aug. 28, 2016).
GenBank Accession No. NP_861445.3, "B- and T-lymphocyte attenuator isoform 1 precursor [*Homo sapiens*]," (Sep. 1, 2016).
GenBank Accession No. NP_932170.1, "T-cell surface glycoprotein CD3 zeta chain isoform 1 precursor [*Homo sapiens*]," (Mar. 15, 2015).
GenBank Accession No. P10747.1, "T-cell-specific surface glycoprotein CD28," (Jul. 6, 2016).
GenBank Accession No. P41273.1, "Tumor necrosis factor ligand superfamily member 9," (Jul. 6, 2016).
GenBank Accession No. P43489.1, "Tumor necrosis factor receptor superfamily member 4," (Jul. 6, 2016).
Gierasch, "Signal sequences," *Biochem.*, 28:923-930 (1989).
Guillonneau et al., "CD8+ regulatory T cells in solid organ transplantation," *Curr. Opin. Organ Transplant.*, 15(6):751-756 (2010).
Haney et al., "Isolation of viable antigen-specific CD8+ T cells based on membrane-bound tumor necrosis factor (TNF)-α expression," *J. Immunol. Methods*, 369:33-41 (2011).
Hollyman et al., "Manufacturing validation of biologically functional T cells targeted to CD19 antigen for autologous adoptive cell therapy," *J. Immunother.*, 32:169-180 (2009).
Huse et al., "Generation of a large combinatorial library of the immunoglobulin repertoire in phage lambda," *Science*, 246:1275-1281 (1989).
Huston et al., "Protein engineering of antibody binding sites: recovery of specific activity in an anti-digoxin single-chain Fv analogue produced in *Escherichia coli,*" *Proc. Nat. Acad. Sci. USA*, 85:5879-5883 (1988).
International Search Report for International Application No. PCT/US2016/050128 dated Feb. 2, 2017.
International Search Report for International Application No. PCT/US2016/065578 dated May 3, 2017.
International Search Report for International Application No. PCT/US2017/049085 dated Jan. 11, 2018.
International Search Report for International Application No. PCT/US2018/021249 dated Aug. 10, 2018.
Ishida et al., "Induced expression of PD-1, a novel member of the immunoglobulin gene superfamily, upon programmed cell death," *Embo K.*, 11:3887-3895 (1992).
Jensen et al., "Design and implementation of adoptive therapy with chimeric antigen receptor-modified T cells," *Immunol. Rev.*, 257:127-133 (2014).

John et al., "Anti-PD-1 antibody therapy potently enhances the eradication of established tumors by gene-modified T cells," *Clin. Cancer Res.*, 19(20):5636-5646 (2013).
Kershaw et al., "Gene-engineered T cells as a superior adjuvant therapy for metastatic cancer," *J. Immunol.*, 173:2143-2150 (2004).
Koehler et al., "CD28 costimulation overcomes transforming growth factor-beta-mediated repression of proliferation of redirected human CD4+ and CD8+ T cells in an antitumor cell attack," *Cancer Res.*, 67(5):2265-2273 (2007).
Koenen et al., "CD27/CFSE-based ex vivo selection of highly suppressive alloantigen-specific human regulatory T cells," *J. Immunol.*, 174(12):7573-7583 (2005).
Krause et al., "Antigen-dependent CD28 signaling selectively enhances survival and proliferation in genetically modified activated human primary T lymphocytes," *J. Exp. Med.*, 188:619-626 (1998).
Lamers et al., "Immune responses to transgene and retroviral vector in patients treated with ex vivo-engineered T cells," *Blood*, 117(1):72-82 (2011).
Lan et al., "Induced Foxp3(+) regulatory T cells: a potential new weapon to treat autoimmune and inflammatory diseases?," *J. Mol. Cell. Biol.*, 4:22-28 (2012).
Le Mercier et al., "Beyond CTLA-4 and PD-1, the Generation Z of Negative Checkpoint Regulators," *Front. Immunol.*, 6:418 (2015).
Lee et al., "In vivo inhibition of human CD19-targeted effector T cells by natural T regulatory cells in a xenotransplant murine model of B cell malignancy," *Cancer Res.*, 71(8):2871-2881 (2011).
Liu et al., "A Chimeric Switch-Receptor Targeting PD1 Augments the Efficacy of Second-Generation CAR T Cells in Advanced Solid Tumors," *Cancer Res.*, 76:1578-1590 (2016).
Liu et al., "CD127 expression inversely correlates with FoxP3 and suppressive function of human CD4+ T reg cells," *J. Exp. Med.*, 203(7):1701-1711 (2006).
Lykken et al., "Regulatory B10 cell development and function," *Int. Immunol.*, 27(10):471-477 (2015).
MacDonald et al., "Alloantigen-specific regulatory T cells generated with a chimeric antigen receptor," *J. Clin. Invest.*, 126(4):1413-1424 (2016).
Magnani et al., "Donor-derived CD19-targeted T cells in allogeneic transplants," *Curr. Opin. Hematol.*, 22(6):497-502 (2015).
Maher et al., "Human T-lymphocyte cytotoxicity and proliferation directed by a single chimeric TCRzeta/CD28 receptor," *Nat. Biotechnol.*, 20:70-75 (2002).
Markley et al., "IL-7 and IL-21 are superior to IL-2 and IL-15 in promoting human T cell-mediated rejection of systemic lymphoma in immunodeficient mice," *Blood*, 115(17):3508-3519 (2010).
Masson et al., "Purification and Immunophenotypic Characterization of Human B Cells with Regulatory Functions," *Regulatory B Cells: Methods and Protocols*, Vitale and Mion eds., Humana Press, New York, Chapter 4, pp. 45-52 (2014).
McGray et al., "Immunotherapy-induced CD8+ T cells instigate immune suppression in the tumor," *Mol. Ther.*, 22(1):206-218 (2014).
Memorial Sloan Kettering Cancer Center, "Malignant Pleural Disease Treated With Autologous T Cells Genetically Engineered to Target the Cancer-Cell Surface Antigen Mesothelin," ClinicalTrials.gov archive, pp. 1-10 (Apr. 12, 2018). Retrieved from the Internet: https://clinicaltrials.gov/ct2/show/NCT02414269, on Aug. 3, 2018.
Miller et al., "CD 19-Targeted CAR T Cells: A New Tool in the Fight against B Cell Malignancies," *Oncol. Res. Treat.*, 38:683-690 (2015).
Miyagaki et al., "Regulatory B cells in human inflammatory and autoimmune diseases: from mouse models to clinical research," *Int. Immunol.*, 27(10):495-504 (2015).
Miyara et al., "TREG-cell therapies for autoimmune rheumatic diseases," *Nat. Rev. Rheumatol.*, 10(9):543-551 (2014).
Montes et al., "Optimum in vitro expansion of human antigen-specific CD8 T cells for adoptive transfer therapy," *Clin. Exp. Immunol.*, 142:292-302 (2005).
Moon et al., "Multifactorial T-cell hypofunction that is reversible can limit the efficacy of chimeric antigen receptor-transduced human T cells in solid tumors," *Clin. Cancer Res.*, 20(16):4262-4273 (2014).

(56) References Cited

OTHER PUBLICATIONS

Morgan et al., "Cancer regression in patients after transfer of genetically engineered lymphocytes," *Science*, 314(5796): 126-129 (2006).
National Cancer Institute, "CAR T Cell Receptor Immunotherapy Targeting Mesothelin for Patients With Metastatic Cancer," ClinicalTrials.gov archive, pp. 1-12 (Aug. 3, 2018). Retrieved from the Internet: https://clinicaltrials.gov/ct2/show/NCT01583686, on Aug. 3, 2018.
Noshimura et al., "Development of lupus-like autoimmune diseases by disruption of the PD-1 gene encoding an IHIM motif-carrying immunoreceptor," *Immunity*, 11(2):141-151 (1999).
Noyan et al., "Isolation of human antigen-specific regulatory T cells with high suppressive function," *Eur. J. Immunol.*, 44:2592-2602 (2014).
Papanicolaou et al., "Rapid expansion of cytomegalovirus-specific cytotoxic T lymphocytes by artificial antigen-presenting cells expressing a single HLA allele," *Blood*, 102:2498-2505 (2003).
Papapetrou et al., "Stoichiometric and temporal requirements of Oct4, Sox2, Klf4, and c-Myc expression for efficient human iPSC induction and differentiation," *Proc. Natl. Acad. Sci. U.S.A.*, 106(31):12759-12764 (2009).
Pardoll, "The blockade of immune checkpoints in cancer immunotherapy," *Nat. Rev. Cancer*, 12(4):252-264 (2012).
Parente-Pereira et al., "Use of retroviral-mediated gene transfer to deliver and test function of chimeric antigen receptors in human T-cells," *J. Biol. Methods*, 1(2):e7 (2014).
Parida et al., "T-Cell Therapy: Options for Infectious Diseases," *Clin. Infect. Dis.*, 61 (Suppl 3):S217-S224 (2015).
Park et al., "PD-1 Upregulated on Regulatory T Cells During Chronic Virus Infection Enhances the Suppression of CD8+ T Cell Immune Response via the Interaction With PD-L1 Expressed on CD8+ T Cells," *J. Immunol.*, 194(12):5801-5811 (2015).
Piccirillo et al., "CD4(+)CD25(+) regulatory T cells can mediate suppressor function in the absence of transforming growth factor beta1 production and responsiveness," *J. Exp. Med.*, 196(2):237-245 (2002).
Polcicova et al., "The extracellular domain of herpes simplex virus gE is indispensable for efficient cell-to-cell spread: evidence for gE/gI receptors," *J. Virol.*, 79(18):11990-12001 (2005).
Prosser et al., "Tumor PD-L1 co-stimulates primary human CD8(+) cytotoxic T cells modified to express a PD1:CD28 chimeric receptor," *Mol. Immunol.*, 51(3-4):263-272 (2012).
Putnam et al., "Clinical grade manufacturing of human alloantigen-reactive regulatory T cells for use in transplantation," *Am. J. Transplant.*, 13(11):3010-3020 (2013).
Putnam et al., "Expansion of human regulatory T-cells from patients with type 1 diabetes," *Diabetes*, 58:652-662 (2009).
Riese et al., "Enhanced effector responses in activated CD8+ T cells deficient in diacylglycerol kinases," *Cancer Res.*, 73:3566-3577 (2013).
Riley et al., "Human T regulatory cell therapy: take a billion or so and call me in the morning," *Immunity*, 30(5):656-665 (2009).
Riviere et al., "Effects of retroviral vector design on expression of human adenosine deaminase in murine bone marrow transplant recipients engrafted with genetically modified cells," *Proc. Natl. Acad. Sci. USA*, 92:6733-6737 (1995).
Rooney et al., "Moving Successful Virus-specific T-cell Therapy for Hematopoietic Stem Cell Recipients to Late Phase Clinical Trials," *Mol. Ther. Nucleic Acids*, 1:e55, doi: 10.1038/mtna.2012.49 (2012).
Sadelain et al., "Targeting tumours with genetically enhanced T lymphocytes," *Nat. Rev. Cancer*, 3:35-45 (2003).
Sadelain et al., "The basic principles of chimeric antigen receptor design," *Cancer Discov.*, 3(4):388-398 (2013).
Sage et al., "The receptor PD-1 controls follicular regulatory T cells in the lymph nodes and blood," *Nat. Immunol.*, 14(2):152-161 (2013).
Sautto et al., "Chimeric antigen receptor (CAR)-engineered T cells redirected against hepatitis C virus (HCV) E2 glycoprotein," *Gut*, 65(3):512-523 (2015).

Scholler et al., "Decade-Long Safety and Function of Retroviral-Modified Chimeric Antigen Receptor T-cells," *Sci. Transl. Med.*, 4:132ra53 (2012).
Seddiki et al., "Expression of interleukin (IL)-2 and IL-7 receptors discriminates between human regulatory and activated T cells," *J. Exp. Med.*, 203(7):1693-1700 (2006).
Servais et al., "An in vivo platform for tumor biomarker assessment," *PLoS One*, 6(10):e26722 (2011).
Servais et al., "Mesothelin overexpression promotes mesothelioma cell invasion and MMP-9 secretion in an orthotopic mouse model and in epithelioid pleural mesothelioma patients," *Clin. Cancer Res.*, 18(9):2478-2489 (2012).
Servais et al., *Current Protocols in Pharmacology*, Enna ed., John Wiley & Sons, Chapter 14, Unit14 21 (2011).
Sharpe et al., "Genetically modified T cells in cancer therapy: opportunities and challenges," *Dis. Model Mech.*, 8(4):337-350 (2015).
Sharpe et al., "The B7-CD28 superfamily," *Nat. Rev. Immunol.*, 2:116-126 (2002).
Sheppard, "Dominant negative mutants: tools for the study of protein function in vitro and in vivo," *Am. J. Respir. Cell Mol. Biol.*, 11:1-6 (1994).
Shin et al., "Enhanced Anti-tumor Reactivity of Cytotoxic T Lymphocytes Expressing PD-1 Decoy," *Immune Netw.*, 16(2):134-139 (2016).
Shin et al., "Positive conversion of negative signaling of CTLA4 potentiates antitumor efficacy of adoptive T-cell therapy in murine tumor models," *Blood*, 119(24):5678-5687 (2012).
Spranger et al., "Up-regulation of PD-L1, IDO, and T(regs) in the melanoma tumor microenvironment is driven by CD8(+) T cells," *Sci. Transl. Med.*, 5(200):200ra116 (2013).
Su et al., "Human CD4+CD25(high)CD127 (low/neg) regulatory T cells," *Methods Mol. Biol.*, 806:287-299 (2012).
Szymczak et al., "Development of 2A peptide-based strategies in the design of multicistronic vectors," *Expert Opin. Biol. Therapy*, 5(5):627-638 (2005).
Ukena et al., "Isolation strategies of regulatory T cells for clinical trials: phenotype, function, stability, and expansion capacity," *Exp. Hematol.*, 39(12):1152-1160 (2011).
University of Pennsylvania, "CART-meso in Mesothelin Expressing Cancers," ClinicalTrials.gov archive, pp. 1-7 (Nov. 9, 2017). Retrieved from the Internet: https://clinicaltrials.gov/ct2/show/NCT02159716, on Aug. 6, 2018.
Van Lent et al., "Functional human antigen-specific T cells produced in vitro using retroviral T cell receptor transfer into hematopoietic progenitors," *J. Immunol.*, 179:4959-4968 (2007).
Virgin et al., "Redefining Chronic Viral Infection," *Cell*, 138(1):30-50 (2009).
Von Heijne, "Signal sequences. The limits of variation," *J. Mol. Biol.*, 184(1):99-105 (1985).
Wang et al., "Overcoming intrinsic inhibitory pathways to augment the antineoplastic activity of adoptively transferred T cells: Re-tuning your CAR before hitting a rocky road," *Oncoimmunology*, 2(11):e26492 (2013).
Wang et al., "Quantitative analysis of clinically relevant mutations occurring in lymphoid cells harboring gamma-retrovirus-encoded hsvtk suicide genes," *Gene Therapy*, 15:1454-1459 (2008).
Ward et al., "Binding activities of a repertoire of single immunoglobulin variable domains secreted from *Escherichia coli*," *Nature*, 341:544-546 (1989).
Wei et al., "Strength of PD-1 signaling differentially affects T-cell effector functions," *Proc. Natl. Acad. Sci. USA*, 110(27):E2480-E2489 (2013).
Wieser et al., "Signaling activity of transforming growth factor beta type II receptors lacking specific domains in the cytoplasmic region," *Mol. Cell. Biol.*, 13:7239-7247 (1993).
Winter et al., "Humanized antibodies," *Immunol. Today*, 14:243-246 (1993).
Wolfl et al., "Antigen-specific activation and cytokine-facilitated expansion of naive, human CD8+ T cells," *Nat. Protocols*, 9:950-966 (2014).
Written Opinion for International Application No. PCT/US2016/050128 dated Feb. 2, 2017.

(56) References Cited

OTHER PUBLICATIONS

Written Opinion for International Application No. PCT/US2016/065578 dated May 3, 2017.
Written Opinion for International Application No. PCT/US2017/049085 dated Jan. 11, 2018.
Written Opinion for International Application No. PCT/US2018/021249 dated Aug. 10, 2018.
Wu et al., "Immunotherapies: the blockade of inhibitory signals," *Int. J. Biol. Sci.*, 8:1420-1430 (2012).
Yamagiwa et al., "A role for TGF-beta in the generation and expansion of CD4+CD25+ regulatory T cells from human peripheral blood," *J. Immunol.*, 166(12):7282-7289 (2001).
Zhang et al., "Dynamic Decrease in PD-1 Expression Correlates With HBV-specific Memory CD8 T-cell Development in Acute Self-Limited Hepatitis B Patients," *J. Hepatol.*, 50(6):1163-1173 (2009).
Zhang et al., "Inhibition of TGF-β signaling in genetically engineered tumor antigen-reactive T cells significantly enhances tumor treatment efficacy," *Gene Ther.*, 20(5):575-580 (2013).
Zheng et al., "Generation ex vivo of TGF-beta-producing regulatory T cells from CD4+CD25-precursors," *J. Immunol.*, 169:4183-4189 (2002).
Zhong et al., "Chimeric antigen receptors combining 4-1BB and CD28 signaling domains augment PI3kinase/AKT/Bcl-XL activation and CD8+ T cell-mediated tumor eradication," *Molecular Therapy*, 18(2):413-420 (2010).
Certified English translation of U.S. Appl. No. 62/126,804, certified Feb. 11, 2020, 24 pp.
Definition of "truncate." The American Heritage® Stedman's Medical Dictionary, Copyright © 2002 by Houghton Mifflin Company, 1 p.
Gorelik et al., "Abrogation of TGFbeta signaling in T cells leads to spontaneous T cell differentiation and autoimmune disease," *Immunity*, 12(2):171-181 (2000).
Amaranth et al., "The PDL1-PD1 axis converts human TH1 cells into regulatory T cells," *Sci. Transl. Med.*, 3(111):111ra120 (2011).
Boldogh et al., "Persistent Viral Infections" in Medical Microbiology, 4th ed., Baron, editor, Chapter 46, The University of Texas Medical Branch at Galveston.
"T Cell Therapies: An Overview" Catapult Cell and Gene Therapy, White Paper 1 (2014).
Sadelain et al., "The promise and potential pitfalls of chimeric antigen receptors," *Curr. Opin. Immunol.* 21(2):215-223 (2009).
Agarwal et al., "Scaffold attachment region-mediated enhancement of retroviral vector expression in primary T cells," *J. Virol.*, 72:3720-3728 (1998).
Anderson, "Prospects for human gene therapy," *Science*, 226:401-409 (1984).
Ashfaq et al., "An overview of HCV molecular biology, replication and immune responses," *Virol. J.*, 8:161, doi: 10.1186/1743-422X-8-161 (2011).
Barese et al., "Thymidine kinase suicide gene-mediated ganciclovir ablation of autologous gene-modified rhesus hematopoiesis," *Mol. Therapy*, 20:1932-1943 (2012).
Bennett et al., Cecil Textbook of Medicine, 20th ed., W.B. Saunders, Philadelphia PA, p. 1770 (1996).
Blomer et al., "Highly efficient and sustained gene transfer in adult neurons with a lentivirus vector," *J. Virol.*, 71:6641-6649 (1997).
Bregni et al., "Human peripheral blood hematopoietic progenitors are optimal targets of retroviral-mediated gene transfer," *Blood*, 80:1418-1422 (1992).
Cayouette et al., "Adenovirus-mediated gene transfer of ciliary neurotrophic factor can prevent photoreceptor degeneration in the retinal degeneration (rd) mouse," *Hum. Gene Ther.*, 8:423-430 (1997).
Chen, "Mesothelin expression in thymic epithelial tumors (TETs)," *J Clin. Oncol.*, 32:503s, abstract 7607 (2014).
Colman PM. 1994, "Effects of amino acid sequence changes on antibody-antigen interactions." Res Immunol. 145(1):33-36.
Cornetta et al., "Gene transfer into primates and prospects for gene therapy in humans," *Prog. Nucleic Acid Res. Mol. Biol.*, 36:311-322 (1989).
Danos et al., "Safe and efficient generation of recombinant retroviruses with amphotropic and ecotropic host ranges," *Proc. Natl. Acad. Sci. USA*, 85:6460-6464 (1988).
Dawson, "The potential role of HCV core antigen testing in diagnosing HCV infection," *Antivir. Ther.*, 17:1431-1435 (2012).
Di Stasi et al., "Inducible apoptosis as a safety switch for adoptive cell therapy," *N. Engl. J. Med.*, 365:1673-1683 (2011).
Eglitis et al., "Retroviral vectors for introduction of genes into mammalian cells," *BioTechniques*, 6:608-614 (1988).
Fauci et al., Harrison's Principles of Internal Medicine, 14th ed., McGraw-Hill, San Francisco CA, pp. 1814-1816 (1998).
Fauci, "The human immunodeficiency virus: infectivity and mechanisms of pathogenesis," *Science*, 239:617-622 (1988).
Friedman, "Progress toward human gene therapy," *Science*, 244:1275-1281 (1989).
Frisancho-Kiss et al., 2006, "Cutting edge: T cell Ig mucin-3 reduces inflammatory heart disease by increasing CTLA-4 during innate immunity." J Immunol. 176(11):6411-6415.
GenBank Accession No. AH002818.2, "*Homo sapiens* FKBP12C (FKBP12) gene, FK506-binding protein 12 (FKBP12) gene, complete cds; and FKBP12A (FKBP12) gene, complete sequence," (Jun. 10, 2016).
GenBank Accession No. NM_001229.4, "*Homo sapiens* caspase 9, apoptosis-related cysteine peptidase (CASP9), transcript variant alpha, mRNA," (Mar. 15, 2015).
Gerdemann et al., "Safety and clinical efficacy of rapidly-generated trivirus-directed T cells as treatment for adenovirus, EBV, and CMV infections after allogeneic hematopoietic stem cell transplant," Mol. Ther., 21:2113-2121 (2013).
Gersbach et al., "Targeted plasmid integration into the human genome by an engineered zinc-finger recombinase," *Nucl. Acids Res.*, 39:7868-7878 (2011).
Gong et al., "Cancer patient T cells genetically targeted to prostate-specific membrane antigen specifically lyse prostate cancer cells and release cytokines in response to prostate-specific membrane antigen," *Neoplasia*, 1:123-127 (1999).
Greco et al., "Improving the safety of cell therapy with the TK-suicide gene," *Frontiers Pharmacol.*, 6:95 (2015).
Hughes et al. "Retroviral gene transfer to primitive normal and leukemic hematopoietic cells using clinically applicable procedures," *J. Clin. Invest.*, 89:1817-1824 (1992).
Johnson, "Gene therapy for cystic fibrosis," *Chest*, 107:77S-83S (1995).
Kachala et al., "Mesothelin overexpression is a marker of tumor aggressiveness and is associated with reduced recurrence-free and overall survival in early-stage lung adenocarcinoma," *Clin. Cancer Res.*, 20(4):1020-1028 (2014).
Kaiser et al., "Towards a commercial process for the manufacture of genetically modified T cells for therapy," *Cancer Gene Therapy*, 22:72-78 (2015).
Kido et al., "Use of a retroviral vector with an internal opsin promoter to direct gene expression to retinal photoreceptor cells," *Curr. Eye Res.*, 15:833-844 (1996).
Krebs et al., "T cells expressing a chimeric antigen receptor that binds hepatitis B virus envelope proteins control virus replication in mice," *Gastroenterology*, 145(2):456-465 (2013).
Latouche et al., "Induction of human cytotoxic T lymphocytes by artificial antigen-presenting cells," *Nat. Biotechnol.*, 18:405-409 (2000).
Le Gal La Salle et al., "An adenovirus vector for gene transfer into neurons and glia in the brain," *Science*, 259:988-990 (1993).
Long et al., "4-1BB costimulation ameliorates T cell exhaustion induced by tonic signaling of chimeric antigen receptors," *Nat. Med.*, 21(6):581-590 (2015).
Lucas et al. 2000, "Disruption of T cell homeostasis in mice expressing a T cell-specific dominant negative transforming growth factor beta II receptor." J Exp Med. 191(7):1187-1196.
McCoy et al., "Chromium-release assay for cell-mediated cytotoxicity of human leukemia and lymphoid tissue-culture cells," *Natl. Cancer Inst. Monogr.*, 37:59-67 (1973).

(56) References Cited

OTHER PUBLICATIONS

Miller et al., "Generation of helper-free amphotropic retroviruses that transduce a dominant-acting, methotrexate-resistant dihydrofolate reductase gene," Mol. Cell. Biol., 5:431-437 (1985).
Miller et al., "Improved Retroviral Vectors for Gene Transfer and Expression," Biotechniques, 7:980-990 (1989).
Miller et al., "Redesign of retrovirus packaging cell lines to avoid recombination leading to helper virus production," Mol. Cell. Biol., 6:2895-2902 (1986).
Miller, "Retrovirus packaging cells," Hum. Gene Ther., 1(1):5-14 (1990).
Mitsuya et al., "Molecular targets for AIDS therapy," Science, 249:1533-1544 (1990).
Miyoshi et al., "Stable and efficient gene transfer into the retina using an HIV-based lentiviral vector," Proc. Natl. Acad. Sci. U.S.A., 94:10319-10323 (1997).
Moen, "Directions in gene therapy," Blood Cells, 17:407-416 (1991).
Moon et al., "A PD1-CD28 "Switch Receptor" Is Abe to Augment Mesothelin-Directed Chimeric Antigen Receptor T Cell Therapy in a Resistant In Vivo Model of Human Tumor," Mol. Ther., 22(1):S201, Abstract 520 (2014).
Movassagh et al., "Retrovirus-mediated gene transfer into T cells: 95% transduction efficiency without further in vitro selection," Hum Gene Ther., 11:1189-1200 (2000).
Naldini et al., "In Vivo Gene Delivery and Stable Transduction of Nondividing Cells by a Lentiviral Vector," Science, 272:263-267 (1996).
Panelli et al., "A tumor-infiltrating lymphocyte from a melanoma metastasis with decreased expression of melanoma differentiation antigens recognizes MAGE-12," J Immunol., 164:4382-4392 (2000).
Panelli et al., "Expansion of tumor-T cell pairs from fine needle aspirates of melanoma metastases," J. Immunol., 164:495-504 (2000).
Pollok et al., "Costimulation of transduced T lymphocytes via T cell receptor-CD3 complex and CD28 leads to increased transcription of integrated retrovirus," Hum. Gene Ther., 10:2221-2236 (1999).
Quinn et al., "T cell activation modulates retrovirus-mediated gene expression," Hum. Gene Ther., 9:1457-1467 (1998).
Relander et al., "Gene transfer to repopulating human CD34+ cells using amphotropic-, GALV-, or RD114-pseudotyped HIV-1-based vectors from stable producer," Mol. Therap., 11:452-459 (2005).
Rettig et al., "Transduction and selection of human T cells with novel CD34/thymidine kinase chimeric suicide genes for the treatment of graft-versus-host disease," Mol. Ther., 8:29-41 (2003).
Riviere et al., 2012, "Hematopoietic stem cell engineering at a crossroads," Blood, 119(5):1107-1116 (Epub 2011).
Rizk et al., "Tissue and serum mesothelin are potential markers of neoplastic progression in Barrett's associated esophageal adenocarcinoma," Cancer Epidemiol. Biomarkers Prev., 21(3):482-486 (2012).
Romanski et al., 2016, "CD19-CAR engineered NK-92 cells are sufficient to overcome NK cell resistance in B-cell malignancies," J. Cell Mol. Med., 20(7):1287-1294.
Rosenberg et al., "Gene transfer into humans—immunotherapy of patients with advanced melanoma, using tumor-infiltrating lymphocytes modified by retroviral gene transduction," N. Engl. J. Med., 323:570-578 (1990).
Rosenberg et al., "Vigorous HIV-1-specific CD4+ T cell responses associated with control of viremia," Science, 278:1447-1450 (1997).
Rudikoff et al., 1982, "Single amino acid substitution altering antigen-binding specificity." Proc Natl Acad Sci U S A. 79(6):1979-1983.
Sharp, "Gene Therapy," Lancet, 337:1277-1278 (1991).
Sillanpää et al., "Hepatitis C virus core, NS3, NS4B and NS5A are the major immunogenic proteins in humoral immunity in chronic HCV infection," Virol J., 6:84, doi: 10.1186/1743-422X-6-84 (2009).
Sontheimer, "The Bacterial Origins of the CRISPR Genome-Editing Revolution," Hum. Gene Ther., 26(7):413-424 (2015).
Szymczak-Workman et al., 2012, "Design and construction of 2A peptide-linked multicistronic vectors," Cold Spring Harb. Protoc., 2012(2):199-204.
Tolstoshev et al., "Gene expression using retroviral vectors," Current Opin. Biotechnol., 1:55-61 (1990).
Tozbikian et al., "Mesothelin expression in triple negative breast carcinomas correlates significantly with basal-like phenotype, distant metastases and decreased survival," PLoS One, 9(12):e114900 (2014).
U.S. Appl. No. 62/126,804, filed Mar. 2, 2015; Modified Cell and Uses Thereof, Wu et al.; with Certified English translation (56 pages).
Vasileva et al., "Genome-editing tools for stem cell biology," Cell Death Dis., 6:e1831. (2015).
Wang et al., 2019, "Chimeric antigen receptor (CAR)-modified NK cells against cancer: Opportunities and challenges," Int. Immunopharmacol., 74:105695 (6 pages).
Xu et al., "Correction of the enzyme deficiency in hematopoietic cells of Gaucher patients using a clinically acceptable retroviral supernatant transduction protocol," Exp. Hemat., 22:223-230 (1994).
Zakrzewski et al., 2008, "Tumor immunotherapy across MHC barriers using allogeneic T-cell precursors." Nat Biotechnol. 26(4):453-461.
Zeltsman et al., 2017, "CAR T-cell therapy for lung cancer and malignant pleural mesothelioma," Transl. Res., 187:1-10.
Zhang et al., 2011, "Improving adoptive T cell therapy by targeting and controlling IL-12 expression to the tumor environment," Mol. Ther., 19(4):751-759.
U.S. Appl. No. 62/126,804, filed Mar. 2, 2015, Wu et al.

* cited by examiner

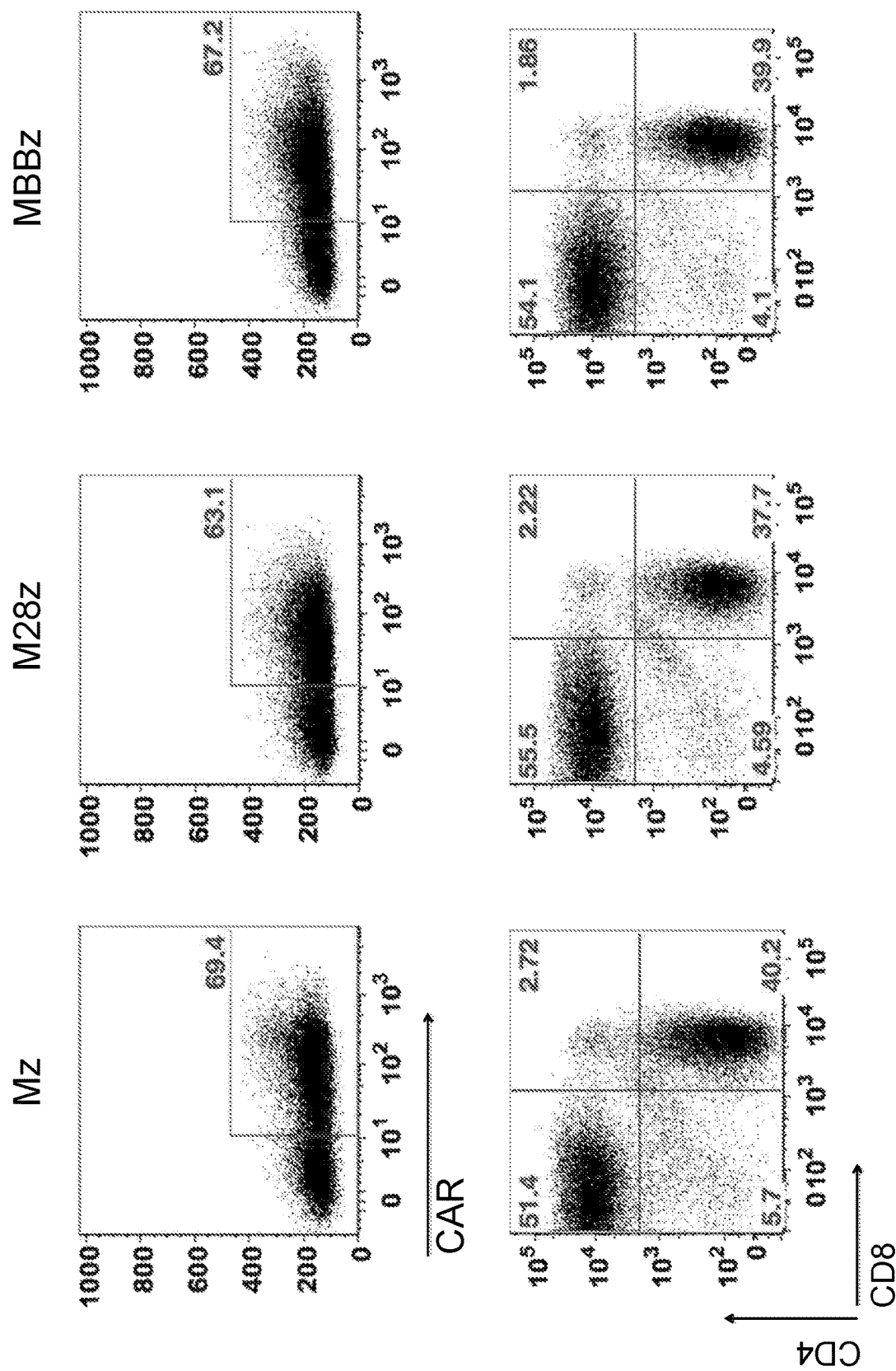

FIG. 3B
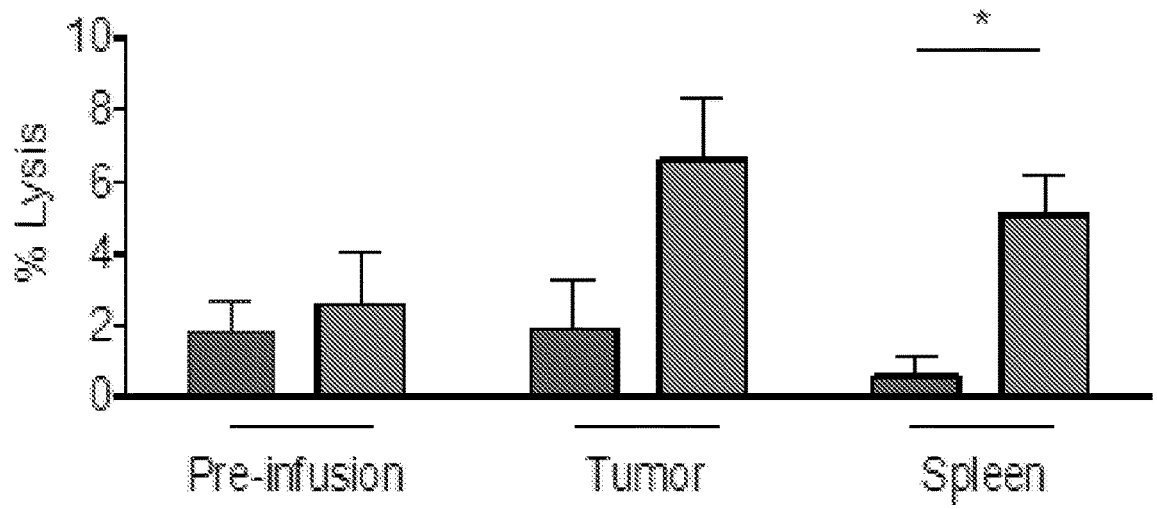
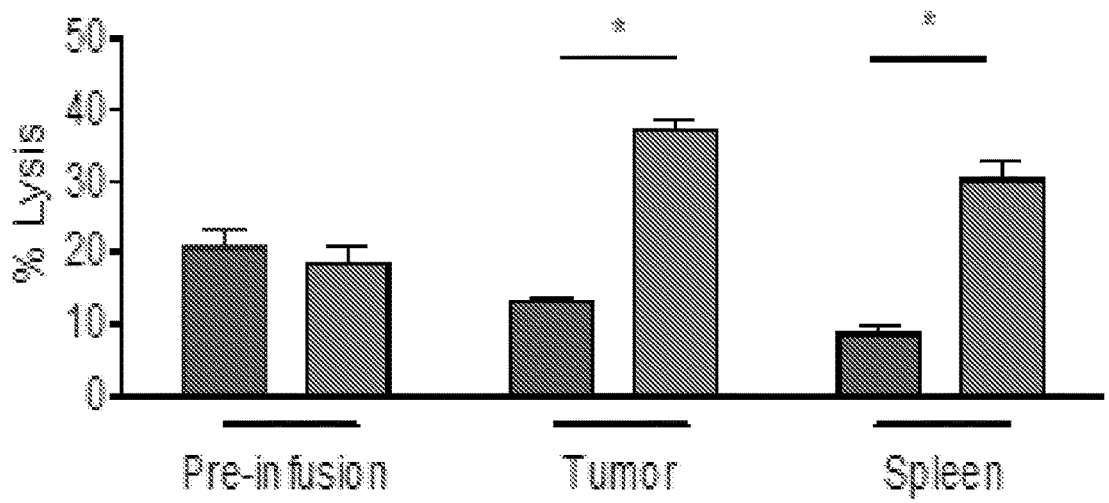

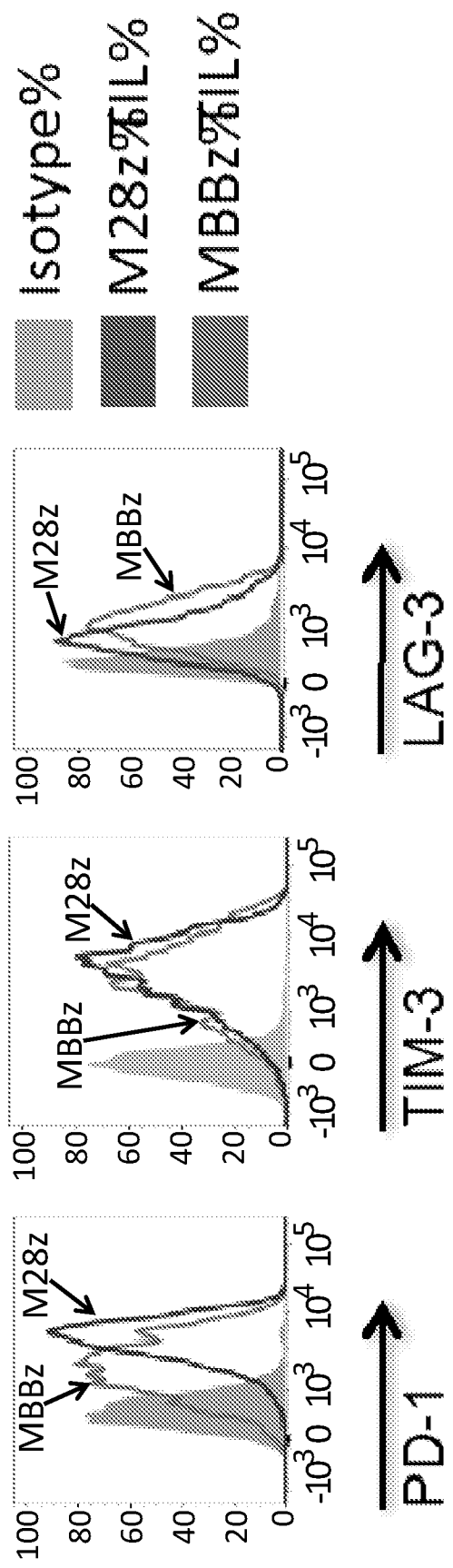

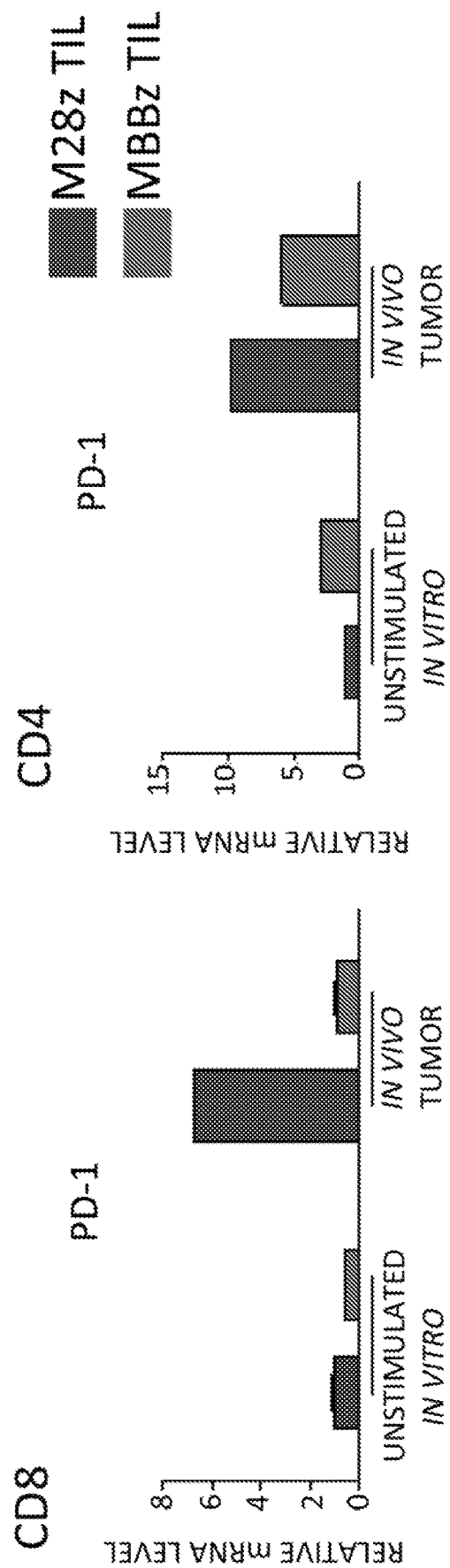

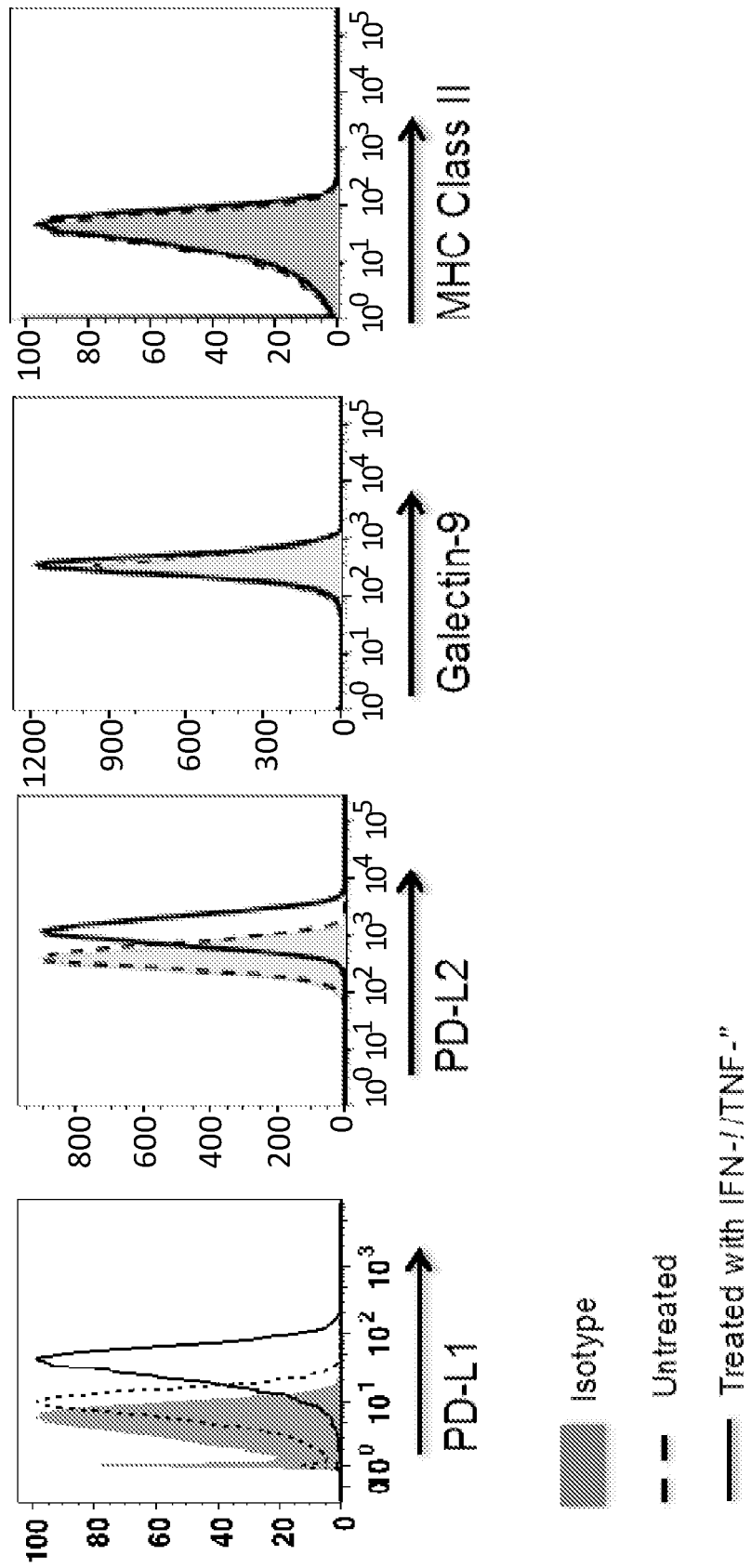

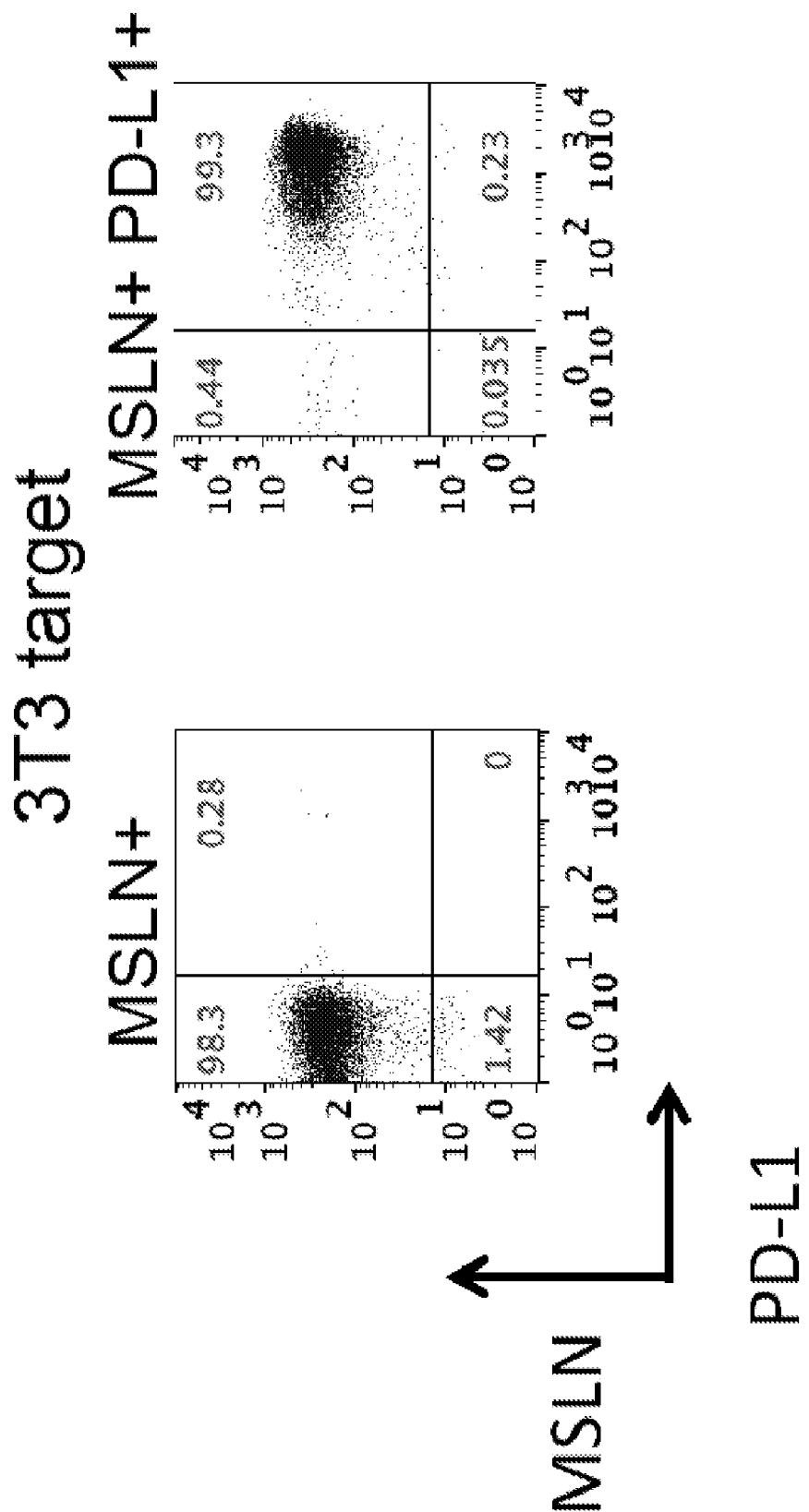

FIG. 8D
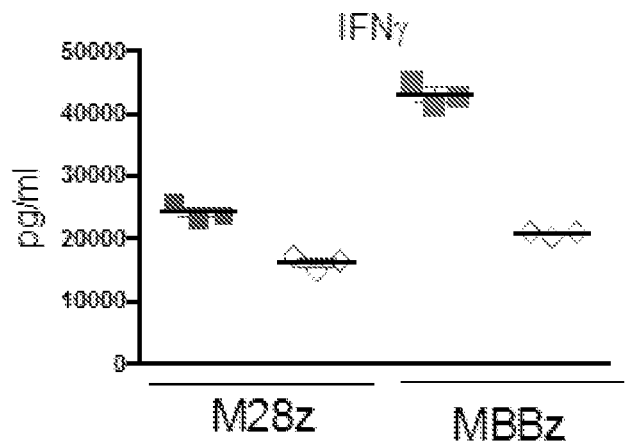
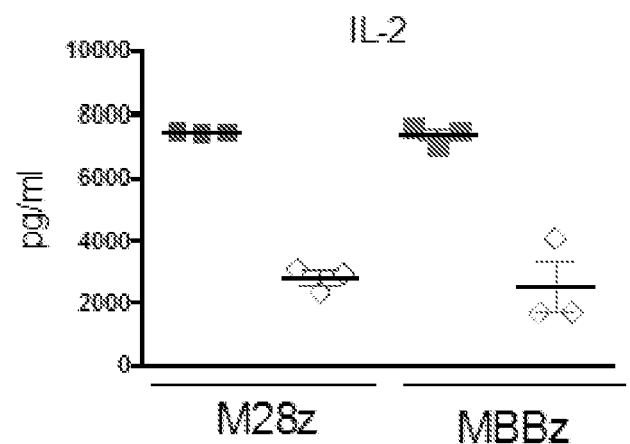
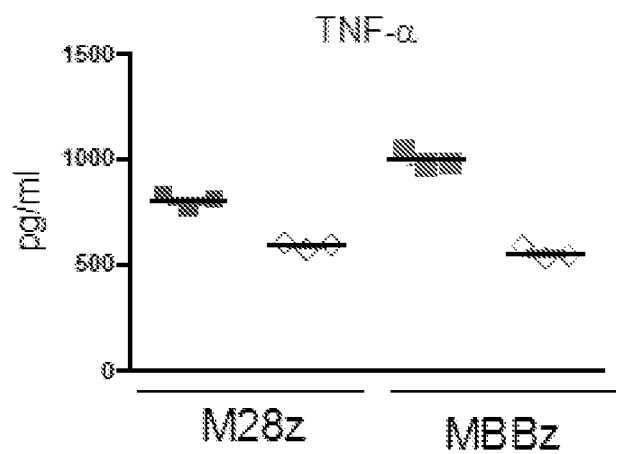

Days Following
Initial antigen stimulation

Effector to Target Ratio

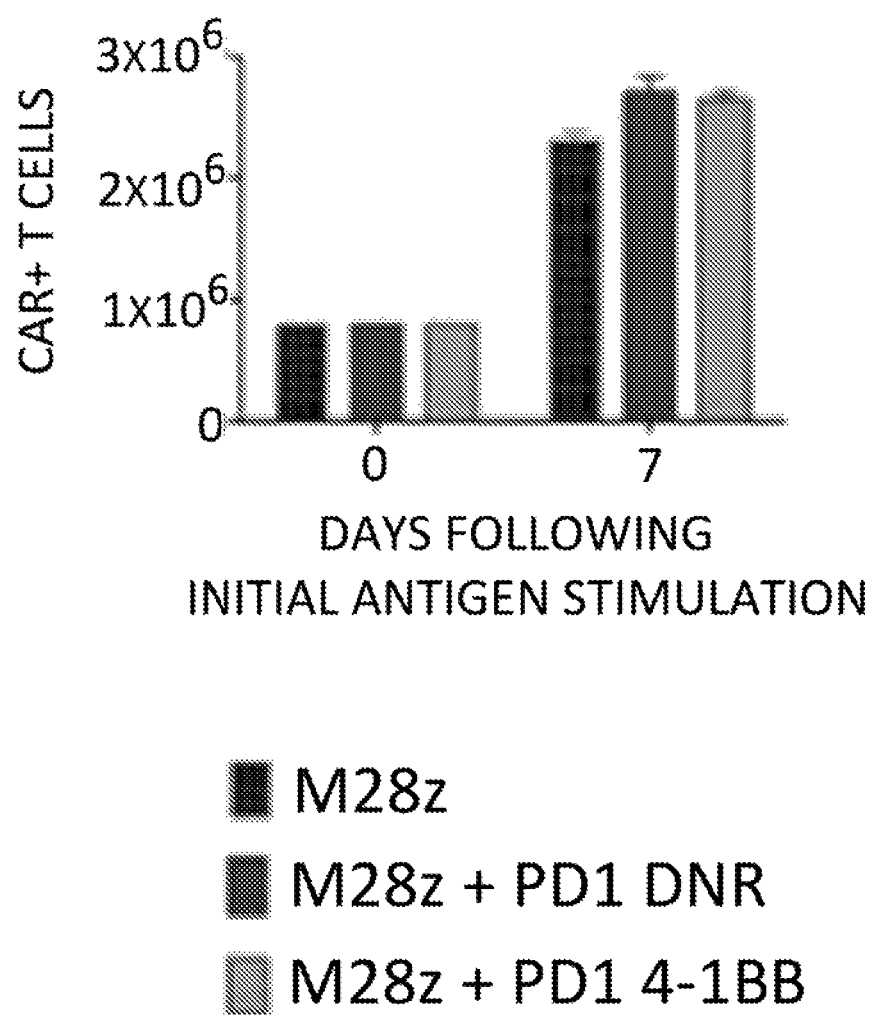

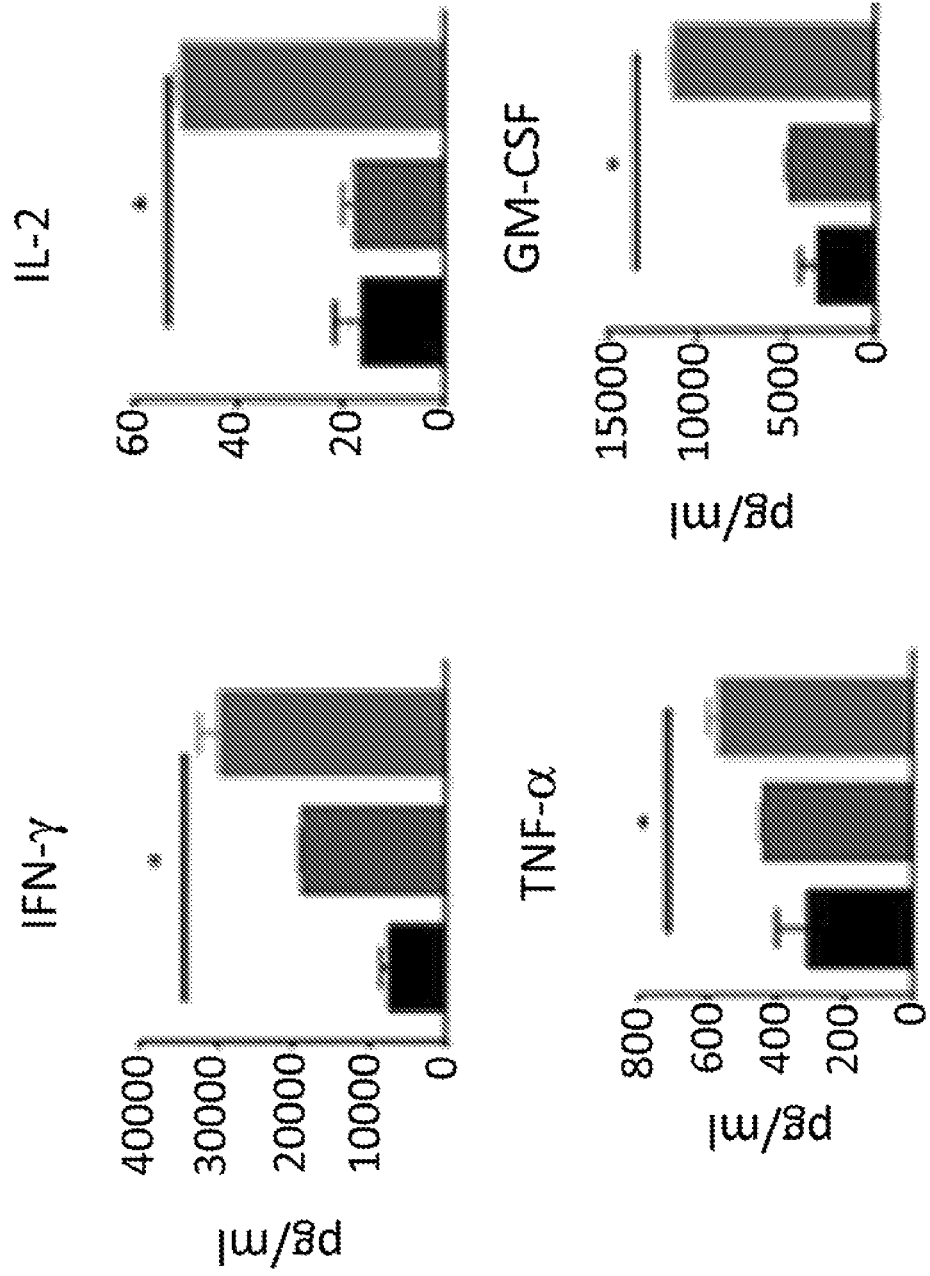

US 11,738,048 B2

SEQUENCE LISTING

<160> NUMBER OF SEQ ID NOS: 29

<210> SEQ ID NO 1
<211> LENGTH: 164
<212> TYPE: PRT
<213> ORGANISM: Homo sapiens

<400> SEQUENCE: 1

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 2
<211> LENGTH: 339
<212> TYPE: DNA
<213> ORGANISM: Homo sapiens

<400> SEQUENCE: 2
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggg aaagccgaga aggaagaacc ctcaggaagg cctgtacaat      180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgctaa                           339

<210> SEQ ID NO 3
<211> LENGTH: 220
<212> TYPE: PRT
<213> ORGANISM: Homo sapiens

<400> SEQUENCE: 3

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

```
Arg Glu Phe Arg Ala Ser Leu His Lys Gly Leu Asp Ser Ala Val Glu
     50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                 85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
210                 215                 220

<210> SEQ ID NO 4
<211> LENGTH: 321
<212> TYPE: DNA
<213> ORGANISM: Homo sapiens

<400> SEQUENCE: 4
attgaagtta tgtatcctcc tccttaccta gacaatgaga agagcaatgg aaccattatc    60
catgtgaaag ggaaacacct tgtccaagt cccctatttc ccggaccttc taagcccttt   120
tgggtgctgg tggtggttgg tggagtcctg gcttgctata gcttgctagt aacagtggcc   180
tttattattt tctgggtgag gagtaagagg agcaggctcc tgcacagtga ctacatgaac   240
atgactcccc gccgccccgg gcccacccgc aagcattacc agccctatgc cccaccacgc   300
gacttcgcag cctatcgctc c                                             321

<210> SEQ ID NO 5
<211> LENGTH: 255
<212> TYPE: PRT
<213> ORGANISM: Homo sapiens

<400> SEQUENCE: 5

Met Gly Asn Ser Cys Tyr Asn Ile Val Ala Thr Leu Leu Leu Val Leu
  1               5                  10                  15

Asn Phe Glu Arg Thr Arg Ser Leu Gln Asp Pro Cys Ser Asn Cys Pro
             20                  25                  30

Ala Gly Thr Phe Cys Asp Asn Asn Arg Asn Gln Ile Cys Ser Pro Cys
         35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                 85                  90                  95
```

```
Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
            130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 6
<211> LENGTH: 277
<212> TYPE: PRT
<213> ORGANISM: Homo sapiens

<400> SEQUENCE: 6

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
            85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
            130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
            210                 215                 220
```

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
            245                 250                 255

Gly Ser Phe Arg Thr Pro Ile Gln Glu Glu Gln Ala Asp Ala His Ser
        260                 265                 270

Thr Leu Ala Lys Ile
        275

<210> SEQ ID NO 7
<211> LENGTH: 199
<212> TYPE: PRT
<213> ORGANISM: Homo sapiens

<400> SEQUENCE: 7

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195

<210> SEQ ID NO 8
<211> LENGTH: 93
<212> TYPE: PRT
<213> ORGANISM: Homo sapiens

<400> SEQUENCE: 8

Met Ile His Leu Gly His Ile Leu Phe Leu Leu Leu Leu Pro Val Ala
1               5                   10                  15

Ala Ala Gln Thr Thr Pro Gly Glu Arg Ser Ser Leu Pro Ala Phe Tyr
            20                  25                  30

Pro Gly Thr Ser Gly Ser Cys Ser Gly Cys Gly Ser Leu Ser Leu Pro
        35                  40                  45

Leu Leu Ala Gly Leu Val Ala Ala Asp Ala Val Ala Ser Leu Leu Ile
    50                  55                  60

Val Gly Ala Val Phe Leu Cys Ala Arg Pro Arg Ser Pro Ala Gln
65                  70                  75                  80

Glu Asp Gly Lys Val Tyr Ile Asn Met Pro Gly Arg Gly
                85                  90

<210> SEQ ID NO 9
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Met Ala Leu Pro Val Thr Ala Leu Leu Leu Pro Leu Ala Leu Leu
1               5                   10                  15

His Ala Ala Arg Pro
                20

<210> SEQ ID NO 10
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Gly Gly Gly Ser Gly Gly Gly Ser Gly Gly Gly Gly Ser
1               5                   10                  15

<210> SEQ ID NO 11
<211> LENGTH: 235
<212> TYPE: PRT
<213> ORGANISM: Homo sapiens

<400> SEQUENCE: 11

Met Ala Leu Pro Val Thr Ala Leu Leu Leu Pro Leu Ala Leu Leu
1               5                   10                  15

His Ala Ala Arg Pro Ser Gln Phe Arg Val Ser Pro Leu Asp Arg Thr
                20                  25                  30

Trp Asn Leu Gly Glu Thr Val Glu Leu Lys Cys Gln Val Leu Leu Ser
                35                  40                  45

Asn Pro Thr Ser Gly Cys Ser Trp Leu Phe Gln Pro Arg Gly Ala Ala
50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
                100                 105                 110

Tyr Phe Cys Ser Ala Leu Ser Asn Ser Ile Met Tyr Phe Ser His Phe
                115                 120                 125

Val Pro Val Phe Leu Pro Ala Lys Pro Thr Thr Thr Pro Ala Pro Arg
                130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly

```
            165                 170                 175
Leu Asp Phe Ala Cys Asp Ile Tyr Ile Trp Ala Pro Leu Ala Gly Thr
            180                 185                 190

Cys Gly Val Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
210                 215                 220

Gly Asp Lys Pro Ser Leu Ser Ala Arg Tyr Val
225                 230                 235

<210> SEQ ID NO 12
<211> LENGTH: 458
<212> TYPE: PRT
<213> ORGANISM: Homo sapiens

<400> SEQUENCE: 12

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Leu Ala Phe Gln Lys Ala Ser
        195                 200                 205

Ser Ile Val Tyr Lys Lys Glu Gly Glu Gln Val Glu Phe Ser Phe Pro
210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
290                 295                 300
```

```
Thr Gly Lys Leu His Gln Glu Val Asn Leu Val Met Arg Ala Thr
305                 310                 315                 320

Gln Leu Gln Lys Asn Leu Thr Cys Glu Val Trp Gly Pro Thr Ser Pro
            325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
            405                 410                 415

Phe Phe Cys Val Arg Cys Arg His Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
    450                 455

<210> SEQ ID NO 13
<211> LENGTH: 288
<212> TYPE: PRT
<213> ORGANISM: Homo sapiens

<400> SEQUENCE: 13

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220
```

```
Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 14
<211> LENGTH: 244
<212> TYPE: PRT
<213> ORGANISM: Homo sapiens

<400> SEQUENCE: 14

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Ala Ala Ala Pro Thr Thr Thr Pro Ala Pro Arg
                165                 170                 175

Pro Pro Thr Pro Ala Pro Thr Ile Ala Ser Gln Pro Leu Ser Leu Arg
            180                 185                 190

Pro Glu Ala Cys Arg Pro Ala Ala Gly Gly Ala Val His Thr Arg Gly
        195                 200                 205

Leu Asp Phe Ala Cys Asp Ile Tyr Ile Trp Ala Pro Leu Ala Gly Thr
    210                 215                 220

Cys Gly Val Leu Leu Leu Ser Leu Val Ile Thr Leu Tyr Cys Asn His
225                 230                 235                 240

Arg Arg Ile Gln

<210> SEQ ID NO 15
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15
```

-continued

Gly Ser Gly Ala Thr Asn Phe Ser Leu Leu Lys Gln Ala Gly Asp Val
1               5                   10                  15

Glu Glu Asn Pro Gly Pro Met
            20

<210> SEQ ID NO 16
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 17
<211> LENGTH: 502
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Met Gln Ile Pro Gln Ala Pro Trp Pro Val Val Trp Ala Val Leu Gln
1               5                   10                  15

-continued

```
Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Ala Ala Ala Pro Thr Thr Thr Pro Ala Pro Arg
                165                 170                 175

Pro Pro Thr Pro Ala Pro Thr Ile Ala Ser Gln Pro Leu Ser Leu Arg
            180                 185                 190

Pro Glu Ala Cys Arg Pro Ala Ala Gly Gly Ala Val His Thr Arg Gly
        195                 200                 205

Leu Asp Phe Ala Cys Asp Ile Tyr Ile Trp Ala Pro Leu Ala Gly Thr
    210                 215                 220

Cys Gly Val Leu Leu Leu Ser Leu Val Ile Thr Leu Tyr Cys Asn His
225                 230                 235                 240

Arg Arg Ile Gln Gly Ser Gly Ala Thr Asn Phe Ser Leu Leu Lys Gln
                245                 250                 255

Ala Gly Asp Val Glu Glu Asn Pro Gly Pro Met Val Ser Lys Gly Glu
            260                 265                 270

Glu Asp Asn Met Ala Ile Ile Lys Glu Phe Met Arg Phe Lys Val His
        275                 280                 285

Met Glu Gly Ser Val Asn Gly His Glu Phe Glu Ile Glu Gly Glu Gly
    290                 295                 300

Glu Gly Arg Pro Tyr Glu Gly Thr Gln Thr Ala Lys Leu Lys Val Thr
305                 310                 315                 320

Lys Gly Gly Pro Leu Pro Phe Ala Trp Asp Ile Leu Ser Pro Gln Phe
                325                 330                 335

Met Tyr Gly Ser Lys Ala Tyr Val Lys His Pro Ala Asp Ile Pro Asp
            340                 345                 350

Tyr Leu Lys Leu Ser Phe Pro Glu Gly Phe Lys Trp Glu Arg Val Met
        355                 360                 365

Asn Phe Glu Asp Gly Gly Val Val Thr Val Thr Gln Asp Ser Ser Leu
    370                 375                 380

Gln Asp Gly Glu Phe Ile Tyr Lys Val Lys Leu Arg Gly Thr Asn Phe
385                 390                 395                 400

Pro Ser Asp Gly Pro Val Met Gln Lys Lys Thr Met Gly Trp Glu Ala
                405                 410                 415

Ser Ser Glu Arg Met Tyr Pro Glu Asp Gly Ala Leu Lys Gly Glu Ile
            420                 425                 430

Lys Gln Arg Leu Lys Leu Lys Asp Gly Gly His Tyr Asp Ala Glu Val
```

|  |  | 435 |  |  |  | 440 |  |  |  | 445 |  |
| --- | --- | --- | --- | --- | --- | --- | --- | --- | --- | --- | --- |

Lys Thr Thr Tyr Lys Ala Lys Lys Pro Val Gln Leu Pro Gly Ala Tyr
    450                         455                  460

Asn Val Asn Ile Lys Leu Asp Ile Thr Ser His Asn Glu Asp Tyr Thr
465                      470                  475                  480

Ile Val Glu Gln Tyr Glu Arg Ala Glu Gly Arg His Ser Thr Gly Gly
            485                  490                  495

Met Asp Glu Leu Tyr Lys
        500

<210> SEQ ID NO 18
<211> LENGTH: 1726
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 18

| | |
|---|---|
| accggtggta cctcacccTT accgagtcgg cgacacagtg tgggtccgcc gacaccagac | 60 |
| taagaaccta gaacctcgct ggaaaggacc ttacacagtc ctgctgacca cccccaccgc | 120 |
| cctcaaagta gacggcatcg cagcttggat acacgccgcc cacgtgaagg ctgccgaccc | 180 |
| cggggggtgga ccatcctcta gactggccac catgcagatc ccacaggcgc cctggccagt | 240 |
| cgtctgggcg gtgctacaac tgggctggcg gccaggatgg ttcttagact ccccagacag | 300 |
| gccctggaac ccccccacct tctccccagc cctgctcgtg gtgaccgaag ggacaacgc | 360 |
| caccttcacc tgcagcttct ccaacacatc ggagagcttc gtgctaaact ggtaccgcat | 420 |
| gagccccagc aaccagacgg acaagctggc cgctttcccc gaggaccgca gccagcccgg | 480 |
| ccaggactgc cgcttccgtg tcacacaact gcccaacggg cgtgacttcc acatgagcgt | 540 |
| ggtcagggcc cggcgcaatg acagcggcac ctacctctgt ggggccatct ccctggcccc | 600 |
| caaggcgcag atcaaagaga gcctgcgggc agagctcagg gtgacagaga agggcagaga | 660 |
| gtgcccaca gcccaccccca gccctcacc caggccagcc ggccaggcgg ccgcaccac | 720 |
| cacgacgcca gcgccgcgac caccaacccc ggcgcccacg atcgcgtcgc agcccctgtc | 780 |
| cctgcgccca gaggcgtgcc ggccagcggc gggggggcgca gtgcacacga gggggctgga | 840 |
| cttcgcctgt gatatctaca tctgggcgcc cctggccggg acttgtgggg tccttctcct | 900 |
| gtcactggtt atcaccctt actgcaacca caggcggatc caaggatctg agcaacaaa | 960 |
| cttctcacta ctcaaacaag caggtgacgt ggaggagaat cccggcccca tggtgagcaa | 1020 |
| gggcgaggag gataacatgg ccatcatcaa ggagttcatg cgcttcaagg tgcacatgga | 1080 |
| gggctccgtg aacggccacg agttcgagat cgagggcgag ggcgagggcc gcccctacga | 1140 |
| gggcacccag accgccaagc tgaaggtgac caagggtggc cccctgccct tcgcctggga | 1200 |
| catcctgtcc cctcagttca tgtacggctc caaggcctac gtgaagcacc ccgccgacat | 1260 |
| ccccgactac ttgaagctgt ccttccccga gggcttcaag tgggagcgcg tgatgaactt | 1320 |
| cgaggacggc ggcgtggtga ccgtgaccca ggactcctcc ctgcaggacg gcgagttcat | 1380 |
| ctacaaggtg aagctgcgcg gcaccaactt ccctctcgac ggccccgtaa tgcagaagaa | 1440 |
| gaccatgggc tgggaggcct cctccgagcg gatgtacccc gaggacggcg ccctgaaggg | 1500 |
| cgagatcaag cagaggctga agctgaagga cggcggccac tacgacgctg aggtcaagac | 1560 |
| cacctacaag gccaagaagc ccgtgcagct gcccggcgcc tacaacgtca acatcaagtt | 1620 |

-continued

```
ggacatcacc tcccacaacg aggactacac catcgtggaa cagtacgaac gcgccgaggg    1680
ccgccactcc accggcggca tggacgagct gtacaagtaa ctcgag                   1726
```

<210> SEQ ID NO 19
<211> LENGTH: 223
<212> TYPE: PRT
<213> ORGANISM: Homo sapiens

<400> SEQUENCE: 19

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```

<210> SEQ ID NO 20
<211> LENGTH: 289
<212> TYPE: PRT
<213> ORGANISM: Homo sapiens

<400> SEQUENCE: 20

```
Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
```

```
                    85                  90                  95
Phe Phe Ile Leu His Phe Glu Pro Val Leu Pro Asn Asp Asn Gly Ser
                100                 105                 110
Tyr Arg Cys Ser Ala Asn Phe Gln Ser Asn Leu Ile Glu Ser His Ser
                115                 120                 125
Thr Thr Leu Tyr Val Thr Asp Val Lys Ser Ala Ser Glu Arg Pro Ser
            130                 135                 140
Lys Asp Glu Met Ala Ser Arg Pro Trp Leu Leu Tyr Ser Leu Leu Pro
145                 150                 155                 160
Leu Gly Gly Leu Pro Leu Leu Ile Thr Thr Cys Phe Cys Leu Phe Cys
                165                 170                 175
Cys Leu Arg Arg His Gln Gly Lys Gln Asn Glu Leu Ser Asp Thr Ala
                180                 185                 190
Gly Arg Glu Ile Asn Leu Val Asp Ala His Leu Lys Ser Glu Gln Thr
            195                 200                 205
Glu Ala Ser Thr Arg Gln Asn Ser Gln Val Leu Leu Ser Glu Thr Gly
            210                 215                 220
Ile Tyr Asp Asn Asp Pro Asp Leu Cys Phe Arg Met Gln Glu Gly Ser
225                 230                 235                 240
Glu Val Tyr Ser Asn Pro Cys Leu Glu Glu Asn Lys Pro Gly Ile Val
                245                 250                 255
Tyr Ala Ser Leu Asn His Ser Val Ile Gly Pro Asn Ser Arg Leu Ala
                260                 265                 270
Arg Asn Val Lys Glu Ala Pro Thr Glu Tyr Ala Ser Ile Cys Val Arg
                275                 280                 285
Ser

<210> SEQ ID NO 21
<211> LENGTH: 301
<212> TYPE: PRT
<213> ORGANISM: Homo sapiens

<400> SEQUENCE: 21

Met Phe Ser His Leu Pro Phe Asp Cys Val Leu Leu Leu Leu Leu Leu
1               5                   10                  15
Leu Leu Thr Arg Ser Ser Glu Val Glu Tyr Arg Ala Glu Val Gly Gln
                20                  25                  30
Asn Ala Tyr Leu Pro Cys Phe Tyr Thr Pro Ala Ala Pro Gly Asn Leu
                35                  40                  45
Val Pro Val Cys Trp Gly Lys Gly Ala Cys Pro Val Phe Glu Cys Gly
            50                  55                  60
Asn Val Val Leu Arg Thr Asp Glu Arg Asp Val Asn Tyr Trp Thr Ser
65                  70                  75                  80
Arg Tyr Trp Leu Asn Gly Asp Phe Arg Lys Gly Asp Val Ser Leu Thr
                85                  90                  95
Ile Glu Asn Val Thr Leu Ala Asp Ser Gly Ile Tyr Cys Cys Arg Ile
                100                 105                 110
Gln Ile Pro Gly Ile Met Asn Asp Glu Lys Phe Asn Leu Lys Leu Val
            115                 120                 125
Ile Lys Pro Ala Lys Val Thr Pro Ala Pro Thr Arg Gln Arg Asp Phe
            130                 135                 140
Thr Ala Ala Phe Pro Arg Met Leu Thr Thr Arg Gly His Gly Pro Ala
145                 150                 155                 160
Glu Thr Gln Thr Leu Gly Ser Leu Pro Asp Ile Asn Leu Thr Gln Ile
```

```
                165                 170                 175
Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
            195                 200                 205

Ile Cys Ala Gly Leu Ala Leu Ala Leu Ile Phe Gly Ala Leu Ile Phe
        210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
        290                 295                 300
```

<210> SEQ ID NO 22
<211> LENGTH: 525
<212> TYPE: PRT
<213> ORGANISM: Homo sapiens

<400> SEQUENCE: 22

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240
```

```
Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Gln Leu
        515                 520                 525

<210> SEQ ID NO 23
<211> LENGTH: 244
<212> TYPE: PRT
<213> ORGANISM: Homo sapiens

<400> SEQUENCE: 23

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95
```

-continued

Ser Leu Thr Val Asn Asp Thr Gly Glu Tyr Phe Cys Ile Tyr His Thr
                100                 105                 110

Tyr Pro Asp Gly Thr Tyr Thr Gly Arg Ile Phe Leu Glu Val Leu Glu
            115                 120                 125

Ser Ser Val Ala Glu His Gly Ala Arg Phe Gln Ile Pro Leu Leu Gly
        130                 135                 140

Ala Met Ala Ala Thr Leu Val Val Ile Cys Thr Ala Val Ile Val Val
145                 150                 155                 160

Val Ala Leu Thr Arg Lys Lys Ala Leu Arg Ile His Ser Val Glu
                165                 170                 175

Gly Asp Leu Arg Arg Lys Ser Ala Gly Gln Glu Glu Trp Ser Pro Ser
                180                 185                 190

Ala Pro Ser Pro Pro Gly Ser Cys Val Gln Ala Glu Ala Ala Pro Ala
            195                 200                 205

Gly Leu Cys Gly Glu Gln Arg Gly Glu Asp Cys Ala Glu Leu His Asp
        210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 24
<211> LENGTH: 287
<212> TYPE: PRT
<213> ORGANISM: Homo sapiens

<400> SEQUENCE: 24

Met Ser Pro His Pro Thr Ala Leu Leu Gly Leu Val Leu Cys Leu Ala
1               5                   10                  15

Gln Thr Ile His Thr Gln Glu Glu Asp Leu Pro Arg Pro Ser Ile Ser
                20                  25                  30

Ala Glu Pro Gly Thr Val Ile Pro Leu Gly Ser His Val Thr Phe Val
            35                  40                  45

Cys Arg Gly Pro Val Gly Val Gln Thr Phe Arg Leu Glu Arg Asp Ser
        50                  55                  60

Arg Ser Thr Tyr Asn Asp Thr Glu Asp Val Ser Gln Ala Ser Pro Ser
65                  70                  75                  80

Glu Ser Glu Ala Arg Phe Arg Ile Asp Ser Val Arg Glu Gly Asn Ala
                85                  90                  95

Gly Leu Tyr Arg Cys Ile Tyr Tyr Lys Pro Pro Lys Trp Ser Glu Gln
            100                 105                 110

Ser Asp Tyr Leu Glu Leu Leu Val Lys Glu Ser Ser Gly Gly Pro Asp
        115                 120                 125

Ser Pro Asp Thr Glu Pro Gly Ser Ser Ala Gly Pro Thr Gln Arg Pro
    130                 135                 140

Ser Asp Asn Ser His Asn Glu His Ala Pro Ser Gln Gly Leu Lys
145                 150                 155                 160

Ala Glu His Leu Tyr Ile Leu Ile Gly Val Ser Val Val Phe Leu Phe
                165                 170                 175

Cys Leu Leu Leu Leu Val Leu Phe Cys Leu His Arg Gln Asn Gln Ile
            180                 185                 190

Lys Gln Gly Pro Pro Arg Ser Lys Asp Glu Glu Gln Lys Pro Gln Gln
        195                 200                 205

Arg Pro Asp Leu Ala Val Asp Val Leu Glu Arg Thr Ala Asp Lys Ala
    210                 215                 220

```
Thr Val Asn Gly Leu Pro Glu Lys Asp Arg Glu Thr Asp Thr Ser Ala
225                 230                 235                 240

Leu Ala Ala Gly Ser Ser Gln Glu Val Thr Tyr Ala Gln Leu Asp His
            245                 250                 255

Trp Ala Leu Thr Gln Arg Thr Ala Arg Ala Val Ser Pro Gln Ser Thr
            260                 265                 270

Lys Pro Met Ala Glu Ser Ile Thr Tyr Ala Ala Val Ala Arg His
            275                 280                 285

<210> SEQ ID NO 25
<211> LENGTH: 370
<212> TYPE: PRT
<213> ORGANISM: Homo sapiens

<400> SEQUENCE: 25

Met Leu Gly Gln Val Val Thr Leu Ile Leu Leu Leu Leu Lys Val
1               5                   10                  15

Tyr Gln Gly Lys Gly Cys Gln Gly Ser Ala Asp His Val Val Ser Ile
            20                  25                  30

Ser Gly Val Pro Leu Gln Leu Gln Pro Asn Ser Ile Gln Thr Lys Val
            35                  40                  45

Asp Ser Ile Ala Trp Lys Lys Leu Leu Pro Ser Gln Asn Gly Phe His
50                  55                  60

His Ile Leu Lys Trp Glu Asn Gly Ser Leu Pro Ser Asn Thr Ser Asn
65                  70                  75                  80

Asp Arg Phe Ser Phe Ile Val Lys Asn Leu Ser Leu Leu Ile Lys Ala
            85                  90                  95

Ala Gln Gln Gln Asp Ser Gly Leu Tyr Cys Leu Glu Val Thr Ser Ile
            100                 105                 110

Ser Gly Lys Val Gln Thr Ala Thr Phe Gln Val Phe Val Phe Glu Ser
            115                 120                 125

Leu Leu Pro Asp Lys Val Glu Lys Pro Arg Leu Gln Gly Gln Gly Lys
            130                 135                 140

Ile Leu Asp Arg Gly Arg Cys Gln Val Ala Leu Ser Cys Leu Val Ser
145                 150                 155                 160

Arg Asp Gly Asn Val Ser Tyr Ala Trp Tyr Arg Gly Ser Lys Leu Ile
                165                 170                 175

Gln Thr Ala Gly Asn Leu Thr Tyr Leu Asp Glu Glu Val Asp Ile Asn
            180                 185                 190

Gly Thr His Thr Tyr Thr Cys Asn Val Ser Asn Pro Val Ser Trp Glu
            195                 200                 205

Ser His Thr Leu Asn Leu Thr Gln Asp Cys Gln Asn Ala His Gln Glu
            210                 215                 220

Phe Arg Phe Trp Pro Phe Leu Val Ile Ile Val Ile Leu Ser Ala Leu
225                 230                 235                 240

Phe Leu Gly Thr Leu Ala Cys Phe Cys Val Trp Arg Arg Lys Arg Lys
            245                 250                 255

Glu Lys Gln Ser Glu Thr Ser Pro Lys Glu Phe Leu Thr Ile Tyr Glu
            260                 265                 270

Asp Val Lys Asp Leu Lys Thr Arg Arg Asn His Glu Gln Glu Gln Thr
            275                 280                 285

Phe Pro Gly Gly Gly Ser Thr Ile Tyr Ser Met Ile Gln Ser Gln Ser
            290                 295                 300

Ser Ala Pro Thr Ser Gln Glu Pro Ala Tyr Thr Leu Tyr Ser Leu Ile
```

```
                305                 310                 315                 320
            Gln Pro Ser Arg Lys Ser Gly Ser Arg Lys Arg Asn His Ser Pro Ser
                            325                 330                 335

Phe Asn Ser Thr Ile Tyr Glu Val Ile Gly Lys Ser Gln Pro Lys Ala
                            340                 345                 350

Gln Asn Pro Ala Arg Leu Ser Arg Lys Glu Leu Glu Asn Phe Asp Val
                            355                 360                 365

Tyr Ser
                370

<210> SEQ ID NO 26
<211> LENGTH: 181
<212> TYPE: PRT
<213> ORGANISM: Homo sapiens

<400> SEQUENCE: 26

Met Leu Leu Glu Pro Gly Arg Gly Cys Cys Ala Leu Ala Ile Leu Leu
1               5                   10                  15

Ala Ile Val Asp Ile Gln Ser Gly Gly Cys Ile Asn Ile Thr Ser Ser
                20                  25                  30

Ala Ser Gln Glu Gly Thr Arg Leu Asn Leu Ile Cys Thr Val Trp His
            35                  40                  45

Lys Lys Glu Glu Ala Glu Gly Phe Val Val Phe Leu Cys Lys Asp Arg
50                  55                  60

Ser Gly Asp Cys Ser Pro Glu Thr Ser Leu Lys Gln Leu Arg Leu Lys
65                  70                  75                  80

Arg Asp Pro Gly Ile Asp Gly Val Gly Glu Ile Ser Ser Gln Leu Met
                85                  90                  95

Phe Thr Ile Ser Gln Val Thr Pro Leu His Ser Gly Thr Tyr Gln Cys
            100                 105                 110

Cys Ala Arg Ser Gln Lys Ser Gly Ile Arg Leu Gln Gly His Phe Phe
        115                 120                 125

Ser Ile Leu Phe Thr Glu Thr Gly Asn Tyr Thr Val Thr Gly Leu Lys
130                 135                 140

Gln Arg Gln His Leu Glu Phe Ser His Asn Glu Gly Thr Leu Ser Ser
145                 150                 155                 160

Gly Phe Leu Gln Glu Lys Val Trp Val Met Leu Val Thr Ser Leu Val
                165                 170                 175

Ala Leu Gln Ala Leu
            180

<210> SEQ ID NO 27
<211> LENGTH: 592
<212> TYPE: PRT
<213> ORGANISM: Homo sapiens

<400> SEQUENCE: 27

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
            35                  40                  45

Arg Thr Ala His Pro Leu Arg His Ile Asn Asn Asp Met Ile Val Thr
        50                  55                  60

Asp Asn Asn Gly Ala Val Lys Phe Pro Gln Leu Cys Lys Phe Cys Asp
```

```
                65                  70                  75                  80
Val Arg Phe Ser Thr Cys Asp Asn Gln Lys Ser Cys Met Ser Asn Cys
                        85                  90                  95

Ser Ile Thr Ser Ile Cys Glu Lys Pro Gln Glu Val Cys Val Ala Val
                        100                 105                 110

Trp Arg Lys Asn Asp Glu Asn Ile Thr Leu Glu Thr Val Cys His Asp
                        115                 120                 125

Pro Lys Leu Pro Tyr His Asp Phe Ile Leu Glu Asp Ala Ala Ser Pro
                130                 135                 140

Lys Cys Ile Met Lys Glu Lys Lys Pro Gly Glu Thr Phe Phe Met
145                     150                 155                 160

Cys Ser Cys Ser Ser Asp Glu Cys Asn Asp Asn Ile Ile Phe Ser Glu
                        165                 170                 175

Glu Tyr Asn Thr Ser Asn Pro Asp Leu Leu Val Ile Phe Gln Val
                180                 185                 190

Thr Gly Ile Ser Leu Leu Pro Pro Leu Gly Val Ala Ile Ser Val Ile
                    195                 200                 205

Ile Ile Phe Tyr Cys Tyr Arg Val Asn Arg Gln Gln Lys Leu Ser Ser
        210                 215                 220

Thr Trp Glu Thr Gly Lys Thr Arg Lys Leu Met Glu Phe Ser Glu His
225                     230                 235                 240

Cys Ala Ile Ile Leu Glu Asp Asp Arg Ser Asp Ile Ser Ser Thr Cys
                        245                 250                 255

Ala Asn Asn Ile Asn His Asn Thr Glu Leu Leu Pro Ile Glu Leu Asp
                    260                 265                 270

Thr Leu Val Gly Lys Gly Arg Phe Ala Glu Val Tyr Lys Ala Lys Leu
            275                 280                 285

Lys Gln Asn Thr Ser Glu Gln Phe Glu Thr Val Ala Val Lys Ile Phe
        290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
                340                 345                 350

His Ala Lys Gly Asn Leu Gln Glu Tyr Leu Thr Arg His Val Ile Ser
            355                 360                 365

Trp Glu Asp Leu Arg Lys Leu Gly Ser Ser Leu Ala Arg Gly Ile Ala
370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
                420                 425                 430

Leu Ser Val Asp Asp Leu Ala Asn Ser Gly Gln Val Gly Thr Ala Arg
            435                 440                 445

Tyr Met Ala Pro Glu Val Leu Glu Ser Arg Met Asn Leu Glu Asn Val
        450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495
```

```
Pro Pro Phe Gly Ser Lys Val Arg Glu His Pro Cys Val Glu Ser Met
            500                 505                 510

Lys Asp Asn Val Leu Arg Asp Arg Gly Arg Pro Glu Ile Pro Ser Phe
            515                 520                 525

Trp Leu Asn His Gln Gly Ile Gln Met Val Cys Glu Thr Leu Thr Glu
        530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ser Gly Gly Gly Ser
1               5

<210> SEQ ID NO 29
<211> LENGTH: 4
<212> TYPE: PRT
<213> ORGANISM: Homo sapiens

<400> SEQUENCE: 29

Tyr Val Lys Met
1
```

IMMUNE CELL COMPOSITIONS AND METHODS OF USE FOR TREATING VIRAL AND OTHER INFECTIONS

1. CROSS-REFERENCE TO RELATED APPLICATIONS

This application is a national stage of International Patent Application No. PCT/US2017/049085, filed Aug. 29, 2017, which claims the benefit of U.S. Provisional application No. 62/381,219, filed Aug. 30, 2016, and U.S. Provisional application No. 62/468,881, filed Mar. 8, 2017; each Provisional application is incorporated by reference herein in its entirety.

2. REFERENCE TO SEQUENCE LISTING SUBMITTED ELECTRONICALLY

This application incorporates by reference a Sequence Listing with this application as an ASCII text file entitled "13542-038-228_SL.TXT" created on Aug. 22, 2017, and having a size of 59,378 bytes.

3. FIELD

The present invention relates generally to treating viral infections, and more specifically to immunotherapy for treating viral infections.

4. BACKGROUND

Viral infections are known to cause a wide range of diseases. An acute viral infection is characterized by viral replication, spread, secondary replication, tissue damage and shedding (Virgin et al., Cell 138(1):30-50 (2009)). If the infected subject survives the acute viral infection, either the host immune system clears the infection, or the infection becomes persistent.

Persistent viral infections are characterized as viral infections that are not cleared from an individual but remain or persist in cells of the individual (see Boldogh et al., "Persistent Viral Infections" in *Medical Microbiology*, 4th ed., Baron, editor, Chapter 46, The University of Texas Medical Branch at Galveston (1996); Virgin et al., Cell 138(1):30-50 (2009)). Persistent viral infections can be classified as latent, chronic or slow infections (Boldogh et al., supra, 1996).

Latent infections lack demonstrable infectious virus between episodes of recurrent disease. In chronic infection, continued presence of infectious virus follows the primary infection and may include chronic or recurrent disease. Slow infection involves a prolonged incubation period followed by progressive disease (Boldogh et al., supra, 1996). Unlike latent and chronic infections, slow infection does not necessarily begin with an acute period of viral multiplication. During persistent infections, the viral genome can be stably integrated into the cellular DNA or maintained episomally (see Boldogh et al., supra, 1996).

A number of viral infections have a tendency to become persistent infections. Examples of such viral infections include infection with human immunodeficiency virus (HIV), hepatitis B virus (HBV) and hepatitis C virus (HCV). Infection with human immunodeficiency virus (HIV) can lead to acquired immunodeficiency syndrome (AIDS) and related medical conditions (Bennett et al., *Cecil Textbook of Medicine*, 20th ed., pp. 1837-1891, W.B. Saunders, Philadelphia Pa. (1996); Fauci et al., *Harrison's Principles of Internal Medicine*, 14th ed., pp. 1791-1856, McGraw-Hill, San Francisco Calif. (1998)). Infection with hepatitis B virus (HBV), which predominantly affects the liver, can lead to progressive chronic liver disease with cirrhosis and, in some cases, hepatocellular carcinoma (Bennett et al., *Cecil Textbook of Medicine*, 20th ed., pp. 762-767, W.B. Saunders, Philadelphia Pa. (1996); Fauci et al., *Harrison's Principles of Internal Medicine*, 14th ed., pp. 1677-1681, McGraw-Hill, San Francisco Calif. (1998)). Infection with hepatitis C virus (HCV), which also predominantly affects the liver, also can lead to progressive chronic liver disease with cirrhosis and, in some cases, hepatocellular carcinoma (Bennett et al., *Cecil Textbook of Medicine*, 20th ed., pp. 762-764, 767-769, W.B. Saunders, Philadelphia Pa. (1996); Fauci et al., *Harrison's Principles of Internal Medicine*, 14th ed., pp. 1677, 1681-1682, McGraw-Hill, San Francisco Calif. (1998)). Such viral infections can lead to persistent infections.

Other viral infections include infection with herpes simplex virus (HSV), varicella zoster virus or (VZV), adenovirus, cytomegalovirus (CMV), and Epstein-Barr Virus (EBV). Infection with HSV can lead to gingivostomatitis, usually caused by HSV-1, for example, herpes simplex labialis (cold sores) (Bennett et al., *Cecil Textbook of Medicine*, 20th ed., pp. 1770-1774, W.B. Saunders, Philadelphia Pa. (1996); Fauci et al., *Harrison's Principles of Internal Medicine*, 14th ed., pp. 1080-1086, McGraw-Hill, San Francisco Calif. (1998)). Infection with HSV can also cause genital herpes, most commonly caused by HSV-2; herpetic keratitis, usually caused by HSV-1 and often accompanied by conjunctivitis; neonatal HSV infection, usually caused by HSV-2; and herpes simplex encephalitis, usually caused by HSV-1. Infection with HSV can become a latent infection (Bennett et al., *Cecil Textbook of Medicine*, 20th ed., pp. 1770-1774, W.B. Saunders, Philadelphia Pa. (1996); Fauci et al., *Harrison's Principles of Internal Medicine*, 14th ed., pp. 1080-1086, McGraw-Hill, San Francisco Calif. (1998)).

Infection with VZV can cause chickenpox (Bennett et al., *Cecil Textbook of Medicine*, 20th ed., pp. 1763-1765, W.B. Saunders, Philadelphia Pa. (1996); Fauci et al., *Harrison's Principles of Internal Medicine*, 14th ed., pp. 1086-1089, McGraw-Hill, San Francisco Calif. (1998)). Latent infections can evolve to herpes zoster (shingles) caused by reactivation of VZV that is normally latent in sensory ganglia (Bennett et al., *Cecil Textbook of Medicine*, 20th ed., pp. 2093-2095, W.B. Saunders, Philadelphia Pa. (1996); Fauci et al., *Harrison's Principles of Internal Medicine*, 14th ed., pp. 1086-1089, McGraw-Hill, San Francisco Calif. (1998)). Infection with adenovirus can cause disease in a variety of human epithelial tissues including the eye (pharyngoconjunctival fever; epidemic keratoconjunctivitis), respiratory tract, including upper respiratory tract illness (acute pharyngitis; exudative tonsillitis) and lower respiratory tract (pneumonia), urinary disease (hemorrhagic cystitis), and gastrointestinal disease (gastroenteritis) (Bennett et al., *Cecil Textbook of Medicine*, 20th ed., pp. 1757-1759, W.B. Saunders, Philadelphia Pa. (1996); Fauci et al., *Harrison's Principles of Internal Medicine*, 14th ed., pp. 1104-1105, McGraw-Hill, San Francisco Calif. (1998)).

Infection with CMV can cause infectious mononucleosis and congenital infection (Bennett et al., *Cecil Textbook of Medicine*, 20th ed., pp. 1774-1776, W.B. Saunders, Philadelphia Pa. (1996); Fauci et al., *Harrison's Principles of Internal Medicine*, 14th ed., pp. 1092-1095, McGraw-Hill, San Francisco Calif. (1998)). Infection with EBV can cause infectious mononucleosis, including chronic mononucleosis or chronic fatigue syndrome, and latent EBV infection is associated with B lymphomas in immunosuppressed patients (Bennett et al., *Cecil Textbook of Medicine*, 20th ed., pp. 1776-1779, W.B. Saunders, Philadelphia Pa. (1996);

Fauci et al., *Harrison's Principles of Internal Medicine*, 14th ed., pp. 1089-1091, McGraw-Hill, San Francisco Calif. (1998)).

Functional impairment of T cells is characteristic of many human viral infections (see Day et al., *Nature* 443:350-354 (2006) and references cited therein). PD-1 is a negative regulator of activated T cells, and is markedly upregulated on the surface of exhausted virus-specific $CD8^+$ T cells (Ishida et al., *EMBO J.* 11:3887-3895 (1992); Noshimura et al., *Immunity* 11:141-151 (1999); Sharpe et al., *Nat. Rev. Immunol.* 2:116-126 (2002); Che, *Nat. Rev. Immunol.* 4:336-347 (2004); Barber et al., *Nature* 439:682-687 (2006)). Blockade of this pathway using antibodies against the PD ligand 1 (PD-L1, also known as CD274) restores $CD8^+$ T-cell function and reduces viral load (Barber et al., *Nature* 439:682-687 (2006)). It was found that PD-1 is significantly upregulated on T cells, and expression correlates with impaired HIV-specific $CD8^+$ T-cell function as well as predictors of disease progression: positively with plasma viral load and inversely with $CD4^+$ T-cell count (Day et al., *Nature* 443:350-354 (2006)). PD-1 expression on $CD4^+$ T cells likewise showed a positive correlation with viral load and an inverse correlation with $CD4^+$ T-cell count, and blockade of the pathway augmented HIV-specific $CD4^+$ and $CD8^+$ T-cell function (Day et al., *Nature* 443:350-354 (2006)). The results described by Day et al. (supra, 2006) indicate that the immunoregulatory PD-1/PD-L1 pathway is operative during a persistent viral infection in humans, and define a reversible defect in HIV-specific T-cell function (Day et al., *Nature* 443:350-354 (2006)).

PD-1-mediated inhibitory signaling not only attenuates HBV-specific $CD8^+$ T-cell effector function during the acute phase of infection but also correlates with the development of HBV-specific memory $CD8^+$ T cells following disease resolution (Zhang et al., *J. Hepatol.* 50:1163-1173 (2009)). In a study of patients with hepatitis B, PD-1 was significantly upregulated and subsequently led to the functional suppression of HBV-specific effector $CD8^+$ T cells, as blocking PD-1/PD-L1 interactions in vitro enhanced their proliferation and IFN-gamma production (Zhang et al., supra, 2009). Following disease resolution, HBV-specific effector $CD8^+$ T cells developed into memory T cells. During this period, the dynamic PD-1 decrease was numerically correlated with the reduction of HBV-specific $CD8^+$ T-cell frequency, phenotypically correlated with an acquisition of CCR7, CD45RA and CD127 expression, and functionally correlated with the increase in proliferation and IFN-gamma production of the memory T cells (Zhang et al., supra, 2009).

Chronic viral infection, unlike acute infection, leads to a large expansion of regulatory T cells (Treg cells) and their upregulation of PD-1 (Park et al., supra, *J. Immunol.* 194:5801-5811 (2015)). Treg cells from chronically infected mice (chronic Treg cells) displayed greater suppressive capacity for inhibiting both $CD8^+$ and $CD4^+$ T cell proliferation and for inhibiting subsequent cytokine production than those from naive or acutely infected mice (Park et al., supra, 2015). A contact between Treg and $CD8^+$ T cells was necessary for the potent suppression of $CD8^+$ T cell immune response. More importantly, the suppression required cell-specific expression and interaction of PD-1 on chronic Treg cells and PD-1 ligand on $CD8^+$ T cells (Park et al., supra, 2015).

T cell therapy has been previously described, in which the host immune system is utilized to treat or eliminate cancer or viral infections (see "T Cell Therapies: An Overview" Catapult Cell and Gene Therapy, White Paper 1 (ct.catapult.org.uk/wp-content/uploads/2016/03/Review-of-T-cell-Receptor-Therapies-2014_v2.pdf) (2014); Rooney et al., *Mol. Ther. Nucleic Acids* 1:e55, doi: 10.1038/mtna.2012.49 (2012)). Such therapies include gene modified T cell receptor (TCR) therapies and chimeric antigen receptor (CAR) therapies (see "T Cell Therapies: An Overview" Catapult Cell and Gene Therapy, White Paper 1 (ct.catapult.org.uk/wp-content/uploads/2016/03/Review-of-T-cell-Receptor-Therapies-2014_v2.pdf) (2014)). The use of CAR therapy in the treatment of conditions such as cancer has been previously described (see, for example, Sadelain et al., *Cancer Discov.* 3(4):388-398 (2013); Jensen et al., *Immunol. Rev.* 257:127-133 (2014); Sharpe et al., *Dis. Model Mech.* 8(4):337-350 (2015); Brentjens et al., *Clin. Cancer Res.* 13:5426-5435 (2007); Gade et al., *Cancer Res.* 65:9080-9088 (2005); Maher et al., *Nat. Biotechnol.* 20:70-75 (2002); Kershaw et al., *J. Immunol.* 173:2143-2150 (2004); Sadelain et al., *Curr. Opin. Immunol.* 21(2):215-223 (2009); Hollyman et al., *J. Immunother.* 32:169-180 (2009); WO/2015/188141).

There exists a need for therapies to provide improved treatment of viral infections, such as chronic viral infections. The object of the present invention is to satisfy this need.

5. SUMMARY OF INVENTION

The present invention relates to cells that are immune cells, which cells recombinantly express a dominant negative form of an inhibitor of a cell-mediated immune response of the immune cell, and optionally recombinantly express a chimeric antigen receptor (CAR), wherein the CAR binds to a viral antigen.

In one aspect, provided herein is a cell that is an immunostimulatory cell or precursor cell thereof, which cell recombinantly expresses (a) a chimeric antigen receptor (CAR), and (b) a dominant negative form of an inhibitor of a cell-mediated immune response of the immunostimulatory cell, wherein the CAR binds to a viral antigen. In another aspect, provided herein is a population of immunostimulatory cells or precursor cells thereof, which cell population comprises cells that recombinantly express (a) a chimeric antigen receptor (CAR), and (b) a dominant negative form of an inhibitor of a cell-mediated immune response of the immunostimulatory cell, wherein the CAR binds to a viral antigen. In certain embodiments, the immunostimulatory cell is a T cell. In certain embodiments, the precursor cell is a hematopoietic stem or hematopoietic progenitor cell. In a specific embodiment, the immunostimulatory cell is a cytotoxic T lymphocyte (CTL). In another specific embodiment, the cell is a T cell. In another specific embodiment, the cell is a Natural Killer (NK) cell. In another specific embodiment, the cell is a memory T cell. In another specific embodiment, the memory T cell is a memory $CD8^+$ T cell.

In another aspect, provided herein is a T cell that recognizes and is sensitized to a viral antigen, which T cell recombinantly expresses a dominant negative form of an inhibitor of a T cell-mediated immune response. In certain embodiments, the T cell is immunostimulatory. In a specific embodiment, the T cell is $CD4^+$. In another specific embodiment, the T cell is $CD8^+$.

In another aspect, provided herein is a population of T cells, which cell population comprises T cells that recognize and are sensitized to a viral antigen and which recombinantly express a dominant negative form of an inhibitor of a T cell-mediated immune response. In certain embodiments, the T cells are immunostimulatory. In a specific embodiment, the T cells are $CD4^+$. In another specific embodiment, the T cells are $CD8^+$.

In certain embodiments of the invention, the cell or cell population is derived from a human. In certain embodiments of the invention, the viral antigen is of a virus that is a human pathogen. In certain embodiments of the invention, the viral antigen can elicit an immune response in a human subject infected with the virus.

In certain embodiments of the invention, the viral antigen is selected from the group consisting of a human immunodeficiency virus (HIV) antigen, a hepatitis B virus (HBV) antigen, a hepatitis C virus (HCV) antigen, a herpes simplex virus (HSV) antigen, a varicella zoster virus (VZV) antigen, an adenovirus antigen, a cytomegalovirus (CMV) antigen, and an Epstein-Barr virus (EBV) antigen. In a specific embodiment, the viral antigen is a HIV antigen selected from the group consisting of group-specific antigen (gag) protein, p55, p24, p18, envelope glycoprotein (env), gp160, gp120, gp41, reverse transcriptase (pol), p66, and p31. In another specific embodiment, the viral antigen is a HBV antigen selected from the group consisting of HBV envelope protein S, HBV envelope protein M, HBV envelope protein L, and the S domain of HBV envelope protein S, M or L. In another specific embodiment, the viral antigen is a HCV antigen selected from the group consisting of core protein, envelope protein E1, envelope protein E2, NS2, NS3, NS4 (e.g., NS4A or NS4B), and NS5 (e.g., NS5A or NS5B). In another specific embodiment, the viral antigen is a HSV antigen selected from the group consisting of gE, gI, gB, gD, gH, gL, gC, gG, gK, gM, and the extracellular domain of gE. In another specific embodiment, the viral antigen is a VZV antigen selected from the group consisting of gE and gI. In another specific embodiment, the viral antigen is an adenovirus antigen selected from the group consisting of hexon protein and penton protein. In another specific embodiment, the viral antigen is a CMV antigen selected from the group consisting of pp65, immediate early (IE) antigen, and IE1. In another specific embodiment, the viral antigen is an EBV antigen selected from the group consisting of latent membrane protein 2 (LMP2), Epstein-Barr nuclear antigen 1 (EBNA1), and BZLF1.

In certain embodiments of the invention, the inhibitor of a cell-mediated immune response is an immune checkpoint inhibitor. In certain embodiments, the immune checkpoint inhibitor is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIR1), natural killer cell receptor 2B4 (2B4), and CD160. In a particular embodiment, the immune checkpoint inhibitor is PD-1. In another embodiment, the inhibitor of a cell-mediated immune response is transforming growth factor β (TGF-β) receptor.

In certain embodiments of the invention, the cell of the invention further recombinantly expresses a suicide gene. In a specific embodiment, the suicide gene comprises inducible Caspase 9.

In another aspect, provided herein is a regulatory T cell that recognizes and is sensitized to a viral antigen, which regulatory T cell recombinantly expresses a dominant negative form of an inhibitor of a regulatory T cell-mediated immune response. In another aspect, provided herein is a population of regulatory T cells, which cell population comprises T cells that recognize and are sensitized to a viral antigen and which recombinantly express a dominant negative form of an inhibitor of a regulatory T cell-mediated immune response. In certain embodiments of the invention, the regulatory T cell is isolated from a subject having a chronic viral infection.

In another aspect, provided herein is a regulatory T cell isolated from a subject having a viral infection, which regulatory T cell recombinantly expresses a dominant negative form of an inhibitor of a regulatory T cell-mediated immune response. In another aspect, provided herein is a population of regulatory T cells isolated from a subject having a viral infection, which cell population comprises regulatory T cells which recombinantly express a dominant negative form of an inhibitor of a regulatory T cell-mediated immune response. In certain embodiments, the cell or cell population is derived from a human. In certain embodiments, the viral infection is infection with a virus that is a human pathogen. In certain embodiments, the viral infection is a chronic viral infection. In certain embodiments, the viral infection is infection with HCV, HBV, HIV, HSV, VZV, adenovirus, CMV or EBV.

In another aspect, provided herein is an immunoinhibitory cell, which cell is isolated from a subject having a viral infection, which immunoinhibitory cell recombinantly expresses a dominant negative form of an inhibitor of an immunoinhibitory cell-mediated immune response. In another aspect, provided herein is a population of immunoinhibitory cells isolated from a subject having a viral infection, which cell population comprises immunoinhibitory cells which recombinantly express a dominant negative form of an inhibitor of an immunoinhibitory cell-mediated immune response. In certain embodiments, the cell or cell population is derived from a human. In certain embodiments, the viral infection is infection with a virus that is a human pathogen. In certain embodiments, the viral infection is a chronic viral infection. In certain embodiments, the immunoinhibitory cell is a regulatory T cell. In certain embodiments, the immunoinhibitory cell recognizes and is sensitized to a viral antigen of the virus of the viral infection. In certain embodiments, the immunoinhibitory cell recombinantly expresses a chimeric antigen receptor (CAR), wherein the CAR binds to a viral antigen of the virus of the viral infection. In a specific embodiment, the regulatory T cell is a human $CD4^+CD25^+$ T cell. In another specific embodiment, the regulatory T cell is a human $CD4^+$ $CD127^{lo/-}CD25^+$ T cell.

In another aspect, provided herein is a polyclonal population of human regulatory T cells that are $CD4^+CD25^+$, are sensitized to a viral antigen, and recombinantly express a dominant negative form of an inhibitor of a regulatory T cell-mediated immune response. In certain embodiments, the human regulatory T cells are $CD127^{lo/-}$.

In certain embodiments, the regulatory T cell or population of regulatory T cells is derived from a human. In certain embodiments, the viral antigen is of a virus that is a human pathogen. In certain embodiments, the viral antigen can elicit an immune response in a human subject infected with the virus.

In certain embodiments of the regulatory T cells or regulatory T cell population, the viral antigen is selected from the group consisting of a hepatitis C virus (HCV) antigen, a human immunodeficiency virus (HIV) antigen, a hepatitis B virus (HBV) antigen, a herpes simplex virus (HSV) antigen, a varicella zoster virus (VZV) antigen, an adenovirus antigen, a cytomegalovirus (CMV) antigen, and an Epstein-Barr virus (EBV) antigen. In a specific embodiment, the viral antigen is a HCV antigen selected from the group consisting of core protein, envelope protein E1, envelope protein E2, NS2, NS3, NS4 (e.g., NS4A or NS4B), and NS5 (e.g., NS5A or NS5B). In another specific embodiment, the viral antigen is a HIV antigen selected from the group consisting of group-specific antigen (gag) protein, p55, p24, p18, envelope glycoprotein (env), gp160, gp120, gp41, reverse transcriptase (pol), p66, and p31. In another specific embodiment, the viral antigen is a HBV antigen selected from the group consisting of HBV envelope protein S, HBV envelope protein M, HBV envelope protein L, and the S domain of HBV envelope protein S, M or L. In another specific embodiment, the viral antigen is a HSV antigen selected from the group consisting of gE, gI, gB, gD, gH, gL, gC, gG, gK, gM, and the extracellular domain of gE. In another specific embodiment, the viral antigen is a VZV antigen selected from the group consisting of gE and gI. In another specific embodiment, the viral antigen is an adenovirus antigen selected from the group consisting of hexon protein and penton protein. In another specific embodiment, the viral antigen is a CMV antigen selected from the group consisting of pp65, immediate early (IE) antigen, and IE1. In another specific embodiment, the viral antigen is an EBV antigen selected from the group consisting of latent membrane protein 2 (LMP2), Epstein-Barr nuclear antigen 1 (EBNA1), and BZLF1.

In certain embodiments of the invention relating to immunoinhibitory cells or regulatory T cells, the inhibitor of a cell-mediated immune response is an immune checkpoint inhibitor. In certain embodiments, the immune checkpoint inhibitor is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIR1), natural killer cell receptor 2B4 (2B4), and CD160. In a specific embodiment, the immune checkpoint inhibitor is PD-1. In certain embodiments of the invention, the inhibitor of a cell-mediated immune response is transforming growth factor β (TGF-β) receptor. In certain embodiments, the immunoinhibitory cell or regulatory T cell, or population thereof, further recombinantly expresses a suicide gene. In a specific embodiment, the suicide gene comprises inducible Caspase 9.

In another aspect, provided herein is a cell that is an immunostimulatory cell or precursor cell thereof, which cell recombinantly expresses (a) a chimeric antigen receptor (CAR), wherein the CAR binds to a viral antigen; (b) a first dominant negative form of an inhibitor of a cell-mediated immune response of the immunostimulatory cell, wherein the first dominant negative form lacks an intracellular signaling domain and is a polypeptide comprising (i) at least a portion of an extracellular domain of an immune checkpoint inhibitor, wherein the portion comprises the ligand binding region, and (ii) a transmembrane domain; and (c) a second dominant negative form of an inhibitor of a cell-mediated immune response of the immunostimulatory cell, wherein the second dominant negative form is a polypeptide comprising (i) at least a portion of an extracellular domain of an immune checkpoint inhibitor, wherein the portion comprises the ligand binding region, (ii) a transmembrane domain, and (iii) a co-stimulatory signaling domain, wherein the co-stimulatory signaling domain is carboxy-terminal to the transmembrane domain of the dominant negative form.

In another aspect, provided herein is a population of immunostimulatory cells or precursor cells thereof, which cell population comprises cells that recombinantly express (a) a chimeric antigen receptor (CAR), wherein the CAR binds to a viral antigen; (b) a first dominant negative form of an inhibitor of a cell-mediated immune response of the immunostimulatory cell, wherein the first dominant negative form lacks an intracellular signaling domain and is a polypeptide comprising (i) at least a portion of an extracellular domain of an immune checkpoint inhibitor, wherein the portion comprises the ligand binding region, and (ii) a transmembrane domain; and (c) a second dominant negative form of an inhibitor of a cell-mediated immune response of the immunostimulatory cell, wherein the second dominant negative form is a polypeptide comprising (i) at least a portion of an extracellular domain of an immune checkpoint inhibitor, wherein the portion comprises the ligand binding region, (ii) a transmembrane domain, and (iii) a co-stimulatory signaling domain, wherein the co-stimulatory signaling domain is carboxy-terminal to the transmembrane domain of the dominant negative form.

In certain embodiments of such cells, the co-stimulatory signaling domain of the second dominant negative form is the intracellular signaling domain of 4-1BB. In certain embodiments of such cells, the CAR comprises a co-stimulatory signaling domain. In certain embodiments of such cells, the co-stimulatory signaling domain of the second dominant negative form is different from the co-stimulatory signaling domain of the CAR. In certain embodiments of such cells, the co-stimulatory signaling domain of the CAR is the intracellular signaling domain of CD28. In certain embodiments of such cells, the immunostimulatory cell is a T cell. In certain embodiments of such cells, the precursor cell is a hematopoietic stem or hematopoietic progenitor cell. In certain embodiments of such cells, the immunostimulatory cell is a cytotoxic T lymphocyte (CTL). In certain embodiments of such cells, the cell is a Natural Killer (NK) cell. In certain embodiments of such cells, the cell is a memory T cell. In certain embodiments of such cells, the memory T cell is a memory $CD8^+$ T cell.

In another aspect, provided herein is an immunoinhibitory cell, which cell is isolated from a subject having a viral infection, which immunoinhibitory cell recombinantly expresses (a) a chimeric antigen receptor (CAR), wherein the CAR binds to a viral antigen of the virus of the viral infection; (b) a first dominant negative form of an inhibitor of a cell-mediated immune response of the immunoinhibitory cell, wherein the first dominant negative form lacks an intracellular signaling domain and is a polypeptide comprising (i) at least a portion of an extracellular domain of an immune checkpoint inhibitor, wherein the portion comprises the ligand binding region, and (ii) a transmembrane domain; and (c) a second dominant negative form of an inhibitor of a cell-mediated immune response of the immunoinhibitory cell, wherein the second dominant negative form is a polypeptide comprising (i) at least a portion of an extracellular domain of an immune checkpoint inhibitor, wherein the portion comprises the ligand binding region, (ii) a transmembrane domain, and (iii) a co-stimulatory signaling domain, wherein the co-stimulatory signaling domain is carboxy-terminal to the transmembrane domain of the dominant negative form.

In another aspect, provided herein is a population of immunoinhibitory cells isolated from a subject having a viral infection, which cell population comprises immunoinhibitory cells which recombinantly express (a) a chimeric antigen receptor (CAR), wherein the CAR binds to a viral antigen of the virus of the viral infection; (b) a first dominant negative form of an inhibitor of a cell-mediated immune response of the immunoinhibitory cell, wherein the first dominant negative form lacks an intracellular signaling domain and is a polypeptide comprising (i) at least a portion of an extracellular domain of an immune checkpoint inhibitor, wherein the portion comprises the ligand binding region, and (ii) a transmembrane domain; and (c) a second dominant negative form of an inhibitor of a cell-mediated immune response of the immunoinhibitory cell, wherein the second dominant negative form is a polypeptide comprising (i) at least a portion of an extracellular domain of an immune checkpoint inhibitor, wherein the portion comprises the ligand binding region, (ii) a transmembrane domain, and (iii) a co-stimulatory signaling domain, wherein the co-stimulatory signaling domain is carboxy-terminal to the transmembrane domain of the dominant negative form.

In certain embodiments of such cells, the co-stimulatory signaling domain is the intracellular signaling domain of 4-1BB. In certain embodiments of such cells, the CAR comprises a co-stimulatory signaling domain. In certain embodiments of such cells, the co-stimulatory signaling domain of the second dominant negative form is different from the co-stimulatory signaling domain of the CAR. In certain embodiments of such cells, the co-stimulatory signaling domain of the CAR is the intracellular signaling domain of CD28. In certain embodiments of such cells, the cell or cell population is derived from a human. In certain embodiments of such cells, the viral infection is infection with a virus that is a human pathogen. In certain embodiments of such cells, the viral infection is a chronic viral infection. In certain embodiments of such cells, the immunoinhibitory cell is a regulatory T cell. In certain embodiments of such cells, the regulatory T cell is a human $CD4^+$ $CD25^+$ T cell. In certain embodiments of such cells, the regulatory T cell is a human $CD4^+CD127^{lo/-}CD25^+$ T cell.

In another aspect, provided herein is a cell that is an immunostimulatory cell or precursor cell thereof, which cell recombinantly expresses (a) a chimeric antigen receptor (CAR), and (b) a dominant negative form of an inhibitor of a cell-mediated immune response of the immunostimulatory cell, wherein the CAR binds to an antigen of a pathogen. In another aspect, provided herein is a population of immunostimulatory cells or precursor cells thereof, which cell population comprises cells that recombinantly express (a) a chimeric antigen receptor (CAR), and (b) a dominant negative form of an inhibitor of a cell-mediated immune response of the immunostimulatory cell, wherein the CAR binds to an antigen of a pathogen.

In certain embodiments of such a cell or cell population, the immunostimulatory cell is a T cell. In certain embodiments, the T cell is $CD4^+$. In certain embodiments, the T cell is $CD8^+$. In certain embodiments of such a cell or cell population, the precursor cell is a hematopoietic stem or hematopoietic progenitor cell. In certain embodiments of such a cell or cell population, the immunostimulatory cell is a cytotoxic T lymphocyte (CTL). In certain embodiments of such a cell or cell population, the cell is a Natural Killer (NK) cell. In certain embodiments of such a cell or cell population, the cell is a memory T cell. In a particular embodiment, the memory T cell is a memory $CD8^+$ T cell.

In another aspect, provided herein is a T cell that recognizes and is sensitized to an antigen of a pathogen, which T cell recombinantly expresses a dominant negative form of an inhibitor of a T cell-mediated immune response. In certain embodiments of such a T cell, the T cell is immunostimulatory. In a particular embodiment, the T cell is $CD4^+$. In another particular embodiment, the T cell is $CD8^+$.

In another aspect, provided herein is a population of T cells, which cell population comprises T cells that recognize and are sensitized to an antigen of a pathogen and which recombinantly express a dominant negative form of an inhibitor of a T cell-mediated immune response. In certain embodiments of such a population of T cells, the T cells are immunostimulatory.

In a particular embodiment of such a T cell or such a population of T cells, the T cells are $CD4^+$. In a particular embodiment of such a T cell or such a population of T cells, the T cells are $CD8^+$. In certain embodiments of such a T cell or such a population of T cells, the cell or cell population is derived from a human. In a particular embodiment of such a T cell or such a population of T cells, the pathogen is a human pathogen. In a particular embodiment, the antigen of the pathogen can elicit an immune response in a human subject infected with the pathogen. In certain embodiments of such a T cell or such a population of T cells, the pathogen is selected from the group consisting of a bacterium, fungus and protozoan.

In certain embodiments of such a T cell or such a population of T cells, the inhibitor of a cell-mediated immune response is an immune checkpoint inhibitor. In certain embodiments, the immune checkpoint inhibitor is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIR1), natural killer cell receptor 2B4 (2B4), and CD160. In a particular embodiment, the immune checkpoint inhibitor is PD-1. In certain embodiments, the inhibitor of a cell-mediated immune response is transforming growth factor β (TGF-β) receptor.

In certain embodiments of such a T cell or such a population of T cells, the cell further recombinantly expresses a suicide gene. In a particular embodiment, the suicide gene comprises inducible Caspase 9.

In another aspect, provided herein are pharmaceutical compositions comprising a therapeutically effective amount of the immune cells or population of immune cells of the invention; and a pharmaceutically acceptable carrier. In certain embodiments, the immune cells or population of immune cells are immunostimulatory cells described above. In certain embodiments, the immune cells or population of immune cells are T cells described above. In certain embodiments, the immune cells or population of immune cells are immunoinhibitory cells described above. In certain embodiments, the immune cells or population of immune cells are regulatory T cells described above.

In another aspect, provided herein is a method of treating a viral infection in a subject in need thereof, comprising administering to the subject a therapeutically effective amount of an immune cell or cell population of the invention, wherein the viral antigen is an antigen associated with the viral infection. In certain embodiments, the immune cells or population of immune cells are immunostimulatory cells described above. In certain embodiments, the immune cells or population of immune cells are T cells described above. In another aspect, provided herein is a method of treating a viral infection in a subject in need thereof, comprising administering to the subject a pharmaceutical composition comprising the immune cells or population of immune cells that are immunostimulatory cells described above, wherein the viral antigen is an antigen associated with the viral infection. In certain embodiments, the immune cells or population of immune cells are T cells described above. In certain embodiments of the methods, the subject is a human. In certain embodiments of the method, the viral infection is infection with a virus that is a human pathogen. In certain embodiments, the viral infection is infection with HIV, HBV, HCV, HSV, VZV, adenovirus, CMV or EBV. In certain embodiments, expression of the dominant negative form promotes production of virus-specific memory cells.

In another aspect, provided herein is a method of treating a viral infection in a subject in need thereof, comprising administering to the subject a therapeutically effective amount of the regulatory T cell or population of regulatory T cells described above, wherein the viral antigen is an antigen associated with the viral infection. In another aspect, provided herein is a method of treating a viral infection in a subject in need thereof, comprising administering to the subject the pharmaceutical composition comprising the regulatory T cell or population of regulatory T cells described above, wherein the viral antigen is an antigen associated with the viral infection.

In another aspect, provided herein is a method of treating a viral infection in a subject in need thereof, comprising administering to the subject a therapeutically effective amount of the immunoinhibitory cell or population of immunoinhibitory cells described above. In another aspect, provided herein is a method of treating a viral infection in a subject in need thereof, comprising administering to the subject the pharmaceutical composition comprising the immunoinhibitory cell or population of immunoinhibitory cells described above.

In certain embodiments of the methods of administering regulatory T cells or immunoinhibitory cells, or populations thereof, or pharmaceutical compositions comprising such cells or cell populations, the subject is a human. In certain of embodiments of the methods of administering regulatory T cells or immunoinhibitory cells, or populations thereof, or pharmaceutical compositions comprising such cells or cell populations, the viral infection is infection with a virus that is a human pathogen. In certain of embodiments of the methods of administering regulatory T cells or immunoinhibitory cells, or populations thereof, or pharmaceutical compositions comprising such cells or cell populations, the viral infection is a chronic viral infection. In certain of embodiments of the methods of administering regulatory T cells or immunoinhibitory cells, or populations thereof, or pharmaceutical compositions comprising such cells or cell populations, the viral infection is infection with HCV, HIV, HBV, HSV, VZV, adenovirus, CMV or EBV.

In another aspect, provided herein is a method of treating a viral infection in a subject in need thereof, comprising: (a) isolating virus-specific T cells from the subject; (b) expressing in the cells a dominant negative form of PD-1; and (c) administering the cells to the subject. In a specific embodiment, the viral infection is infection with HIV. In another aspect, provided herein is a method of treating a viral infection in a subject in need thereof, comprising: (a) isolating virus-specific T cells from the subject; (b) expressing in the cells a dominant negative form of PD-1, wherein expression of the dominant negative form of PD-1 promotes production of virus-specific memory cells; and (c) administering the cells to the subject. In a specific embodiment, the viral infection is infection with HBV. In another aspect, provided herein is a method of treating a viral infection in a subject in need thereof, comprising: (a) isolating regulatory T cells from a subject having a chronic viral infection; (b) expressing in the cells a dominant negative form of PD-1; and (c) administering the cells to the subject. In a specific embodiment, the viral infection is infection with HCV. In certain embodiments of the methods, the subject is a human. In certain embodiments of the methods, the viral infection is infection with a virus that is a human pathogen. In certain embodiments of the methods, the viral infection is infection with HIV, HBV, HCV, HSV, VZV, adenovirus, CMV or EBV.

In certain embodiments of the methods of the invention, the administering of the immune cell or immune cell population, or pharmaceutical composition comprising the immune cells or immune cell populations, is by intrapleural administration, intravenous administration, subcutaneous administration, intranodal administration, intrahepatic administration, intrathecal administration, intraperitoneal administration, intracranial administration, or direct administration to the thymus. In certain embodiments of the methods of the invention, the cell is administered in a dose in the range of $10^4$ to $10^{10}$ cells per kilogram of body weight. In a specific embodiment, the dose is in the range of $3\times10^5$ to $3\times10^6$ cells per kilogram of body weight. In certain embodiments of methods of the invention the cell or cell population is autologous to the subject.

In another aspect, provided herein is a method of treating a viral infection in a subject in need thereof, comprising administering to the subject a therapeutically effective amount of the cell or cell population, where the cell recombinantly expresses (a) a chimeric antigen receptor (CAR), wherein the CAR binds to a viral antigen; (b) a first dominant negative form of an inhibitor of a cell-mediated immune response of the immunostimulatory cell, wherein the first dominant negative form lacks an intracellular signaling domain and is a polypeptide comprising (i) at least a portion of an extracellular domain of an immune checkpoint inhibitor, wherein the portion comprises the ligand binding region, and (ii) a transmembrane domain; and (c) a second dominant negative form of an inhibitor of a cell-mediated immune response of the immunostimulatory cell, wherein the second dominant negative form is a polypeptide comprising (i) at least a portion of an extracellular domain of an immune checkpoint inhibitor, wherein the portion comprises the ligand binding region, (ii) a transmembrane domain, and (iii) a co-stimulatory signaling domain, wherein the co-stimulatory signaling domain is carboxy-terminal to the transmembrane domain of the dominant negative form and wherein the viral antigen is an antigen associated with the viral infection. In another embodiment, the invention provides a method of treating a viral infection in a subject in need thereof, comprising administering to the subject the pharmaceutical composition of such cells, wherein the viral antigen is an antigen associated with the viral infection.

In certain embodiments of such methods of the invention, the subject is a human. In certain embodiments of such methods, the viral infection is infection with a virus that is a human pathogen. In certain embodiments, the viral infection is infection with HIV, HBV, HCV, HSV, VZV, adenovirus, CMV or EBV. In certain embodiments of such methods, expression of the first dominant negative form promotes production in the subject of virus-specific memory cells.

In another aspect, provided herein is a method of treating a viral infection in a subject in need thereof, comprising administering to the subject a therapeutically effective amount of the cell or cell population, wherein the cell is isolated from a subject having a viral infection, which immunoinhibitory cell recombinantly expresses (a) a chimeric antigen receptor (CAR), wherein the CAR binds to a viral antigen of the virus of the viral infection; (b) a first dominant negative form of an inhibitor of a cell-mediated immune response of the immunoinhibitory cell, wherein the first dominant negative form lacks an intracellular signaling domain and is a polypeptide comprising (i) at least a portion of an extracellular domain of an immune checkpoint inhibitor, wherein the portion comprises the ligand binding region, and (ii) a transmembrane domain; and (c) a second dominant negative form of an inhibitor of a cell-mediated immune response of the immunoinhibitory cell, wherein the second dominant negative form is a polypeptide comprising (i) at least a portion of an extracellular domain of an immune checkpoint inhibitor, wherein the portion comprises the ligand binding region, (ii) a transmembrane domain, and (iii) a co-stimulatory signaling domain, wherein the co-stimulatory signaling domain is carboxy-terminal to the transmembrane domain of the dominant negative form; wherein the viral antigen is an antigen associated with the viral infection. In another embodiment, the provided herein is a method of treating a viral infection in a subject in need thereof, comprising administering to the subject a pharmaceutical composition of such cells, wherein the viral antigen is an antigen associated with the viral infection.

In certain embodiments of such methods of the invention, the subject is a human. In certain embodiments of such methods of the invention, the viral infection is infection with a virus that is a human pathogen. In certain embodiments, the viral infection is infection with HIV, HBV, HCV, HSV, VZV, adenovirus, CMV or EBV. In certain embodiments of such methods of the invention, expression of the first dominant negative form promotes production in the subject of virus-specific memory cells.

In another aspect, provided herein is a method of treating a viral infection in a subject in need thereof, comprising administering to the subject a therapeutically effective amount of (a) a first cell or first population of said first cell, wherein the first cell is an immunostimulatory cell and recombinantly expresses (i) a chimeric antigen receptor (CAR), wherein the CAR binds to a viral antigen and wherein the viral antigen is an antigen associated with the viral infection, and (ii) a dominant negative form of an inhibitor of a cell-mediated immune response of the immunostimulatory cell, wherein the dominant negative form lacks an intracellular signaling domain and is a polypeptide comprising (A) at least a portion of an extracellular domain of an immune checkpoint inhibitor, wherein the portion comprises the ligand binding region, and (B) a transmembrane domain; and (b) a second cell or second population of said second cell, wherein the second cell is an immunostimulatory cell and recombinantly expresses (i) a chimeric antigen receptor (CAR), wherein the CAR binds to a viral antigen and wherein the viral antigen is an antigen associated with the viral infection, and (ii) a dominant negative form of an inhibitor of a cell-mediated immune response of the immunostimulatory cell, wherein the dominant negative form is a polypeptide comprising (A) at least a portion of an extracellular domain of an immune checkpoint inhibitor, wherein the portion comprises the ligand binding region, (B) a transmembrane domain, and (C) a co-stimulatory signaling domain, wherein the co-stimulatory signaling domain is carboxy-terminal to the transmembrane domain of the dominant negative form. In certain embodiments of such methods, the subject is a human. In certain embodiments of such methods, the viral infection is infection with a virus that is a human pathogen. In certain embodiments, the viral infection is infection with HIV, HBV, HCV, HSV, VZV, adenovirus, CMV or EBV.

In another aspect, provided herein is a method of treating a viral infection in a subject in need thereof, comprising administering to the subject a therapeutically effective amount of (a) a first cell or first population of said first cell, wherein the first cell is an immunoinhibitory cell and recombinantly expresses (i) a chimeric antigen receptor (CAR), wherein the CAR binds to a viral antigen and wherein the viral antigen is an antigen associated with the viral infection, and (ii) a dominant negative form of an inhibitor of a cell-mediated immune response of the immunoinhibitory cell, wherein the dominant negative form lacks an intracellular signaling domain and is a polypeptide comprising (A) at least a portion of an extracellular domain of an immune checkpoint inhibitor, wherein the portion comprises the ligand binding region, and (B) a transmembrane domain; and (b) a second cell or second population of said second cell, wherein the second cell is an immunoinhibitory cell and recombinantly expresses (i) a chimeric antigen receptor (CAR), wherein the CAR binds to a viral antigen and wherein the viral antigen is an antigen associated with the viral infection, and (ii) a dominant negative form of an inhibitor of a cell-mediated immune response of the immunoinhibitory cell, wherein the dominant negative form is a polypeptide comprising (A) at least a portion of an extracellular domain of an immune checkpoint inhibitor, wherein the portion comprises the ligand binding region, (B) a transmembrane domain, and (C) a fusion to a co-stimulatory signaling domain, wherein the co-stimulatory signaling domain is carboxy-terminal to the transmembrane domain of the dominant negative form.

In certain embodiments of such methods, the subject is a human. In certain embodiments of such methods, the viral infection is infection with a virus that is a human pathogen. In certain embodiments, the viral infection is infection with HIV, HBV, HCV, HSV, VZV, adenovirus, CMV or EBV. In certain embodiments of such methods, the cell or cell population is autologous to the subject.

In another aspect, provided herein is a method of treating an infection caused by a pathogen in a subject in need thereof, comprising administering to the subject a therapeutically effective amount of a cell or cell population, wherein the cell or cell population recombinantly expresses (a) a chimeric antigen receptor (CAR), and (b) a dominant negative form of an inhibitor of a cell-mediated immune response of the immunostimulatory cell, wherein the CAR binds to an antigen of a pathogen, wherein the antigen of the pathogen to which the CAR binds is an antigen of the pathogen causing the infection. In another aspect, provided herein is a method of treating an infection caused a pathogen in a subject in need thereof, comprising administering to the subject a therapeutically effective amount of a cell or cell population, wherein the cell is, or cell population comprises, a T cell that recognizes and is sensitized to an antigen of a pathogen, which T cell recombinantly expresses a dominant negative form of an inhibitor of a T cell-mediated immune response, wherein the antigen of the pathogen to which the T cell is sensitized is an antigen of the pathogen causing the infection. In certain embodiments, the T cell is immunostimulatory. In certain embodiments, the T cell is CD4$^+$. In certain embodiments, the T cell is CD8$^+$.

In another aspect, provided herein is a method of treating an infection caused by a pathogen in a subject in need thereof, comprising administering to the subject a pharmaceutical composition comprising a cell or cell population, wherein the cell or cell population recombinantly expresses (a) a chimeric antigen receptor (CAR), and (b) a dominant negative form of an inhibitor of a cell-mediated immune response of the immunostimulatory cell, wherein the CAR binds to an antigen of a pathogen, wherein the antigen of the pathogen to which the CAR binds is an antigen of the pathogen causing the infection. In another aspect, provided herein is a method of treating an infection caused by a pathogen in a subject in need thereof, comprising administering to the subject a pharmaceutical composition comprising a T cell, or population of T cells, that recognizes and is sensitized to an antigen of the pathogen, which T cell recombinantly expresses a dominant negative form of an inhibitor of a T cell-mediated immune response, wherein the antigen of the pathogen to which the T cell is sensitized is an antigen of the pathogen causing the infection.

In certain embodiments of methods for treating an infection caused by a pathogen, the subject is a human. In certain embodiments of such methods, the pathogen is a human pathogen.

6. DESCRIPTION OF THE DRAWINGS

Figure 1B:
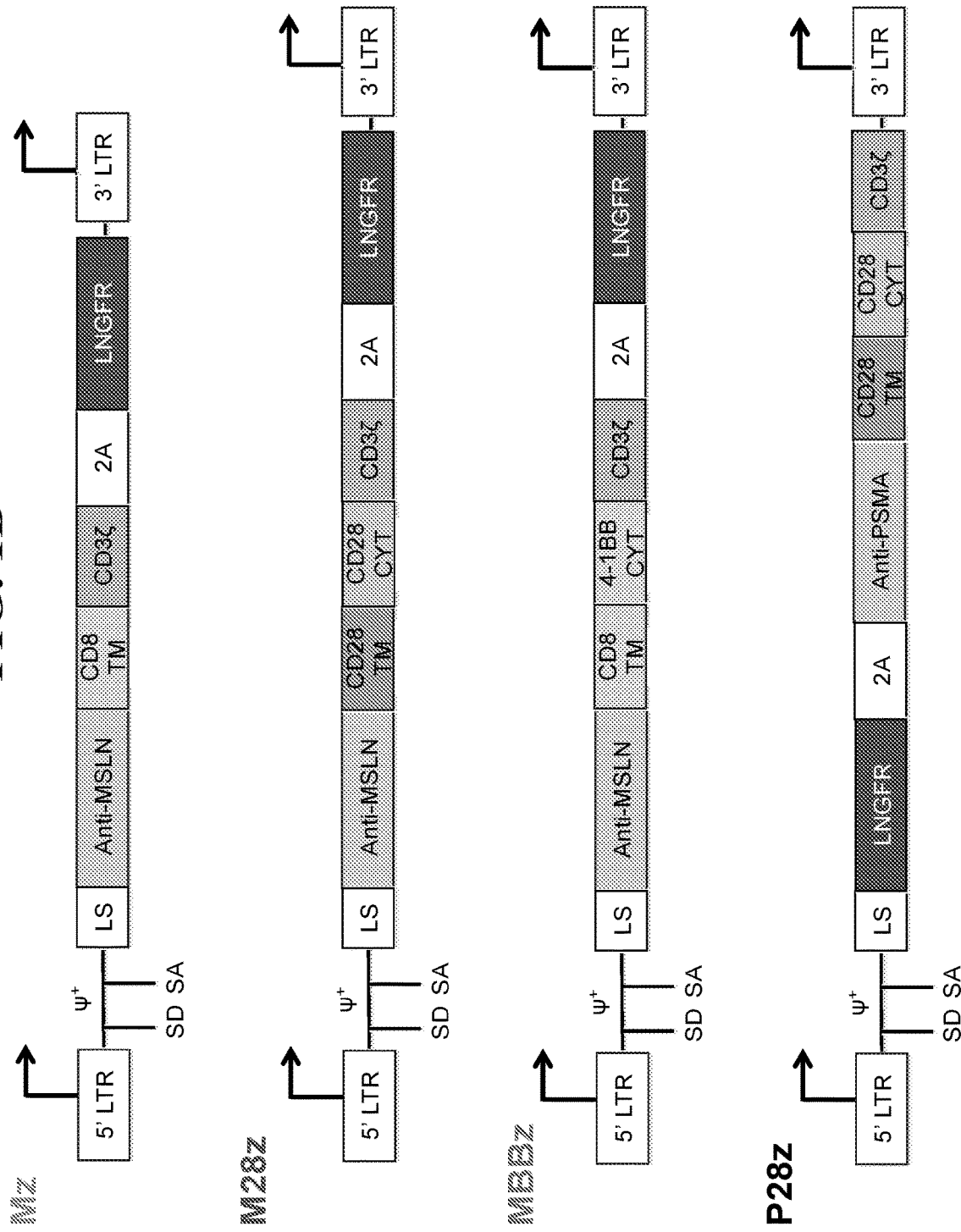
Figure 1C:
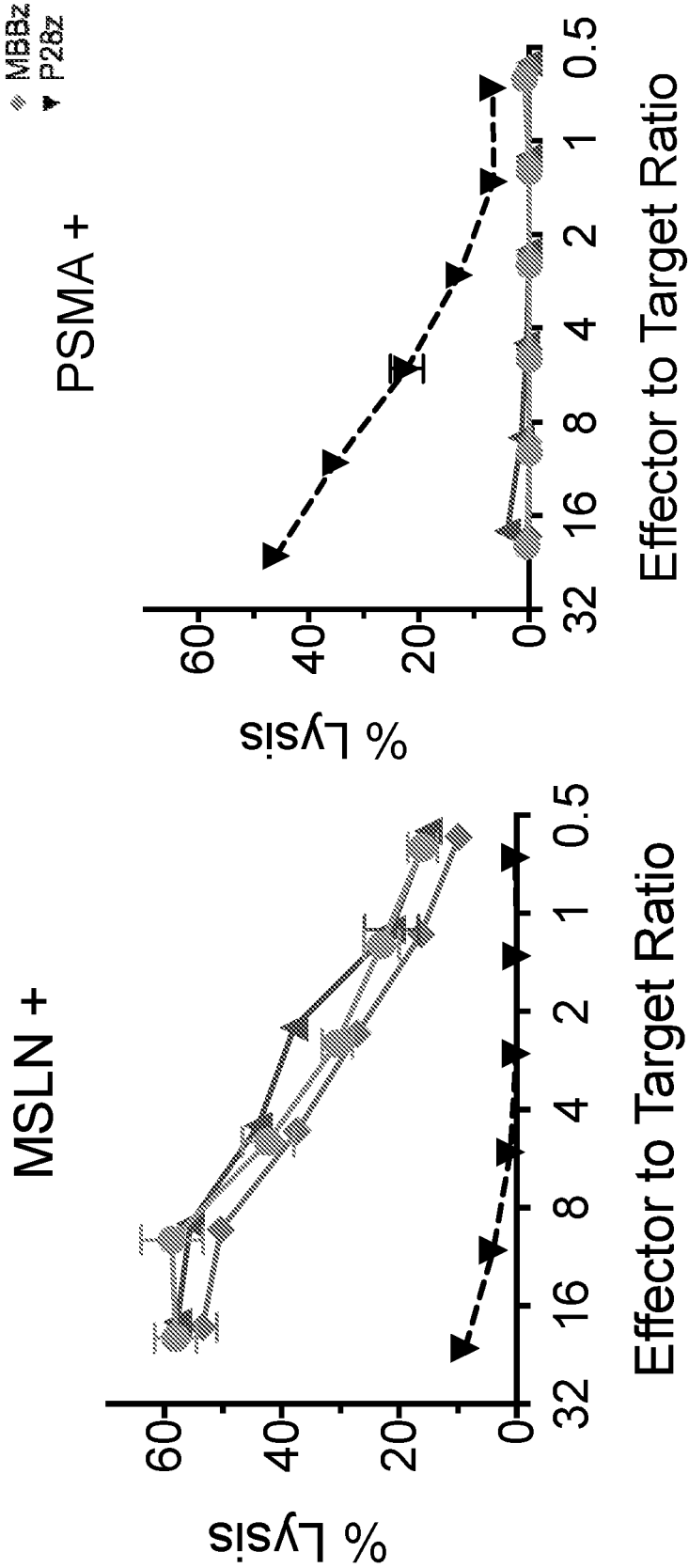
Figure 1D:
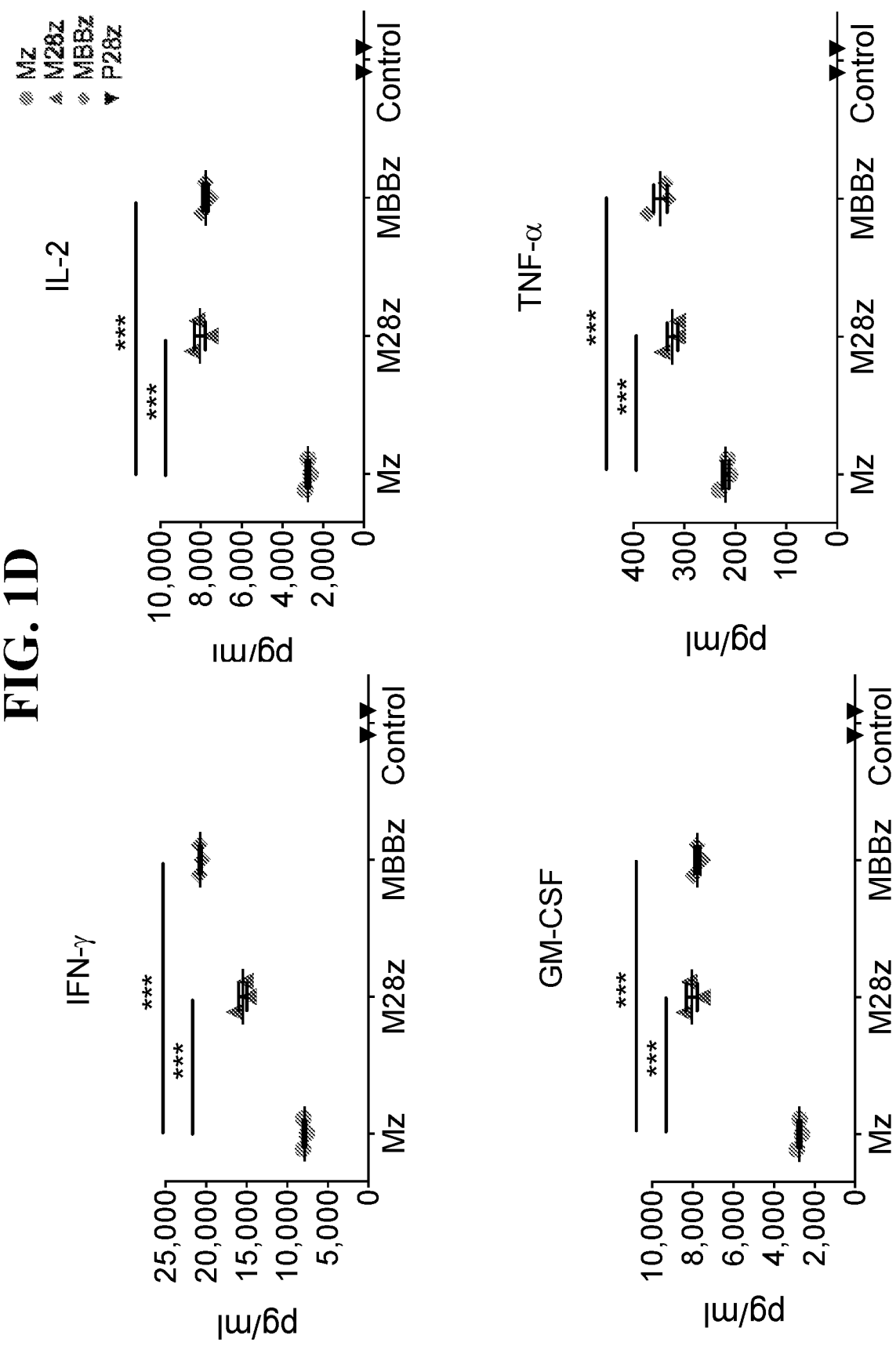
Figure 1E:
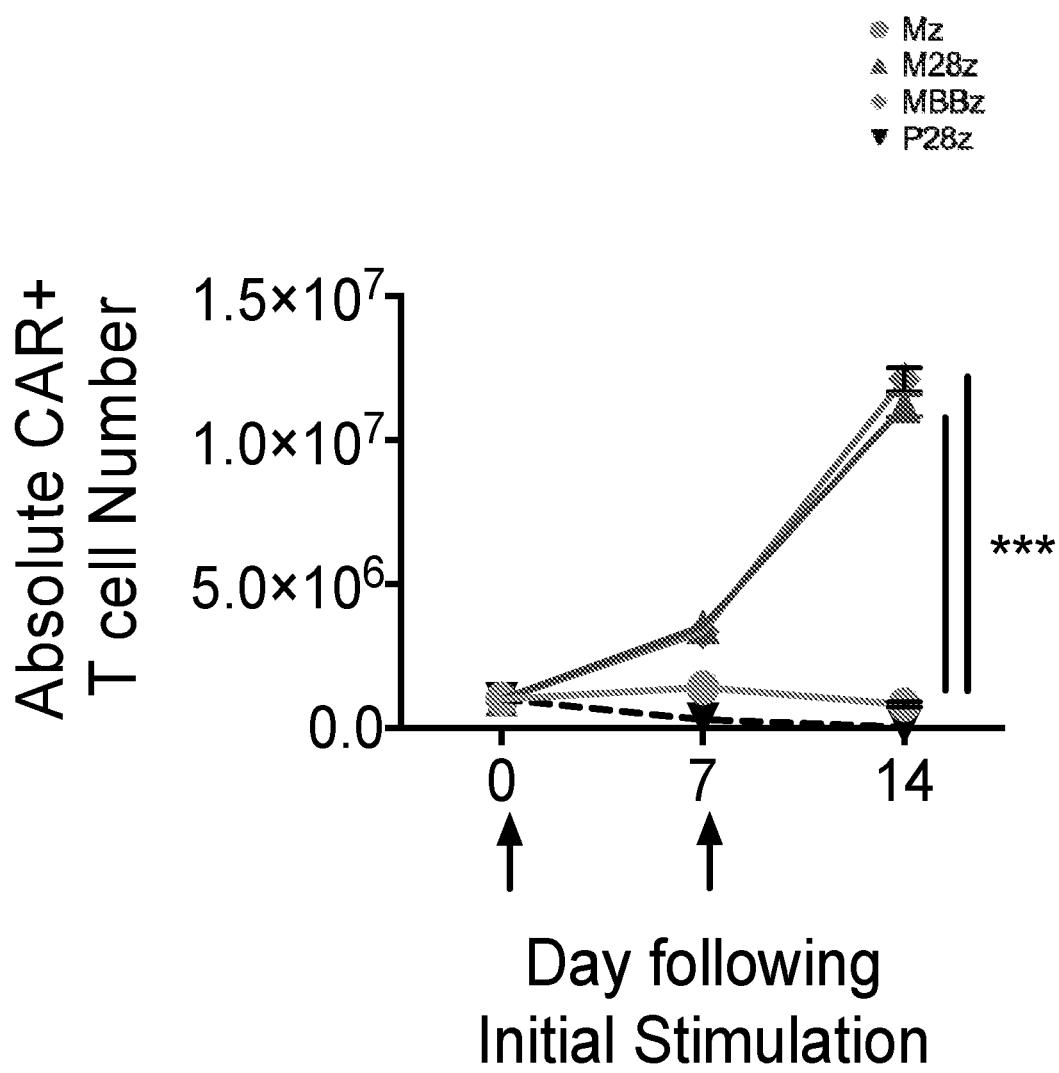

FIGS. 1A-1E show that chimeric antigen receptors (CARs) with CD28 or 4-1BB costimulation exhibit equivalent effector cytokine secretion and proliferation in vitro upon initial antigen stimulation. FIG. 1A. First- and second-generation CARs. FIG. 1B. Mesothelin (MSLN)-targeted CARs contain the CD3ζ endodomain either alone (Mz, first-generation CAR) or in combination with the CD28 (M28z) or 4-1BB (MBBz) costimulatory domain (second-generation CAR). A prostate-specific membrane antigen (PSMA)-directed CAR with CD28 costimulation (P28z) as well as PSMA-expressing targets (PSMA+) are included in experiments as negative controls. CYT, cytoplasmic domain; LS, leader sequence; LTR, long terminal repeat; SA, splice acceptor; SD, splice donor; TM, transmembrane. FIGS. 1C-1E. Antigen-specific effector functions of CAR-transduced T cells. FIG. 1C. Lysis of MSLN-expressing targets (MSLN+), but not PSMA+ targets, as measured by chromium-release assays. FIG. 1D. 4-1BB and CD28 costimulations enhance cytokine secretion, as assessed by Luminex assay, after coculture of CAR T cells with MSLN+ cells. FIG. 1E. M28z and MBBz CARs facilitate robust T-cell accumulation after stimulation with MSLN+ cells. Data represent the mean±SEM (FIGS. 1C, 1E) of three replicates or are plotted as individual points (FIG. 1D). ***P<0.001, comparing costimulated CAR T cells (M28z or MBBz) with the first-generation receptor (Mz), by Student's t test; significance was determined using the Bonferroni correction for multiple comparisons.

FIG. 2 shows efficient retroviral transduction of human T cells to express Mz, M28z, and MBBz CARs. (Top) Shown is representative FACS analysis 4 days after gene transfer. Fluorescence minus one staining was used to set positive gates after a live/dead stain excluded nonviable cells. All experiments used T cells with 50% to 70% CAR transduction efficiency; transduction percentages between T-cell groups were within 5% of each other. (Bottom) Both CD4+ and CD8+ T-cell subsets were efficiently transduced. CD4+ and CD8+ percentages after gating for CAR T cells are shown.

Figure 3A:
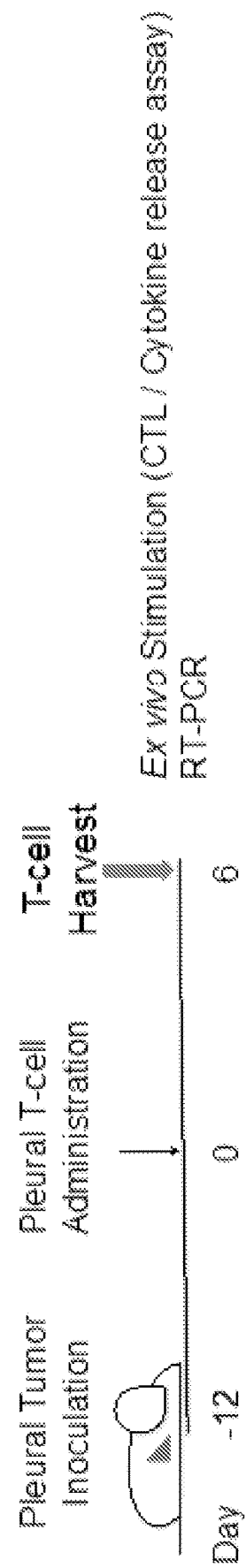
Figure 3C:
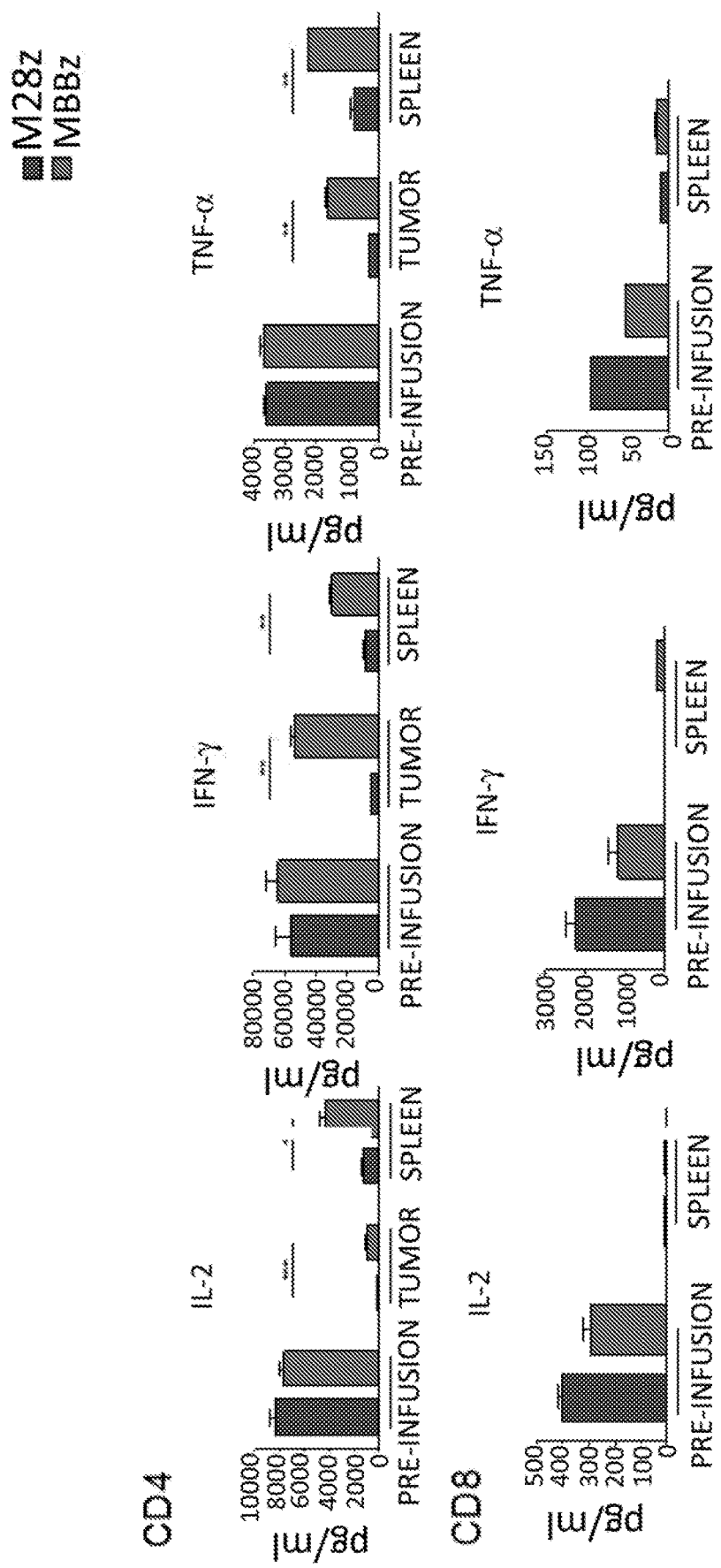
Figure 3D:
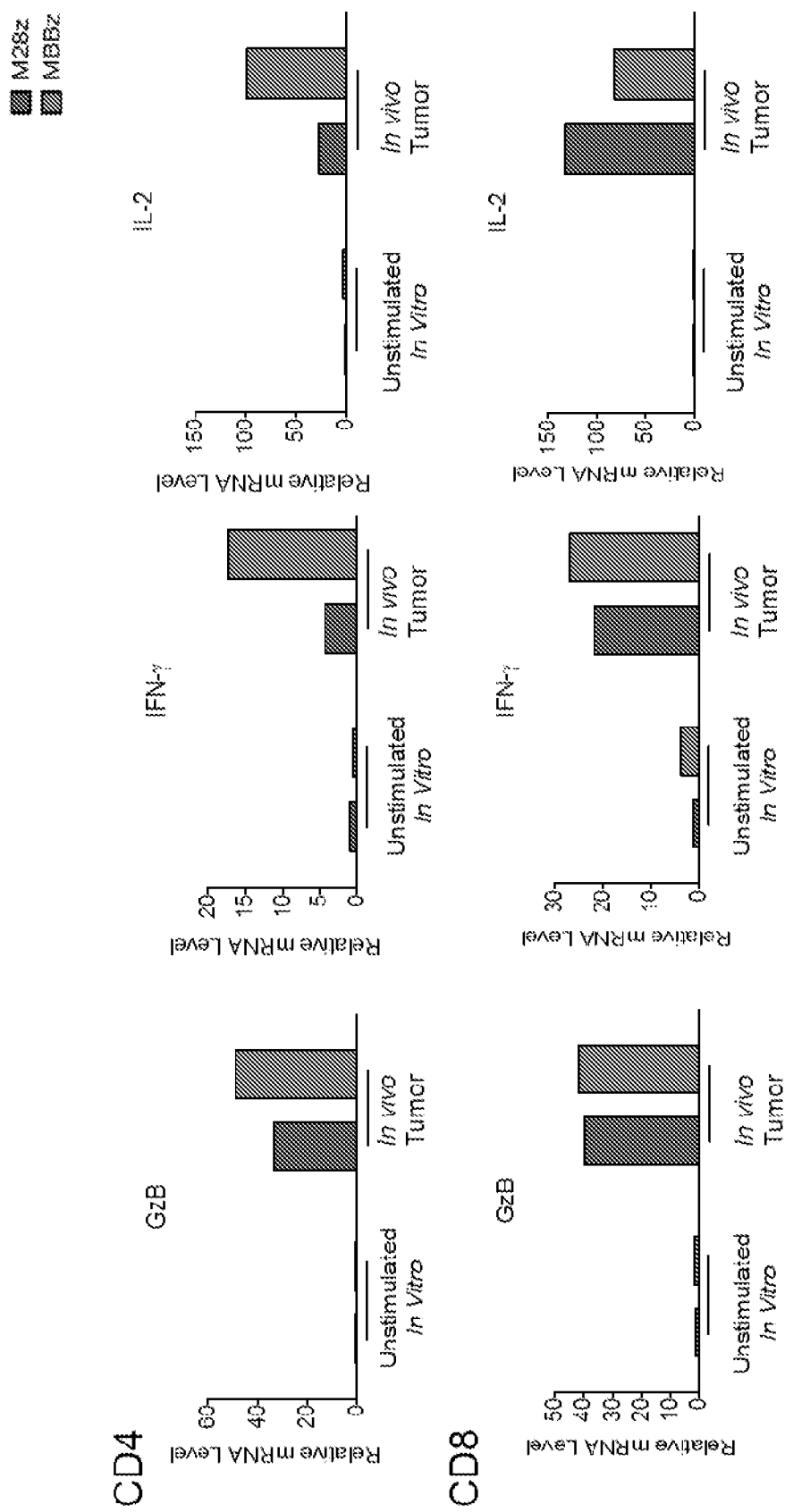

FIGS. 3A-3D show that CAR T cells become exhausted following in vivo antigen exposure, although MBBz CAR T cells preferentially retain effector cytokine secretion and cytotoxicity. FIG. 3A. Six days after intrapleural administration of CAR T cells, M28z and MBBz CAR T cells were isolated from the tumor and spleen and subjected to ex vivo antigen stimulation. FIG. 3B. Chromium-release assay upon ex vivo stimulation demonstrates a decrease in M28z but persistent MBBz cytolytic function (E:T ratio 1:5). FIG. 3C. Cytokine secretion measurements demonstrate decreases in effector cytokine secretion by CAR T cells, although MBBz CAR T cells are better able to retain secretion. FIG. 3D. RT-PCR measurements of GzB, IFN-γ, and TL-2 expression by harvested CAR T cells correlate well with protein level measurements. Data represent the fold-change relative to the mRNA expression of unstimulated M28z CAR T cell in vitro. Data represent the mean±SEM of three individual wells per condition. Student's t tests were performed, and statistical significance was determined using the Bonferroni correction for multiple comparisons (*P<0.05; P<0.01; *P<0.001). Results are reproduced in two separate cohorts of mice used for each of the two experiments. In each of FIGS. 3B-3D, each pair of bar graphs show, from left to right, M28z, MBBZ.

Figure 4A:
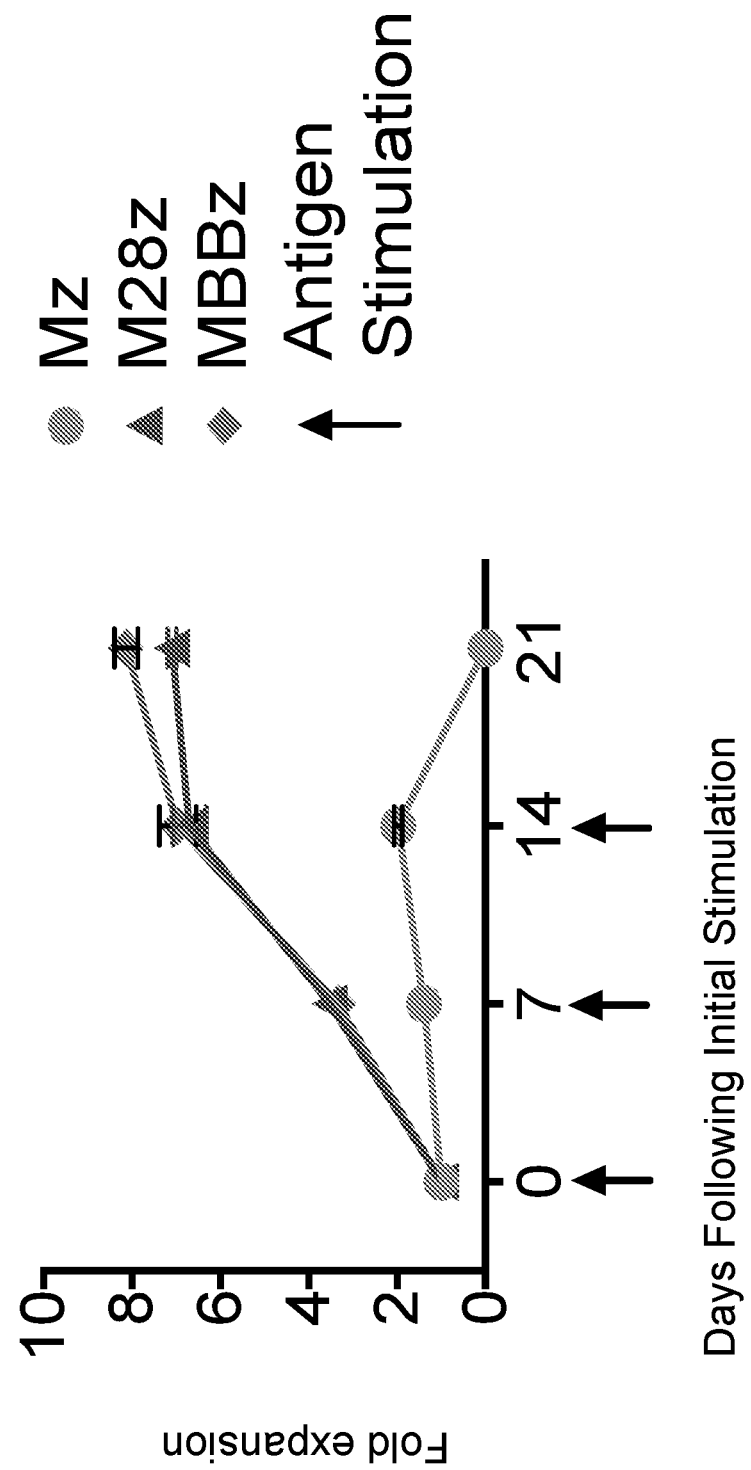
Figure 4B:
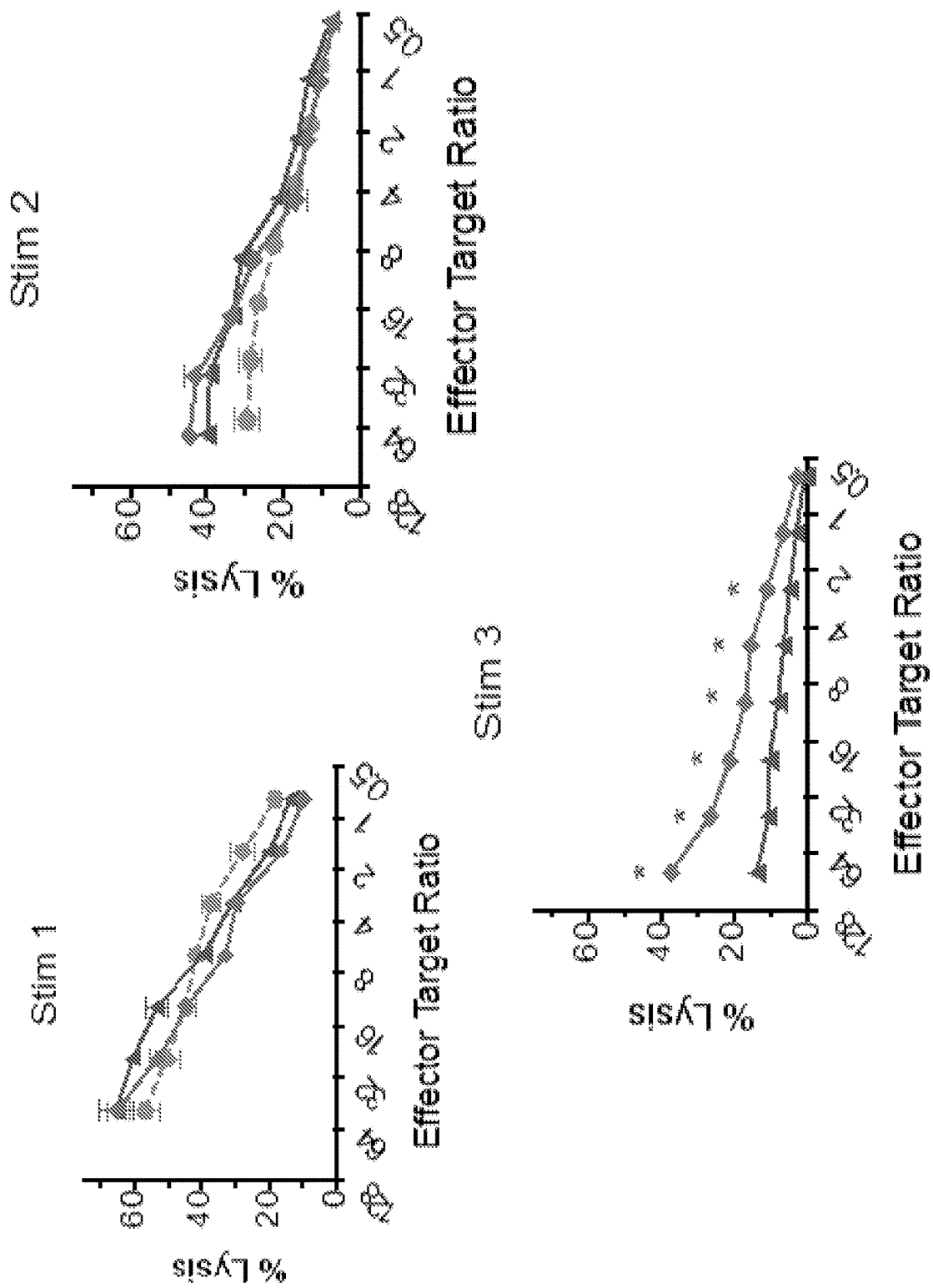
Figure 4C:
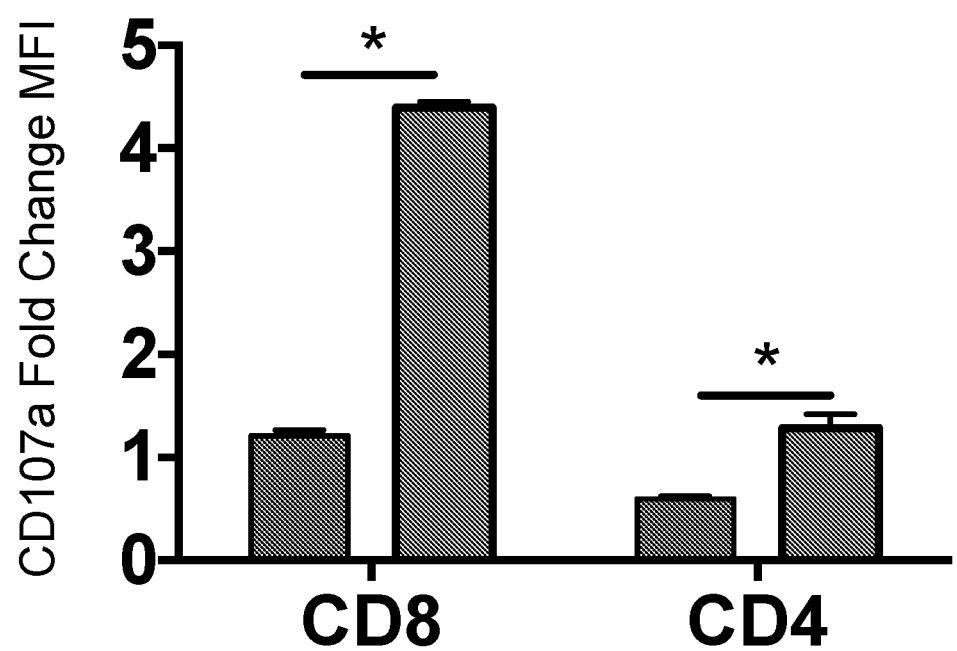
Figure 4D:
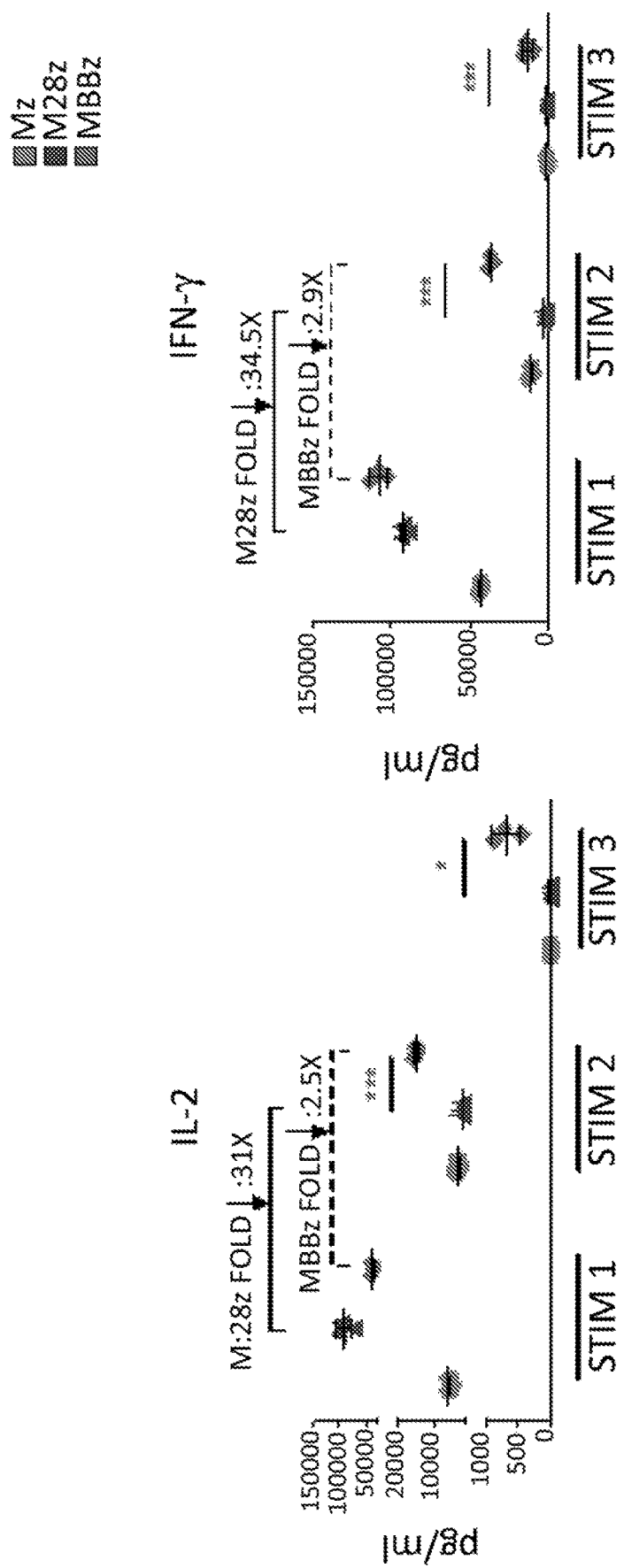
Figure 4E:
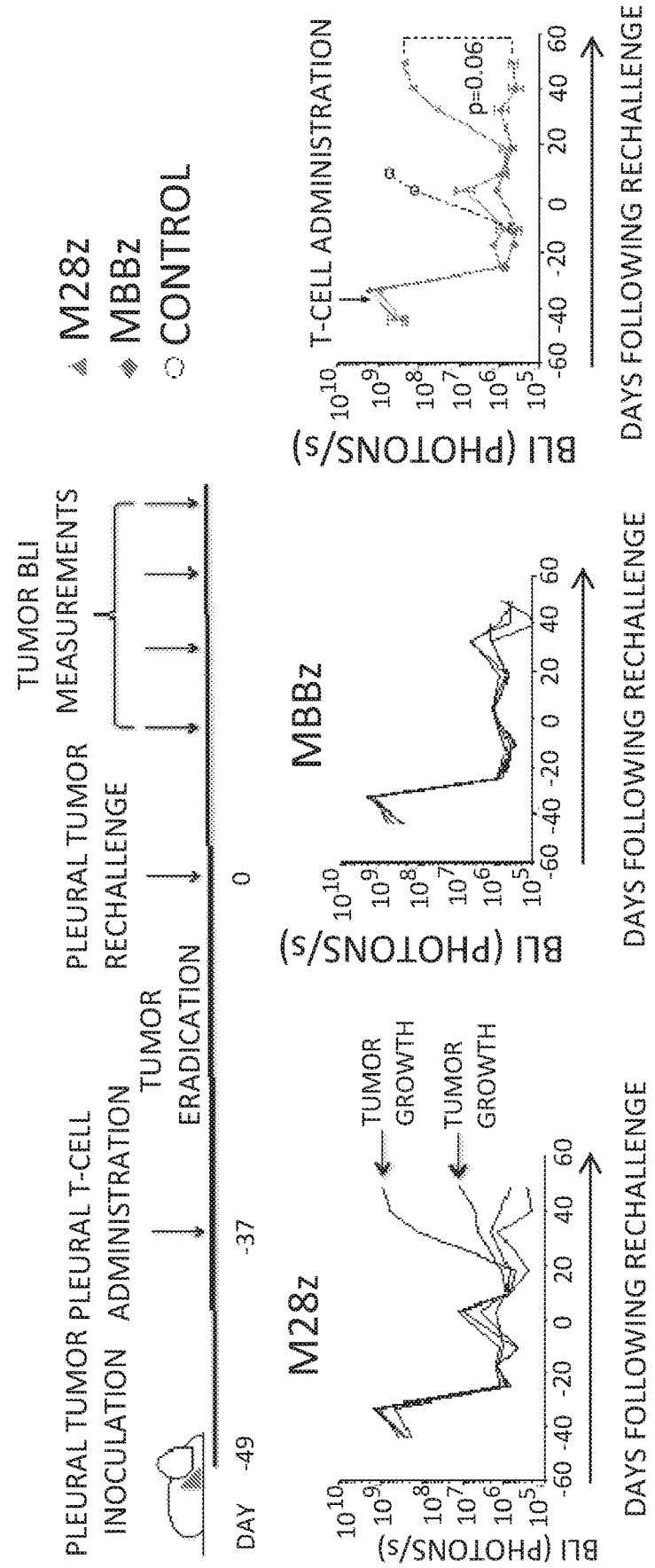

FIGS. 4A-4E show that CAR T cells become exhausted upon repeated antigen stimulation in vitro, although MBBz CAR T cells preferentially retain effector cytokine secretion and cytotoxicity in vitro and upon tumor rechallenge in vivo. FIG. 4A. Both M28z and MBBz CAR T cells retain proliferative capacity in vitro upon repeated antigen stimulation. T cells were also tested for cytotoxicity by chromium-release assay and for cytokine secretion by Luminex assay (FIGS. 4B-4D). FIG. 4B. CAR T cells demonstrate equal killing at the first stimulation (left) and loss of cytolytic function upon repeated antigen stimulation, although MBBz CAR T cells are better able to retain cytolytic function as measured by chromium-release assay (circles, MZ; triangles, M28z; diamonds, MBBz). FIG. 4C. Cytotoxic granule release as measured by CD107a expression (shown at the third stimulation) correlates with chromium release assay (FIG. 4B). Data represent the mean±SD (triplicates) of the fold-change relative to the CD107a MFI of unstimulated CAR T cells (each pair of bar graphs shows, from left to right, M28z, MBBz). FIG. 4D. Cytokine secretion measurements similarly demonstrate loss of CAR T-cell effector function upon repeated antigen encounter; again, MBBz CAR T cells are better able to preserve their function (each set of symbols above "Stim 1," "Stim 2" and "Stim 3" are, from left to right, Mz, M28z, MBBz). FIG. 4E. Although equally persistent, MBBz CAR T cells demonstrate superior functional persistence. Twenty-eight days after pleural tumor eradication (following a single dose of $1e^5$ CAR T cells), $1e^6$ MSLN+ tumor cells were injected into the pleural cavity (tumor rechallenge). MBBz CAR T cells prevented tumor growth in all mice, whereas tumor growth and death were observed in 2 of 4 mice initially treated with M28z CAR T cells. Student's t tests were performed and statistical significance was determined using the Bonferroni correction (*P<0.05; ***P<0.001). Data represent the mean±SEM of three replicates or are plotted as individual points.

Figure 5:
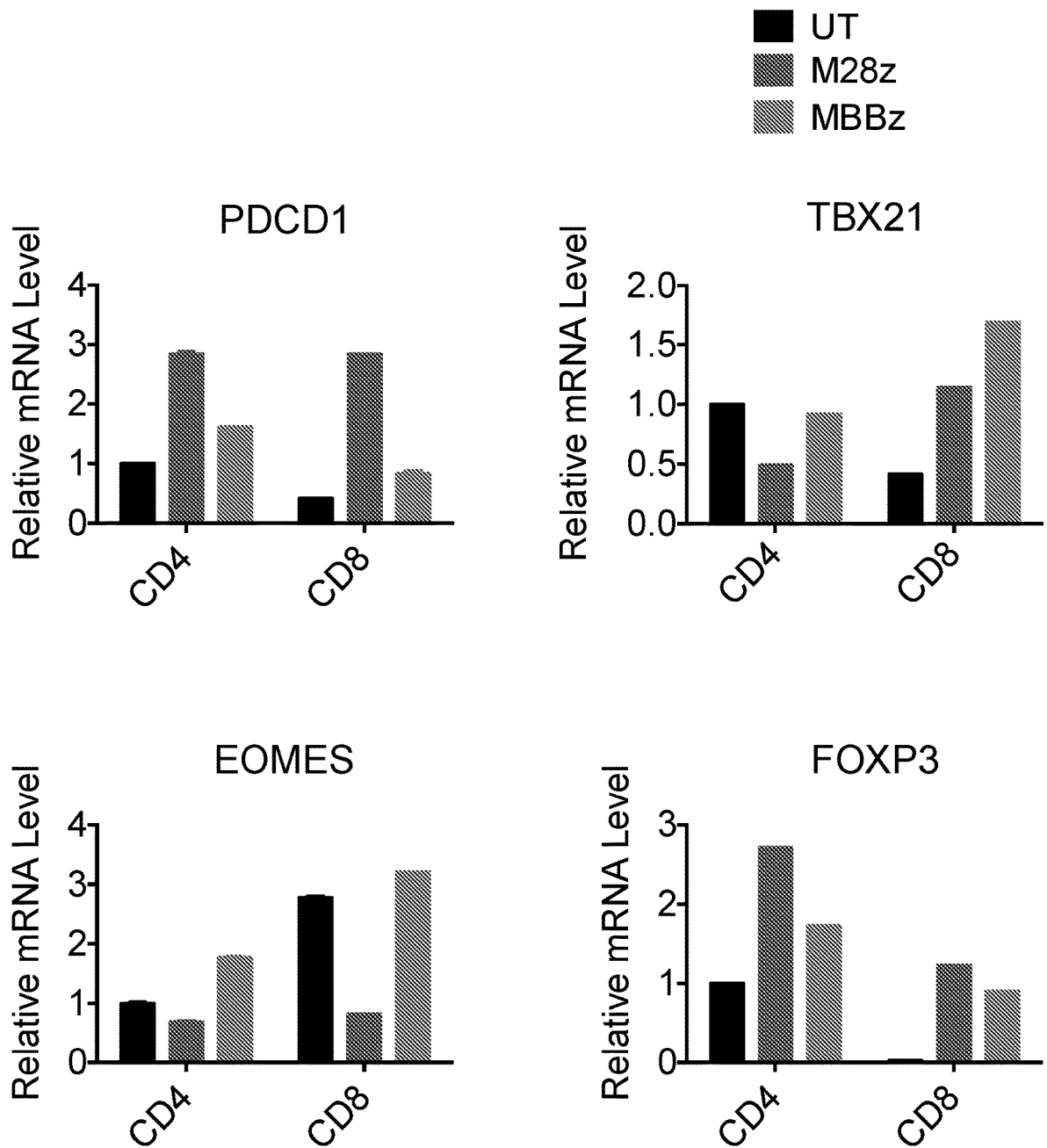

FIG. 5 shows that MBBz CAR T cells express a less exhausted, more potent phenotype compared to M28z CAR T cells. 4-1BB- and CD28-costimulated T cells were expanded with repeated antigen stimulation, and mRNA was extracted and subjected to RT-PCR analysis 20 h after the third stimulation. Data are represented in fold change relative to the mRNA expression of CD4+ unstransduced T cells. MBBz CAR T cells express higher levels of EOMES (Eomesodermin) and TBX21 (T-bet), and lower levels of PDCD1 (PD-1) and FOXP3 (Foxp3). All comparisons were significant at P<0.001. Results were similar in 3 separate experiments using different donors. Each group of bar graphs shows, left to right, UT (untransduced T cells used as a control), M28z, MBBz.

Figure 6B:
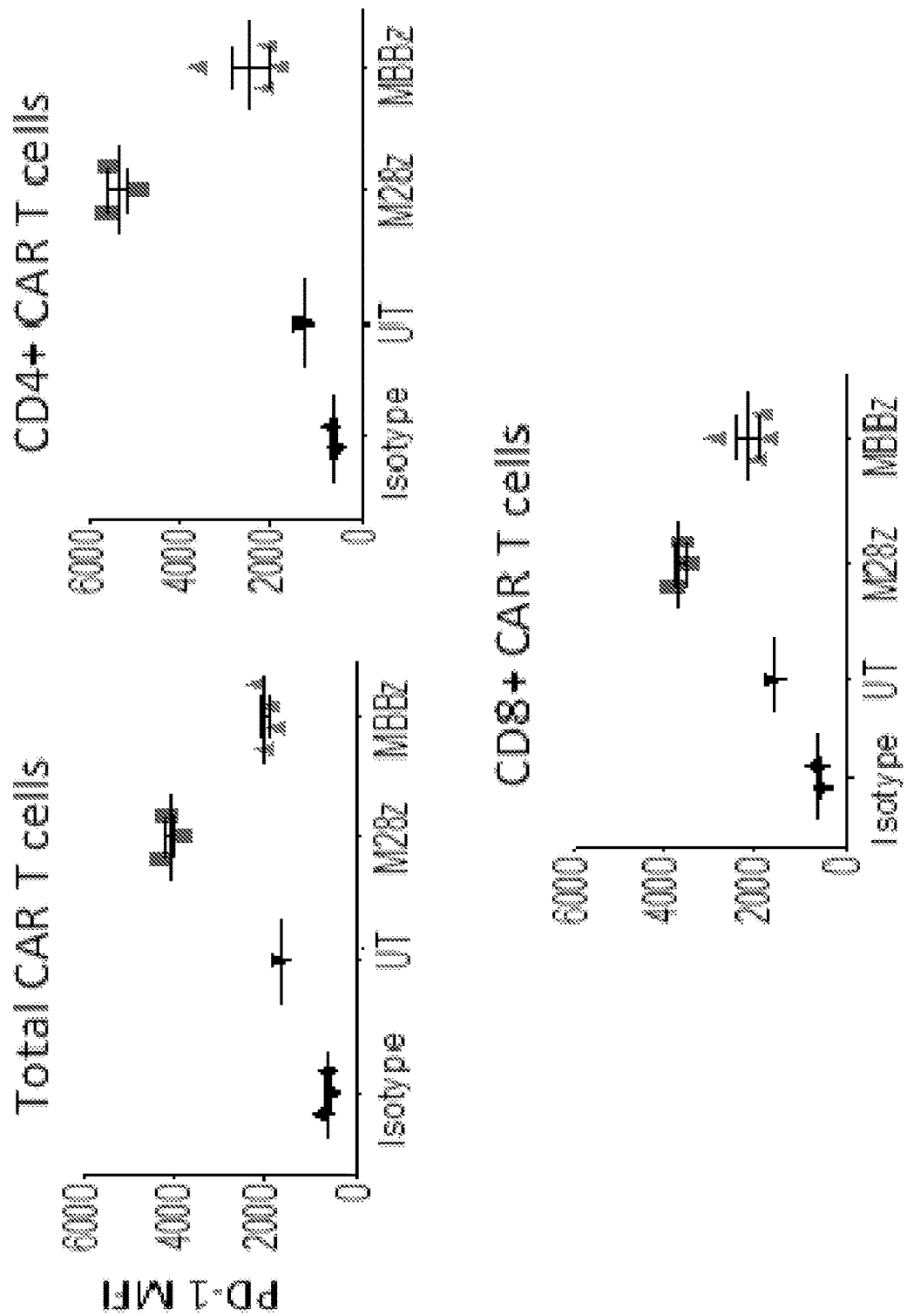
Figure 6D:
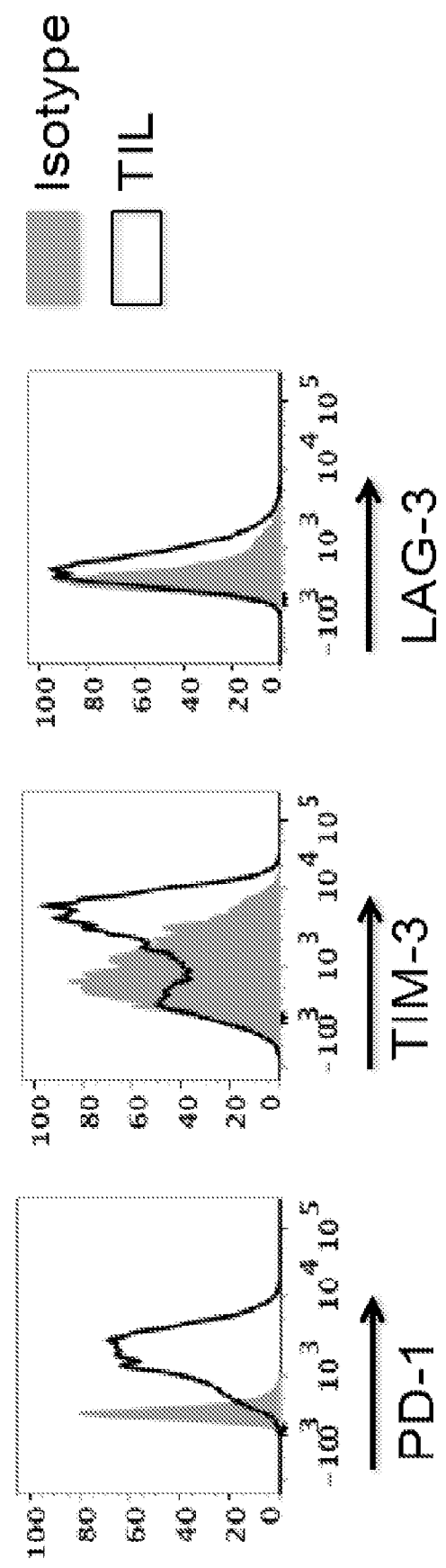
Figure 6E:
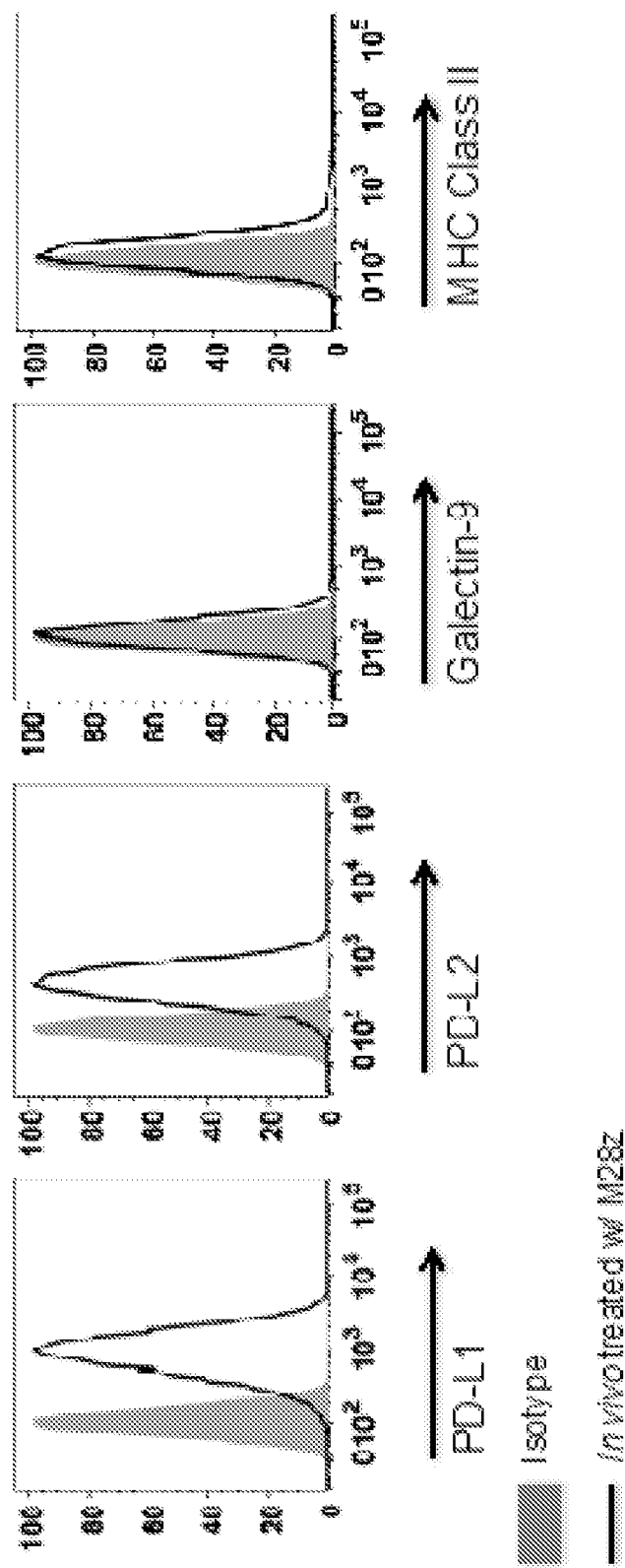

FIGS. 6A-6F show that PD-1 receptor and its ligands are upregulated in vivo (FIGS. 6A-6D, harvested T cells; FIGS. 6E-6F, tumor cells). FIG. 6A. Tumor-infiltrating M28z and MBBz CAR T cells express inhibitory receptors 6 days after their administration, but MBBz CAR T cells express lower levels of PD-1. FIG. 6B. Mean fluorescence intensity (MFI) of PD-1 receptor expression of tumor-infiltrating CAR T cells (TIL) 6 days after intrapleural administration. FIG. 6C. Relative expression of PD-1 mRNA in CD4 and CD8 subsets of tumor-infiltrating CAR T cells 6 days after intrapleural administration. Data are represented in fold-change relative to the PD-1 mRNA expression of unstimulated M28z T cells (for each pair of bar graphs, M28z, left, MBBz, right). FIG. 6D. Tumor-infiltrating M28z CAR T cells isolated from progressing tumors express inhibitory receptors PD-1, Tim-3, and Lag-3. FIG. 6E. Single-cell tumor suspensions harvested from mice treated with M28z CAR T cells express high levels of PD-1 binding ligands. FIG. 6F. In vitro cultured mesothelioma tumor cells express the ligands (PD-L1, PD-L2) for the PD-1 receptor, and expression is further upregulated following incubation for 24 h with IFN-γ and TNF-α.

Figure 7:
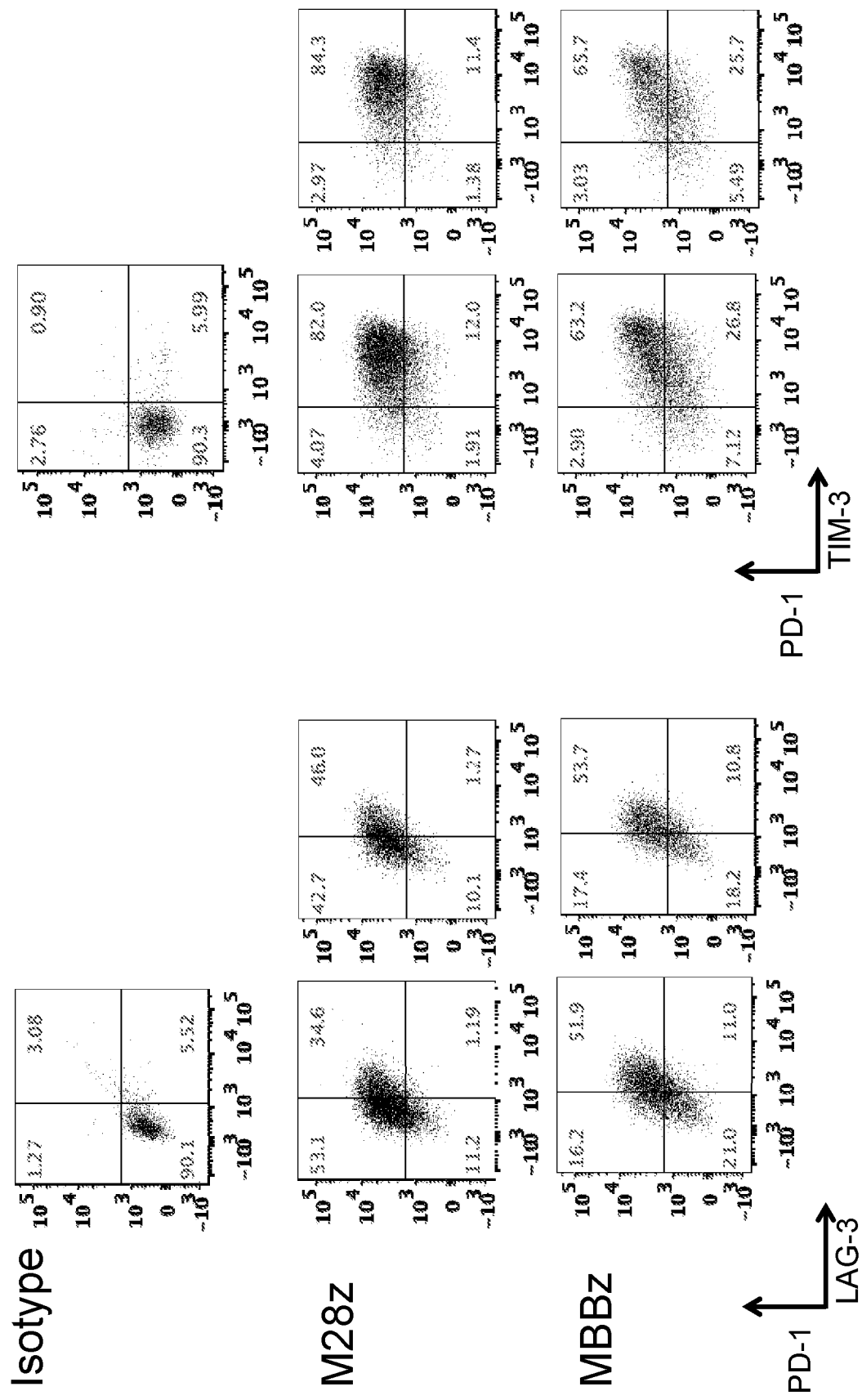

FIG. 7 shows M28z and MBBz CAR T cells coexpress PD-1 along with other inhibitory receptors. Tumor-infiltrating M28z and MBBz CAR T cells were harvested 6 days following intrapleural administration to pleural tumor bearing mice. Cells were costained with antibodies for PD-1 and for either LAG-3 (left) or TIM-3 (right) and analyzed by flow cytometry. Isotype staining controls (top) were used to establish positive gates.

Figure 8B:
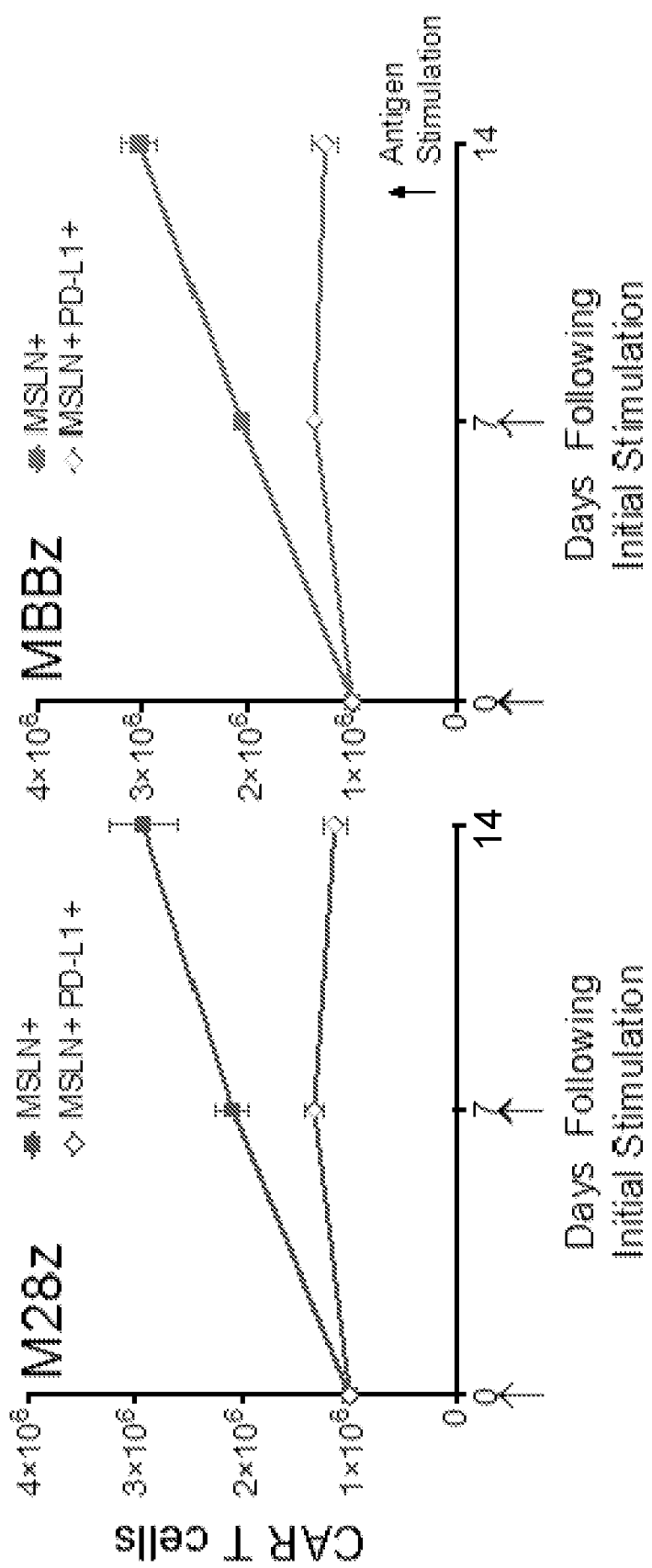
Figure 8C:
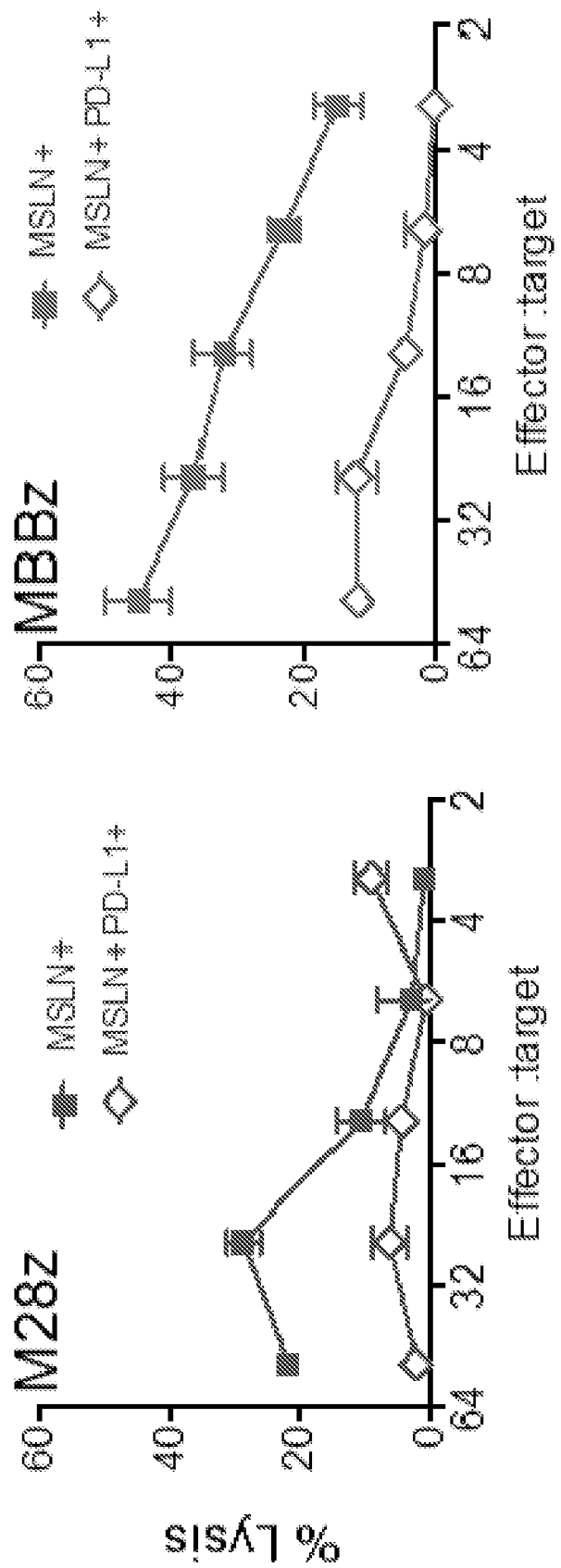

FIGS. 8A-8D show that PD-L1 inhibits CAR T-cell effector function. FIG. 8A. 3T3 fibroblasts were transduced to either express mesothelin alone (MSLN+, left) or coexpress MSLN in addition to PD-L1 (MSLN+PD-L1+, right). FIGS. 8B-8D. M28z and MBBz CAR T-cell effector functions were assessed after stimulation with 3T3 MSLN+ or MSLN+PD-L1+ targets. PD-L1 inhibits M28z and MBBz CAR T-cell accumulation upon repeated antigen stimulation (FIG. 8B), cytolytic function following two stimulations with MSLN+PD-L1+ tumor cells (FIG. 8C), and Th1 effector cytokine secretion upon the first stimulation (FIG. 8D). Data represent the mean±SEM of three replicates or are plotted as individual points.

Figure 9A:
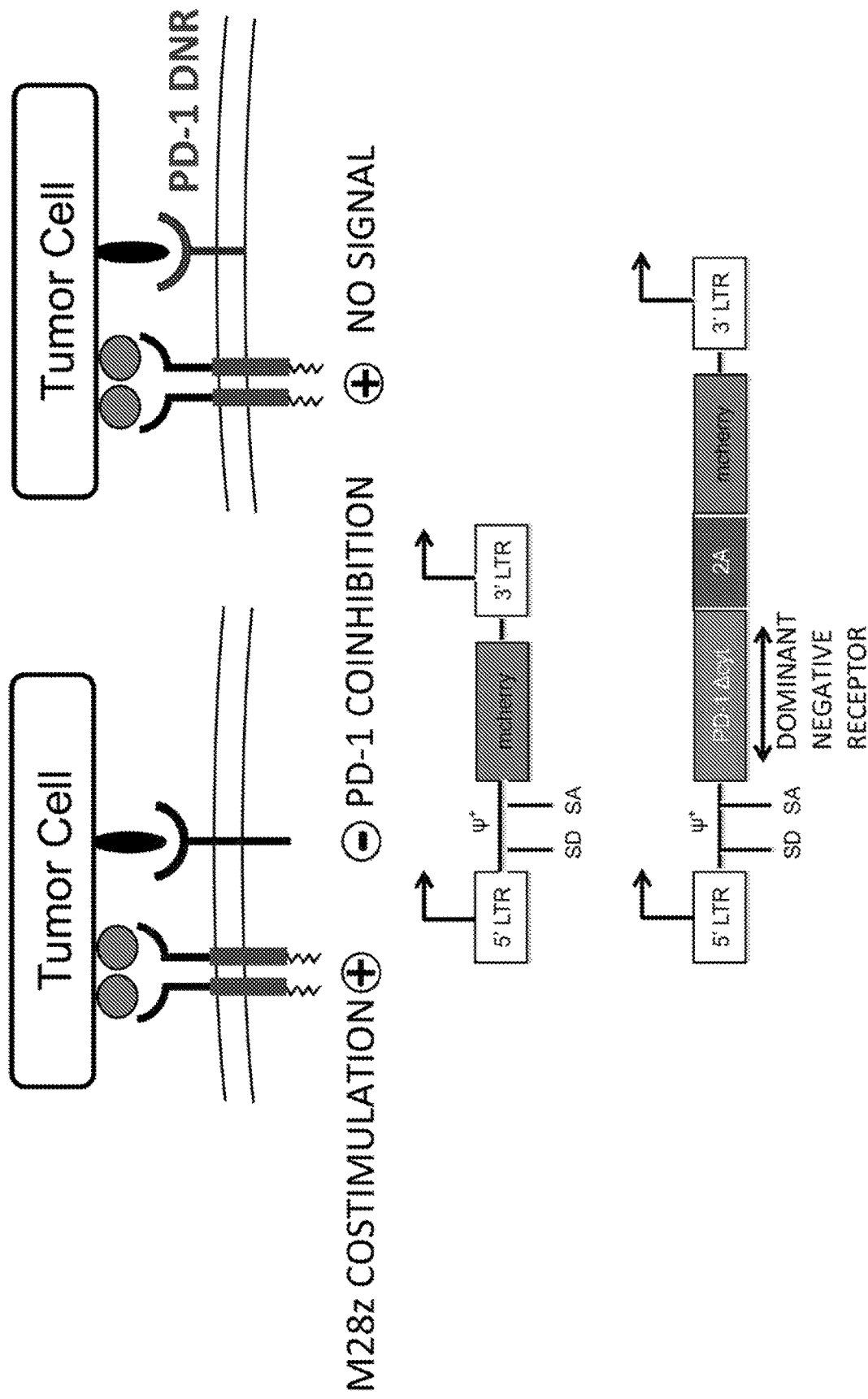
Figure 9B:
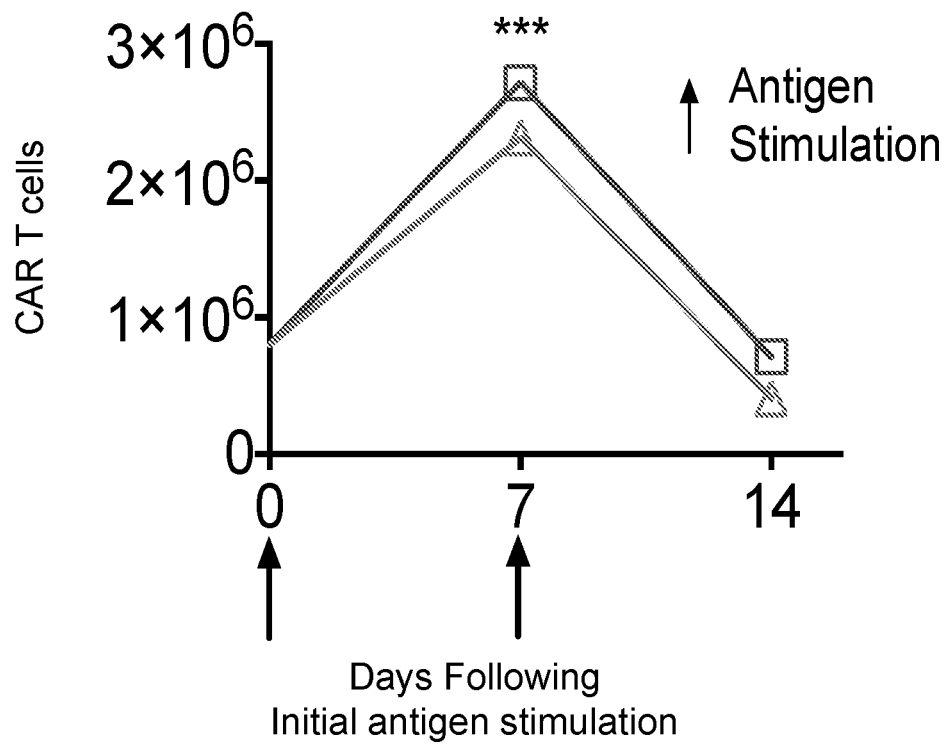
Figure 9C:
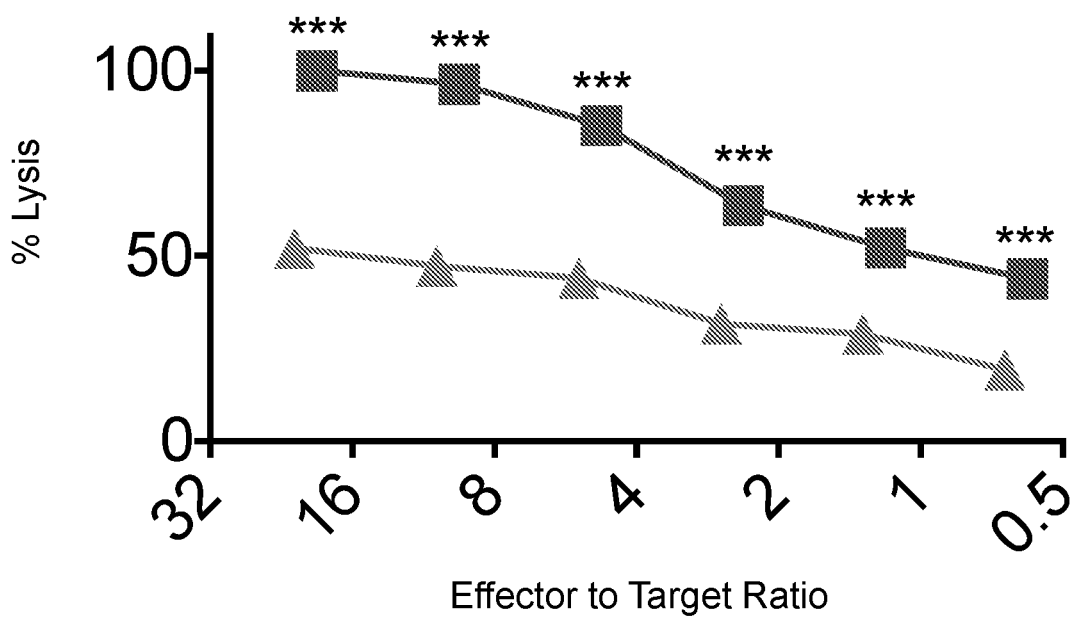
Figure 9D:
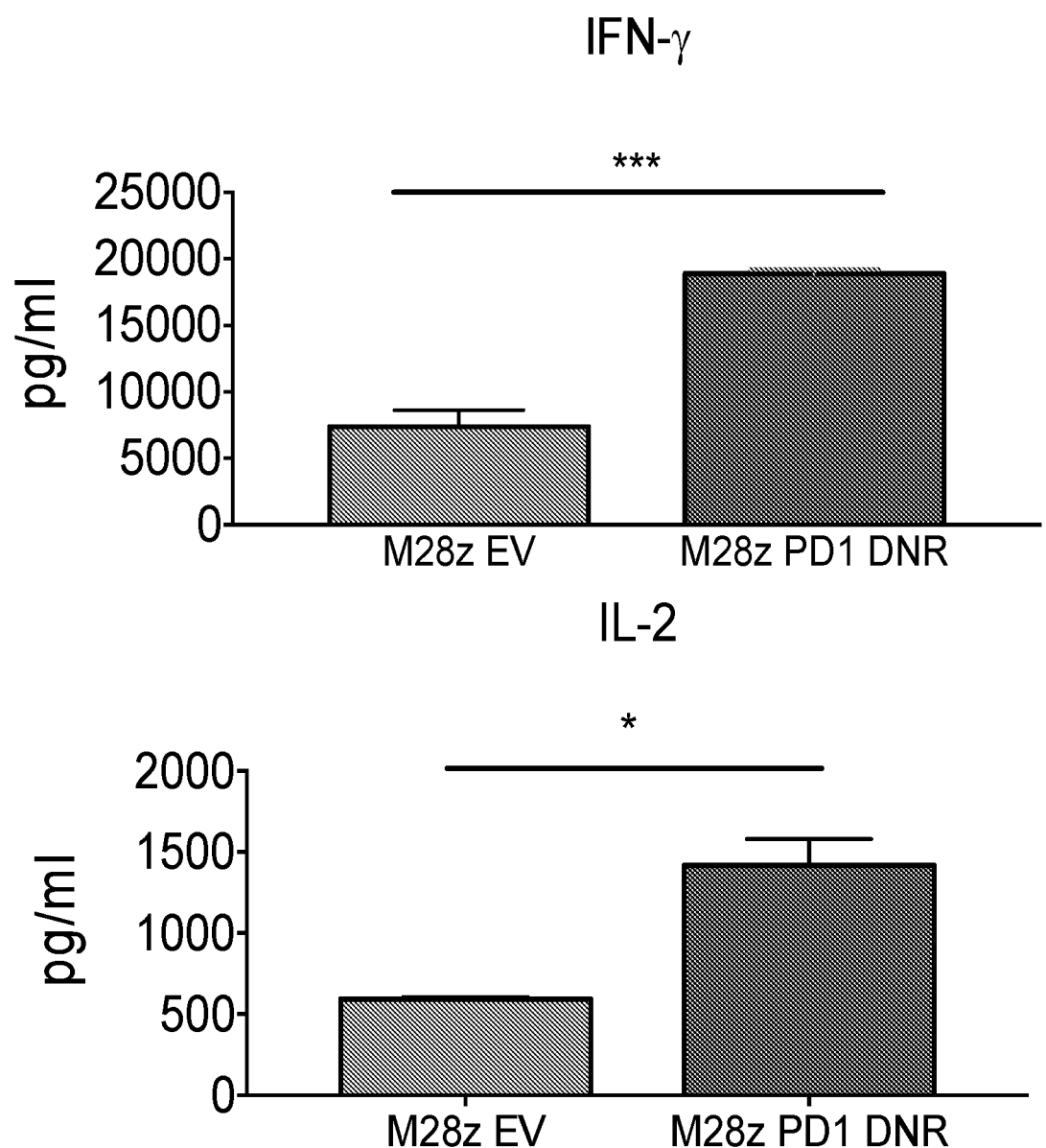
Figure 9E:
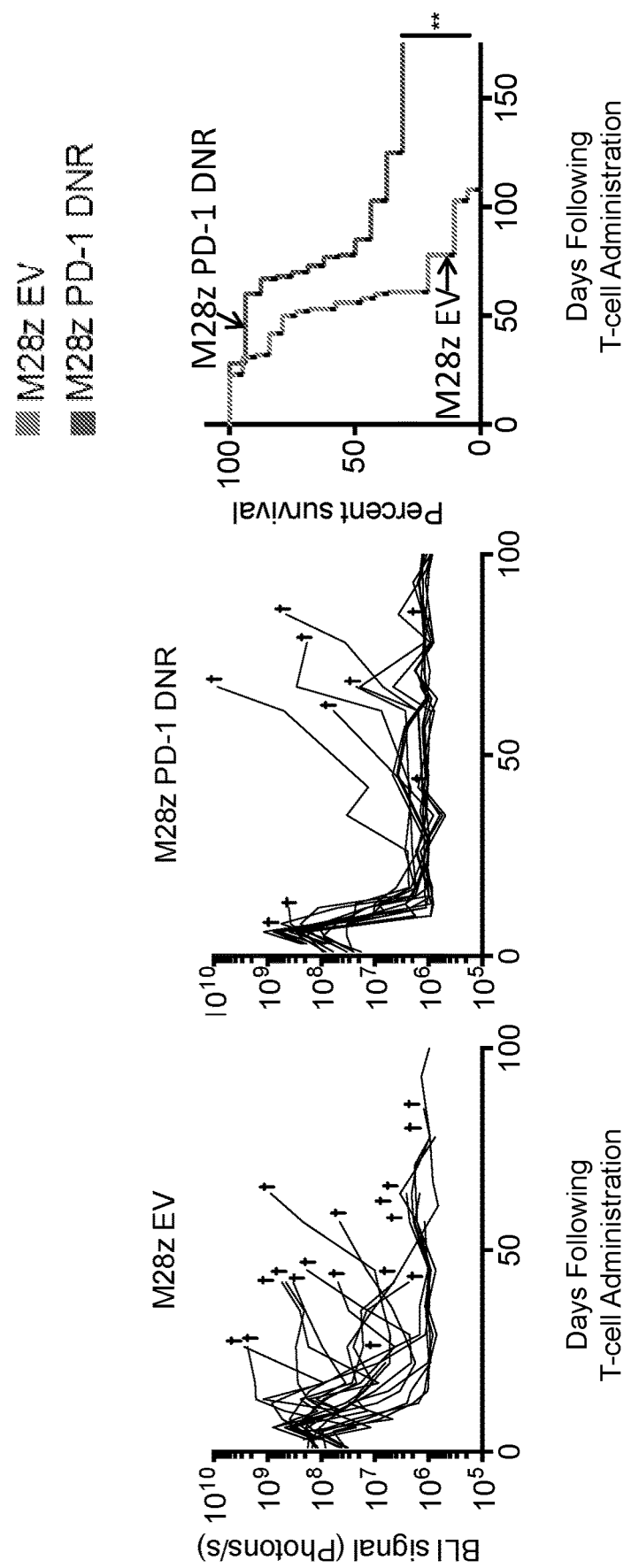

FIGS. 9A-9E show that cotransduction of a PD-1 dominant negative receptor (PD-1 DNR) rescues M28z CAR T cells from PD-1 Ligand-mediated inhibition in vitro and in vivo. FIG. 9A. (Left) Schematic representations of CD28-costimulated T cells binding tumor ligand via the endogenous PD-1 receptor (transmitting a coinhibitory signal) or a cotransduced PD-1 DNR lacking an inhibitory signaling domain. (Right) For in vitro and in vivo experiments, M28z CAR T cells were cotransduced with either empty vector (EV; SFG-mCherry) or PD-1 DNR (SFG-2A-PD-1 DNR). CAR T cells sorted for mCherry expression were then incubated for 24 h with MSLN+ tumor cells that had been treated with IFN-γ and TNF-α to upregulate PD-1 ligands. M28z PD-1 DNR CAR T cells demonstrated a small but statistically significant enhancement in accumulation upon repeated antigen stimulation (FIG. 9B; triangles, M28z EV; squares, M28z PD-1 DNR), an enhanced cytolytic function, as measured by chromium release assay upon the 3rd stimulation with MSLN+PD-L1+ tumor cells (FIG. 9C; triangles, M28z EV; squares, M28z PD-1 DNR), and an increased expression of Th1 supernatant cytokines upon initial stimulation (FIG. 9D). Student's t tests were performed, and statistical significance was determined using the Bonferroni correction for multiple comparisons (*P<0.05; P<0.01; *P<0.001). Data represent the mean±SEM of triplicates or are plotted as individual points. FIG. 9E. Tumor BLI (left) and Kaplan-Meier survival analysis (right) comparing the in vivo efficacy of a single dose of 5e4 M28z EV (n=19) or M28z PD-1 DNR (n=16) plurally administrated. Data shown are a combination of two independent experiments. The (†) symbol indicates death. Median survival is shown in days. The survival curve was analyzed using the log-rank test (P=0.001). The log-rank test for each independent experiment was significant to the P<0.05 level; two experiments are combined for illustration. A cohort of the mice (M28z PD-1 DNR) in this experiment survived beyond 450 days in spite of repeated tumor rechallenge, demonstrating the "functional persistence" of CAR T cells transduced with PD-1 DNR.

Figure 10A:
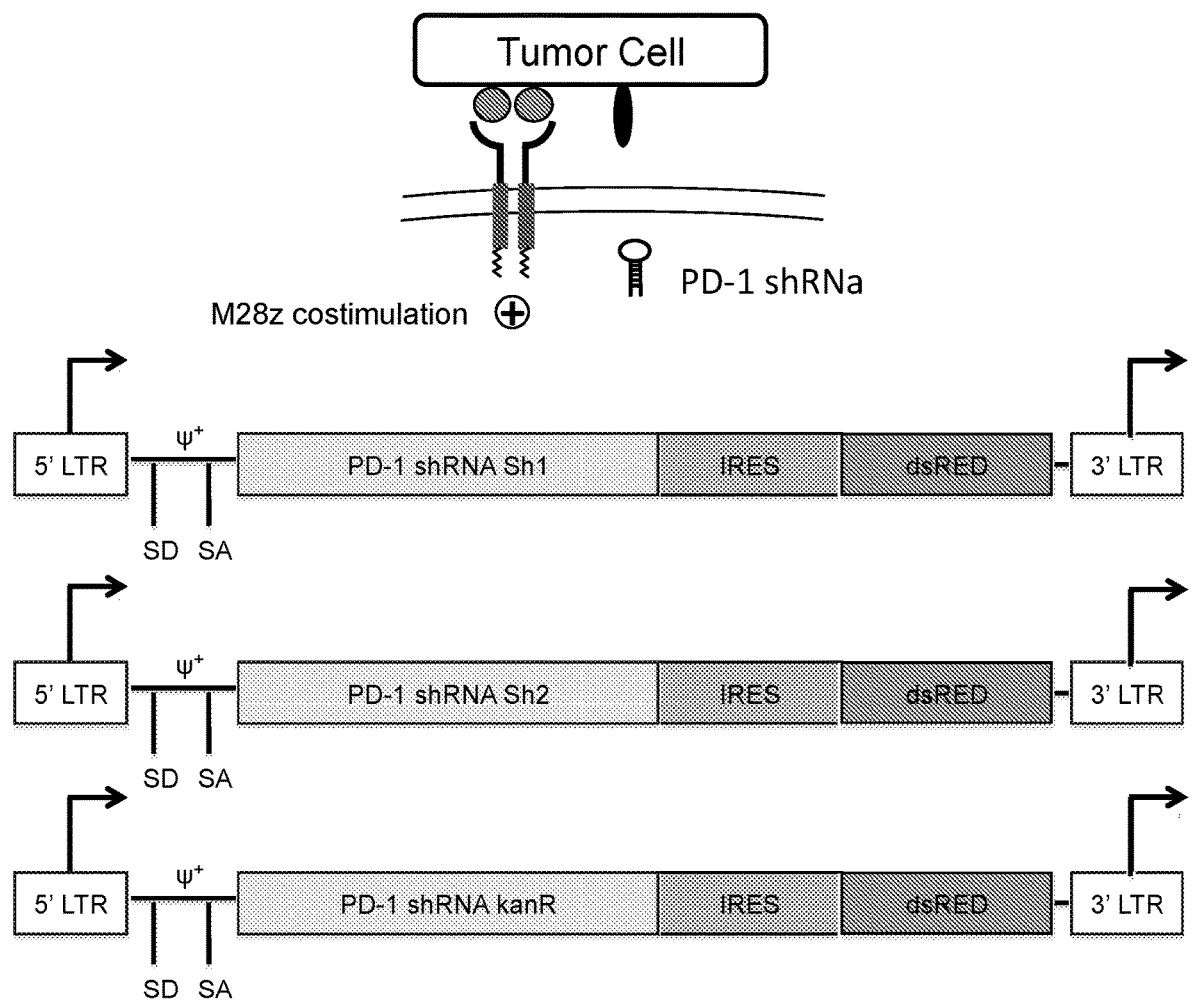
Figure 10B:
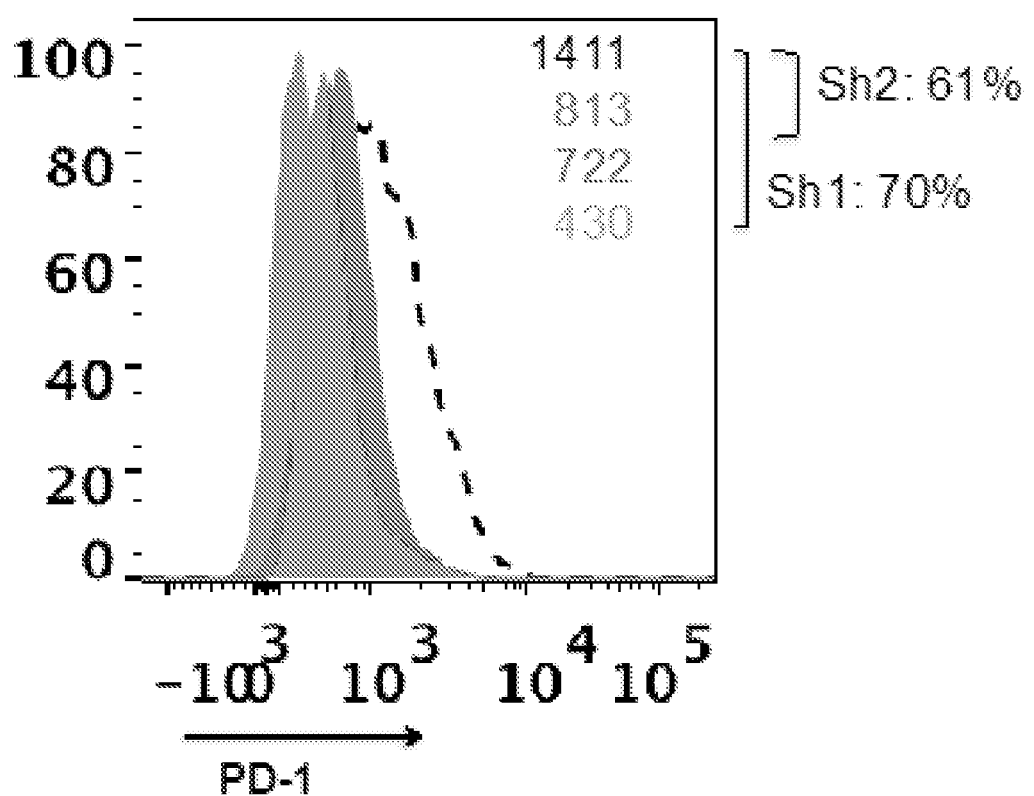
Figure 10C:
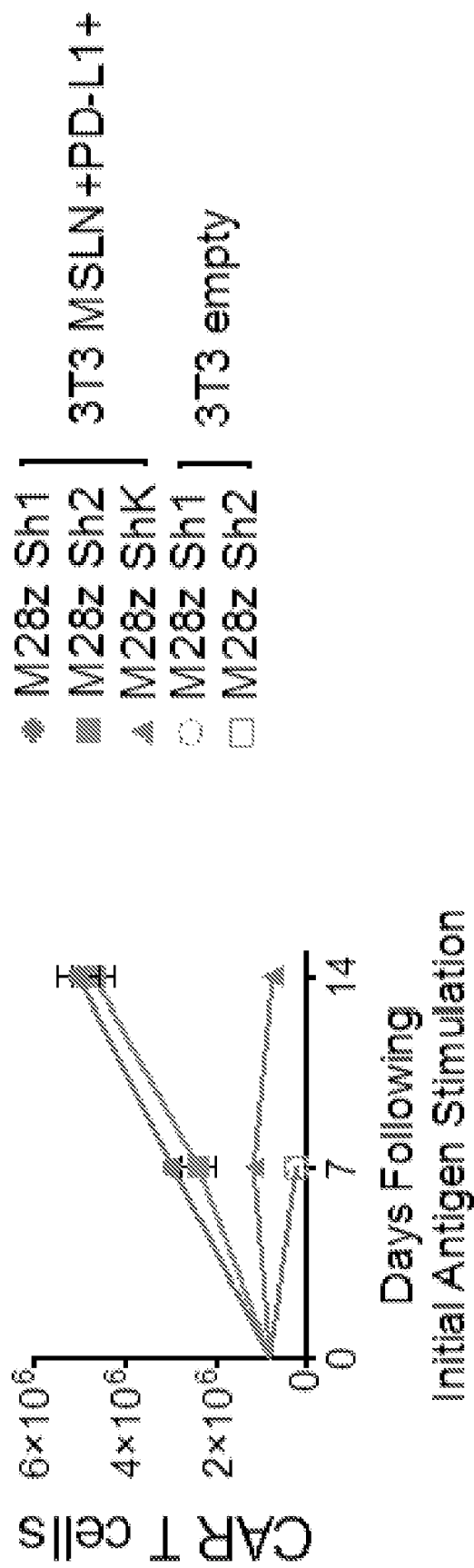
Figure 10D:
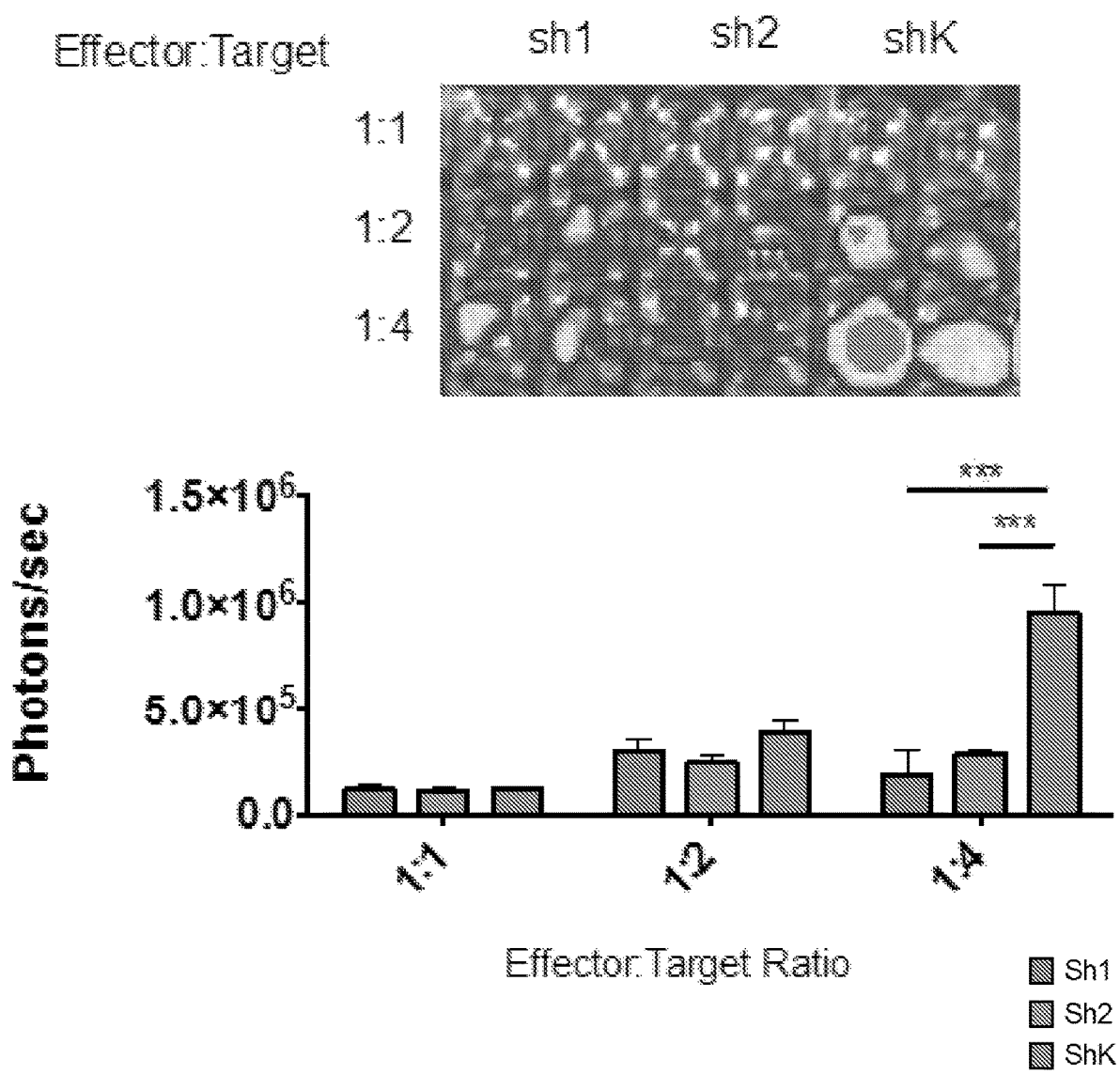
Figure 10E:
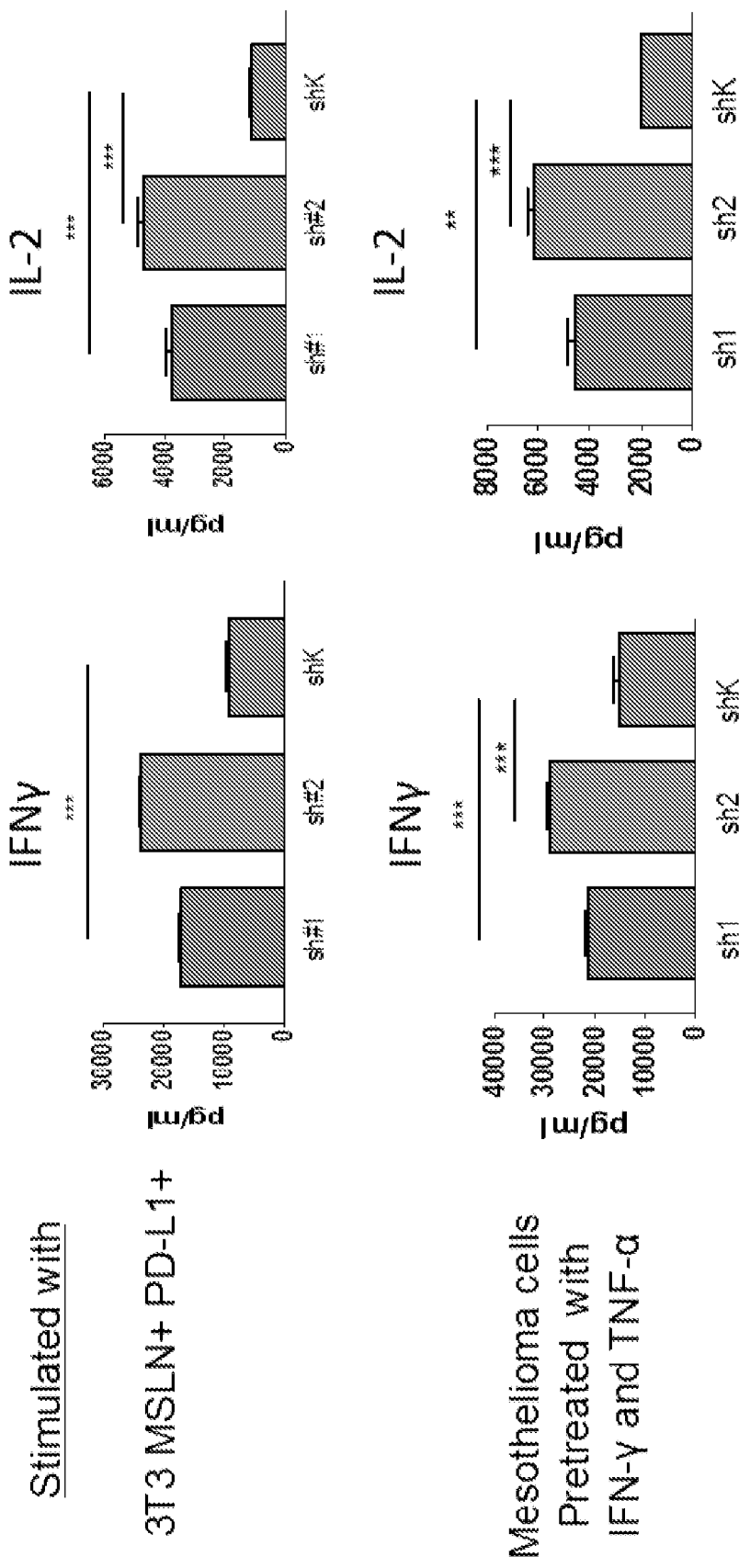

FIGS. 10A-10E show that cotransduction of PD-1 receptor-targeting shRNAs rescues M28z CAR T cells from PD-L1/PD-1-mediated inhibition in vitro. FIG. 10A. (Left) Schematic representation of CD28-costimulated T cells binding tumor-expressed PD-L1 via endogenous PD-1 receptor, with or without coexpression of PD-1-targeting shRNA. (Right) All experiments included M28z CAR T cells cotransduced with one of two PD-1-targeting shRNAs (sh1 or sh2 coexpressing a dsRED reporter) or with an shRNA targeting a bacterial sequence (KanR). FIG. 10B. Compared with KanR-transduced cells, M28z CAR T cells cotransduced with PD-1-targeting shRNAs demonstrated a 60% to 70% knockdown in PD-1 receptor protein expression upon stimulation with phytohemagglutinin (graphs left to right correspond to 430, 722, 813 and 1411). Cells were incubated with either 3T3 fibroblasts overexpressing PD-L1 (3T3 MSLN+PD-L1+) or mesothelioma tumor cells that had been treated with IFN-γ and TNF-α in order to upregulate PD-L1 and PD-L2. M28z PD1 shRNA CAR T cells demonstrate enhanced accumulation upon repeated antigen stimulation (FIG. 10C), enhanced cytolytic function at low effector to target ratios, as measured by luciferase activity of remaining live tumor cells (FIG. 10D; each group of bar grafts, from left to right, Sh1, Sh2, ShK), and increased Th1 cytokine secretion (FIG. 10E; each group of bar grafts, from left to right, Sh1, Sh2, ShK) (P<0.01; *P<0.001). Student's t tests were performed and statistical significance was determined using the Bonferroni correction for multiple comparisons. Data represent the mean±SEM of three replicates.

Figure 11:
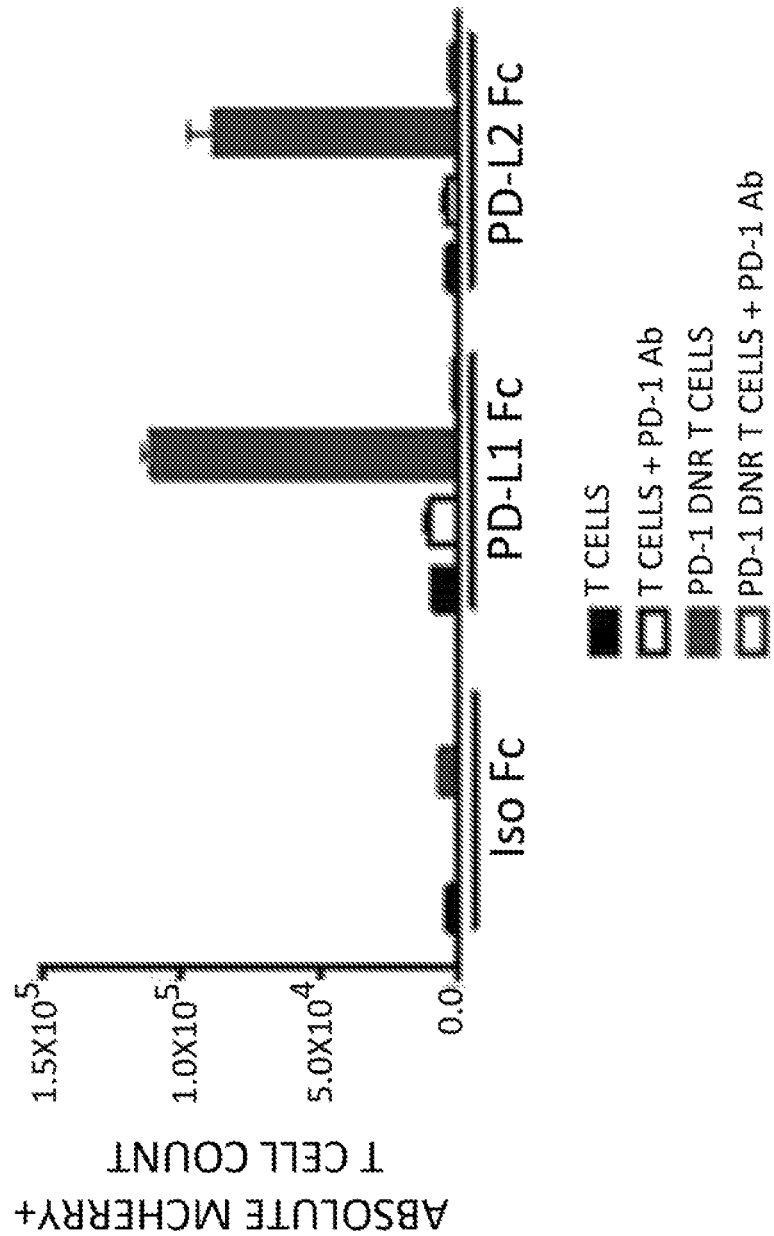

FIG. 11 shows an adhesion assay of PD-1 DNR to PD-L1 and PD-L2 recombinant proteins fused to an Fc domain. T cells labeled with mCherry and transduced with PD-1 DNR were exposed to plates coated with PD-L1 fused to Fc ("PD-L1 Fc"), PD-L2 fused to Fc ("PD-L2 Fc"), or control isotype Fc ("Iso Fc"). T cells bound to the plates were measured as absolute mcherry+ T cell count in the presence ("+PD-1 Ab") or absence of PD-1 antibody. The bar graphs show the binding for each of the respectively coated plates, from left to right, T cells alone ("T cells"), T cells in the presence of PD-1 antibody (T cells+PD-1 ab"), T cells transduced with PD-1 DNR ("PD-1 DNR T cells"), and T cells transduced with PD-1 DNR in the presence of PD-1 antibody ("PD-1 DNR T cells+PD-1 Ab").

Figure 12A:
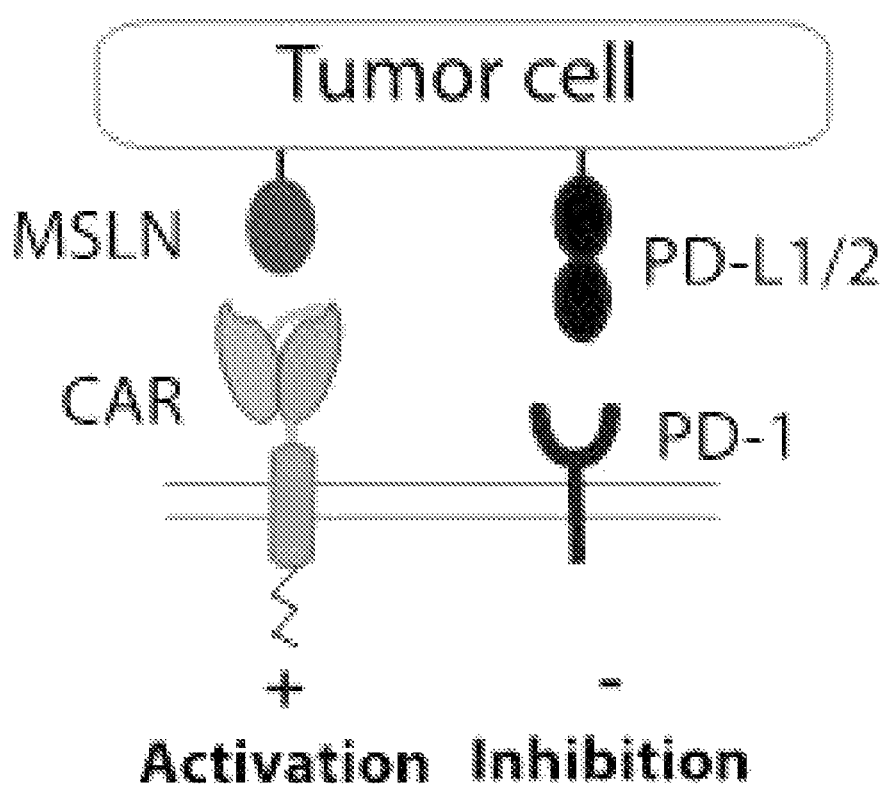
Figure 12B:
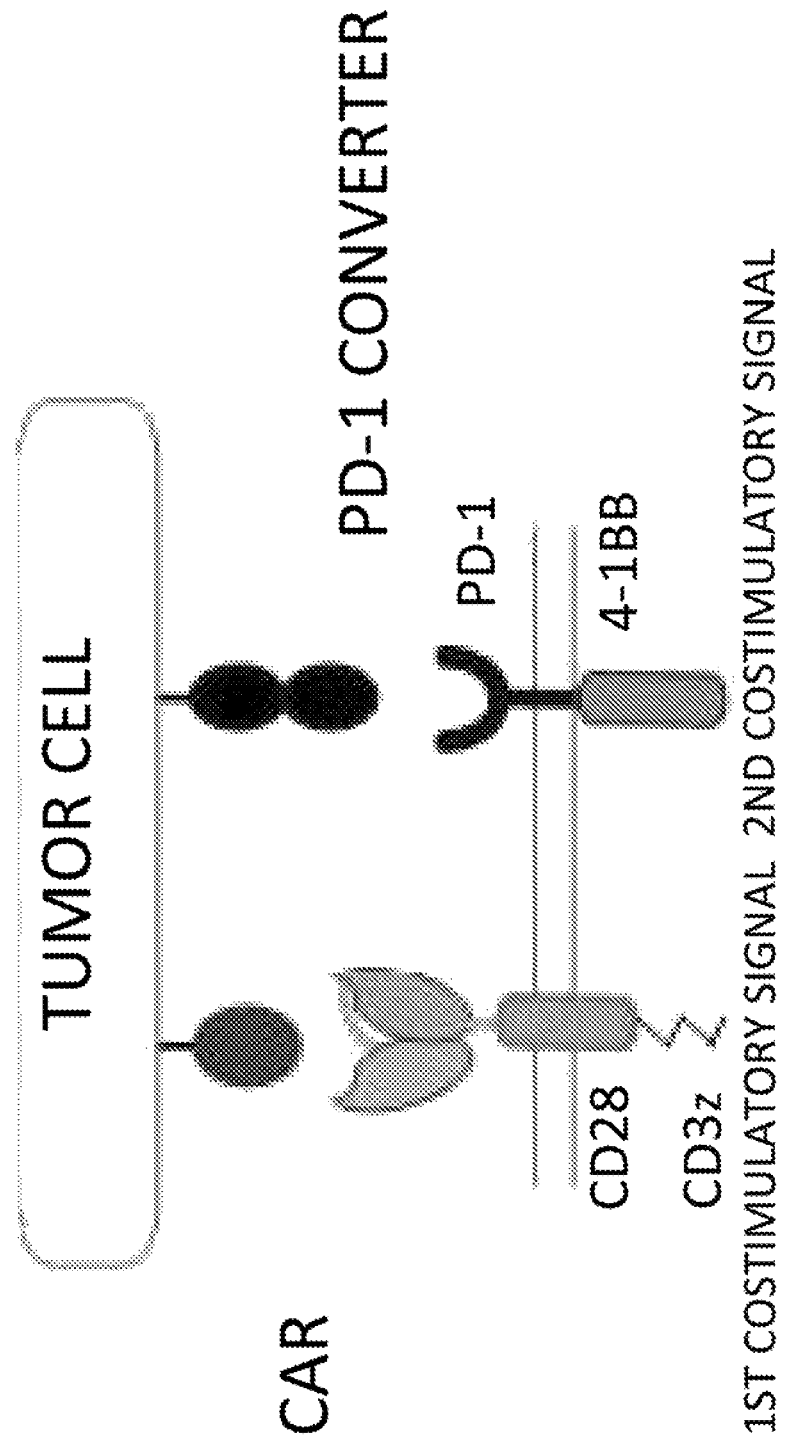

FIGS. 12A-12D show that a PD-1 DNR, which inhibits PD-L1- or PD-L2-mediated inhibition of T cell activation, can be converted into a positive co-stimulatory signal. FIG. 12A shows a schematic diagram illustrating co-expression of a CAR and a PD-1 DNR. FIG. 12B shows a schematic diagram illustrating co-expression of a CAR and a PD-1 DNR converted into a costimulatory construct by fusing a costimulatory domain, exemplified as 4-1 BB, to a transmembrane domain fused to the ligand binding domain of PD-1. FIG. 12C shows accumulation of CAR T cells at day 0 and day 7 in T cells transduced with M28z CAR, M28z CAR plus PD-1 DNR, or M28z CAR plus a PD-1 4-1BB switch receptor construct. Bars left to right respectively: M28z CAR, M28z CAR+PD-1 DNR, and M28z CAR+PD-1 4-1BB switch receptor construct. FIG. 12D shows cytokine secretion of interferon gamma (IFN-γ), interleukin 2 (IL-2), tumor necrosis factor alpha (TNF-α) and granulocyte-macrophage colony-stimulating factor (GM-CSF) in T cells transduced with M28z CAR, M28z CAR plus PD-1 DNR or M28z CAR plus a PD-1 4-1BB switch receptor construct. Bars left to right respectively: M28z CAR, M28z CAR+PD-1 DNR, and M28z CAR+PD-1 4-1BB switch receptor construct.

7. DETAILED DESCRIPTION OF THE INVENTION

The present invention relates to compositions and methods for treating viral infections. Such viral infections include, but are not limited to, infection with human immunodeficiency virus (HIV), hepatitis B virus (HBV), hepatitis C virus (HCV), and the like. As described herein, immunostimulatory immune cells can be genetically engineered to intrinsically express proteins that are dominant negative mutants and that inhibit blockades that limit the activity of the immune cells. By inhibiting the blockade, the genetically engineered immune cells that are immunostimulatory are permitted to provide a more effective immune response against a viral infection. In another embodiment, immunoinhibitory cells, such as regulatory T cells, that exhibit immunosuppression of the immune activity of immunostimulatory cells targeted to a viral antigen, such as $CD8^+$ and/or $CD4^+$ T cells, can be genetically engineered to intrinsically express proteins that are dominant negative mutants and that inhibit the immunosuppressive effect of the immunoinhibitory cells on immune stimulatory cells.

7.1 Cells

In one embodiment, the invention provides cells that are immune cells, in particular immunostimulatory cells, or precursor cells thereof, that recombinantly express (i) a CAR that binds to a viral antigen and (ii) a dominant negative form (hereinafter "DN form") of an inhibitor of a cell-mediated immune response, preferably of the immune cell. The immune cells in such an embodiment are preferably $CD4^+$ or $CD8^+$ T cells or a combination thereof. In another embodiment, the invention provides an immune cell, such as a T cell, in particular, an immunostimulatory T cell, that is sensitized to a viral antigen, where the cell expresses a DN form of an inhibitor of a cell-mediated immune response, preferably of the T cell. In yet another embodiment, the invention provides an immune cell that is an immunoinhibitory cell, such as a regulatory T cell, where the cell expresses a DN form of an inhibitor of a cell-mediated immune response, preferably of the regulatory T cell. In a particular embodiment, the immunoinhibitory cells, such as regulatory T cells, are isolated from a subject having a chronic viral infection. The recombinant cells can be used to enhance or provide an immune response against a target such as a virus. Preferably, the cells are derived from a human (are of human origin prior to being made recombinant) (and human-derived cells are particularly preferred for administration to a human in the methods of treatment of the invention).

Immune Cells that are Immunostimulatory Cells. The immune cells of the invention can be immunostimulatory cells of the lymphoid lineage. The immunostimulatory cells mediate an immune response in a subject. Non-limiting examples of cells of the lymphoid lineage that can be used as immunostimulatory cells include T cells and Natural Killer (NK) cells. T cells express the T cell receptor (TCR), with most cells expressing α and β chains and a smaller population expressing γ and δ chains. T cells useful as immunostimulatory cells of the invention can be $CD4^+$ or $CD8^+$ and can include, but are not limited to, T helper cells ($CD4^+$), cytotoxic T cells (also referred to as cytotoxic T lymphocytes, CTL; $CD8^+$ T cells), and memory T cells, including central memory T cells, stem-cell-like memory T cells (or stem-like memory T cells), and effector memory T cells, for example, $T_{EM}$ cells and $T_{EMRA}$ ($CD45RA^+$) cells, natural killer T cells, mucosal associated invariant T cells (MAIT), and γδ T cells. Other exemplary immunostimulatory cells include, but are not limited to, macrophages, antigen presenting cells (APCs) such as dendritic cells, or any immune cell that mediates an immune response and expresses an inhibitor of a cell-mediated immune response, for example, an immune checkpoint inhibitor pathway receptor, e.g., PD-1 (while not intending to be bound by mechanism, it is submitted that expression of the DN form in the cell inhibits the inhibitor of the cell-mediated immune response to promote sustained activation of the cell). Precursor cells of immunostimulatory cells that can be used according to the invention, which recombinantly express a DN form or co-express a CAR and a DN form, as described above, are, by way of example, hematopoietic stem and/or progenitor cells. Hematopoietic stem and/or progenitor cells can be derived from bone marrow, umbilical cord blood, adult peripheral blood after cytokine mobilization, and the like, by methods known in the art, and then are genetically engineered to recombinantly express a DN form or co-express a CAR and DN form. Particularly useful precursor cells are those that can differentiate into the lymphoid lineage, for example, hematopoietic stem cells or progenitor cells of the lymphoid lineage.

Immune cells that are immunostimulatory cells, and precursor cells thereof, can be isolated by methods well known in the art, including commercially available isolation methods (see, for example, Rowland-Jones et al., *Lymphocytes: A Practical Approach*, Oxford University Press, New York (1999)). Sources for the immune cells or precursor cells thereof include, but are not limited to, peripheral blood, umbilical cord blood, bone marrow, or other sources of hematopoietic cells. Various techniques can be employed to separate the cells to isolate or enrich for desired immune cells. For instance, negative selection methods can be used to remove cells that are not the desired immune cells. Additionally, positive selection methods can be used to isolate or enrich for desired immune cells or precursor cells thereof, or a combination of positive and negative selection methods can be employed. Monoclonal antibodies (MAbs) are particularly useful for identifying markers associated with particular cell lineages and/or stages of differentiation for both positive and negative selections. If a particular type of cell is to be isolated, for example, a particular type of T cell, various cell surface markers or combinations of markers, including but not limited to, CD3, CD4, CD8, CD34 (for hematopoietic stem and progenitor cells) and the like, can be used to separate the cells, as is well known in the art (see Kearse, *T Cell Protocols: Development and Activation*, Humana Press, Totowa N.J. (2000); De Libero, *T Cell Protocols*, Vol. 514 of *Methods in Molecular Biology*, Humana Press, Totowa N.J. (2009)).

Various methods for isolating immune cells that can be used for recombinant expression of a CAR have been described previously, and can be used, including but not limited to, using peripheral donor lymphocytes (Sadelain et al., *Nat. Rev. Cancer* 3:35-45 (2003); Morgan et al., *Science* 314:126-129 (2006), and using selectively in vitro-expanded antigen-specific peripheral blood leukocytes employing artificial antigen-presenting cells (AAPCs) or dendritic cells (Dupont et al., *Cancer Res.* 65:5417-5427 (2005); Papanicolaou et al., *Blood* 102:2498-2505 (2003)). In the case of using stem cells, the cells can be isolated by methods well known in the art (see, for example, Klug et al., *Hematopoietic Stem Cell Protocols*, Humana Press, New Jersey (2002); Freshney et al., *Culture of Human Stem Cells*, John Wiley & Sons (2007)).

In another embodiment, the invention provides immune cells, such as T cells, that recognize and are sensitized to a viral antigen, and also which recombinantly express a DN form of an inhibitor of an immune cell-mediated immune response, such as a T cell-mediated immune response in the case of a T cell. Such immune cells, such as T cells, can but need not express a CAR that binds to a viral antigen, since the cells already are viral antigen-specific so that their immune response (for example, cytotoxicity) is stimulated specifically by such viral antigen. Such immune cells, such as T cells, that recognize and are sensitized to a viral antigen can be obtained by known methods, by way of example, in vitro sensitization methods using naive T cells (see, for example, Wolfl et al., *Nat. Protocols* 9:950-966 (2014)) or hematopoietic progenitor cells (see van Lent et al., *J. Immunol.* 179:4959-4968 (2007)); or obtained from a subject that has been exposed to and is mounting an immune response against the viral antigen, such as a subject having a viral infection (i.e., in vivo sensitized immune cells). Methods for isolating an antigen-specific T cell from a subject are well known in the art. Such methods include, but are not limited to, a cytokine capture system or cytokine secretion assay, which is based on the secretion of cytokines from antigen stimulated T cells that can be used to identify and isolate antigen-specific, and expansion of cells in vitro (see Assenmacher et al., *Cytometric Cytokine Secretion Assay*, in *Analyzing T Cell Responses: How to Analyze Cellular Immune Responses Against Tumor Associated Antigens*, Nagorsen et al., eds., Chapter 10, pp. 183-195, Springer, The Netherlands (2005); Haney et al., *J. Immunol. Methods* 369:33-41 (2011); Bunos et al., *Vox Sanguinis* DOI: 10.1111/vox.12291 (2015); Montes et al., *Clin. Exp. Immunol.* 142:292-302 (2005); Adusumilli et al., *Sci Transl Med.* 6:261ra151 (2014)). Such cytokines include, but are not limited to interferon-γ and tumor necrosis factor-α. The antigen-specific T cells can be isolated using well known techniques as described above for isolating immune cells, which include, but are not limited to, flow cytometry, magnetic beads, panning on a solid phase, and so forth. Antigen-specific T cell isolation techniques are also commercially available, which can be used or adapted for clinical applications (see, for example, Miltenyi Biotec, Cambridge, Mass.; Proimmune, Oxford, UK; and the like).

Immune Cells that are Immunoinhibitory Cells. The immune cells of the invention that are immunoinhibitory cells can be cells of the lymphoid lineage. Non-limiting examples of cells of the lymphoid lineage that can be used as immunoinhibitory cells include regulatory T cells (Tregs), follicular regulatory T cells, regulatory B cells, and the like. The immunoinhibitory cells of the invention express an inhibitor of a cell-mediated immune response, for example, an immune checkpoint inhibitor pathway receptor, e.g., PD-1.

Immunoinhibitory cells that can be genetically engineered to recombinantly express a DN form of an inhibitor of a cell-mediated immune response can be isolated by methods well known in the art, including commercially available isolation methods (see, for example, Rowland-Jones et al., *Lymphocytes: A Practical Approach*, Oxford University Press, New York (1999)). Sources for the immunoinhibitory cells thereof include, but are not limited to, peripheral blood, umbilical cord blood, bone marrow, or other sources of cells of the lymphoid lineage. Various techniques can be employed to separate the cells to isolate or enrich for desired immunoinhibitory cells. For instance, negative selection methods can be used to remove cells that are not the desired immunoinhibitory cells. Additionally, positive selection methods can be used to isolate or enrich for desired immunoinhibitory cells, or a combination of positive and negative selection methods can be employed. Monoclonal antibodies (MAbs) are particularly useful for identifying markers associated with particular cell lineages and/or stages of differentiation and can be used as reagents for both positive and negative selections. A particular type of immunoinhibitory cell can be isolated based on various cell surface markers or combinations of markers, or the absence of markers, including but not limited to CD4 and/or CD8 for positive selection combined with CD127 for negative selection, as is well known in the art (see Kearse, *T Cell Protocols: Development and Activation*, Humana Press, Totowa N.J. (2000); De Libero, *T Cell Protocols*, Vol. 514 of *Methods in Molecular Biology*, Humana Press, Totowa N.J. (2009); Su et al., *Methods Mol. Biol.* 806:287-299 (2012); Bluestone et al., *Sci. Transl. Med.* 7(315) (doi: 10.1126/scitranslmed.aad4134)(2015); Miyara et al., *Nat. Rev. Rheumatol.* 10:543-551 (2014); Liu et al., *J. Exp. Med.* 203:1701-1711 (2006); Seddiki et al., *J. Exp. Med.* 203:1693-1700 (2006); Ukena et al., *Exp. Hematol.* 39:1152-1160 (2011); Chen et al., *J. Immunol.* 183:4094-4102 (2009); Putnam et al., *Diabetes* 58:652-662 (2009); Putnam et al., *Am. J. Tranplant.* 13:3010-3020 (2013)). In a specific embodiment, $CD4^+CD25^+$ regulatory T cells are isolated, for example, using a $CD4^+CD25^+$ Regulatory T Cell Isolation Kit (Dynal brand, Invitrogen, Carlsbad, Calif.) (see Lee et al., *Cancer Res.* 71:2871-2881 (2011)). In vitro generation of regulatory T cells (iTregs) have also been described (see, for example, Lan et al., *J. Mol. Cell. Biol.* 4:22-28 (2012); Yamagiwa et al., *J. Immunol.* 166:7282-7289 (2001); Zheng et al., *J. Immunol.* 169:4183-4189 (2002)). Various methods for isolating immune cells that can be used for recombinant expression of a CAR have been described previously (Sadelain et al., *Nat. Rev. Cancer* 3:35-45 (2003); Morgan et al., *Science* 314:126-129 (2006); Panelli et al., *J. Immunol.* 164:495-504 (2000); Panelli et al., *J Immunol.* 164:4382-4392 (2000); Dupont et al., *Cancer Res.* 65:5417-5427 (2005); Papanicolaou et al., *Blood* 102:2498-2505 (2003); MacDonald et al., *J Clin. Invest.* 126:1413-1424 (2016)). In a particular embodiment, the immunoinhibitory cells, in particular regulatory T cells, are isolated from a subject having a viral infection, e.g., a chronic viral infection, such as a chronic infection with HCV, HBV or HIV. In a specific embodiment, regulatory T cells are isolated from a patient with a chronic viral infection when the patient is in remission of acute infection. In the case of immunoinhibitory cells isolated from a patient having a viral infection, the immunoinhibitory cells, such as regulatory T cells, need not be, but can be, antigen specific for a viral antigen.

Optionally, the immunoinhibitory cells, such as regulatory T cells, can be sensitized to a viral antigen. Methods for isolating an antigen-specific immunoinhibitory cell, such as a regulatory T cell, from a subject are well known in the art (see, for example, Noyan et al., *Eur. J. Immunol.* 44:2592-2602 (2014); Brusko et al., *PLoS One* 5(7) e11726 (doi: 10.1371) (2010); Bacher et al., *Mucosal Immunol.* 7:916-928 (2014); Koenen et al., *J. Immunol.* 174:7573-7583 (2005)).

In one embodiment, immunoinhibitory cells, such as regulatory T cells, are isolated from a patient having a viral infection, e.g., a chronic viral infection. Such isolated cells or their progeny can optionally be genetically modified to express a CAR that binds to an antigen of the virus responsible for the viral infection.

Methods for isolating and expanding regulatory T cells are well known in the art (see, for example, Su et al., *Methods Mol. Biol.* 806:287-299 (2012); Bluestone et al., *Sci. Transl. Med.* 7(315) (doi: 10.1126/scitranslmed.aad4134)(2015); Miyara et al., *Nat. Rev. Rheumatol.* 10:543-551 (2014); Liu et al., *J. Exp. Med.* 203:1701-1711 (2006); Seddiki et al., *J. Exp. Med.* 203:1693-1700 (2006); Ukena et al., *Exp. Hematol.* 39:1152-1160 (2011); Chen et al., *J. Immunol.* 183:4094-4102 (2009); Putnam et al., *Diabetes* 58:652-662 (2009); Putnam et al., *Am. J. Tranplant.* 13:3010-3020 (2013); Lee et al., *Cancer Res.* 71:2871-2881 (2011); MacDonald et al., *J Clin. Invest.* 126:1413-1424 (2016)). In vitro generation of regulatory T cells (iTregs) has also been described (see, for example, Lan et al., *J. Mol. Cell. Biol.* 4:22-28 (2012); Yamagiwa et al., *J. Immunol.* 166:7282-7289 (2001); Zheng et al., *J. Immunol.* 169:4183-4189 (2002)). Generally, regulatory T cells of the invention are $CD4^+$, for example, $CD4^+CD25^+$, and in particular $CD4^+CD127^{lo/-}CD25^+$. Such regulatory T cells express Foxp3 (forkhead box P3), which is in the forkhead/winged-helix family of transcription factors (Bluestone et al., *J. Clin. Invest.* 125:2250-2260 (2015); Riley et al., *Immunity* 30:656-665 (2009)). A regulatory T cell that is an immunoinhibitory cell of the invention can also be a $CD8^+$ regulatory T cell (Guillonneau et al., *Curr. Opin. Organ Transplant.* 15:751-756 (2010)). Methods for isolating and expanding regulatory T cells are also commercially available (see, for example, BD Biosciences, San Jose, Calif.; STEMCELL Technologies Inc., Vancouver, Canada; eBioscience, San Diego, Calif.; Invitrogen, Carlsbad, Calif.). An immunoinhibitory cell of the invention can also be a follicular regulatory T cell (T(FR)) (Sage et al., *Nat. Immunol.* 14:152-161 (2013)). In a particular embodiment, the follicular regulatory T cells of the invention are $CD4^+CXCR5^+$ and express Foxp3 (Sage et al., supra, 2013).

In some embodiments, the immunoinhibitory cells of the invention are regulatory B cells. Regulatory B cells have the unique ability in B cells to produce interleukin 10 (IL10) (see, for example, Lykken et al., *International Immunol.* 27:471-477 (2015); Miyagaki et al., *International Immunol.* 27:495-504 (2015)). Methods of isolating regulatory B cells have been described (see, for example, Masson et al., in *Regulatory B Cells: Methods and Protocols*, Vitale and Mion, eds., Chapter 4, pp. 45-52, Humana Press, New York (2014)). Such methods are based on the expression of cell surface markers, such as $CD24^{high}CD38^{high}$, and the expression of IL10 (Masson et al., supra, 2014). Other markers for regulatory B cells include $CD24^{hi}CD27^+$ (see Lykken et al., supra, 2015).

Procedures for separation of immune cells include, but are not limited to, density gradient centrifugation, coupling to particles that modify cell density, magnetic separation with antibody-coated magnetic beads, affinity chromatography; cytotoxic agents joined to or used in conjunction with a monoclonal antibody (mAb), including, but not limited to, complement and cytotoxins, and panning with an antibody attached to a solid matrix, for example, a plate or chip, elutriation, flow cytometry, or any other convenient technique (see, for example, Recktenwald et al., *Cell Separation Methods and Applications*, Marcel Dekker, Inc., New York (1998)). It is understood that the immune cells used in methods of the invention can be substantially pure cells or can be a polyclonal population. In some embodiments, a polyclonal population can be enriched for a desired immune cell. Such an enrichment can take place prior to or after genetically engineering the cells to express a DN form, or a CAR and DN form, as desired.

The immune cells, or precursor cells thereof, can be autologous or non-autologous to the subject to which they are administered in the methods of treatment of the invention. Autologous cells are isolated from the subject to which the engineered cells are to be administered. Optionally, the cells can be obtained by leukapheresis, where leukocytes are selectively removed from withdrawn blood, made recombinant, and then retransfused into the donor. Alternatively, allogeneic cells from a non-autologous donor that is not the subject can be used. In the case of a non-autologous donor, the cells are typed and matched for human leukocyte antigen (HLA) to determine an appropriate level of compatibility, as is well known in the art. For both autologous and non-autologous cells, the cells can optionally be cryopreserved until ready to be used for genetic manipulation and/or administration to a subject using methods well known in the art.

The immune cells, or precursor cells thereof, can be subjected to conditions that favor maintenance or expansion of the immune cells, or precursor cells thereof (see Kearse, *T Cell Protocols: Development and Activation*, Humana Press, Totowa N.J. (2000); De Libero, *T Cell Protocols*, Vol. 514 of *Methods in Molecular Biology*, Humana Press, Totowa N.J. (2009); Parente-Pereira et al., *J. Biol. Methods* 1(2) e7 (doi 10.14440/jbm.2014.30) (2014); Movassagh et al., *Hum. Gene Ther.* 11:1189-1200 (2000); Rettig et al., *Mol. Ther.* 8:29-41 (2003); Agarwal et al., *J. Virol.* 72:3720-3728 (1998); Pollok et al., *Hum. Gene Ther.* 10:2221-2236 (1999); Quinn et al., *Hum. Gene Ther.* 9:1457-1467 (1998); Su et al., *Methods Mol. Biol.* 806:287-299 (2012); Bluestone et al., *Sci. Transl. Med.* 7(315) (doi: 10.1126/scitranslmed.aad4134)(2015); Miyara et al., *Nat. Rev. Rheumatol.* 10:543-551 (2014); Liu et al., *J. Exp. Med.* 203:1701-1711 (2006); Seddiki et al., *J. Exp. Med.* 203:1693-1700 (2006); Ukena et al., *Exp. Hematol.* 39:1152-1160 (2011); Chen et al., *J. Immunol.* 183:4094-4102 (2009); Putnam et al., *Diabetes* 58:652-662 (2009); Putnam et al., *Am. J. Tranplant.* 13:3010-3020 (2013); Lee et al., *Cancer Res.* 71:2871-2881 (2011); MacDonald et al., *J Clin. Invest.* 126:1413-1424 (2016); see also commercially available methods such as Dynabeads™ human T cell activator products, Thermo Fisher Scientific, Waltham, Mass.)). The immune cells, or precursor cells thereof, or viral antigen sensitized immune cells, such as T cells, can optionally be expanded prior to or after ex vivo genetic engineering. Expansion of the cells is particularly useful to increase the number of cells for administration to a subject. Such methods for expansion of immune cells are well known in the art (see Kaiser et al., *Cancer Gene Therapy* 22:72-78 (2015); Wolfl et al., *Nat. Protocols* 9:950-966 (2014); Su et al., *Methods Mol. Biol.* 806:287-299 (2012); Bluestone et al., *Sci. Transl. Med.* 7(315) (doi: 10.1126/scitranslmed.aad4134)(2015); Miyara et al., *Nat. Rev. Rheumatol.* 10:543-551 (2014); Liu et al., *J. Exp. Med.* 203:1701-1711 (2006); Seddiki et al., *J. Exp. Med.* 203:1693-1700 (2006); Ukena et al., *Exp. Hematol.* 39:1152-1160 (2011); Chen et al., *J. Immunol.* 183:4094-4102 (2009); Putnam et al., *Diabetes* 58:652-662 (2009); Putnam et al., *Am. J. Tranplant.* 13:3010-3020 (2013); Lee et al., *Cancer Res.* 71:2871-2881 (2011)). Furthermore, the cells can optionally be cryopreserved after isolation and/or genetic engineering, and/or expansion of genetically engineered cells (see Kaiser et al., supra, 2015)). Methods for cyropreserving cells are well known in the art (see, for example, Freshney, *Culture of Animal Cells: A Manual of Basic Techniques,* 4th ed., Wiley-Liss, New York (2000); Harrison and Rae, *General Techniques of Cell Culture,* Cambridge University Press (1997)).

In a specific embodiment, isolated immune cells that are immunostimulatory cells, or precursor cells thereof, are genetically engineered ex vivo for recombinant expression of a DN form and a CAR. In a specific embodiment, isolated T cells are genetically engineered ex vivo for recombinant expression of a DN form. In a specific embodiment, immunoinhibitory cells, such as regulatory T cells, are genetically engineered ex vivo for recombinant expression of a DN form. The cells can be genetically engineered for recombinant expression by methods well known in the art.

In an embodiment where viral antigen sensitized immune cells, such as T cells, that recombinantly express a DN form are used, and wherein such cells are obtained by in vitro sensitization, the sensitization can occur before or after the immune cells are genetically engineered to recombinantly express a DN form. In an embodiment where the sensitized immune cells, such T cells, are isolated from in vivo sources, it will be self-evident that genetic engineering occurs of the already-sensitized immune cells.

With respect to generating cells recombinantly expressing a DN form or a CAR and DN form, one or more nucleic acids encoding the DN form or the CAR and DN form is introduced into the immune cell, or precursor cell thereof, using a suitable expression vector. The immune cells (for example, T cells or regulatory T cells), or precursor cells thereof, are preferably transduced with one or more nucleic acids encoding a DN form, or a CAR and DN form. In the case of expressing both a CAR and DN form, the CAR and DN form encoding nucleic acids can be on separate vectors or on the same vector, as desired. For example, a polynucleotide encoding a CAR or DN form of the invention can be cloned into a suitable vector, such as a retroviral vector, and introduced into the immune cell using well known molecular biology techniques (see Ausubel et al., *Current Protocols in Molecular Biology,* John Wiley and Sons, Baltimore, Md. (1999)). Any vector suitable for expression in a cell of the invention, particularly a human immune cell or a precursor cell thereof, can be employed. The vectors contain suitable expression elements such as promoters that provide for expression of the encoded nucleic acids in the immune cell. In the case of a retroviral vector, cells can optionally be activated to increase transduction efficiency (see Parente-Pereira et al., *J. Biol. Methods* 1(2) e7 (doi 10.14440/jbm.2014.30) (2014); Movassagh et al., *Hum. Gene Ther.* 11:1189-1200 (2000); Rettig et al., *Mol. Ther.* 8:29-41 (2003); Agarwal et al., *J. Virol.* 72:3720-3728 (1998); Pollok et al., *Hum. Gene Ther.* 10:2221-2236 (1998); Quinn et al., *Hum. Gene Ther.* 9:1457-1467 (1998); see also commercially available methods such as Dynabeads™ human T cell activator products, Thermo Fisher Scientific, Waltham, Mass.). Methods for use in expressing a polypeptide, such as a CAR, in a regulatory T cell can be any known in the art, e.g., those described in Lee et al., *Cancer Res.* 71:2871-2881 (2011).

In one embodiment, the vector is a retroviral vector, for example, a gamma retroviral or lentiviral vector, which is employed for the introduction of a CAR or DN form into the immune cell, or precursor cell thereof. For genetic modification of the cells to express a CAR and/or DN form, a retroviral vector is generally employed for transduction. However, it is understood that any suitable viral vector or non-viral delivery system can be used. Combinations of a retroviral vector and an appropriate packaging line are also suitable, where the capsid proteins will be functional for infecting human cells. Various amphotropic virus-producing cell lines are known, including, but not limited to, PA12 (Miller et al., *Mol. Cell. Biol.* 5:431-437 (1985)); PA317 (Miller et al., *Mol. Cell. Biol.* 6:2895-2902(1986)); and CRIP (Danos et al., *Proc. Natl. Acad. Sci. USA* 85:6460-6464 (1988)). Non-amphotropic particles are suitable too, for example, particles pseudotyped with VSVG, RD114 or GALV envelope and any other known in the art (Relander et al., *Mol. Therap.* 11:452-459 (2005)). Possible methods of transduction also include direct co-culture of the cells with producer cells (for example, Bregni et al., *Blood* 80:1418-1422 (1992)), or culturing with viral supernatant alone or concentrated vector stocks with or without appropriate growth factors and polycations (see, for example, Xu et al., *Exp. Hemat.* 22:223-230 (1994); Hughes, et al. *J. Clin. Invest.* 89:1817-1824 (1992)).

Generally, the chosen vector exhibits high efficiency of infection and stable integration and expression (see, for example, Cayouette et al., *Human Gene Therapy* 8:423-430 (1997); Kido et al., *Current Eye Research* 15:833-844 (1996); Bloomer et al., *J. Virol.* 71:6641-6649 (1997); Naldini et al., *Science* 272:263 267 (1996); and Miyoshi et al., *Proc. Natl. Acad. Sci. U.S.A.* 94:10319-10323 (1997)). Other viral vectors that can be used include, for example, adenoviral, lentiviral, and adeno-associated viral vectors, vaccinia virus, a bovine papilloma virus derived vector, or a herpes virus, such as Epstein-Barr Virus (see, for example, Miller, *Hum. Gene Ther.* 1(1):5-14 (1990); Friedman, *Science* 244:1275-1281 (1989); Eglitis et al., *BioTechniques* 6:608-614 (1988); Tolstoshev et al., *Current Opin. Biotechnol.* 1:55-61 (1990); Sharp, *Lancet* 337:1277-1278 (1991); Cornetta et al., *Prog. Nucleic Acid Res. Mol. Biol.* 36:311-322 (1989); Anderson, *Science* 226:401-409 (1984); Moen, *Blood Cells* 17:407-416 (1991); Miller et al., *Biotechnology* 7:980-990 (1989); Le Gal La Salle et al., *Science* 259:988-990 (1993); and Johnson, *Chest* 107:775-83S (1995)). Retroviral vectors are particularly well developed and have been used in clinical settings (Rosenberg et al., *N. Engl. J. Med.* 323:370 (1990); Anderson et al., U.S. Pat. No. 5,399,346).

Particularly useful vectors for expressing a CAR and/or DN form of the invention include vectors that have been used in human gene therapy. In one non-limiting embodiment, a vector is a retroviral vector. The use of retroviral vectors for expression in T cells or other immune cells, including engineered CAR T cells, has been described (see Scholler et al., *Sci. Transl. Med.* 4:132-153 (2012; Parente-Pereira et al., *J. Biol. Methods* 1(2):e7 (1-9)(2014); Lamers et al., *Blood* 117(1):72-82 (2011); Reviere et al., *Proc. Natl. Acad. Sci. USA* 92:6733-6737 (1995)). In one embodiment, the vector is an SGF retroviral vector such as an SGF γ-retroviral vector, which is Moloney murine leukemia-based retroviral vector. SGF vectors have been described previously (see, for example, Wang et al., *Gene Therapy* 15:1454-1459 (2008)).

The vectors of the invention employ suitable promoters for expression in a particular host cell. The promoter can be an inducible promoter or a constitutive promoter. In a particular embodiment, the promoter of an expression vector provides expression in an immune cell, such as a T cell, or precursor cell thereof, or a regulatory T cell. Non-viral vectors can be used as well, so long as the vector contains suitable expression elements for expression in the immune cell, or precursor cell thereof. Some vectors, such as retroviral vectors, can integrate into the host genome. If desired, targeted integration can be implemented using technologies such as a nuclease, transcription activator-like effector nucleases (TALENs), Zinc-finger nucleases (ZFNs), and/or clustered regularly interspaced short palindromic repeats (CRISPRs), by homologous recombination, and the like (Gersbach et al., *Nucl. Acids Res.* 39:7868-7878 (2011); Vasileva, et al. *Cell Death Dis.* 6:e1831. (Jul. 23, 2015); Sontheimer, *Hum. Gene Ther.* 26(7):413-424 (2015)).

The vectors and constructs can optionally be designed to include a reporter. For example, the vector can be designed to express a reporter protein, which can be useful to identify cells comprising the vector or nucleic acids provided on the vector, such as nucleic acids that have integrated into the host chromosome. In one embodiment, the reporter can be expressed as a bicistronic or multicistronic expression construct with the CAR or DN form. Exemplary reporter proteins include, but are not limited to, fluorescent proteins, such as mCherry, green fluorescent protein (GFP), blue fluorescent protein, for example, EBFP, EBFP2, Azurite, and mKalamal, cyan fluorescent protein, for example, ECFP, Cerulean, and CyPet, and yellow fluorescent protein, for example, YFP, Citrine, Venus, and YPet. In an additional embodiment, a vector construct can comprise a P2A sequence, which provides for optional co-expression of a reporter molecule. P2A is a self-cleaving peptide sequence, which can be used for bicistronic or multicistronic expression of protein sequences (see Szymczak et al., *Expert Opin. Biol. Therapy* 5(5):627-638 (2005)).

Assays can be used to determine the transduction efficiency of a CAR and/or DN form using routine molecular biology techniques. If a marker has been included in the construct, such as a fluorescent protein, gene transfer efficiency can be monitored by FACS analysis to quantify the fraction of transduced (for example, GFP$^+$) immune cells, such as T cells, or precursor cells thereof, or regulatory T cells, and/or by quantitative PCR. Using a well-established cocultivation system (Gade et al., *Cancer Res.* 65:9080-9088 (2005); Gong et al., *Neoplasia* 1:123-127 (1999); Latouche et al., *Nat. Biotechnol.* 18:405-409 (2000)) it can be determined whether fibroblast AAPCs expressing viral antigen (vs. controls) direct cytokine release from transduced immune cells, such as T cells, expressing a CAR (cell supernatant LUMINEX (Austin Tex.) assay for IL-2, IL-4, IL-10, IFN-γ, TNF-α, and GM-CSF), T cell proliferation (by carboxyfluorescein succinimidyl ester (CFSE) labeling), and T cell survival (by Annexin V staining). The influence of CD80 and/or 4-1BBL on T cell survival, proliferation, and efficacy can be evaluated. T cells can be exposed to repeated stimulation by viral antigen positive target cells, and it can be determined whether T cell proliferation and cytokine response remain similar or diminished with repeated stimulation. Cells with and without the viral antigen CAR constructs can be compared side by side under equivalent assay conditions. Cytotoxicity assays with multiple E:T ratios can be conducted using chromium-release assays.

If desired, a nucleic acid encoding a polypeptide for genetic engineering of a cell of the invention, such as a DN form or a CAR, can be codon optimized to increase efficiency of expression in an immune cell, or precursor cell thereof. Codon optimization can be used to achieve higher levels of expression in a given cell. Factors that are involved in different stages of protein expression include codon adaptability, mRNA structure, and various cis-elements in transcription and translation. Any suitable codon optimization methods or technologies that are known to one skilled in the art can be used to modify the polynucleotides encoding the polypeptides. Such codon optimization methods are well known, including commercially available codon optimization services, for example, OptimumGene™ (GenScript; Piscataway, N.J.), Encor optimization (EnCor Biotechnology; Gainseville Fla.), Blue Heron (Blue Heron Biotech; Bothell, Wash.), and the like. Optionally, multiple codon optimizations can be performed based on different algorithms, and the optimization results blended to generate a codon optimized nucleic acid encoding a polypeptide.

Further modification can be introduced to the immune cells, or precursor cells thereof, of the invention. For example, the cells can be modified to address immunological complications and/or targeting of the immune cells to healthy or non-target tissues. For example, a suicide gene can be introduced into the cells to provide for depletion of the cells when desired. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. Agents are administered to the subject to which the cells containing the suicide genes have been administered, including but not limited to, gancilovir (GCV) for hsv-tk (Greco et al., *Frontiers Pharmacol.* 6:95 (2015); Barese et al., *Mol. Therapy* 20:1932-1943 (2012)), AP1903 for iCasp-9 (Di Stasi et al., *N. Engl. J. Med.* 365:1673-1683 (2011), and cetuximab for EGFRt (U.S. Pat. No. 8,802,374), to promote cell death. In one embodiment, administration of a prodrug designed to activate the suicide gene, for example, a prodrug such as AP1903 that can activate iCasp-9, triggers apoptosis in the suicide gene-activated cells. In one embodiment, iCasp9 consists of the sequence of the human FK506-binding protein (FKBP12; GenBank number, AH002818 (AH002818.2, GI:1036032368)) with an F36V mutation, connected through a Ser-Gly-Gly-Gly-Ser (SEQ ID NO:28) linker to the gene encoding human caspase 9 (CASP9; GenBank number, NM001229 (NM_001229.4, GI:493798577)), which has had its endogenous caspase activation and recruitment domain deleted. FKBP12-F36V binds with high affinity to an otherwise bioinert small-molecule dimerizing agent, AP1903. In the presence of AP1903, the iCasp9 promolecule dimerizes and activates the intrinsic apoptotic pathway, leading to cell death (Di Stasi et al., *N. Engl. J. Med.* 365:1673-1683 (2011)). In another embodiment, the suicide gene is an EGFRt polypeptide. The EGFRt polypeptide can provide for cell elimination by administering anti-EGFR monoclonal antibody, for example, cetuximab. The suicide gene can be expressed on a separate vector or, optionally, expressed within the vector encoding a CAR or DN form, and can be a bicistronic or multicistronic construct joined to a CAR or DN form encoding nucleic acid.

7.2 Chimeric Antigen Receptors (CARs)

The CAR that is recombinantly expressed by a cell of the invention has an antigen binding domain that binds to a viral antigen. In specific embodiments, the CAR can be a "first generation," "second generation" or "third generation" CAR (see, for example, Sadelain et al., *Cancer Discov.* 3(4):388-398 (2013); Jensen et al., *Immunol. Rev.* 257:127-133 (2014); Sharpe et al., *Dis. Model Mech.* 8(4):337-350 (2015); Brentjens et al., *Clin. Cancer Res.* 13:5426-5435 (2007); Gade et al., *Cancer Res.* 65:9080-9088 (2005); Maher et al., *Nat. Biotechnol.* 20:70-75 (2002); Kershaw et al., *J. Immunol.* 173:2143-2150 (2004); Sadelain et al., *Curr. Opin. Immunol.* 21(2):215-223 (2009); Hollyman et al., *J. Immunother.* 32:169-180 (2009)).

"First generation" CARs are typically composed of an extracellular antigen binding domain, for example, a single-chain variable fragment (scFv), fused to a transmembrane domain, which is fused to a cytoplasmic/intracellular domain of the T cell receptor chain. "First generation" CARs typically have the intracellular domain from the CD3ζ-chain, which is the primary transmitter of signals from endogenous T cell receptors (TCRs) (see exemplary first generation CAR in FIG. 1A). "First generation" CARs can provide de novo antigen recognition and cause activation of T cells, including both CD4$^+$ and CD8$^+$ T cells, through their CD3ζ chain signaling domain in a single fusion molecule, independent of HLA-mediated antigen presentation. "Second-generation" CARs for use in the invention comprise a viral antigen-binding domain fused to an intracellular signaling domain capable of activating immune cells such as T cells and a co-stimulatory domain designed to augment immune cell, such as T cell, potency and persistence (Sadelain et al., *Cancer Discov.* 3:388-398 (2013)). CAR design can therefore combine antigen recognition with signal transduction, two functions that are physiologically borne by two separate complexes, the TCR heterodimer and the CD3 complex. "Second generation" CARs include an intracellular domain from various co-stimulatory molecules, for example, CD28, 4-1BB, ICOS, OX40, and the like, in the cytoplasmic tail of the CAR to provide additional signals to the cell (see exemplary second generation CAR in FIG. 1A). "Second generation" CARs provide both co-stimulation, for example, by CD28 or 4-1BB domains, and activation, for example, by a CD3ζ signaling domain. "Third generation" CARs provide multiple co-stimulation, for example, by comprising both CD28 and 4-1BB domains, and activation, for example, by comprising a CD3ζ activation domain.

In the embodiments disclosed herein, the CARs generally comprise an extracellular antigen binding domain, a transmembrane domain and an intracellular domain, as described above, where the extracellular antigen binding domain binds to a viral antigen. In a particular non-limiting embodiment, the extracellular antigen-binding domain is an scFv.

As disclosed herein, the methods of the invention can involve administering cells that have been engineered to co-express a viral antigen CAR and a dominant negative form ("DN form") of an inhibitor of a cell-mediated immune response. The extracellular antigen-binding domain of a CAR is usually derived from a monoclonal antibody (mAb) or from receptors or their ligands.

The design of CARs is well known in the art (see, for example, reviews by Sadelain et al., *Cancer Discov.* 3(4): 388-398 (2013); Jensen et al., *Immunol. Rev.* 257:127-133 (2014); Sharpe et al., *Dis. Model Mech.* 8(4):337-350 (2015), and references cited therein). A CAR directed to a desired viral antigen can be generated using well known methods for designing a CAR, including those as described herein. A CAR, whether a first, second or third generation CAR, can be readily designed by fusing a viral antigen binding activity, for example, an scFv antibody directed to the viral antigen, to an immune cell signaling domain, such as a T cell receptor cytoplasmic/intracellular domain. As described above, the CAR generally has the structure of a cell surface receptor, with the viral antigen binding activity, such as an scFv, as at least a portion of the extracellular domain, fused to a transmembrane domain, which is fused to an intracellular domain that has cell signaling activity in an immune cell, such as a T cell, or precursor cell thereof. The viral antigen CAR can include co-stimulatory molecules, as described herein. One skilled in the art can readily select appropriate transmembrane domains, as described herein and known in the art, and intracellular domains to provide the desired signaling capability in the immune cell, such as a T cell, or precursor cell thereof.

A CAR for use in the present invention comprises an extracellular domain that includes an antigen binding domain that binds to a viral antigen. The antigen binding domain binds to an antigen on the target virus, or to a viral antigen expressed in a target cell or tissue. Such an antigen binding domain is generally derived from an antibody. In one embodiment, the antigen binding domain can be an scFv or a Fab, or any suitable antigen binding fragment of an antibody (see Sadelain et al., *Cancer Discov.* 3:388-398 (2013)). Many antibodies or antigen binding domains derived from antibodies that bind to a viral antigen are known in the art. Alternatively, such antibodies or antigen binding domains can be produced by routine methods. Methods of generating an antibody are well known in the art, including methods of producing a monoclonal antibody or screening a library to obtain an antigen binding polypeptide, including screening a library of human Fabs (Winter and Harris, *Immunol. Today* 14:243-246 (1993); Ward et al., *Nature* 341:544-546 (1989); Harlow and Lane, Antibodies: A Laboratory Manual, Cold Spring Harbor Laboratory Press (1988); Hilyard et al., *Protein Engineering: A practical approach* (IRL Press 1992); Borrabeck, *Antibody Engineering,* 2nd ed. (Oxford University Press 1995); Huse et al., *Science* 246:1275-1281 (1989)). For the CAR, the antigen binding domain derived from an antibody can be human, humanized, chimeric, CDR-grafted, and the like, as desired. For example, if a mouse monoclonal antibody is a source antibody for generating the antigen binding domain of a CAR, such an antibody can be humanized by grafting CDRs of the mouse antibody onto a human framework (see Borrabeck, supra, 1995), which can be beneficial for administering the CAR to a human subject. In a preferred embodiment, the antigen binding domain is an scFv. The generation of scFvs is well known in the art (see, for example, Huston, et al., *Proc. Nat. Acad. Sci. USA* 85:5879-5883 (1988); Ahmad et al., *Clin. Dev. Immunol.* 2012: ID980250 (2012); U.S. Pat. Nos. 5,091,513, 5,132,405 and 4,956,778; and U.S. Patent Publication Nos. 20050196754 and 20050196754)).

With respect to obtaining a viral antigen binding activity, one skilled in the art can readily obtain a suitable viral antigen binding activity, such as an antibody, using any of the well known methods for generating and screening for an antibody that binds to a desired antigen, as disclosed herein, including the generation of an scFv that binds to a viral antigen, which is particularly useful in a CAR. In addition, a number viral antigen antibodies, in particular monoclonal antibodies, are commercially available and can also be used as a source for a viral antigen binding activity, such as an scFv, to generate a CAR (see, for example, Sigma-Aldrich, St. Louis, Mo.; Meridian Life Science, Memphis, Tenn.; ProSpec-Tany Technogene, East Brunswick, N.J., and the like).

Alternatively to using an antigen binding domain derived from an antibody, a CAR extracellular domain can comprise a ligand or extracellular ligand binding domain of a receptor (see Sadelain et al., *Cancer Discov.* 3:388-398 (2013); Sharpe et al., *Dis. Model Mech.* 8:337-350 (2015)). In this case, the ligand or extracellular ligand binding domain of a receptor provides to the CAR the ability to target the cell expressing the CAR to the corresponding receptor or ligand. In the case of targeting a virus, an exemplary embodiment is the use of the gE/gI glycoprotein of herpes simplex virus (HSV) (see Polcicova et al., *J. Virol.* 79:11990-12001 (2005). The HSV gE/gI glycoprotein accumulates at cell junctions and mediates cell-to-cell spread of HSV (Polcicova et al., supra, 2005). In a specific embodiment, a CAR extracellular domain comprises the extracellular domain of HSV gE, so as to target the immune cell expressing the CAR to cell junctions, where HSV spreads from cell to cell.

For a CAR directed to a viral antigen, the antigen binding domain of the CAR is selected to bind to a viral antigen of the target virus or a viral antigen expressed on a cell containing the virus, for example, an infected cell expressing viral antigen on its cell surface. Such a viral antigen can be uniquely expressed on a virus, or the viral antigen can be overexpressed on a virus or in a virus infected tissue or cell relative to non-virally infected cells or tissues. Generally, a viral antigen is uniquely expressed by the virus or a virally infected cell or tissue and is not naturally expressed in an infected organism. The viral antigen to be bound by the CAR is chosen to provide targeting of the cell expressing the CAR over non-virally infected cells or tissues. In one embodiment of the methods of the invention for treating a viral infection, an immune cell or precursor cell thereof is designed to treat a patient with a viral infection by expressing in the cell a CAR that binds to a suitable viral antigen of the patient's viral infection, along with a DN form, as described herein.

Any suitable viral antigen can be chosen based on the type of viral infection exhibited by a subject (patient with a viral infection) to be treated. It is understood that the selected viral antigen is expressed in a manner such that the viral antigen is accessible for binding by the CAR. Generally, the viral antigen to be targeted by a cell expressing a CAR is expressed on the surface of the virus or the surface of a virally infected cell or tissue of the subject. However, it is understood that any viral antigen that is accessible for binding to a CAR is suitable for targeting the CAR expressing cell to the site of a viral infection or virally infected tissue. Preferred viruses include those that are pathogenic, particularly human pathogens, and that elicit a viral antigen-specific immune response. In a specific embodiment, the targeted viral antigen is of a virus that is a human pathogen, and in a particular embodiment, such a viral antigen of a human pathogen is one that can elicit an immune response in a human patient infected with the virus. Exemplary viruses and their viral antigens that can be targeted include, but are not limited to, those provided below in Table 1.

TABLE 1

Viruses and Viral Antigens

| Virus | Viral Antigen | Reference[1] |
|---|---|---|
| human immunodeficiency virus (HIV) | group-specific antigen (gag) protein (p55, p24, or p18), envelope glycoprotein (env) (gp160, gp120 or gp41) or reverse transcriptase (pol) (p66 or p31) | Mitsuya, 1990; Fauci, 1998; Fauci, 1988; Rosenberg, 1997 |
| hepatitis B virus (HBV) | HBV envelope protein S, M or L | Krebs, 2013 |
| hepatitis C virus (HCV) | core protein, envelope protein E1 or E2, nostructural protein NS2, NS3, NS4 (NS4A or NS4B), NS5 (NS5A or NS5B) | Ashfaq (2011); Sillanpää (2009); Dawson (2012) |
| herpes simplex virus (HSV) | gE, gI, gB, gD, gH, gL, gC, gG, gK or gM | Polcicova, 2005; Bennett, 1996 |
| varicella zoster virus or (VZV) | gE or gI | Polcicova, 2005 |
| adenovirus | hexon protein or penton protein | Gerdemann, 2013 |
| cytomegalovirus (CMV) | pp65, immediate early (IE) antigen or IE1 | Gerdemann, 2013; Rooney, 2012 |
| Epstein-Barr virus (EBV) | LMP2 (latent membrane protein 2), EBNA1 (Epstein-Barr nuclear antigen 1) or immediate early protein BZLF1 (also known as Zta, ZEBRA, EB1) | Gerdemann, 2013; Rooney, 2012 |

[1]Mitsuya et al., *Science* 249: 1533-1544 (1990); Fauci et al., *Harrison's Principles of Internal Medicine*, 14th ed., pp. 1814-1816, McGraw-Hill, San Francisco CA (1998); Fauci, *Science* 239: 617-622 (1988); Rosenberg et al., *Science* 278: 1447-1450 (1997); Krebs et al., *Gastroenterol.* 145: 456-465 (2013); Ashfaq et al., *Virol. J.* 8: 161 (doi: 10.1186/1743-422X-8-161); Sillanpää et al., *Virol. J.* 6: 84 (doi: 10.1186/1743-422X-6-84); Dawson, *Antiviral Therap.* 17: 1431-1435 (2012); Polcicova et al., *J. Virol.* 79: 11990-12001 (2005); Bennett et al., *Cecil Textbook of Medicine*, 20th ed., p. 1770, W. B. Saunders, Philadelphia PA (1996); Gerdemann et al., *Mol. Ther.* 21: 2113-2121 (2013); Rooney et al., *Mol. Ther. Nucleic Acids* 1: e55, doi: 10.1038/mtna.2012.49 (2012)

In a specific embodiment in the case of HBV, the S domain of an S, M or L envelope protein is targeted (see Krebs et al., supra, 2013). In another specific embodiment in the case of HSV, the extracellular domain of gE is targeted (see Polcicova et al., supra, 2005). It is understood that a person skilled in the art can readily determine a viral antigen, or domain of a viral antigen, suitable for targeting by an immune cell of the invention.

It is further understood that reference to a virus, such as those listed in Table 1, includes different strains or types of the same virus. For example, HSV exists as herpes simplex virus type 1 (HSV-1) and herpes simplex virus type 2 (HSV-2), which can be distinguished by the respective glycoprotein G (gG) (Bennett et al., *Cecil Textbook of Medicine,* 20th ed., p. 1770, W.B. Saunders, Philadelphia Pa. (1996)). In a particular embodiment, the viral antigen can be selected such that the antigen is common to different strains or types of the same virus or is a distinct antigen specific to a particular strain or type of virus, such as for HSV-1 and HSV-2.

It is to be understood that any of the above-described viral antigens or epitopes thereof, as well as any known in the art, can be targeted by the immune cells of the invention (that express a DN form), for example, by using such an immune cell that recombinantly expresses a CAR that binds to such antigen or epitope, or using such an immune cell sensitized ex vivo to such antigen or epitope, or using such an immune cell that is in vivo sensitized to such antigen or epitope. In a specific embodiment, one or more nucleic acids encoding a CAR and a DN form are used to transduce both $CD4^+$ and CD8+ T cells. In such an embodiment, administration of the transduced T cells to a subject should generate both helper and cytotoxic T lymphocyte (CTL) responses in the subject, resulting in a sustained anti-viral response.

Exemplary polypeptides are described herein with reference to GenBank numbers, GI numbers and/or SEQ ID NOS. It is understood that one skilled in the art can readily identify homologous sequences by reference to sequence sources, including but not limited to GenBank (ncbi.nlm.nih.gov/genbank/) and EMBL (embl.org/).

It is further understood that embodiments described herein relating to immune cells for treating a viral infection and methods of using such cells for treating a viral infection can be modified and similarly applied to treating an infection by another pathogen, e.g., a pathogen that is a bacterium, fungus, or protozoan. In one embodiment, the pathogen is a human pathogen. It is additionally understood that an antigen of the pathogen can be targeted, for example, by targeting a cell surface antigen of the pathogen.

As described above, a CAR also contains a signaling domain that functions in the immune cell, or precursor cell thereof, expressing the CAR. Such a signaling domain can be, for example, derived from CDζ or Fc receptor γ (see Sadelain et al., Cancer Discov. 3:388-398 (2013)). In general, the signaling domain will induce persistence, trafficking and/or effector functions in the transduced immune cells such as T cells, or precursor cells thereof (Sharpe et al., Dis. Model Mech. 8:337-350 (2015); Finney et al., J. Immunol. 161:2791-2797 (1998); Krause et al., J. Exp. Med. 188:619-626 (1998)). In the case of CDζ or Fc receptor γ, the signaling domain corresponds to the intracellular domain of the respective polypeptides, or a fragment of the intracellular domain that is sufficient for signaling. Exemplary signaling domains are described below in more detail.

CD3ζ. In a non-limiting embodiment, a CAR can comprise a signaling domain derived from a CD3ζ polypeptide, for example, a signaling domain derived from the intracellular domain of CD3ζ, which can activate or stimulate an immune cell, for example, a T cell, or precursor cell thereof. CD3ζ comprises 3 Immune-receptor-Tyrosine-based-Activation-Motifs (ITAMs), and transmits an activation signal to the cell, for example, a cell of the lymphoid lineage such as a T cell, after antigen is bound. A CD3ζ polypeptide can have an amino acid sequence corresponding to the sequence having GenBank No. NP_932170 (NP_932170.1, GI:37595565; see below), or fragments thereof. In one embodiment, the CD3ζ polypeptide has an amino acid sequence of amino acids 52 to 164 of the CD3ζ polypeptide sequence provided below, or a fragment thereof that is sufficient for signaling activity. An exemplary CAR is Mz, which has an intracellular domain comprising a CD3ζ polypeptide comprising amino acids 52 to 164 of the CD3ζ polypeptide sequence provided below. Another exemplary CAR is M28z, which has an intracellular domain comprising a CD3ζ polypeptide comprising amino acids 52 to 164 of the CD3ζ polypeptide provided below. Still another exemplary CAR is MBBz, which has an intracellular domain comprising a CD3ζ polypeptide comprising amino acids 52 to 164 of the CD3ζ polypeptide provided below. Yet another exemplary CAR is P28z, which has an intracellular domain derived from a CD3ζ polypeptide. See GenBank NP_932170 for reference to domains within CD3ζ, for example, signal peptide, amino acids 1 to 21; extracellular domain, amino acids 22 to 30; transmembrane domain, amino acids 31 to 51; intracellular domain, amino acids 52 to 164.

```
  1 MKWKALFTAA ILQAQLPITE AQSFGLLDPK LCYLLDGILF IYGVILTALF LRVKFSRSAD

61 APAYQQGQNQ LYNELNLGRR EEYDVLDKRR GRDPEMGGKP QRRKNPQEGL YNELQKDKMA

121 EAYSEIGMKG ERRRGKGHDG LYQGLSTATK DTYDALHMQA LPPR
```

(NP_932170; SEQ ID NO: 1)

It is understood that a "CD3ζ nucleic acid molecule" refers to a polynucleotide encoding a CD3ζ polypeptide. In one embodiment, the CD3ζ nucleic acid molecule encoding the CD3ζ polypeptide comprised in the intracellular domain of a CAR, including exemplary CARs Mz, M28z, or MBBz, comprises a nucleotide sequence as set forth below.

(SEQ ID NO:2)
AGAGTGAAGTTCAGCAGGAGCGCAGACGCCCCCGCGTACCAGCAGGGCC

AGAACCAGCTCTATAACGAGCTCAATCTAGGACGAAGAGAGGAGTACGA

TGTTTTGGACAAGAGACGTGGCCGGGACCCTGAGATGGGGGGAAAGCCG

AGAAGGAAGAACCCTCAGGAAGGCCTGTACAATGAACTGCAGAAAGATA

AGATGGCGGAGGCCTACAGTGAGATTGGGATGAAAGGCGAGCGCCGGAG

GGGCAAGGGGCACGATGGCCTTTACCAGGGTCTCAGTACAGCCACCAAG

GACACCTACGACGCCCTTCACATGCAGGCCCTGCCCCCTCGCTAA

In certain non-limiting embodiments, an intracellular domain of a CAR can further comprise at least one co-stimulatory signaling domain. Such a co-stimulatory signaling domain can provide increased activation of an immune cell, or precursor cell thereof. A co-stimulatory signaling domain can be derived from a CD28 polypeptide, a 4-1BB polypeptide, an OX40 polypeptide, an ICOS polypeptide, a DAP10 polypeptide, a 2B4 polypeptide, and the like. CARs comprising an intracellular domain that comprises a co-stimulatory signaling region comprising 4-1BB, ICOS or DAP-10 have been described previously (see U.S. Pat. No. 7,446,190, which is incorporated herein by reference, which also describes representative sequences for 4-1BB, ICOS and DAP-10). In some embodiments, the intracellular domain of a CAR can comprise a co-stimulatory signaling region that comprises two co-stimulatory molecules, such as CD28 and 4-1BB (see Sadelain et al., *Cancer Discov.* 3(4):388-398 (2013)), or CD28 and OX40, or other combinations of co-stimulatory ligands, as disclosed herein.

CD28. Cluster of Differentiation 28 (CD28) is a protein expressed on T cells that provides co-stimulatory signals for T cell activation and survival. CD28 is the receptor for CD80 (B7.1) and CD86 (B7.2) proteins. In one embodiment, a CAR can comprise a co-stimulatory signaling domain derived from CD28. For example, as disclosed herein, a CAR can include at least a portion of an intracellular/cytoplasmic domain of CD28, for example an intracellular/cytoplasmic domain that can function as a co-stimulatory signaling domain (see FIG. 1B). A CD28 polypeptide can have an amino acid sequence corresponding to the sequence having GenBank No. P10747 (P10747.1, GI:115973) or NP_006130 (NP_006130.1, GI:5453611), as provided below, or fragments thereof. If desired, CD28 sequences additional to the intracellular domain can be included in a CAR of the invention. For example, a CAR can comprise the transmembrane of a CD28 polypeptide. In one embodiment, a CAR can have an amino acid sequence comprising the intracellular domain of CD28 corresponding to amino acids 180 to 220 of CD28, or a fragment thereof. In another embodiment, a CAR can have an amino acid sequence comprising the transmembrane domain of CD28 corresponding to amino acids 153 to 179, or a fragment thereof. M28z is an exemplary CAR, which comprises a co-stimulatory signaling domain corresponding to an intracellular domain of CD28 (see FIG. 1B). M28z also comprises a transmembrane domain derived from CD28 (see FIG. 1B). Thus, M28z exemplifies a CAR that comprises two domains from CD28, a co-stimulatory signaling domain and a transmembrane domain. In one embodiment, a CAR has an amino acid sequence comprising the transmembrane domain and the intracellular domain of CD28 and comprises amino acids 153 to 220 of CD28. In another embodiment, a CAR is exemplified by M28z CAR and comprises amino acids 117 to 220 of CD28. Another exemplary CAR having a transmembrane domain and intracellular domain of CD28 is P28z (see FIG. 1B). In one embodiment, a CAR can comprise a transmembrane domain derived from a CD28 polypeptide comprising amino acids 153 to 179 of the CD28 polypeptide provided below. See GenBank NP_006130 for reference to domains within CD28, for example, signal peptide, amino acids 1 to 18; extracellular domain, amino acids 19 to 152; transmembrane domain, amino acids 153 to 179; intracellular domain, amino acids 180 to 220. It is understood that sequences of CD28 that are shorter or longer than a specific delineated domain can be included in a CAR, if desired.

```
  1 MLRLLLALNL FPSIQVTGNK ILVKQSPMLV AYDNAVNLSC KYSYNLFSRE FRASLHKGLD

61 SAVEVCVVYG NYSQQLQVYS KTGFNCDGKL GNESVTFYLQ NLYVNQTDIY FCKIEVMYPP

121 PYLDNEKSNG TIIHVKGKHL CPSPLFPGPS KPFWVLVVVG GVLACYSLLV TVAFIIFWVR

181 SKRSRLLHSD YMNMTPRRPG PTRKHYQPYA PPRDFAAYRS (NP_006130; SEQ ID NO:3)
```

It is understood that a "CD28 nucleic acid molecule" refers to a polynucleotide encoding a CD28 polypeptide. In one embodiment, the CD28 nucleic acid molecule encoding the CD28 polypeptide of M28z comprising the transmembrane domain and the intracellular domain, for example, the co-stimulatory signaling region, comprises a nucleotide sequence as set forth below.

(SEQ ID NO:4)
ATTGAAGTTATGTATCCTCCTCCTTACCTAGACAATGAGAAGAGCAATG

GAACCATTATCCATGTGAAAGGGAAACACCTTTGTCCAAGTCCCCTATT

TCCCGGACCTTCTAAGCCCTTTTGGGTGCTGGTGGTGGTTGGTGGAGTC

CTGGCTTGCTATAGCTTGCTAGTAACAGTGGCCTTTATTATTTTCTGGG

TGAGGAGTAAGAGGAGCAGGCTCCTGCACAGTGACTACATGAACATGAC

TCCCCGCCGCCCCGGGCCCACCCGCAAGCATTACCAGCCCTATGCCCCA

CCACGCGACTTCGCAGCCTATCGCTCC 4-1BB. 4-1BB, also referred to as tumor necrosis factor receptor superfamily member 9, can act as a tumor necrosis factor (TNF) ligand and have stimulatory activity. In one embodiment, a CAR can comprise a co-stimulatory signaling domain derived from 4-1BB. A 4-1BB polypeptide can have an amino acid sequence corresponding to the sequence having GenBank No. P41273 (P41273.1, GI:728739) or NP_001552 (NP_001552.2, GI:5730095) or fragments thereof. In one embodiment, a CAR can have a co-stimulatory domain comprising the intracellular domain of 4-1BB corresponding to amino acids 214 to 255, or a fragment thereof. In another embodiment, a CAR can have a transmembrane domain of 4-1BB corresponding to amino acids 187 to 213, or a fragment thereof. An exemplary CAR is MBBz, which has an intracellular domain comprising a 4-1BB polypeptide (for example, amino acids 214 to 255 of NP_001552, SEQ ID NO:5) (see FIG. 1B). See GenBank NP_001552 for reference to domains within 4-1BB, for example, signal peptide, amino acids 1 to 17; extracellular domain, amino acids 18 to 186; transmembrane domain, amino acids 187 to 213; intracellular domain, amino acids 214 to 255. It is understood that sequences of 4-1BB that are shorter or longer than a specific delineated domain can be included in a CAR, if desired. It is also understood that a "4-1BB nucleic acid molecule" refers to a polynucleotide encoding a 4-1BB polypeptide.

```
  1 MGNSCYNIVA TLLLVLNFER TRSLQDPCSN CPAGTFCDNN RNQICSPCPP NSFSSAGGQR

61 TCDICRQCKG VFRTRKECSS TSNAECDCTP GFHCLGAGCS MCEQDCKQGQ ELTKKGCKDC

121 CFGTFNDQKR GICRPWTNCS LDGKSVLVNG TKERDVVCGP SPADLSPGAS SVTPPAPARE

181 PGHSPQIISF FLALTSTALL FLLFFLTLRF SVVKRGRKKL LYIFKQPFMR PVQTTQEEDG

241 CSCRFPEEEE GGCEL  (NP_001552; SEQ ID NO:5)
```

OX40. OX40, also referred to as tumor necrosis factor receptor superfamily member 4 precursor or CD134, is a member of the TNFR-superfamily of receptors. In one embodiment, a CAR can comprise a co-stimulatory signaling domain derived from OX40. An OX40 polypeptide can have an amino acid sequence corresponding to the sequence having GenBank No. P43489 (P43489.1, GI:1171933) or NP_003318 (NP_003318.1, GI:4507579), provided below, or fragments thereof. In one embodiment, a CAR can have a co-stimulatory domain comprising the intracellular domain of OX40 corresponding to amino acids 236 to 277, or a fragment thereof. In another embodiment, a CAR can have an amino acid sequence comprising the transmembrane domain of OX40 corresponding to amino acids 215 to 235 of OX40, or a fragment thereof. See GenBank NP_003318 for reference to domains within OX40, for example, signal peptide, amino acids 1 to 28; extracellular domain, amino acids 29 to 214; transmembrane domain, amino acids 215 to 235; intracellular domain, amino acids 236 to 277. It is understood that sequences of OX40 that are shorter or longer than a specific delineated domain can be included in a CAR, if desired. It is also understood that an "OX40 nucleic acid molecule" refers to a polynucleotide encoding an OX40 polypeptide.

```
  1 MCVGARRLGR GPCAALLLLG LGLSTVTGLH CVGDTYPSND RCCHECRPGN GMVSRCSRSQ

61 NTVCRPCGPG FYNDVVSSKP CKPCTWCNLR SGSERKQLCT ATQDTVCRCR AGTQPLDSYK

121 PGVDCAPCPP GHFSPGDNQA CKPWTNCTLA GKHTLQPASN SSDAICEDRD PPATQPQETQ
```

```
181 GPPARPITVQ PTEAWPRTSQ GPSTRPVEVP GGRAVAAILG LGLVLGLLGP LAILLALYLL

241 RRDQRLPPDA HKPPGGGSFR TPIQEEQADA HSTLAKI  (NP_003318; SEQ ID NO:6)
```

ICOS. Inducible T-cell costimulator precursor (ICOS), also referred to as CD278, is a CD28-superfamily costimulatory molecule that is expressed on activated T cells. In one embodiment, a CAR can comprise a co-stimulatory signaling domain derived from ICOS. An ICOS polypeptide can have an amino acid sequence corresponding to the sequence having GenBank No. NP_036224 (NP_036224.1, GI:15029518), provided below, or fragments thereof. In one embodiment, a CAR can have a co-stimulatory domain comprising the intracellular domain of ICOS corresponding to amino acids 162 to 199 of ICOS. In another embodiment, a CAR can have an amino acid sequence comprising the transmembrane domain of ICOS corresponding to amino acids 141 to 161 of ICOS, or a fragment thereof. See GenBank NP_036224 for reference to domains within ICOS, for example, signal peptide, amino acids 1 to 20; extracellular domain, amino acids 21 to 140; transmembrane domain, amino acids 141 to 161; intracellular domain, amino acids 162 to 199. It is understood that sequences of ICOS that are shorter or longer than a specific delineated domain can be included in a CAR, if desired. It is also understood that an "ICOS nucleic acid molecule" refers to a polynucleotide encoding an ICOS polypeptide.

```
  1 MKSGLWYFFL FCLRIKVLTG EINGSANYEM FIFHNGGVQI LCKYPDIVQQ FKMQLLKGGQ

61 ILCDLTKTKG SGNTVSIKSL KFCHSQLSNN SVSFFLYNLD HSHANYYFCN LSIFDPPPFK

121 VTLTGGYLHI YESQLCCQLK FWLPIGCAAF VVVCILGCIL ICWLTKKKYS SSVHDPNGEY

181 MFMRAVNTAK KSRLTDVTL  (NP_036224; SEQ ID NO:7)
```

DAP10. DAP10, also referred to as hematopoietic cell signal transducer, is a signaling subunit that associates with a large family of receptors in hematopoietic cells. In one embodiment, a CAR can comprise a co-stimulatory domain derived from DAP10. A DAP10 polypeptide can have an amino acid sequence corresponding to the sequence having GenBank No. NP_055081.1 (GI:15826850), provided below, or fragments thereof. In one embodiment, a CAR can have a co-stimulatory domain comprising the intracellular domain of DAP10 corresponding to amino acids 70 to 93, or a fragment thereof. In another embodiment, a CAR can have a transmembrane domain of DAP10 corresponding to amino acids 49 to 69, or a fragment thereof. See GenBank NP_055081.1 for reference to domains within DAP10, for example, signal peptide, amino acids 1 to 19; extracellular domain, amino acids 20 to 48; transmembrane domain, amino acids 49 to 69; intracellular domain, amino acids 70 to 93. It is understood that sequences of DAP10 that are shorter or longer than a specific delineated domain can be included in a CAR, if desired. It is also understood that a "DAP10 nucleic acid molecule" refers to a polynucleotide encoding an DAP10 polypeptide.

```
 1 MIHLGHILFL LLLPVAAAQT TPGERSSLPA FYPGTSGSCS GCGSLSLPLL AGLVAADAVA

61 SLLIVGAVFL CARPRRSPAQ EDGKVYINMP GRG  (NP_055081.1; SEQ ID NO:8)
```

The extracellular domain of a CAR can be fused to a leader or a signal peptide that directs the nascent protein into the endoplasmic reticulum and subsequent translocation to the cell surface. It is understood that, once a polypeptide containing a signal peptide is expressed at the cell surface, the signal peptide has generally been proteolytically removed during processing of the polypeptide in the endoplasmic reticulum and translocation to the cell surface. Thus, a polypeptide such as a CAR is generally expressed at the cell surface as a mature protein lacking the signal peptide, whereas the precursor form of the polypeptide includes the signal peptide. A signal peptide or leader can be essential if a CAR is to be glycosylated and/or anchored in the cell membrane. The signal sequence or leader is a peptide sequence generally present at the N-terminus of newly synthesized proteins that directs their entry into the secretory pathway. The signal peptide is covalently joined to the N-terminus of the extracellular antigen-binding domain of a CAR as a fusion protein. In one embodiment, the signal peptide comprises a CD8 polypeptide comprising amino acids MALPVTALLLPLALLLHAARP (SEQ ID NO:9). It is understood that use of a CD8 signal peptide is exemplary. Any suitable signal peptide, as are well known in the art, can be applied to a CAR to provide cell surface expression in an immune cell (see Gierasch *Biochem.* 28:923-930 (1989); von Heijne, *J. Mol. Biol.* 184 (1):99-105 (1985)). Particularly useful signal peptides can be derived from cell surface proteins naturally expressed in the immune cell, or precursor cell thereof, including any of the signal peptides of the polypeptides disclosed herein. Thus, any suitable signal peptide can be utilized to direct a CAR to be expressed at the cell surface of an immune cell, or precursor cell thereof.

In certain non-limiting embodiments, an extracellular antigen-binding domain of a CAR can comprise a linker sequence or peptide linker connecting the heavy chain variable region and light chain variable region of the extracellular antigen-binding domain. In one non-limiting example, the linker comprises amino acids having the sequence set forth in

GGGGSGGGGSGGGGS. (SEQ ID NO:10)

In certain non-limiting embodiments, a CAR can also comprise a spacer region or sequence that links the domains of the CAR to each other. For example, a spacer can be included between a signal peptide and an antigen binding domain, between the antigen binding domain and the transmembrane domain, between the transmembrane domain and the intracellular domain, and/or between domains within the intracellular domain, for example, between a stimulatory domain and a co-stimulatory domain. The spacer region can be flexible enough to allow interactions of various domains with other polypeptides, for example, to allow the antigen binding domain to have flexibility in orientation in order to facilitate antigen recognition. The spacer region can be, for example, the hinge region from an IgG, the $CH_2CH_3$ (constant) region of an immunoglobulin, and/or portions of CD3 (cluster of differentiation 3) or some other sequence suitable as a spacer.

The transmembrane domain of a CAR generally comprises a hydrophobic alpha helix that spans at least a portion of the membrane. Different transmembrane domains result in different receptor stability. After antigen recognition, receptors cluster and a signal is transmitted to the cell. In an embodiment, the transmembrane domain of a CAR can be derived from another polypeptide that is naturally expressed in the immune cell, or precursor cell thereof. In one embodiment, a CAR can have a transmembrane domain derived from CD8, CD28, CD3ζ, CD4, 4-1BB, OX40, ICOS, CTLA-4, PD-1, LAG-3, 2B4, BTLA, or other polypeptides expressed in the immune cell, or precursor cell thereof, having a transmembrane domain, including others as disclosed herein. Optionally, the transmembrane domain can be derived from a polypeptide that is not naturally expressed in the immune cell, or precursor cell thereof, so long as the transmembrane domain can function in transducing signal from antigen bound to the CAR to the intracellular signaling and/or co-stimulatory domains. It is understood that the portion of the polypeptide that comprises a transmembrane domain of the polypeptide can include additional sequences from the polypeptide, for example, additional sequences adjacent on the N-terminal or C-terminal end of the transmembrane domain, or other regions of the polypeptide, as desired.

CD8. Cluster of differentiation 8 (CD8) is a transmembrane glycoprotein that serves as a co-receptor for the T cell receptor (TCR). CD8 binds to a major histocompatibility complex (MHC) molecule and is specific for the class I MHC protein. In one embodiment, a CAR can comprise a transmembrane domain derived from CD8. A CD8 polypeptide can have an amino acid sequence corresponding to the sequence having GenBank No. NP_001139345.1 (GI: 225007536), as provided below, or fragments thereof. In one embodiment, a CAR can have an amino acid sequence comprising the transmembrane domain of CD8 corresponding to amino acids 183 to 203, or fragments thereof. In one embodiment, an exemplary CAR is Mz, which has a transmembrane domain derived from a CD8 polypeptide (see FIG. 1B). In another embodiment, an exemplary CAR is MBBz, which has a transmembrane domain derived from a CD8 polypeptide (see FIG. 1B). In one non-limiting embodiment, a CAR can comprise a transmembrane domain derived from a CD8 polypeptide comprising amino acids 183 to 203. In addition, a CAR can comprise a hinge domain comprising amino acids 137-182 of the CD8 polypeptide provided below. In another embodiment, a CAR can comprise amino acids 137-203 of the CD8 polypeptide provided below. In yet another embodiment, a CAR can comprise amino acids 137 to 209 of the CD8 polypeptide provided below. See GenBank NP_001139345.1 for reference to domains within CD8, for example, signal peptide, amino acids 1 to 21; extracellular domain, amino acids 22 to 182; transmembrane domain amino acids, 183 to 203; intracellular domain, amino acids 204 to 235. It is understood that additional sequence of CD8 beyond the transmembrane domain of amino acids 183 to 203 can be included in a CAR, if desired. It is further understood that sequences of CD8 that are shorter or longer than a specific delineated domain can be included in a CAR, if desired. It also is understood that a "CD8 nucleic acid molecule" refers to a polynucleotide encoding a CD8 polypeptide.

```
  1 MALPVTALLL PLALLLHAAR PSQFRVSPLD RTWNLGETVE LKCQVLLSNP TSGCSWLFQP
 61 RGAAASPTFL LYLSQNKPKA AEGLDTQRFS GKRLGDTFVL TLSDFRRENE GYYFCSALSN
```

```
121 SIMYFSHFVP VFLPAKPTTT PAPRPPTPAP TIASQPLSLR PEACRPAAGG AVHTRGLDFA

181 CDIYIWAPLA GTCGVLLLSL VITLYCNHRN RRRVCKCPRP VVKSGDKPSL SARYV
```

(NP_001139345.1; SEQ ID NO:11)

CD4. Cluster of differentiation 4 (CD4), also referred to as T-cell surface glycoprotein CD4, is a glycoprotein found on the surface of immune cells such as T helper cells, monocytes, macrophages, and dendritic cells. In one embodiment, a CAR can comprise a transmembrane domain derived from CD4. CD4 exists in various isoforms. It is understood that any isoform can be selected to achieve a desired function. Exemplary isoforms include isoform 1 (NP_000607.1, GI:10835167), isoform 2 (NP_001181943.1, GI:303522479), isoform 3 (NP_001181944.1, GI:303522485; or NP_001181945.1, GI:303522491; or NP_001181946.1, GI:303522569), and the like. One exemplary isoform sequence, isoform 1, is provided below. In one embodiment, a CAR can have an amino acid sequence comprising the transmembrane domain of CD4 corresponding to amino acids 397 to 418, or fragments thereof. See GenBank NP_000607.1 for reference to domains within CD4, for example, signal peptide, amino acids 1 to 25; extracellular domain, amino acids 26 to 396; transmembrane domain amino acids, 397 to 418; intracellular domain, amino acids 419 to 458. It is understood that additional sequence of CD4 beyond the transmembrane domain of amino acids 397 to 418 can be included in a CAR, if desired. It is further understood that sequences of CD4 that are shorter or longer than a specific delineated domain can be included in a CAR, if desired. It also is understood that a "CD4 nucleic acid molecule" refers to a polynucleotide encoding a CD4 polypeptide.

particular function to a CAR of the invention. Possible desirable functions can include, but are not limited to, providing a signal peptide and/or transmembrane domain.

7.3. Dominant Negative Forms of an Inhibitor of a Cell-Mediated Immune Response According to the invention, an immune cell that is an immunostimulatory cell, such as a T cell, or a precursor cell thereof, or an immune cell that is an immunoinhibitory cell, such as a regulatory T cell, is engineered to express a dominant negative form (DN form) of an inhibitor of a cell-mediated immune response.

An inhibitor of a cell-mediated immune response of the immune cell, or precursor cell thereof, refers to a molecule that acts to inhibit or suppress the immune response effected by the immune cell, or precursor cell thereof. In one embodiment, the inhibitor of a cell-mediated immune response is an immune checkpoint inhibitor, also referred to as a checkpoint blockade.

In one embodiment, the invention provides immune cells, such as T cells, or precursor cells thereof, or regulatory T cells that express a dominant negative form of an inhibitor of a cell-mediated immune response of the immune cell, or that co-express a CAR and a dominant negative form of an inhibitor of a cell-mediated immune response of the immune cell, for example, a receptor that functions in an immune checkpoint inhibitor pathway. Immune checkpoint pathways are inhibitory pathways that suppress the immune response of an immune cell. The pathways deliver negative signals to

```
  1 MNRGVPFRHL LLVLQLALLP AATQGKKVVL GKKGDTVELT CTASQKKSIQ FHW-
    KNSNQIK

61 ILGNQGSFLT KGPSKLNDRA DSRRSLWDQG NFPLIIKNLK IEDSDTYICE VEDQ-
    KEEVQL

121 LVFGLTANSD THLLQGQSLT LTLESPPGSS PSVQCR-
    SPRG KNIQGGKTLS VSQLELQDSG

181 TWTCTVLQNQ KKVEFKIDIV VLAFQKASSI VYKKEGEQVE FSF-
    PLAFTVE KLTGSGELWW

241 QAER-
    ASSSKS WITFDLKNKE VSVKRVTQDP KLQMGKKLPL HLTLPQALPQ YAGSGNLTLA

301 LEAKTGKLHQ EVNLVVMRAT QLQKNLTCEV WGPTSPKLML SLKLEN-
    KEAK VSKREKAVWV

361 LNPEAGMWQC LLSDSGQVLL ESNIKVLPTW STPVQPMALI VLGGVAGLLL FIGL-
    GIFFCV

421 RCRHRRRQAE RMSQIKRLLS EKKTCQCPHR FQKTCSPI
```

(NP_000607.1; SEQ ID NO:12)

As disclosed herein, mesothelin CARs exemplify CARs that can target an antigen, and CARs directed to other antigens can be generated using similar methods and others well known in the art, as described above. It is understood that domains of the polypeptides described herein can be used in a CAR, as useful to provide a desired function such as a signal peptide, antigen binding domain, transmembrane domain, intracellular signaling domain and/or co-stimulatory domain. For example, a domain can be selected such as a signal peptide, a transmembrane domain, an intracellular signaling domain, or other domain, as desired, to provide a the immune cells, such as T cells, and attenuate TCR-mediated signals, leading to decreased cell proliferation, cytokine production and cell cycle progression (see Pardoll, *Nat. Rev.* 12:252-264 (2012); Wu et al., *Int. J. Biol. Sci.* 8:1420-1430 (2012)). The immune checkpoint inhibitor pathway generally involves a ligand-receptor pair. Exemplary immune checkpoint inhibitor pathway receptors include, for example, PD-1, CTLA-4, BTLA, TIM-3, LAG-3, CD160, TIGIT, LAIR1, 2B4, and the like (see Chen et al., *Nat. Rev. Immunol.* 13(4):227-242 (2013)). The corresponding ligands for these receptors include, for example, PD-L1

(for PD-1); PD-L2 (for PD-1); CD80, CD86 (for CTLA-4); HVEM (for BTLA); Galectin-9, HMGB1 (for TIM-3); MHC II (for LAG-3); HVEM (for CD160); CD155, CD 112, CD 113 (for TIGIT); C1q, collagen (for LAIR1); CD48 (for 2B4), and the like (Chen et al., supra, 2013). Expression of a DN form in the immune cell, such as a T cell, or precursor cell thereof, provides for inhibition of a checkpoint inhibitor pathway that is intrinsic to the cell.

A DN form of an inhibitor of a cell-mediated immune response that is a cell-surface receptor such as an immune checkpoint inhibitor pathway receptor can be generated by deleting some portion of the receptor to prevent intracellular signaling, thereby suppressing the immune checkpoint pathway and sustaining activation of the immune cell, such as a T cell. A DN form of the invention is a polypeptide comprising (a) at least a portion of an extracellular domain of an immune checkpoint inhibitor, where the portion comprises the ligand binding region, and (b) a transmembrane domain, where the polypeptide is a dominant negative form of the immune checkpoint inhibitor. Generally, a DN form of an inhibitor of an immune checkpoint inhibitor pathway receptor retains most or all of an extracellular domain of the receptor such that the extracellular domain retains sufficient protein interaction activity to bind to its respective ligand. Thus, in a specific embodiment, a polypeptide encoding a DN form comprises substantially all of an extracellular domain of an immune checkpoint inhibitor. It is understood that a polypeptide comprising "substantially all" of an extracellular domain includes a polypeptide that comprises the entire extracellular domain or a portion of the extracellular domain in which one to a few amino acids have been deleted from the N-terminus and/or C-terminus of the extracellular domain, for example deletion of 1, 2, 3, 4, or 5 amino acids from the N-terminus and/or C-terminus, so long as the remaining portion of the extracellular domain retains sufficient protein interaction activity to bind to its respective ligand. A DN form of the invention generally also lacks some portion or all of a signaling domain, such as the intracellular/cytoplasmic domain, such that the DN form has reduced activity or is inactive for signaling in the immune checkpoint pathway. Without being bound by a particular mechanism or theory, binding of the ligand to the DN form decreases binding of the ligand to the intact endogenous receptor, and/or the DN form complexes with signaling molecules, including the endogenous receptor, resulting in decreased signaling of an immune checkpoint pathway.

A DN form of the invention generally has certain functional characteristics including, but not limited to, the ability to be expressed at the cell surface of an immune cell such as a T cell, or precursor cell thereof, the ability to bind to its respective ligand, and the inability or reduced ability to propagate an intracellular signal of an immune checkpoint pathway. One skilled in the art can readily generate a DN form of an inhibitor of a cell-mediated immune response by engineering the inhibitor to have such functional characteristics. In one embodiment, a DN form is constructed to retain the extracellular domain of inhibitor of a cell-mediated immune response, or at least a sufficient portion of the extracellular domain to retain ligand binding activity. In an exemplary embodiment, a DN form can be constructed using the extracellular domain of an inhibitor of a cell-mediated immune response, including, but not limited to, the extracellular domains of PD-1, CTLA-4, BTLA, TIM-3, LAG-3, CD160, TIGIT, LAIR1, 2B4, as disclosed herein. One skilled in the art will readily understand that it is not required to retain the entire extracellular domain of an inhibitor of a cell-mediated immune response, and that deletions from the N-terminus and/or C-terminus of the extracellular domain can be introduced so long as ligand binding activity is retained. One skilled in the art can readily determine the appropriateness of such N-terminal and/or C-terminal deletions based on the analysis of the receptor sequence to identify protein motifs known to provide ligand binding activity (see, for example, ExPASy (expasy.org), in particular PROSITE (prosite.expasy.org)). In addition or alternatively, suitable N-terminal and/or C-terminal deletions can be determined empirically by introducing deletions in a polypeptide and measuring binding activity for the respective ligand. Thus, one skilled in the art can readily determine an appropriate sequence of an inhibitor of a cell-mediated immune response to provide ligand binding activity to a DN form of the invention.

It is understood that, whether an entire extracellular domain or a portion of the extracellular domain of a receptor is used in a DN form, additional sequences can optionally be included in the extracellular domain of the DN form. Such additional sequences can be derived from the parent polypeptide of the DN form, or the additional sequences can be derived from a different polypeptide. Such a polypeptide comprising sequences from a parent polypeptide and a different polypeptide is a non-naturally occurring, chimeric polypeptide. For example, a signal peptide or leader peptide is generally included so that the DN form will be expressed at the cell surface of the immune cell such as a T cell, or precursor cell thereof, or a regulatory T cell. It is understood that, once a polypeptide containing a signal peptide is expressed at the cell surface, the signal peptide has generally been proteolytically removed during processing of the polypeptide in the endoplasmic reticulum and translocation to the cell surface. Thus, a polypeptide such as a DN form is generally expressed at the cell surface as a mature protein lacking the signal peptide, whereas the precursor form of the polypeptide includes the signal peptide. The signal peptide can be the naturally occurring signal peptide of the receptor, or alternatively can be derived from a different protein. Exemplary signal peptides are described herein, including those described herein as being suitable for a CAR. To additionally provide expression at the cell surface, the DN form will generally include a transmembrane domain that provides for retention of the DN form at the cell surface. The transmembrane domain can be the naturally occurring transmembrane of the receptor, or alternatively can be derived from a different protein. In a particular embodiment, the transmembrane domain derived from another protein is derived from another receptor expressed on the cell surface of the immune cell such as a T cell, or precursor cell thereof, or a regulatory T cell. Exemplary transmembrane domains are described herein, including those described herein as being suitable for a CAR.

In the case of an immune checkpoint pathway receptor, generally the signaling domain resides within the intracellular/cytoplasmic domain. The signaling activity of an immune checkpoint pathway receptor is generally mediated by protein-protein interactions with cell surface receptor(s) and/or intracellular signaling molecules. In one embodiment, a DN form lacks the entire intracellular domain, or a portion thereof, that functions in propagating the signal of an immune checkpoint pathway. It is understood that it is not necessary to delete the entire intracellular domain of the receptor so long as a sufficient portion of the intracellular signaling domain is deleted to inhibit or reduce signaling from the DN form. In addition or alternatively, mutations can be introduced into the intracellular signaling domain to inhibit or reduce signaling from the DN form. In addition or alternatively, a heterologous sequence with no signaling activity can be substituted for the intracellular signaling domain of the receptor to generate a DN form. One skilled in the art will readily understand that these and other well known methods can be utilized to generate a DN form of the invention.

One exemplary embodiment of a dominant negative form of an immune checkpoint inhibitor is a dominant negative form of PD-1. A dominant negative form of PD-1 is exemplary of a DN form of an inhibitor of a cell-mediated immune response, including an immune checkpoint inhibitor. It is understood that a PD-1 DN form as disclosed herein is exemplary.

As described herein, a DN form of an inhibitor of a cell-mediated immune response is designed to have reduced or inhibited intracellular signaling. The DN forms of the invention are generally based on inhibiting a receptor of an immune checkpoint pathway, which function to inhibit activation of an immune cell, such as T cell, for example, cell proliferation, cytokine production and/or cell cycle progression. The DN forms of the invention are designed to remove the intracellular signaling domain, or a portion thereof, so that the signaling ability of the receptor is reduced or inhibited. The DN form also functions to inhibit signaling of the endogenous receptor. In a particular embodiment, the reduced or inhibited signaling overcomes the checkpoint blockade, resulting in sustained signaling and activation of the immune cell, such as a T cell, or precursor cell thereof. It is understood that the signaling activity of the DN form can be completely knocked out or partially knocked out, so long as the partial reduction in activity is sufficient for the effect of providing enhanced activation of the immune cell, or precursor cell thereof, in comparison to the absence of the DN form. Also, the DN form is not required to result in complete inactivation of signaling from the endogenous receptor but can reduce the activation of the endogenous receptor sufficient to overcome the checkpoint blockade and allow activation of the immune cell, such as a T cell, or precursor cell thereof. One skilled in the art can readily determine the effect of a DN form on the activity of a parent receptor using assay methods well known in the art, including assays using in vivo models, such as animal models, to assess the effect of the DN form on the activity of the immune cell in which the DN form is expressed, including assays such as those disclosed herein.

In the case of using regulatory T cells isolated from a subject having a chronic viral infection, expression of a DN form of an inhibitor of a cell-mediated immune response of the immune cell, such as PD-1, inhibits the suppressive activity of the regulatory T cells resulting from interactions between the regulatory T cells that express the inhibitor of a cell-mediated immune response of the immune cell, e.g., PD-1, and immunostimulatory T cells, such as CD8$^+$ T cells, that express the corresponding ligand, e.g., PD-L1. In such a case, the suppressive activity of the regulatory T cells on the immune response mediated by ligand-expressing immunostimulatory cells is reduced, thereby promoting the immune response against the virus.

As with a CAR for use in the invention, optional linker or spacer sequences can be included in a DN form, for example, a linker or spacer between a signal peptide and the extracellular ligand binding domain, particularly when heterologous sequences are fused. A linker or spacer can also optionally be included between the extracellular ligand binding domain and the transmembrane domain. Similarly, a linker or spacer can optionally be included between the transmembrane domain and any remaining intracellular domain. Such optional linkers or spacers are described herein. In addition, such linkers or spacers can be derived from a heterologous sequence. For example, as described above, a transmembrane domain derived from a heterologous polypeptide can optionally include additional sequences at the N-terminus and/or C-terminus derived from the heterologous polypeptide. Such additional sequences can function as a linker or spacer.

In one embodiment, as described above, a DN form can lack any signaling domain carboxy-terminal to the transmembrane domain of the DN form (i.e., the DN form can lack an intracellular signaling domain).

In a different specific embodiment, a DN form of the invention can optionally further comprise a fusion to a co-stimulatory signaling domain, wherein the co-stimulatory signaling domain is carboxy-terminal to the transmembrane domain of the dominant negative form. Such a DN form is also referred to herein as a "switch receptor." Such a DN form, or switch receptor, comprises at least a ligand binding domain of the extracellular region of an inhibitor of a cell-mediated immune response of the cell, such as an immune checkpoint inhibitor, fused to a transmembrane domain, fused to a co-stimulatory domain (i.e., cytoplasmic signaling domain) of an immunostimulatory molecule, thereby switching the activity upon ligand binding from inhibitory of the cell immune activity to stimulatory of the cell immune activity (see e.g., Liu et al., *Cancer Res.* 76:1578-1590 (2016)). A DN form further comprising a fusion to a co-stimulatory domain (i.e., switch receptor) also functions as a dominant negative form in such a construct since the signaling domain of the immune checkpoint inhibitor has been deleted. In one embodiment, a DN form further comprising a fusion to a co-stimulatory signaling domain is expressed in an immunostimulatory cell. In one embodiment, a DN form further comprising a fusion to a co-stimulatory signaling domain is expressed in an immunoinhibitory cell. In another embodiment, a DN form further comprising a fusion to a co-stimulatory signaling domain is co-expressed with a CAR in an immunostimulatory cell. In another embodiment, a DN form further comprising a fusion to a co-stimulatory signaling domain is co-expressed with a CAR in an immunostimulatory cell.

A co-stimulatory signaling domain in a DN form fusion polypeptide can be derived, for example, from a cytoplasmic signaling domain of a receptor such as the co-stimulatory molecules described herein for use in a CAR, including but not limited to a 4-1BB polypeptide, a CD28 polypeptide, an OX40 polypeptide, an ICOS polypeptide, a DAP10 polypeptide, and a 2B4 polypeptide. In a DN form comprising a fusion to a co-stimulatory signaling domain, the transmembrane domain can be derived from the polypeptide from which the co-stimulatory domain is derived, from the polypeptide from which the extracellular ligand binding domain of DN form is derived, or it can be a transmembrane domain from another polypeptide, similar to the description herein of the transmembrane domains that can be utilized to generate a CAR or DN form.

In one embodiment, the invention provides an immune cell (which can be immunostimulatory or immunoinhibitory, as desired) that recombinantly expresses a DN form, wherein the DN form further comprises a fusion to a co-stimulatory signaling domain, wherein the co-stimulatory signaling domain is fused carboxy-terminal to the transmembrane domain of the DN form. In certain embodiments of the invention, the cell or population of the invention recombinantly expresses a dominant negative form of an inhibitor of a cell-mediated immune response of the cell, wherein the dominant negative form further comprises a co-stimulatory signaling domain, wherein the co-stimulatory signaling domain is fused to the transmembrane domain of the dominant negative form (which in turn is fused to the at least a portion of the extracellular domain of an immune checkpoint inhibitor containing the ligand binding region of the dominant negative form). Such cells optionally can co-express a dominant negative form that lacks an intracellular signaling domain. Such cells can be used to treat a viral infection as disclosed herein. The invention provides for recombinant expression by an immune cell of a switch receptor (i.e., a DN form further comprising a co-stimulatory signaling domain), which switch receptor comprises (i) at least the extracellular ligand binding domain of an immune checkpoint inhibitor, (ii) a transmembrane domain, and (iii) a co-stimulatory signaling domain. Such recombinant cells optionally can co-express a DN form that lacks an intracellular signaling domain. The invention also provides for recombinant expression by an immune cell of both a CAR and a DN form, which DN form further comprises a fusion to a co-stimulatory signaling domain (switch receptor), which DN form comprises (i) at least the extracellular ligand binding domain of an immune checkpoint inhibitor, (ii) a transmembrane domain, and (iii) a co-stimulatory signaling domain. Such cells optionally can co-express a DN form that lacks an intracellular signaling domain. It is understood that, in such immune cells co-expressing a CAR, and a DN form further comprising a fusion to a co-stimulatory signaling domain (switch receptor), and optionally a DN form lacking an intracellular signaling domain, the CAR binds to an antigen of the viral infection as being treated, i.e., the same virus of the viral infection. In one embodiment of cells co-expressing a CAR and a DN form comprising a fusion to a co-stimulatory signaling domain, the co-stimulatory signaling domain of the DN form is different from the co-stimulatory signaling domain of the CAR. In a particular embodiment, the co-stimulatory signaling domain of the DN form is the intracellular signaling domain of 4-1BB. In another particular embodiment, in an immune cell co-expressing a CAR and a DN form that further comprises a fusion to a co-stimulatory signaling domain, the co-stimulatory signaling domain of the CAR is the intracellular signaling domain of CD28. In another particular embodiment, the invention provides an immune cell co-expressing a CAR and a DN form that further comprises a fusion to a co-stimulatory signaling domain, and optionally co-expresses a DN form that lacks an intracellular signaling domain, where the co-stimulatory signaling domain of the DN form is the intracellular signaling domain of 4-1BB and the co-stimulatory signaling domain of the CAR is the intracellular signaling domain of CD28.

Exemplary DN forms of immune checkpoint inhibitors are described below in more detail. DN forms consisting essentially of the described sequences are also envisioned.

PD-1. Programmed cell death protein 1 (PD-1) is a negative immune regulator of activated T cells upon engagement with its corresponding ligands, PD-L1 and PD-L2, expressed on endogenous macrophages and dendritic cells. PD-1 is a type I membrane protein of 268 amino acids. PD-1 has two ligands, PD-L1 and PD-L2, which are members of the B7 family. The protein's structure comprises an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif. PD-1 negatively regulates TCR signals. SUP-1 and SHP-2 phosphatases bind to the cytoplasmic tail of PD-1 upon ligand binding. Upregulation of PD-L1 is one mechanism tumor cells use to evade the host immune system. In pre-clinical and clinical trials, PD-1 blockade by antagonistic antibodies induced anti-tumor responses mediated through the host endogenous immune system.

A PD-1 polypeptide can have an amino acid corresponding to GenBank No. NP_005009.2 (GI:167857792), as provided below, or fragments thereof. See GenBank NP_005009.2 for reference to domains within PD-1, for example, signal peptide, amino acids 1 to 20; extracellular domain, amino acids 21 to 170; transmembrane domain, amino acids 171 to 191; intracellular domain, amino acids 192 to 288. It is understood that an "PD-1 nucleic acid molecule" refers to a polynucleotide encoding an PD-1 polypeptide.

```
  1 MQIPQAPWPV VWAVLQLGWR PGWFLDSPDR PWNPPTFSPA LLVVTEGDNA TFTCSFSNTS
 61 ESFVLNWYRM SPSNQTDKLA AFPEDRSQPG QDCRFRVTQL PNGRDFHMSV VRARRNDSGT
121 YLCGAISLAP KAQIKESLRA ELRVTERRAE VPTAHPSPSP RPAGQFQTLV VGWGGLLGS
181 LVLLVWVLAV ICSRAARGTI GARRTGQPLK EDPSAVPVFS VDYGELDFQW REKTPEPPVP
241 CVPEQTEYAT IVFPSGMGTS SPARRGSADG PRSAQPLRPE DGHCSWPL (NP_005009.2; SEQ ID NO:13)
```

In one embodiment, the invention provides an inhibitor of a cell-mediated immune response that is a PD-1 dominant negative form (DN form). In one embodiment, the PD-1 DN form comprises the extracellular ligand binding domain of PD-1. In one embodiment, the PD-1 DN form comprises the extracellular ligand binding domain of PD-1 and a transmembrane domain (e.g., mature form). In another embodiment, the PD-1 DN form comprises the extracellular ligand binding domain of PD-1, a transmembrane domain and a signal peptide (e.g., precursor form). The invention also provides encoding polypeptides and nucleic acids of the PD-1 DN forms of the invention. In a particular embodiment, the PD-1 extracellular ligand binding domain is fused to one or more heterologous polypeptide sequences, that is, the PD-1 DN form is a chimeric sequence. For example, the PD-1 extracellular ligand binding domain can be fused at its N-terminus to a signal peptide that is optionally a heterologous signal peptide, including various signal peptides described herein. In addition, a PD-1 DN form can comprise a transmembrane domain that is optionally a heterologous transmembrane domain, including any of various transmembrane domains described herein. Although the PD-1 DN form exemplified in the Example herein comprises heterologous sequences fused to the extracellular domain of PD-1, it is understood that a PD-1 DN form can comprise PD-1 sequence only.

In one embodiment, the invention provides a PD-1 DN form that comprises the extracellular domain, or a ligand binding portion thereof, of PD-1, for example, amino acids 21 to 170 corresponding to the extracellular domain of PD-1 (GenBank NP_005009.2; SEQ ID NO:13). A cell expressing such a PD-1 DN form should lack the ability or have reduced ability to signal in a PD-1 immune checkpoint pathway. In one embodiment, a PD-1 DN form is a deletion mutant having a deletion of the intracellular domain, for example, amino acids 192 to 288 of PD-1 (GenBank NP_005009.2; SEQ ID NO:13), or a portion thereof, such that intracellular signaling of the immune checkpoint pathway mediated by PD-1 is reduced or inhibited. Additional embodiments of a DN form of PD-1 are described below.

In one embodiment, a PD-1 DN form comprises an amino acid sequence comprising the extracellular domain of PD-1 fused to the transmembrane and hinge domains of CD8. In one embodiment, a PD-1 DN form comprises amino acids 21 to 165 of a PD-1 sequence (NP_005009.2; SEQ ID NO:13). Such a PD-1 DN form comprises the extracellular domain of PD-1. In another embodiment, the invention provides a PD-1 DN form comprising amino acids 1 to 165 (precursor form) or amino acids 21 to 165 (mature form) of a PD-1 sequence (NP_005009.2; SEQ ID NO:13). Such a DN form comprises the signal peptide of PD-1, amino acids 1 to 20, and extracellular domain amino acids 21 to 165, whereas the mature form lacks the signal peptide. In one embodiment, a PD-1 DN form comprises amino acids 21 to 151 of a PD-1 sequence (NP_005009.2; SEQ ID NO:13). In another embodiment, the invention provides a PD-1 DN form comprising amino acids 1 to 151 (precursor form) or amino acids 21 to 151 (mature form) of a PD-1 sequence (NP_005009.2; SEQ ID NO:13). Optionally, a PD-1 DN form comprises an extracellular ligand binding domain starting at amino acid 21 through an amino acid between amino acids 151 to 165 of a PD-1 sequence (NP_005009.2; SEQ ID NO:13). In another embodiment, a PD-1 DN form comprises the transmembrane domain of CD8, amino acids 183 to 203 of a CD8 sequence (NP_001139345.1; SEQ ID NO:11). Such an embodiment is representative of a chimeric DN form comprising a transmembrane domain from a different (heterologous) polypeptide. As described above, a DN form comprising a heterologous domain such as a transmembrane domain can optionally include additional sequence from the heterologous polypeptide. In one such embodiment, a DN form is provided that comprises additional sequence from the heterologous polypeptide N-terminal of the transmembrane domain. In one embodiment, the DN form comprises the hinge domain of CD8. In a particular embodiment, the heterologous sequence comprises additional N-terminal sequence of amino acids 137 to 182, or optionally starting at amino acids 138 or 139, of a CD8 sequence (NP_001139345.1; SEQ ID NO:11). In another embodiment, a DN form is provided that comprises additional sequence from the heterologous polypeptide C-terminal of the transmembrane domain. In a particular embodiment, the heterologous sequence comprises additional C-terminal sequence from amino acids 204 to 209 of a CD8 sequence (NP_001139345.1; SEQ ID NO:11). In one embodiment, the PD-1 DN form comprises the transmembrane domain of CD8, amino acids 183 to 203, optionally a hinge domain comprising amino acids 137 to 182 (or optionally starting at amino acids 138 or 139), and/or additional C-terminal sequence comprising amino acids 204 to 209. In a particular embodiment of the invention, a PD-1 DN form is provided that comprises amino acids 1 to 165 of a PD-1 sequence (NP_005009.2; SEQ ID NO:13), and amino acids 137 to 209, optionally starting at amino acids 138 or 139, of a CD8 sequence (NP_001139345.1; SEQ ID NO:11).

In a further particular embodiment, the invention provides a PD-1 DN form comprising the sequence provided below, where the underlined sequence is derived from PD-1 and the italicized sequence is derived from CD8.

(SEQ ID NO:14)
MQIPQAPWPVVWAVLQLGWRPGWFLDSPDRPWNPPTFSPALLVVTEGDN

ATFTCSFSNTSESFVLNWYRMSPSNQTDKLAAFPEDRSQPGQDCRFRVT

QLPNGRDFHMSVVRARRNDSGTYLCGAISLAPKAQIKESLRAELRVTER

RAEVPTAHPSPSPRPAGQAAA*PTTTPAPRPPTPAPTIASQPLSLRPEAC*

*RPAAGGAVHTRGLDFACDIYIWAPLAGTCGVLLLSLVITLYCNHRRIQ*

In an additional embodiment, a DN form of the invention optionally comprises a P2A sequence, which provides for optional co-expression of a reporter molecule. P2A is a self-cleaving peptide sequence, which can be used for bicistronic or multicistronic expression of protein sequences (see Szymczak et al., *Expert Opin. Biol. Therapy* 5(5):627-638 (2005)). An exemplary P2A sequence is GSGATNFSLLKQAGDVEENPGPM (SEQ ID NO:15). In a further embodiment, a DN form of the invention is co-expressed with a reporter protein. In a particular embodiment, the reporter protein is mCherry fluorescent protein. In a particular embodiment, the mCherry polypeptide sequence is as provided below. It is understood that mCherry is merely exemplary and that any desired reporter molecule, such as a fluorescent protein can be included as a reporter, as described herein.

(SEQ ID NO:16)
MVSKGEEDNMAIIKEFMRFKVHMEGSVNGHEFEIEGEGEGRPYEGTQTA

KLKVTKGGPLPFAWDILSPQFMYGSKAYVKHPADIPDYLKLSFPEGFKW

ERVMNFEDGGVVTVTQDSSLQDGEFIYKVKLRGTNFPSDGPVMQKKTMG

WEASSERMYPEDGALKGEIKQRLKLKDGGHYDAEVKTTYKAKKPVQLPG

AYNVNIKLDITSHNEDYTIVEQYERAEGRHSTGGMDELYK

In a further particular embodiment, a PD-1 DN form is expressed as a polypeptide construct as provided below, where the underlined sequence is derived from PD-1, the italicized sequence is derived from CD8, the P2A sequence is double underlined, and the mCherry sequence is underlined and italicized.

(SEQ ID NO:17)
MQIPQAPWPVVWAVLQLGWRPGWFLDSPDRPWNPPTFSPALLVVTEGDN

ATFTCSFSNTSESFVLNWYRMSPSNQTDKLAAFPEDRSQPGQDCRFRVT

QLPNGRDFHMSVVRARRNDSGTYLCGAISLAPKAQIKESLRAELRVTER

RAEVPTAHPSPSPRPAGQAAA*PTTTPAPRPPTPAPTIASQPLSLRPEAC*

*RPAAGGAVHTRGLDFACDIYIWAPLAGTCGVLLLSLVITLYCNHRRIQ*G

SGATNFSLLKQAGDVEENPGPMVSKGEEDNMAIIKEFMRFKVHMEGSVN

-continued

GHEFEIEGEGEGRPYEGTQTAKLKVTKGGPLPFAWDILSPQFMYGSKAY

VKHPADIPDYLKLSFPEGFKWERVMNFEDGGWTVTQDSSLQDGEFIYKV

KLRGTNFPSDGPVMQKKTMGWEASSERMYPEDGALKGEIKQRLKLKDGG

HYDAEVKTTYKAKKPVQLPGAYNVNIKLDITSHNEDYTIVEQYERAEGR

HSTGGMDELYK

In a particular embodiment, a nucleic acid encoding a PD-1 DNR form construct is provided below, where the underlined sequence encodes amino acids derived from PD-1 DN, the italicized sequence encodes amino acids derived from CD8, the P2A encoding sequence is double underlined, the mCherry encoding sequence is underlined and italicized, a Kozak sequence is bolded with a dashed underline, and restriction sites Age I and Xho I are underlined with a dotted line at the 5' and 3' ends, respectively.

(SEQ ID NO: 18)

ACCGGTGGTACCTCACCCTTACCGAGTCGGCGACACAGTGTGGGTCCGCCGACACC

AGACTAAGAACCTAGAACCTCGCTGGAAAGGACCTTACACAGTCCTGCTGACCACC

CCCACCGCCCTCAAAGTAGACGGCATCGCAGCTTGGATACACGCCGCCCACGTGAA

GGCTGCCGACCCCGGGGGTGGACCATCCTCTAGACTGGCCACCATGCAGATCCCAC

AGGCGCCCTGGCCAGTCGTCTGGGCGGTGCTACAACTGGGCTGGCGGCCAGGATGG

TTCTTAGACTCCCCAGACAGGCCCTGGAACCCCCCCACCTTCTCCCCAGCCCTGCTC

GTGGTGACCGAAGGGGACAACGCCACCTTCACCTGCAGCTTCTCCAACACATCGGA

GAGCTTCGTGCTAAACTGGTACCGCATGAGCCCCAGCAACCAGACGGACAAGCTGG

CCGCTTTCCCCGAGGACCGCAGCCAGCCCGGCCAGGACTGCCGCTTCCGTGTCACAC

AACTGCCCAACGGGCGTGACTTCCACATGAGCGTGGTCAGGGCCCGGCGCAATGAC

AGCGGCACCTACCTCTGTGGGGCCATCTCCCTGGCCCCCAAGGCGCAGATCAAAGA

GAGCCTGCGGGCAGAGCTCAGGGTGACAGAGAGAAGGGCAGAAGTGCCCACAGCC

CACCCCAGCCCCTCACCCAGGCCAGCCGGCCAGGCGGCCGCACCCACCACGACGCCA

GCGCCGCGACCACCAACCCCGGCGCCCACGATCGCGTCGCAGCCCCTGTCCCTGCGCC

CAGAGGCGTGCCGGCCAGCGGCGGGGGCGCAGTGCACACGAGGGGGCTGGACTTCG

CCTGTGATATCTACATCTGGGCGCCCCTGGCCGGGACTTGTGGGGTCCTTCTCCTGTCAC

TGGTTATCACCCTTTACTGCAACCACAGGCGGATCCAAGGATCTGGAGCAACAAACTT

CTCACTACTCAAACAAGCAGGTGACGTGGAGGAGAATCCCGGCCCCATGGTGAGCAA

GGGCGAGGAGGATAACATGGCCATCATCAAGGAGTTCATGCGCTTCAAGGTGCACATGGA

GGGCTCCGTGAACGGCCACGAGTTCGAGATCGAGGGCGAGGGCGAGGGCCGCCCCTAC

GAGGGCACCCAGACCGCCAAGCTGAAGGTGACCAAGGGTGGCCCCCTGCCCTTCGCCT

GGGACATCCTGTCCCCTCAGTTCATGTACGGCTCCAAGGCCTACGTGAAGCACCCCGCC

GACATCCCCGACTACTTGAAGCTGTCCTTCCCCGAGGGCTTCAAGTGGGAGCGCGTGATG

AACTTCGAGGACGGCGGCGTGGTGACCGTGACCCAGGACTCCTCCCTGCAGGACGGCG

AGTTCATCTACAAGGTGAAGCTGCGCGGCACCAACTTCCCCTCCGACGGCCCCGTAATGC

AGAAGAAGACCATGGGCTGGGAGGCCTCCTCCGAGCGGATGTACCCCGAGGACGGCGC

CCTGAAGGGCGAGATCAAGCAGAGGCTGAAGCTGAAGGACGGCGGCCACTACGACGCT

GAGGTCAAGACCACCTACAAGGCCAAGAAGCCCGTGCAGCTGCCCGGCGCCTACAACGT

CAACATCAAGTTGGACATCACCTCCCACAACGAGGACTACACCATCGTGGAACAGTACGA

ACGCGCCGAGGGCCGCCACTCCACCGGCGGCATGGACGAGCTGTACAAGTAACTCGAG

CTLA-4. Cytotoxic T-lymphocyte-associated protein 4 (CTLA-4) is an inhibitory receptor expressed by activated T cells, which when engaged by its corresponding ligands (CD80 and CD86; B7-1 and B7-2, respectively), mediates activated T cell inhibition or anergy. In both preclinical and clinical studies, CTLA-4 blockade by systemic antibody infusion enhanced the endogenous anti-tumor response albeit, in the clinical setting, with significant unforeseen toxicities. CTLA-4 contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM (SEQ ID NO:29) motif able to bind PI3K, PP2A and SHP-2 and one proline-rich motif able to bind SH3 containing proteins. One role of CTLA-4 in inhibiting T cell responses seems to be directly via SHP-2 and PP2A dephosphorylation of TCR-proximal signaling proteins such as CD3 and LAT. CTLA-4 can also affect signaling indirectly via competing with CD28 for CD80/86 binding. CTLA-4 has also been shown to bind and/or interact with PI3K, CD80, AP2M1, and PPP2R5A.

A CTLA-4 polypeptide can have an amino acid sequence corresponding to GenBank No. AAH69566.1 (GI: 46854814) or NP_005205.2 (GI:21361212), sequence as provided below, or fragments thereof. See GenBank NP_005205.2 for reference to domains within CTLA-4, for example, signal peptide, amino acids 1 to 35; extracellular domain, amino acids 36 to 161; transmembrane domain, amino acids 162 to 182; intracellular domain, amino acids 183 to 223. It is understood that a "CTLA-4 nucleic acid molecule" refers to a polynucleotide encoding a CTLA-4 polypeptide.

```
  1 MACLGFQRHK AQLNLATRTW PCTLLFFLLF IPVFCKAMHV AQPAVVLASS RGIASFVCEY

61 ASPGKATEVR VTVLRQADSQ VTEVCAATYM MGNELTFLDD SICTGTSSGN QVNLTIQGLR

121 AMDTGLYICK VELMYPPPYY LGIGNGTQIY VIDPEPCPDS DFLLWILAAV SSGLFFYSFL

181 LTAVSLSKML KKRSPLTTGV YVKMPPTEPE CEKQFQPYFI PIN (NP_005205.2; SEQ ID NO:19)
```

In one embodiment, the invention provides a CTLA-4 DN form. In one embodiment, the CTLA-4 DN form comprises the extracellular ligand binding domain of CTLA-4. In one embodiment, the CTLA-4 DN form comprises the extracellular ligand binding domain of CTLA-4 and a transmembrane domain (e.g., mature form). In another embodiment, the CTLA-4 DN form comprises the extracellular ligand binding domain of CTLA-4, a transmembrane domain and a signal peptide (e.g., precursor form). The invention also provides encoding polypeptides and nucleic acids of the CTLA-4 DN forms of the invention. In a particular embodiment, the CTLA-4 extracellular ligand binding domain is fused to one or more heterologous polypeptide sequences, that is, the CTLA-4 DN form is chimeric. For example, the CTLA-4 extracellular ligand binding domain can be fused at its N-terminus to a signal peptide that is optionally a heterologous signal peptide, including various signal peptides described herein. In addition, a CTLA-4 DN form can comprise a transmembrane domain that is optionally a heterologous transmembrane domain, including any of various transmembrane domains described herein.

In an embodiment of the invention, the CTLA-4 DN form can comprise the extracellular domain, or a ligand binding portion thereof, of CTLA-4, for example, amino acids 36 to 161 corresponding to the extracellular domain of CTLA-4 (GenBank NP_005205.2; SEQ ID NO:19). A cell expressing such a CTLA-4 DN form should lack the ability or have reduced ability to signal in a CTLA-4 immune checkpoint pathway. In one embodiment, a CTLA-4 DN form is a deletion mutant having a deletion of the intracellular domain, for example, amino acids 183 to 223 of CTLA-4 (GenBank NP_005205.2; SEQ ID NO:19), or a portion thereof, such that intracellular signaling of the immune checkpoint pathway mediated by CTLA-4 is reduced or inhibited.

BTLA. B- and T-lymphocyte attenuator (BTLA) expression is induced during activation of T cells, and BTLA remains expressed on Th1 cells but not Th2 cells. BTLA interacts with a B7 homolog, B7H4. BTLA displays T-Cell inhibition via interaction with tumor necrosis family receptors (TNF-R), not just the B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses. BTLA activation has been shown to inhibit the function of human CD8+ cancer-specific T cells. BTLA has also been designated as CD272 (cluster of differentiation 272).

A BTLA polypeptide can have an amino acid sequence corresponding to GenBank No. AAP44003.1 (GI:31880027) or NP_861445.3 (GI:145580621), sequence provided below, or fragments thereof. See GenBank NP_861445.3 for reference to domains within BTLA, for example, signal peptide, amino acids 1 to 30; extracellular domain, amino acids 31 to 157; transmembrane domain, amino acids 158 to 178; intracellular domain, amino acids 179 to 289. It is understood that a "BTLA nucleic acid molecule" refers to a polynucleotide encoding a BTLA polypeptide.

```
  1 MKTLPAMLGT GKLFWVFFLI PYLDIWNIHG KESCDVQLYI KRQSEHSILA GDPFELECPV

61 KYCANRPHVT WCKLNGTTCV KLEDRQTSWK EEKNISFFIL HFEPVLPNDN GSYRCSANFQ

121 SNLIESHSTT LYVTDVKSAS ERPSKDEMAS RPWLLYSLLP LGGLPLLITT CFCLFCCLRR

181 HQGKQNELSD TAGREINLVD AHLKSEQTEA STRQNSQVLL SETGIYDNDP DLCFRMQEGS

241 EVYSNPCLEE NKPGIVYASL NHSVIGPNSR LARNVKEAPT EYASICVRS (NP_861445.3; SEQ ID NO:20)
```

In one embodiment, the invention provides a BTLA DN form. In one embodiment, the BTLA DN form comprises the extracellular ligand binding domain of BTLA. In one embodiment, the BTLA DN form comprises the extracellular ligand binding domain of BTLA and a transmembrane domain (e.g., mature form). In another embodiment, the BTLA DN form comprises the extracellular ligand binding domain of BTLA, a transmembrane domain and a signal peptide (e.g., precursor form). The invention also provides encoding polypeptides and nucleic acids of the BTLA DN forms of the invention. In a particular embodiment, the BTLA extracellular ligand binding domain is fused to one or more heterologous polypeptide sequences, that is, the BTLA DN form is chimeric. For example, the BTLA extracellular ligand binding domain can be fused at its N-terminus to a signal peptide that is optionally a heterologous signal peptide, including various signal peptides described herein. In addition, a BTLA DN form can comprise a transmembrane domain that is optionally a heterologous transmembrane domain, including any of various transmembrane domains described herein.

In an embodiment of the invention, the BTLA DN form can comprise the extracellular domain, or a ligand binding portion thereof, of BTLA, for example, amino acids 31 to 157 corresponding to the extracellular domain of BTLA (GenBank NP_861445.3; SEQ ID NO:20). A cell expressing such a BTLA DN form should lack the ability or have reduced ability to signal in a BTLA immune checkpoint pathway. In one embodiment, a BTLA DN form is a deletion mutant having a deletion of the intracellular domain, for example, amino acids 179 to 289 of BTLA (GenBank NP_861445.3; SEQ ID NO:20), or a portion thereof, such that intracellular signaling of the immune checkpoint pathway mediated by BTLA is reduced or inhibited.

TIM-3. T cell immunoglobulin mucin-3 (TIM-3), also referred to as hepatitis A virus cellular receptor 2 precursor, is a Th1-specific cell surface protein that regulates macrophage activation. Tim-3 was first identified as a molecule selectively expressed on IFN-γ-producing CD4$^+$ T helper 1 (Th1) and CD8$^+$ T cytotoxic 1 (Tc1) T cells. TIM-3 possess an N-terminal Ig domain of the V type, followed by a mucin domain.

A TIM-3 polypeptide can have an amino acid sequence corresponding to GenBank No. NP_116171.3 (GI: 49574534), sequence provided below, or fragments thereof. See GenBank NP_116171.3 for reference to domains within TIM-3, for example, signal peptide, amino acids 1 to 21; extracellular domain, amino acids 22 to 202; transmembrane domain, amino acids 203 to 223; intracellular domain, amino acids 224 to 301. It is understood that a "TIM-3 nucleic acid molecule" refers to a polynucleotide encoding a TIM-3 polypeptide.

```
  1 MFSHLPFDCV LLLLLLLLTR SSEVEYRAEV GQNAYLPCFY TPAAPGNLVP VCWGKGACPV

61 FECGNVVLRT DERDVNYWTS RYWLNGDFRK GDVSLTIENV TLADSGIYCC RIQIPGIMND

121 EKFNLKLVIK PAKVTPAPTR QRDFTAAFPR MLTTRGHGPA ETQTLGSLPD INLTQISTLA

181 NELRDSRLAN DLRDSGATIR IGIYIGAGIC AGLALALIFG ALIFKWYSHS KEKIQNLSLI

241 SLANLPPSGL ANAVAEGIRS EENIYTIEEN VYEVEEPNEY YCYVSSRQQP SQPLGCRFAM

301 P (NP_116171.3; SEQ ID NO:21)
```

In one embodiment, the invention provides a TIM-3 DN form. In one embodiment, the TIM-3 DN form comprises the extracellular ligand binding domain of TIM-3. In one embodiment, the TIM-3 DN form comprises the extracellular ligand binding domain of TIM-3 and a transmembrane domain, amino acids 23 to 450; transmembrane domain, amino acids 451 to 471; intracellular domain, amino acids 472 to 525. It is understood that a "LAG-3 nucleic acid molecule" refers to a polynucleotide encoding a LAG-3 polypeptide.

```
  1 MWEAQFLGLL FLQPLWVAPV KPLQPGAEVP VVWAQEGAPA QLPCSPTIPL QDLSLLRRAG

61 VTWQHQPDSG PPAAAPGHPL APGPHPAAPS SWGPRPRRYT VLSVGPGGLR SGRLPLQPRV

121 QLDERGRQRG DFSLWLRPAR RADAGEYRAA VHLRDRALSC RLRLRLGQAS MTASPPGSLR

181 ASDWVILNCS FSRPDRPASV HWFRNRGQGR VPVRESPHHH LAESFLFLPQ VSPMDSGPWG

241 CILTYRDGFN VSIMYNLTVL GLEPPTPLTV YAGAGSRVGL PCRLPAGVGT RSFLTAKWTP

301 PGGGPDLLVT GDNGDFTLRL EDVSQAQAGT YTCHIHLQEQ QLNATVTLAI ITVTPKSFGS

361 PGSLGKLLCE VTPVSGQERF VWSSLDTPSQ RSFSGPWLEA QEAQLLSQPW QCQLYQGERL

421 LGAAVYFTEL SSPGAQRSGR APGALPAGHL LLFLILGVLS LLLLVTGAFG FHLWRRQWRP

481 RRFSALEQGI HPPQAQSKIE ELEQEPEPEP EPEPEPEPEP EPEQL (NP_302277.4; SEQ ID NO: 22)
``` domain (e.g., mature form). In another embodiment, the TIM-3 DN form comprises the extracellular ligand binding domain of TIM-3, a transmembrane domain and a signal peptide (e.g., precursor form). The invention also provides encoding polypeptides and nucleic acids of the TIM-3 DN forms of the invention. In a particular embodiment, the TIM-3 extracellular ligand binding domain is fused to one or more heterologous polypeptide sequences, that is, the TIM-3 DN form is chimeric. For example, the TIM-3 extracellular ligand binding domain can be fused at its N-terminus to a signal peptide that is optionally a heterologous signal peptide, including various signal peptides described herein. In addition, a TIM-3 DN form can comprise a transmembrane domain that is optionally a heterologous transmembrane domain, including any of various transmembrane domains described herein.

In an embodiment of the invention, the TIM-3 DN form can comprise the extracellular domain, or a ligand binding portion thereof, of TIM-3, for example, amino acids 22 to 202 corresponding to the extracellular domain of TIM-3 (GenBank NP_116171.3; SEQ ID NO:21). A cell expressing such a TIM-3 DN form should lack the ability or have reduced ability to signal in a TIM-3 immune checkpoint pathway. In one embodiment, a TIM-3 DN form is a deletion mutant having a deletion of the intracellular domain, for example, amino acids 224 to 301 of TIM-3 (GenBank NP_116171.3; SEQ ID NO:21), or a portion thereof, such that intracellular signaling of the immune checkpoint pathway mediated by TIM-3 is reduced or inhibited.

LAG-3. Lymphocyte-activation protein 3 (LAG-3) is a negative immune regulator of immune cells. LAG-3 belongs to the immunoglobulin (Ig) superfamily and contains 4 extracellular Ig-like domains. The LAG3 gene contains 8 exons. The sequence data, exon/intron organization, and chromosomal localization all indicate a close relationship of LAG-3 to CD4. LAG-3 has also been designated CD223 (cluster of differentiation 223).

A LAG-3 polypeptide can have an amino acid sequence corresponding to GenBank No. CAA36243.3 (GI: 15617341) or NP_002277.4 (GI:167614500), sequence provided below, or fragments thereof. See GenBank NP_002277.4 for reference to domains within LAG-3, for example, signal peptide, amino acids 1 to 22; extracellular In one embodiment, the invention provides a LAG-3 DN form. In one embodiment, the LAG-3 DN form comprises the extracellular ligand binding domain of LAG-3. In one embodiment, the LAG-3 DN form comprises the extracellular ligand binding domain of LAG-3 and a transmembrane domain (e.g., mature form). In another embodiment, the LAG-3 DN form comprises the extracellular ligand binding domain of LAG-3, a transmembrane domain and a signal peptide (e.g., precursor form). The invention also provides encoding polypeptides and nucleic acids of the LAG-3 DN forms of the invention. In a particular embodiment, the LAG-3 extracellular ligand binding domain is fused to one or more heterologous polypeptide sequences, that is, the LAG-3 DN form is chimeric. For example, the LAG-3 extracellular ligand binding domain can be fused at its N-terminus to a signal peptide that is optionally a heterologous signal peptide, including various signal peptides described herein. In addition, a LAG-3 DN form can comprise a transmembrane domain that is optionally a heterologous transmembrane domain, including any of various transmembrane domains described herein.

In an embodiment of the invention, the LAG-3 DN form can comprise the extracellular domain, or a ligand binding portion thereof, of LAG-3, for example, amino acids 23 to 450 corresponding to the extracellular domain of LAG-3 (GenBank NP_002277.4; SEQ ID NO:22). A cell expressing such a LAG-3 DN form should lack the ability or have reduced ability to signal in a LAG-3 immune checkpoint pathway. In one embodiment, a LAG-3 DN form is a deletion mutant having a deletion of the intracellular domain, for example, amino acids 472 to 525 of LAG-3 (GenBank NP_002277.4; SEQ ID NO:22), or a portion thereof, such that intracellular signaling of the immune checkpoint pathway mediated by LAG-3 is reduced or inhibited.

TIGIT. T-cell immunoreceptor with Ig and ITIM domains (TIGIT) is a cell surface protein that suppresses T-cell activation. It belongs to the poliovirus receptor (PVR) family of immunoglobulin (Ig) proteins that share 3 conserved sequence motifs in their N-terminal Ig domains. A TIGIT polypeptide can have an amino acid sequence corresponding to GenBank No. NP_776160.2 (GI:256600228), sequence provided below, or fragments thereof. See Gen- Bank NP_776160.2 for reference to domains within TIGIT, for example, signal peptide, amino acids 1 to 21; extracellular domain, amino acids 22 to 141; transmembrane domain, amino acids 142 to 162; intracellular domain, amino acids 163 to 244. It is understood that a "TIGIT nucleic acid molecule" refers to a polynucleotide encoding a TIGIT polypeptide.

LAIR1. Leukocyte-associated immunoglobulin-like receptor 1 (LAIR1) is an inhibitory receptor that plays a constitutive negative regulatory role on cytolytic function of natural killer (NK) cells, B-cells and T-cells. LAIR exists in various isoforms. It is understood that any isoform can be selected to achieve a desired function. Exemplary isoforms include isoform a (NP_002278.2, GI:612407859), isoform b

```
  1 MRWCLLLIWA QGLRQAPLAS GMMTGTIETT GNISAEKGGS IILQCHLSST TAQVTQVNWE

61 QQDQLLAICN ADLGWHISPS FKDRVAPGPG LGLTLQSLTV NDTGEYFGIY HTYPDGTYTG

121 RIFLEVLESS VAEHGARFQI PLLGAMAATL VVICTAVIVV VALTRKKKAL RIHSVEGDLR

181 RKSAGQEEWS PSAPSPPGSC VQAEAAPAGL CGEQRGEDCA ELHDYFNVLS YRSLGNCSFF

241 TETG (NP_776160.2; SEQ ID NO:23)
```

In one embodiment, the invention provides a TIGIT DN form. In one embodiment, the TIGIT DN form comprises the extracellular ligand binding domain of TIGIT. In one embodiment, the TIGIT DN form comprises the extracellular ligand binding domain of TIGIT and a transmembrane domain (e.g., mature form). In another embodiment, the TIGIT DN form comprises the extracellular ligand binding domain of TIGIT, a transmembrane domain and a signal peptide (e.g., precursor form). The invention also provides encoding polypeptides and nucleic acids of the TIGIT DN forms of the invention. In a particular embodiment, the TIGIT extracellular ligand binding domain is fused to one or more heterologous polypeptide sequences, that is, the TIGIT DN form is chimeric. For example, the TIGIT extracellular ligand binding domain can be fused at its N-terminus to a (NP_068352.2, GI:612407861), isoform c (NP_001275952.2, GI:612407867), isoform e (NP_001275954.2, GI:612407869), isoform f (NP_001275955.2, GI:612407863), isoform g (NP_001275956.2, GI:612407865), and the like. One exemplary isoform sequence, isoform a, is provided below. In one embodiment, a LAIR1 polypeptide can have an amino acid sequence corresponding to NP_002278.2, sequence provided below, or fragments thereof. See GenBank NP_002278.2 for reference to domains within LAIR1, for example, signal peptide, amino acids 1 to 21; extracellular domain, amino acids 22 to 165; transmembrane domain, amino acids 166 to 186; intracellular domain, amino acids 187 to 287. It is understood that a "LAIR1 nucleic acid molecule" refers to a polynucleotide encoding a LAIR1 polypeptide.

```
  1 MSPHPTALLG LVLCLAQTIH TQEEDLPRPS ISAEPGTVIP LGSHVTFVCR GPVGVQTFRL

61 ERDSRSTYND TEDVSQASPS ESEARFRIDS VREGNAGLYR CIYYKPPKWS EQSDYLELLV

121 KESSGGPDSP DTEPGSSAGP TQRPSDNSHN EHAPASQGLK AEHLYILIGV SVVFLFCLLL

181 LVLFCLHRQN QIKQGPPRSK DEEQKPQQRP DLAVDVLERT ADKATVNGLP EKDRETDTSA

241 LAAGSSQEVT YAQLDHWALT QRTARAVSPQ STKPMAESIT YAAVARH (NP_002278.2;

SEQ ID NO:24)
``` signal peptide that is optionally a heterologous signal peptide, including various signal peptides described herein. In addition, a TIGIT DN form can comprise a transmembrane domain that is optionally a heterologous transmembrane domain, including any of various transmembrane domains described herein.

In an embodiment of the invention, the TIGIT DN form can comprise the extracellular domain, or a ligand binding portion thereof, of TIGIT, for example, amino acids 22 to 141 corresponding to the extracellular domain of TIGIT (GenBank NP_776160.2; SEQ ID NO:23). A cell expressing such a TIGIT DN form should lack the ability or have reduced ability to signal in a TIGIT immune checkpoint pathway. In one embodiment, a TIGIT DN form is a deletion mutant having a deletion of the intracellular domain, for example, amino acids 163 to 244 of TIGIT (GenBank NP_776160.2; SEQ ID NO:23), or a portion thereof, such that intracellular signaling of the immune checkpoint pathway mediated by TIGIT is reduced or inhibited.

In one embodiment, the invention provides a LAIR1 DN form. In one embodiment, the LAIR1 DN form comprises the extracellular ligand binding domain of LAIR1. In one embodiment, the LAIR1 DN form comprises the extracellular ligand binding domain of LAIR1 and a transmembrane domain (e.g., mature form). In another embodiment, the LAIR1 DN form comprises the extracellular ligand binding domain of LAIR1, a transmembrane domain and a signal peptide (e.g., precursor form). The invention also provides encoding polypeptides and nucleic acids of the LAIR1 DN forms of the invention. In a particular embodiment, the LAIR1 extracellular ligand binding domain is fused to one or more heterologous polypeptide sequences, that is, the LAIR1 DN form is chimeric. For example, the LAIR1 extracellular ligand binding domain can be fused at its N-terminus to a signal peptide that is optionally a heterologous signal peptide, including various signal peptides described herein. In addition, a LAIR1 DN form can comprise a transmembrane domain that is optionally a heterologous transmembrane domain, including any of various transmembrane domains described herein.

In an embodiment of the invention, the LAIR1 DN form can comprise the extracellular domain, or a ligand binding portion thereof, of LAIR1, for example, amino acids 22 to 165 corresponding to the extracellular domain of LAIR1 (GenBank NP_002278.2; SEQ ID NO:24). A cell expressing such a LAIR1 DN form should lack the ability or have reduced ability to signal in a LAIR1 immune checkpoint pathway. In one embodiment, a LAIR1 DN form is a deletion mutant having a deletion of the intracellular domain, for example, amino acids 187 to 287 of LAIR1 (GenBank NP_002278.2; SEQ ID NO:24), or a portion thereof, such that intracellular signaling of the immune checkpoint pathway mediated by LAIR1 is reduced or inhibited.

2B4. Natural Killer Cell Receptor 2B4 (2B4) mediates non-MHC restricted cell killing on NK cells and subsets of T cells. The 2B4-S isoform is believed to be an activating receptor, and the 2B4-L isoform is believed to be a negative immune regulator of immune cells. 2B4 becomes engaged upon binding its high-affinity ligand, CD48. 2B4 contains a tyrosine-based switch motif, a molecular switch that allows the protein to associate with various phosphatases. 2B4 has also been designated CD244 (cluster of differentiation 244).

A 2B4 polypeptide can have an amino acid sequence corresponding to GenBank No. NP_001160135.1 (GI: 262263435), sequence provided below, or fragments thereof. See GenBank NP_001160135.1 for reference to domains within 2B4, for example, signal peptide, amino acids 1 to 18; extracellular domain, amino acids 19 to 229; transmembrane domain, amino acids 230 to 250; intracellular domain, amino acids 251 to 370. It is understood that a "2B4 nucleic acid molecule" refers to a polynucleotide encoding a 2B4 polypeptide.

transmembrane domain and a signal peptide (e.g., precursor form). The invention also provides encoding polypeptides and nucleic acids of the 2B4 DN forms of the invention. In a particular embodiment, the 2B4 extracellular ligand binding domain is fused to one or more heterologous polypeptide sequences, that is, the 2B4 DN form is chimeric. For example, the 2B4 extracellular ligand binding domain can be fused at its N-terminus to a signal peptide that is optionally a heterologous signal peptide, including various signal peptides described herein. In addition, a 2B4 DN form can comprise a transmembrane domain that is optionally a heterologous transmembrane domain, including any of various transmembrane domains described herein.

In an embodiment of the invention, the 2B4 DN form can comprise the extracellular domain, or a ligand binding portion thereof, of 2B4, for example, amino acids 19 to 229 corresponding to the extracellular domain of 2B4 (GenBank NP_001160135.1; SEQ ID NO:25). A cell expressing such a 2B4 DN form should lack the ability or have reduced ability to signal in a 2B4 immune checkpoint pathway. In one embodiment, a 2B4 DN form is a deletion mutant having a deletion of the intracellular domain, for example, amino acids 251 to 370 of 2B4 (GenBank NP_001160135.1; SEQ ID NO:25), or a portion thereof, such that intracellular signaling of the immune checkpoint pathway mediated by 2B4 is reduced or inhibited.

CD160. CD160 is a glycosylphosphatidylinositol-anchored molecule containing a single IgV-like domain that binds to HVEM and functions as a co-inhibitory receptor on T cells. A CD160 polypeptide can have an amino acid

```
  1 MLGQVVTLIL LLLLKVYQGK GCQGSADHVV SISGVPLQLQ PNSIQTKVDS IAWKKLLPSQ

61 NGFHHILKWE NGSLPSNTSN DRFSFIVKNL SLLIKAAQQQ DSGLYCLEVT SISGKVQTAT

121 FQVFVFESLL PDKVEKPRLQ GQGKILDRGR CQVALSCLVS RDGNVSYAWY RGSKLIQTAG

181 NLTYLDEEVD INGTHTYTCN VSNPVSWESH TLNLTQDCQN AHQEFRFWPF LVIIVILSAL

241 FLGTLACFCV WRRKRKEKQS ETSPKEFLTI YEDVKDLKTR RNHEQEQTFP GGGSTIYSMI

301 QSQSSAPTSQ EPAYTLYSLI QPSRKSGSRK RNHSPSFNST IYEVIGKSQP KAQNPARLSR

361 KELENFDVYS (NP_001160135.1; SEQ ID NO:25)
```

In one embodiment, the invention provides a 2B4 DN form. In one embodiment, the 2B4 DN form comprises the extracellular ligand binding domain of 2B4. In one embodiment, the 2B4 DN form comprises the extracellular ligand binding domain of 2B4 and a transmembrane domain (e.g., mature form). In another embodiment, the 2B4 DN form comprises the extracellular ligand binding domain of 2B4, a sequence corresponding to GenBank NP_008984.1 (GI: 5901910), sequence provided below, or fragments thereof. See GenBank NP_008984.1 for reference to domains within CD160, for example, signal peptide, amino acids 1 to 26; extracellular domain, amino acids 27 to 159. It is understood that a "CD160 nucleic acid molecule" refers to a polynucleotide encoding a CD160 polypeptide.

```
  1 MLLEPGRGCC ALAILLAIVD IQSGGCINIT SSASQEGTRL NLICTVWHKK EEAEGFVVFL

61 CKDRSGDCSP ETSLKQLRLK RDPGIDGVGE ISSQLMFTIS QVTPLHSGTY QCCARSQKSG

121 IRLQGHFFSI LFTETGNYTV TGLKQRQHLE FSHNEGTLSS GFLQEKVWVM LVTSLVALQA

181 L (NP_008984.1; SEQ ID NO:26)
```

In one embodiment, the invention provides a CD160 DN form. In one embodiment, the CD160 DN form comprises the extracellular ligand binding domain of CD160. In one embodiment, the CD160 DN form comprises the extracellular ligand binding domain of CD160 and a transmembrane domain (e.g., mature form). In another embodiment, the CD160 DN form comprises the extracellular ligand binding domain of CD160, a transmembrane domain and a signal peptide (e.g., precursor form). The invention also provides encoding polypeptides and nucleic acids of the CD160 DN forms of the invention. In a particular embodiment, the CD160 extracellular ligand binding domain is fused to one or more heterologous polypeptide sequences, that is, the CD160 DN form is chimeric. For example, the CD160 extracellular ligand binding domain can be fused at its N-terminus to a signal peptide that is optionally a heterologous signal peptide, including various signal peptides described herein. In addition, a CD160 DN form can comprise a transmembrane domain that is a heterologous transmembrane domain, including any of various transmembrane domains described herein.

In an embodiment of the invention, the CD160 DN form can comprise the extracellular domain, or a ligand binding portion thereof, of CD160, for example, amino acids 27 to 159 corresponding to the extracellular domain of CD160 (GenBank NP_008984.1; SEQ ID NO:26). A cell expressing such a CD160 DN form should lack the ability or have reduced ability to signal in an immune checkpoint pathway. In one embodiment, the CD160 DN form comprises the extracellular domain of CD160, or a ligand binding portion thereof, and a transmembrane domain derived from a heterologous polypeptide, including but not limited to one of the transmembrane domains described herein. In one non-limiting embodiment, the CD160 DN form comprises the transmembrane domain of CD8. In a cell expressing the CD160 DN form, intracellular signaling of the immune checkpoint pathway mediated by CD160 should be reduced or inhibited.

TGF-β Receptor Type 2. TGF-β receptor type 2 binds to TGF-β and a type I receptor dimer forming a heterotetrameric complex with the ligand. A TGF-β receptor type 2 polypeptide can have an amino acid sequence corresponding to GenBank No. NP_001020018.1 (GI:67782326), sequence provided below, or fragments thereof. See GenBank NP_001020018.1 for reference to domains within TGF-β receptor type 2, for example, signal peptide, amino acids 1 to 22; extracellular domain, amino acids 23 to 191; transmembrane domain, amino acids 192 to 212; intracellular domain, amino acids 213 to 592 (see also annotation in UniProtKB—P37173). It is understood that a "TGF-0 receptor type 2 nucleic acid molecule" refers to a polynucleotide encoding a TGF-β receptor type 2 polypeptide.

```
  1 MGRGLLRGLW PLHIVLWTRI ASTIPPHVQK SDVEMEAQKD EIICPSCNRT AHPLRHINND

61 MIVTDNNGAV KFPQLCKFCD VRFSTCDNQK SCMSNCSITS ICEKPQEVCV AVWRKNDENI

121 TLETVCHDPK LPYHDFILED AASPKCIMKE KKKPGETFFM CSCSSDECND NIIFSEEYNT

181 SNPDLLLVIF QVTGISLLPP LGVAISVIII FYCYRVNRQQ KLSSTWETGK TRKLMEFSEH

241 CAIILEDDRS DISSTCANNI NHNTELLPIE LDTLVGKGRF AEVYKAKLKQ NTSEQFETVA

301 VKIFPYEEYA SWKTEKDIFS DINLKHENIL QFLTAEERKT ELGKQYWLIT AFHAKGNLQE

361 YLTRHVISWE DLRKLGSSLA RGIAHLHSDH TPCGRPKMPI VHRDLKSSNI LVKNDLTCCL

421 CDFGLSLRLD PTLSVDDLAN SGQVGTARYM APEVLESRMN LENVESFKQT DVYSMALVLW

481 EMTSRCNAVG EVKDYEPPFG SKVREHPCVE SMKDNVLRDR GRPEIPSFWL NHQGIQMVCE

541 TLTECWDHDP EARLTAQCVA ERFSELEHLD RLSGRSCSEE KIPEDGSLNT TK (NP_001020018.1 SEQ ID NO:27)
```

In one embodiment, the invention provides a TGFβ receptor DN form. In one embodiment, the TGFβ receptor DN form comprises the extracellular ligand binding domain of TGFβ receptor. In one embodiment, the TGFβ receptor DN form comprises the extracellular ligand binding domain of TGFβ receptor and a transmembrane domain (e.g., mature form). In another embodiment, the TGFβ receptor DN form comprises the extracellular ligand binding domain of TGFβ receptor, a transmembrane domain and a signal peptide (e.g., precursor form). The invention also provides encoding polypeptides and nucleic acids of the TGF-β receptor DN forms of the invention. In a particular embodiment, the TGFβ receptor extracellular ligand binding domain is fused to one or more heterologous polypeptide sequences, that is, the TGFβ receptor DN form is chimeric. For example, the TGFβ receptor extracellular ligand binding domain can be fused at its N-terminus to a signal peptide that is optionally a heterologous signal peptide, including various signal peptides described herein. In addition, a TGFβ receptor DN form can comprise a transmembrane domain that is a heterologous transmembrane domain, including any of various transmembrane domains described herein.

TGFβ receptor DN forms have been described previously (see, for example, Bottinger et al., *EMBO J.* 16:2621-2633 (1997), describing a DN form comprising TGFβ receptor extracellular and transmembrane domains; Foster et al., *J. Immunother.* 31:500-505 (2008); Bollard et al., *Blood* 99:3179-3187 (2002); Wieser et al., *Mol. Cell. Biol.* 13:7239-7247 (1993)). In an embodiment of the invention, the TGFβ receptor DN form can comprise the extracellular domain, or a ligand binding portion thereof, of TGFβ receptor, for example, amino acids 23 to 191 corresponding to the extracellular domain of TGFβ receptor (GenBank NP_001020018.1, SEQ ID NO:27). A cell expressing such a TGFβ receptor DN form lacks the ability or has reduced ability to signal in the cell. In one embodiment, a TGFβ receptor DN form is a deletion mutant having a deletion of the intracellular domain, for example, amino acids 213 to 592 of TGFβ receptor (GenBank NP_001020018.1, SEQ ID NO:27), or a portion thereof, such that intracellular signaling of mediated by TGFβ receptor is reduced or inhibited (see also Bottinger et al., *EMBO J.* 16:2621-2633 (1997); Foster et al., *J. Immunother.* 31:500-505 (2008); Bollard et al., *Blood* 99:3179-3187 (2002); Wieser et al., *Mol. Cell. Biol.* 13:7239-7247 (1993)).

It is understood that, optionally, a second DN form of an inhibitor of a cell-mediated immune response, such as an immune checkpoint inhibitor, can be expressed in a cell of the invention. In this case, it can be desirable to inhibit more than one cell-mediated immune response in the same cell. Thus, a cell can express two or more DN forms, each directed to a different inhibitor of a cell-mediated immune response, including those described above. For example, a DN form of PD-1 can be co-expressed in a cell with a DN form of TGF-β receptor, a DN form of PD-1 can be co-expressed with a DN form of CTLA-4, a CTLA-4 DN form can be co-expressed with a DN form of TGF-β, and so forth, as desired, including combinations of any of the DN forms described above.

In a specific embodiment, a nucleic acid encoding a DN form is used to transduce both CD4$^+$ and CD8$^+$ T cells. In such an embodiment, administration of the transduced T cells to a subject should generate both helper and cytotoxic T lymphocyte (CTL) responses in the subject, resulting in a sustained anti-viral response.

7.4. Methods of Treatment

The invention also relates to methods of treating a viral infection using the cells of the invention or pharmaceutical compositions comprising the cells and a pharmaceutically acceptable carrier. In one embodiment, the methods can include administering an immune cell that is an immunostimulatory cell, or precursor cell thereof, expressing a viral antigen-binding CAR and a DN form of an inhibitor of a cell-mediated immune response. The viral antigen is chosen to target a viral infection in the subject. In another embodiment, the methods can include administering a viral-antigen specific immune cell, such as a T cell that recognizes and is sensitized to a viral antigen, where the cell recombinantly expresses a DN form of an inhibitor of a cell-mediated immune response (and may, but need not, express a viral antigen-binding CAR). In another embodiment, the methods can include administering an immune cell that is an immunoinhibitory cell, such as a regulatory T cell, in particular a regulatory T cell isolated from a subject having a chronic viral infection, where the cell recombinantly expresses a DN form of an inhibitor of a cell-mediated immune response.

The methods of the invention can be used to treat a viral infection. In a particular embodiment, the viral infection can be, but is not limited to, infection with HIV (e.g., HIV-1 and/or HIV-2), HBV or HCV. The methods of the invention can be used to treat persistent viral infections, such as latent infections, chronic infections or slow infections, for example, persistent viral infections with HIV, HBV or HCV.

Sustaining Activation of Viral-Specific Immunostimulatory Cells. In one embodiment, the invention provides methods of treating a viral infection comprising administering to a patient immune cells of the invention, in particular immunostimulatory cells, or precursor cells thereof, that are virus specific and that express a DN form of an inhibitor of a cell-mediated immune response. In one particular embodiment, the immunostimulatory cells are made virus specific by expressing a CAR that binds to a viral antigen. In one particular embodiment, the immunostimulatory cells that are virus specific are isolated from a subject having a viral infection. In a particular embodiment, the virus specific immunostimulatory cell is a T cell that recognizes and is sensitized to a viral antigen. In a particular embodiment, the T cell is a CD4$^+$ T cell and/or a CD8$^+$ T cell. In a particular embodiment, the inhibitor of a cell-mediated immune response is PD-1.

The methods can be used to treat a viral infection. Such viral infections include, but are not limited to, infection with HIV, HBV or HCV. The methods of the invention can be used to reduce or eliminate viral load or a persistent viral infection, such as a chronic, latent or slow viral infection, or to prevent or reduce the severity of relapse or recurrent viral infection.

Promoting Virus-Specific Memory Cells. In one embodiment, the invention provides methods of treating a viral infection comprising administering to a patient immune cells of the invention, in particular immunostimulatory cells, or precursor cells thereof, that are virus specific and that express a DN form of an inhibitor of a cell-mediated immune response. In such an embodiment, expression of the DN form can promote production of virus-specific memory cells. In one particular embodiment, the immunostimulatory cells are made virus specific by expressing a CAR that binds to a viral antigen. In one particular embodiment, the immunostimulatory cells that are virus specific are isolated from a subject having a viral infection. In a particular embodiment, the virus specific immunostimulatory cell is a T cell that recognizes and is sensitized to a viral antigen. In a particular embodiment, the T cell is a CD4$^+$ T cell and/or a CD8+ T cell. In a particular embodiment, the inhibitor of a cell-mediated immune response is PD-1.

The methods can be used to treat a viral infection. Such viral infections include, but are not limited to, infection with HBV, HCV or HIV. The methods of the invention can be used to reduce or eliminate viral load or a persistent viral infection, such as a chronic, latent or slow viral infection, or to prevent or reduce the severity of relapse or recurrent viral infection, by promoting the production of virus-specific memory cells.

Inhibiting Immune Suppression Activity of Immunoinhibitory Cells. In one embodiment, the invention provides methods of treating a viral infection comprising administering to a patient immune cells that are immunoinhibitory cells, in particular regulatory T cells, and that express a DN form of an inhibitor of a cell-mediated immune response. In such an embodiment, regulatory T cells can be isolated from a subject, in particular a subject having a chronic viral infection. Expression of the DN form in the regulatory T cell can be used to inhibit the suppressive effect of the regulatory T cell upon immunostimulatory cells, in particular a suppressive effect associated with the expression of the inhibitor of a cell-mediated immune response by the regulatory T cell. In an embodiment, the inhibition of the suppressive effect promotes an immune response mediated by T cells, in particular CD8+ T cells. In a particular embodiment, the inhibitor of a cell-mediated immune response is PD-1. In a particular embodiment, the inhibition of the suppressive effect promotes an immune response mediated by T cells, in particular CD8+ T cells, that express PD-L1 and which are suppressed by PD-1-expressing regulatory T cells.

The methods can be used to treat a viral infection. Such viral infections include, but are not limited to, infection with HCV, HBV or HIV (e.g., HIV-1 and/or HIV-2). The methods of the invention can be used to reduce or eliminate viral load or a persistent viral infection, such as a chronic, latent or slow viral infection, or to prevent or reduce the severity of relapse or recurring viral infection. Without intending to be limited by mechanism, the methods inhibit immunosuppression by the regulatory T cells, where the suppression is mediated by an inhibitor of a cell-mediated immune response, e.g., PD-1. In a particular embodiment, regulatory T cells are harvested from a subject having a chronic viral infection, such as with HCV, HBV or HIV, and then genetically engineered to express the DN form. For example, the cells can be harvested from a subject in remission and not exhibiting signs or symptoms of acute infection. In a specific embodiment, the method can be used to treat a chronic infection and to prevent relapse into an active infection.

Dosages and Administration. In the methods of the invention, the immune cells of the invention are administered to a subject or patient in need of treatment. The subject or patient can be a mammal, in particular a human. Preferably, the subject or patient is a human. The human can be a child or an adult.

For treatment, the amount administered is an amount effective for producing the desired effect. An effective amount or therapeutically effective amount is an amount sufficient to provide a beneficial or desired clinical result upon treatment. An effective amount can be provided in a single administration or a series of administrations (one or more doses). An effective amount can be provided in a bolus or by continuous perfusion. In terms of treatment, an effective amount is an amount that is sufficient to palliate, ameliorate, stabilize, reverse or slow the progression of the disease, or otherwise reduce the pathological consequences of the disease. The effective amount can be determined by the physician for a particular subject. Several factors are typically taken into account when determining an appropriate dosage to achieve an effective amount. These factors include age, sex and weight of the subject, the condition being treated, the severity of the condition and the form and effective concentration of the cells of the invention being administered.

The cells of the invention are generally administered as a dose based on cells per kilogram (cells/kg) of body weight of the subject to which the cells are administered. Generally the cell doses are in the range of about $10^4$ to about $10^{10}$ cells/kg of body weight, for example, about $10^5$ to about $10^9$, about $10^5$ to about $10^8$, about $10^5$ to about $10^7$, or about $10^5$ to $10^6$ cells/kg, depending on the mode and location of administration. In general, in the case of systemic administration, a higher dose is used than in regional administration, where the immune cells of the invention are administered in the region of a viral infection or virally infected cells or tissue. Exemplary dose ranges include, but are not limited to, $1\times10^4$ to $1\times10^8$, $2\times10^4$ to $1\times10^8$, $3\times10^4$ to $1\times10^8$, $4\times10^4$ to $1\times10^8$, $5\times10^4$ to $1\times10^8$, $6\times10^4$, to $1\times10^8$, $7\times10^4$ to $1\times10^8$, $8\times10^4$ to $1\times10^8$, $9\times10^4$ to $1\times10^8$, $1\times10^5$ to $1\times10^8$, for example, $1\times10^5$ to $9\times10^7$, $1\times10^5$ to $8\times10^7$, $1\times10^5$ to $7\times10^7$, $1\times10^5$ to $6\times10^7$, $1\times10^5$ to $5\times10^7$, $1\times10^5$ to $4\times10^7$, $1\times10^5$ to $3\times10^7$, $1\times10^5$ to $2\times10^7$, $1\times10^5$ to $1\times10^7$, $1\times10^5$ to $9\times10^6$, $1\times10^5$ to $8\times10^6$, $1\times10^5$ to $7\times10^6$, $1\times10^5$ to $6\times10^6$, $1\times10^5$ to $5\times10^6$, $1\times10^5$ to $4\times10^6$, $1\times10^5$ to $3\times10^6$, $1\times10^5$ to $2\times10^6$, $1\times10^5$ to $1\times10^6$, $2\times10^5$ to $9\times10^7$, $2\times10^5$ to $8\times10^7$, $2\times10^5$ to $7\times10^7$, $2\times10^5$ to $6\times10^7$, $2\times10^5$ to $5\times10^7$, $2\times10^5$ to $4\times10^7$, $2\times10^5$ to $3\times10^7$, $2\times10^5$ to $2\times10^7$, $2\times10^5$ to $1\times10^7$, $2\times10^5$ to $9\times10^6$, $2\times10^5$ to $8\times10^6$, $2\times10^5$ to $7\times10^6$, $2\times10^5$ to $6\times10^6$, $2\times10^5$ to $5\times10^6$, $2\times10^5$ to $4\times10^6$, $3\times10^5$ to $3\times10^6$ cells/kg, and the like. Such dose ranges can be particularly useful for regional administration. In a particular embodiment, cells are provided in a dose of $1\times10^5$ to $1\times10^8$, for example $1\times10^5$ to $1\times10^7$, $1\times10^5$ to $1\times10^6$, $1\times10^6$ to $1\times10^8$, $1\times10^6$ to $1\times10^7$, $1\times10^7$ to $1\times10^8$, $1\times10^5$ to $5\times10^6$, $1\times10^5$ to $3\times10^6$ or $3\times10^5$ to $3\times10^6$ cells/kg for regional administration. Exemplary dose ranges also can include, but are not limited to, $5\times10^5$ to $1\times10^8$, for example, $6\times10^5$ to $1\times10^8$, $7\times10^5$ to $1\times10^8$, $8\times10^5$ to $1\times10^8$, $9\times10^5$ to $1\times10^8$, $1\times10^6$ to $1\times10^8$, $1\times10^6$ to $9\times10^7$, $1\times10^6$ to $8\times10^7$, $1\times10^6$ to $7\times10^7$, $1\times10^6$ to $6\times10^7$, $1\times10^6$ to $5\times10^7$, $1\times10^6$ to $4\times10^7$, $1\times10^6$ to $3\times10^7$ cells/kg, and the like. Such does can be particularly useful for systemic administration. In a particular embodiment, cells are provided in a dose of $1\times10^6$ to $3\times10^7$ cells/kg for systemic administration. Exemplary cell doses include, but are not limited to, a dose of $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$ and so forth in the range of about $10^4$ to about $10^{10}$ cells/kg. In addition, the dose can also be adjusted to account for whether a single dose is being administered or whether multiple doses are being administered. The precise determination of what would be considered an effective dose can be based on factors individual to each subject, including their size, age, sex, weight, and condition of the particular subject, as described above. Dosages can be readily determined by those skilled in the art based on the disclosure herein and knowledge in the art.

In a specific embodiment, the dosage for human administration is in the range of $1\times10^5$ to $1\times10^8$ cells/kg body weight of the human.

The cells of the invention can be administered by any methods known in the art, including, but not limited to, pleural administration, intravenous administration, subcutaneous administration, intranodal administration, intrahepatic administration, intrathecal administration, intrapleural administration, intraperitoneal administration, intracranial administration, intratracheal administration, intraarticular administration, intrauterine administration, intraocular administration, intranasal administration, intraspinal administration, epidural administration, direct administration at a tendon insertion site, and direct administration to the thymus. In one embodiment, the cells of the invention can be delivered regionally to desired site using well known methods, including but not limited to, hepatic or aortic pump; limb, lung or liver perfusion; in the portal vein; through a venous shunt; in a cavity or in a vein that is nearby a desired site, and the like, such that the cells of the invention are delivered to a region of viral infection or where virally infected cells or tissue occur. For example, the cells can be delivered to a region or tissue in which a latent or chronic viral infection occurs. In another embodiment, the cells of the invention can be administered systemically. In a preferred embodiment, the cells are administered regionally at a desired site. One skilled in the art can select a suitable mode of administration based on the type of viral infection to be treated. The cells can be introduced by injection or catheter. In one embodiment, the cells are administered by intravenous infusion. Optionally, expansion and/or differentiation agents can be administered to the subject prior to, during or after administration of cells to increase production of the cells of the invention in vivo.

Proliferation of the cells of the invention is generally done ex vivo, prior to administration to a subject, and can be desirable in vivo after administration to a subject (see Kaiser et al., *Cancer Gene Therapy* 22:72-78 (2015)). Cell proliferation should be accompanied by cell survival to permit cell expansion and persistence. Cell isolation and/or expansion can be carried out using any method known in the art, e.g., as described in Lee et al., Cancer Res. 71:2871-2881 (2011).

The methods of the invention can further comprise adjuvant therapy in combination with, either prior to, during, or after treatment with the cells of the invention. Thus, the cell therapy methods of the invention can be used with other standard care and/or therapies for treating a particular viral infection that are compatible with administration of the cells of the invention.

Optionally, the methods of administering cells of the invention can additionally include combination therapy that comprises immunomodulation of the host to facilitate the effectiveness of the administered cells of the invention. In an embodiment of the invention, the methods of the invention can further comprise administering at least one immunomodulatory agent. Non-limiting examples of immunomodulatory agents include immunostimulatory agents when immunostimulatory cells are administered, or immunoinhibitory agents when immunoinhibitory cells are administered.

In one embodiment, the immune cells of the invention expressing a DN form lacking an intracellular signaling domain, as disclosed herein), or such a DN form and a CAR, can be co-administered with immune cells co-expressing a CAR and a switch receptor (i.e., a DN form that further comprises a co-stimulatory signaling domain, where the co-stimulatory signaling domain is carboxy-terminal to the transmembrane domain of the dominant negative form). In such immune cells co-expressing a CAR and a switch receptor that are to be co-administered with immune cells expressing a DN form that does not contain an intracellular signaling domain (and thus lacks the co-stimulatory domain) (i.e., is not a switch receptor), the CAR binds to an antigen of the same viral infection as being treated, i.e., the same virus of the viral infection. In another embodiment, the switch receptor can be transduced into the same cell in which a DN form lacking an intracellular signaling domain, and a CAR, are transduced, so that the cell recombinantly expresses all three constructs. Alternatively and preferably, the switch receptor is transduced into a cell in which the CAR, but not the DN form is transduced, so as to produce a cell expressing both the switch receptor and CAR, which can be used in combination therapy with cells that express the DN form, or both the CAR and DN form, but not the switch receptor. In this case, two types of cells, either cells expressing a DN form lacking an intracellular signaling domain and cells expressing a CAR and a switch receptor, or cells expressing a CAR and the DN form and cells expressing a CAR and a switch receptor, are administered to the subject. Generally, the two types of cells are administered concurrently, but can also be administered sequentially, for example, within 1 or 2 hours, or within 1 or 2 days, or on the same day, as each other, as desired. In a particular embodiment, the co-stimulatory signaling domain of the CAR is different than the co-stimulatory signaling domain of the switch receptor being expressed in the same cell. This should result in two co-stimulatory signaling domains in the same cell and enhanced efficacy of the cells for immune cell therapy. In the case where it is believed that the administered immune cells will proliferate sufficiently in the subject being treated such that additional doses of cells need not be administered, it may be suitable to administer the immune cells of the invention at the initiation of immune cell therapy. Optionally, the immune cells of the invention, including optionally immune cells that express a switch receptor, can be administered more than once, as needed.

Administering an immunomodulatory agent, or cells expressing a CAR and a switch receptor, in a combination therapy with an immune cell of the invention expressing a DN form lacking an intracellular signaling domain, can occur concurrently with administration of the immune cells of the invention, for example, when immune cell therapy is initiated, or can occur sequentially at any time during the course of immune cell therapy, as desired. A person skilled in the art can readily determine appropriate regimens for administering cells of the invention and an immunomodulatory agent, or cells expressing a CAR and a switch receptor, in a combination therapy, including the timing and dosing of an immunomodulatory agent to be used in a combination therapy, based on the needs of the subject being treated.

7.5. Pharmaceutical Compositions

The invention additionally provides pharmaceutical compositions comprising the cells of the invention. The pharmaceutical composition comprises an effective amount of a cell of the invention and a pharmaceutically acceptable carrier. The cells of the invention and compositions comprising the cells can be conveniently provided in sterile liquid preparations, for example, typically isotonic aqueous solutions with cell suspensions, or optionally as emulsions, dispersions, or the like, which are typically buffered to a selected pH. The compositions can comprise carriers, for example, water, saline, phosphate buffered saline, and the like, suitable for the integrity and viability of the cells, and for administration of a cell composition.

Sterile injectable solutions can be prepared by incorporating cells of the invention in a suitable amount of the appropriate solvent with various amounts of the other ingredients, as desired. Such compositions can include a pharmaceutically acceptable carrier, diluent, or excipient such as sterile water, physiological saline, glucose, dextrose, or the like, that are suitable for use with a cell composition and for administration to a subject such as a human. Suitable buffers for providing a cell composition are well known in the art. Any vehicle, diluent, or additive used is compatible with preserving the integrity and viability of the cells of the invention.

The compositions will generally be isotonic, that is, they have the same osmotic pressure as blood and lacrimal fluid. The desired isotonicity of the cell compositions of the invention can be accomplished using sodium chloride, or other pharmaceutically acceptable agents such as dextrose, boric acid, sodium tartrate, or other inorganic or organic solutes. Sodium chloride is preferred particularly for buffers containing sodium ions. One particularly useful buffer is saline, for example, normal saline. Those skilled in the art will recognize that the components of the compositions should be selected to be chemically inert and will not affect the viability or efficacy of the cells of the invention and will be compatible for administration to a subject, such as a human. The skilled artisan can readily determine the amount of cells and optional additives, vehicles, and/or carrier in compositions to be administered in methods of the invention.

The cells of the invention can be administered in any physiologically acceptable vehicle. Suitable doses for administration are described herein. A cell population comprising cells of the invention can comprise a purified population of cells. Those skilled in the art can readily determine the percentage of cells in a cell population using various well-known methods, as described herein. The ranges of purity in cell populations comprising genetically modified cells of the invention can be from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. Dosages can be readily adjusted by those skilled in the art; for example, a decrease in purity may require an increase in dosage.

The invention also provides kits for preparation of cells of the invention. In one embodiment, the kit comprises one or more vectors for generating a genetically engineered immune cell, such as a T cell or regulatory T cell, that expresses a DN form or co-expresses a CAR and DN form of an inhibitor of a cell-mediated immune response. The kits can be used to generate genetically engineered immune cells from autologous cells derived from a subject or from non-autologous cells to be administered to a compatible subject. In another embodiment, the kits can comprise cells of the invention, for example, autologous or non-autologous cells, for administration to a subject. In specific embodiments, the kits comprise the immune cells of the invention in one or more containers.

It is understood that modifications which do not substantially affect the activity of the various embodiments of this invention are also provided within the definition of the invention provided herein. Accordingly, the following example is intended to illustrate but not limit the present invention.

8. EXAMPLE

This example describes the construction and use of T cells expressing CARs and a dominant negative PD-1 mutant. Although this example relates to the use of CD4$^+$ T cells and CD8$^+$ T cells that are directed to cancer antigens instead of viral antigens, it describes methodology that can be applied in the instant invention. Furthermore, the results described below, although with CD4$^+$ T cells and CD8$^+$ T cells, show that a dominant negative form of PD-1 can function as a dominant negative and can sustain the activity of a T cell expressing the dominant negative form of PD-1.

8.1. Methods and Procedures

The experimental procedures were approved by the Institutional Animal Care and Use Committee of Memorial Sloan Kettering Cancer Center (MSKCC). Each experiment was performed multiple times, using different donor T cells. To avoid confounding variables—such as differences due to transduction efficiencies, donor-related variability, and E:T ratios—data are presented using a representative experiment, with sample replicates of more than 3.

Cell lines. MSTO-211H human pleural mesothelioma cells (ATCC, Manassas, Va.) were retrovirally transduced to express GFP and firefly luciferase fusion protein (MSTO GFP-ffLuc$^+$). These cells were then transduced with the human MSLN variant 1 subcloned into an SFG retroviral vector to generate MSTO MSLN$^+$ GFP-ffLuc$^+$. Similarly, A549 cells and 3T3 murine fibroblasts were transduced with human MSLN variant 1 alone to generate A549 MSLN+ and 3T3 MSLN+ cell lines. 3T3 cells were also cotransduced with PD-L1 to generate 3T3 MSLN+PDL1+ cells.

γ-Retroviral vector construction and viral production. To generate MSLN-specific CARs, a cDNA encoding for a fully human scFv m912 specific for MSLN (provided by D. Dimitrov, National Cancer Institute at Frederick) (Feng et al., *Mol. Cancer Ther.* 8(5):1113-1118 (2009)), linked to the human CD8 leader domain and the CD8/CD3ζ, CD28/CD3ζ, or CD8/4-1BB/CD3ζ domain was engineered, as previously described (Zhong et al., *Mol. Ther.* 18(2):413-420 (2010)). The control PSMA-specific CAR was generated similarly, using a previously characterized PSMA-targeting scFv (Gade et al., *Cancer Res.* 65(19):9080-9088 (2005)). For construction of the PD-1 DNR, commercial gene synthesis was used to encode the extracellular portion of the PD-1 receptor (amino acids 1-151) fused to the CD8 transmembrane and hinge domains. The CAR sequence was inserted into the SFG γ-retroviral vector (provided by I. Riviere, MSKCC) and linked to a P2A sequence to induce coexpression of the LNGFR reporter (truncated low-affinity nerve growth factor receptor) or, in the case of the PD-1 DNR, the mCherry fluorescent protein reporter (Markley et al., *Blood* 115(17):3508-3519 (2010); Papapetrou et al., *Proc. Natl. Acad. Sci. USA* 106(31):12759-12764 (2009)). The CAR and PD-1 DNR encoding plasmids were then transfected into 293T H29 packaging cell lines to produce the retrovirus, as previously described (Hollyman et al., *J. Immunother.* 32(2):169-180 (2009)).

T-cell isolation, gene transfer, and CD4/CD8 isolation. Peripheral blood leukocytes were isolated from the blood of healthy volunteer donors under an institutional review board-approved protocol. Peripheral blood mononuclear cells (PBMCs) were isolated by low-density centrifugation on Lymphoprep (Stem Cell Technology, Vancouver, Canada) and activated with phytohemagglutinin (2 µg/mL; Remel, Lenexa, Kans.). Two days after isolation, PBMCs were transduced with 293T RD114-produced retroviral particles encoding for CARs and PD-1 DNR and spinoculated for 1 h at 3000 rpm on plates coated with retronectin (15 µg/mL; r-Fibronectin, Takara, Tokyo, Japan). After 1 day, transduced PBMCs were maintained in IL-2 (20 UI/mL; Novartis, Basel, Switzerland). Transduction efficiencies were determined by flow cytometric analysis. Pure populations of CD4+ and CD8+ CAR+ T cells, or mCherry-positive PD-1 DNR-expressing and mCherry-positive EV-expressing CAR+ T cells, were obtained by flow cytometric-based sorting (BD Aria Sorter; BD Biosciences, San Jose, Calif.).

Flow cytometry. Human MSLN expression was detected using a phycoerythrin- or allophycocyanin-conjugated anti-human MSLN rat IgG2a (R&D Systems, Minneapolis, Minn.). Expression of costimulation or inhibitory proteins on tumor cells was analyzed using the following antibodies: 4-1BBL (PE, clone 5F4; BioLegend, San Diego, Calif.), MHC HLA-DR (PE, clone L203; R&D Systems), PD-L1 (APC, clone MI11; eBioscience, San Diego, Calif.), PD-L2 (APC, clone MIH18; eBioscience), and galectin-9 (APC, clone 9M13; BioLegend). T-cell phenotype and transduction efficiency were determined with monoclonal antibodies for CD3, CD4, CD8, and CD69m LNGFR. Expression of T-cell inhibitory receptors was analyzed using PD1 (APC, eBio-JIU5; eBioscience), TIM-3 (PE, clone 344823; R&D Systems), and Lag-3 (PE, clone C9B7W; BioLegend). Cell staining was analyzed using a BD LSRII flow cytometer (BD, Franklin Lakes, N.J.) and FlowJo analysis software (FlowJo, Ashland, Oreg.).

T-cell functional assays. The cytotoxicity of T cells transduced with a CAR or vector control was determined by standard $^{51}$Cr-release assays, as previously described (McCoy et al., *National Cancer Institute Monograph* 37:59-67 (1973)). To perform the luciferase-activity assay, CAR+ T cells and MSTO-211H cells expressing MSLN and firefly luciferase were incubated for 18 h at different E:T ratios. Tumor-cell quantity was determined by BLI using IVIS 100/lumina II, after the addition of 100 μL of D-luciferin (15 mg/mL) per well, and was compared to the signal emitted by the tumor cells alone. CD107a and intracellular staining were performed after incubation of effector cells and irradiated MSTO-211H MSLN tumor cells for 18 h in 24-well plates at a ratio of 5:1. For the CD107a assay, 5 μL of CD107a-PeCy7 antibody (BD Biosciences, San Jose, Calif.) and Golgi STOP (4 μL/6 mL; BD Biosciences) were added at the time of stimulation. For intracellular staining, Golgi Plug (1 μL/1 mL; BD Biosciences) was added at the time of stimulation. After incubation, effector cells were stained for CD4, CD8, LNGFR, and CD3 marker, then fixed and permeabilized in accordance with the manufacturer's instructions (Cytofix/Cytoperm Kit; BD Biosciences). Staining for intracellular cytokines was performed using granzyme B-APC, perforin-PE, and IFN-γ-FITC antibodies (BD Biosciences).

Cytokine-release assays were performed by coculturing $3 \times 10^4$ to $5 \times 10^3$ T cells with target cells in a 1:1 to 5:1 ratio, in 200 μL of medium, in 96-well round-bottomed plates as triplicates. After 6 to 24 h of coculture, supernatants were collected. Cytokine levels were determined using a multiplex bead Human Cytokine Detection kit, in accordance with the manufacturer's instructions (Millipore, Darmstadt, Germany).

To analyze the proliferation capacity of T cells, $1 \times 10^6$ CAR+ T cells were stimulated over irradiated MSTO-211H or 3T3 cells with or without MSLN expression (and, in the case of 3T3, with or without PD-L1). Proliferation assays were performed in the absence of exogenous IL-2. Cells were counted every 7 days and then overlaid on irradiated target cells for repeated stimulations. The CAR+ T cell number versus time was plotted for each T-cell group.

Orthotopic pleural mesothelioma animal model and ex vivo experiments. To develop the orthotopic mouse model of pleural mesothelioma, female NOD/SCIDγ mice (The Jackson Laboratory, Bar Harbor, Me.) aged 4 to 6 weeks were used. All procedures were performed under approved Institutional Animal Care and Use Committee protocols. Mice were anesthetized using inhaled isoflurane and oxygen, with bupivacaine administered for analgesia. Direct intrapleural injection of $1 \times 10^5$ to $1 \times 10^6$ tumor cells in 200 μL of serum-free medium via a right thoracic incision was performed to establish orthotopic MPM tumors, as previously described (Adusumilli et al., *Science Translational Medicine* 6(261):261ra151 (2014); Servais et al., *Clin. Cancer Res.* 18(9):2478-2489 (2012); Servais et al., in *Current Protocols in Pharmacology*, Enna, ed., Chapter 14 (Unit14 21), John Wiley & Sons (2011)). In total, $3 \times 10^4$ to $1 \times 10^5$ transduced T cells (in 200 μL of serum-free medium) were adoptively transferred into tumor-bearing mice, either into the thoracic cavity by direct intrapleural injection or systemically by tail vein injection. Tumor growth was monitored and quantified in vivo by BLI performed 20 minutes after a single intraperitoneal dose of D-luciferin (150 mg/kg; Perkin Elmer, Waltham, Mass.). BLI data were analyzed using Living Image software (version 2.60; Perkin Elmer); BLI signal was reported as total flux (photons per second), which represents the average of ventral and dorsal flux. To analyze the functional capacity of CAR T cells ex vivo, tumor tissues and mouse spleen were processed as follows: Tissues were weighed and harvested into ice-cold RPMI 1640. The tissues were manually morselized with a scalpel and then mechanically disaggregated through 40- to 100-μm filters. Next, samples were analyzed by FACS (fluorescence activated cell sorting) for phenotyping, or CAR+ CD4+ or CD8+ T cells were sorted using a FACS Aria sorter then rested for 24 h in RPMI with IL-2 (60 UI/mL), and $^{51}$Cr-release and cytokine-release assays were performed as described above.

Histologic analysis and immunostaining. Histopathologic evaluation of tumors was performed after hematoxylin and eosin (H&E) staining of paraffin-embedded, 4% paraformaldehyde-fixed tissue samples. Immunohistochemical analysis for human MSLN was performed with mouse anti-human MSLN immunoglobulin G, as previously described (Kachala et al., *Clin. Cancer Res.* 20(4):1020-1028 (2014); Rizk et al., *Cancer Epidemiol. Biomarkers Prev.* 21(3):482-486 (2012); Tozbikian et al., *PLoS One* 9(12):e114900 (2014)).

Quantitative Real-time PCR. The mRNA from CD4+ LNGFR+ or CD8+ LNGFR+ sorted T cells were extracted and reverse transcribed into cDNA using MACS One-Step cDNA kit (MACS molecular, Miltenyi Biotech Inc, Auburn, USA). Quantitative Real Time PCR (RT-PCR) was performed with the Taqman® method using Applied Biosystems® 7500 systems (Foster, Calif., USA), Taqman® Universal PCR Mastermix and Taqman® probes labeled with 6-carboxyfluorescein (FAM-MBG) and designed by Life Technologies (Carlsbad, Calif.): Tbet (Hs00203436_m1); Eomes (Hs00172872_m1); Granzyme B (Hs01554355_m1); IFNγ (Hs00989291_m1); IL-2 (Hs00174114_m1); PD-1 (Hs01550088_m1). The comparative threshold cycle (CT) of the gene of interest was used and normalized to the β2m housekeeping gene using the following formula: ΔCt (sample)=Ct (gene of interest)−Ct (β2m). Then, the $2^{-\Delta\Delta Ct}$ method was used to analyze the relative fold change expression compared to control condition and calculated as follow: $2^{\Delta\Delta Ct}=2\hat{}-(\Delta Ct$ (sample)$-\Delta Ct$ (control)).

Statistical methods. Data were analyzed using Prism (version 6.0; GraphPad Software, La Jolla, Calif.) software and are presented as mean±SEM, as stated in the figure legends. Results were analyzed using the unpaired Student's t test (two-tailed), with the Bonferroni correction used for multiple comparisons, when applicable. Survival curves were analyzed using the log-rank test. Statistical significance was defined as P<0.05. All statistical analyses were performed with Prism software.

8.2. CARs with CD28 or 4-1BB Costimulation Exhibit Equivalent Effector Cytokine Secretion and Proliferation In Vitro Upon Initial Antigen Stimulation Three CARs were constructed that incorporated a human MSLN-specific scFv (Feng et al., *Mol. Cancer Ther.* 8(5): 1113-1118 (2009)) and either CD3ζ, CD28/CD3ζ or 4-1BB/CD3ζ signaling domains (Mz, M28z, MBBz) (FIGS. 1A and 1B). The P28z CAR, which is specific for prostate-specific membrane antigen (PSMA), served as a negative effector control for alloreactivity and xenoreactivity. Both CD4+ and CD8+ human peripheral blood T lymphocytes were effectively transduced using the SFG-retroviral vector (50%-70% transduction) (FIG. 2). MSLN-transduced MSTO-211H cells (MSLN+) and PSMA-transduced EL-4 mouse lymphoma cells (MSLN-) served as MSLN-positive and -negative targets in the in vitro experiments. Mz-, M28z-, and MBBz-transduced T cells demonstrated similar MSLN-specific lysis in vitro (FIG. 1C). P28z CAR T cells did not lyse MSTO MSLN+ cells, and MSLN-targeted CARs did not lyse EL4 PSMA+ cells, demonstrating that lysis is antigen specific. Validating the functionality of costimulatory signaling (Brentjens et al., *Clin. Cancer Res.* 13(18 Pt 1):5426-5435 (2007)), M28z and MBBz CAR T cells secreted 2- to 15-fold higher levels of Th1 cytokines (FIG. 1D) and achieved 14-fold greater T-cell accumulation upon repeated exposure to MSLN+ cells when compared to Mz in the absence of exogenous IL-2 (FIG. 1E). Having established antigen specificity and validated the functionality of costimulatory signaling domains, evaluation of the therapeutic potential of MSLN-targeted CAR T cells in mice bearing established pleural tumors was performed.

These results demonstrate that CARs with CD28 or 4-1BB costimulation exhibit equivalent effector cytokine secretion and proliferation in vitro upon initial antigen stimulation.

8.3. Mesothelin CAR T Cells Become Exhausted Following In Vivo Antigen Exposure

To assess whether there is ongoing immuno inhibition of CAR T cells and to compare the relative abilities of M28z and MBBz CAR T cells to overcome tumor-mediated immuno inhibition, $1 \times 10^6$ CAR T cells were injected into the pleural cavities of MSTO MSLN+ tumor-bearing mice, allowed sufficient time for repeated antigen encounter and T-cell activation (confirmed by forward- and side-scatter and upregulation of the activation marker CD69), and then performed ex vivo stimulation of harvested CD4 or CD8 CAR tumor-infiltrating or splenic T cells with MSLN+ targets (schematic shown in FIG. 3A). Uninjected in vitro resting T cells ("preinfusion cells") were used to establish the baseline level of function (before antigen exposure). Compared with resting M28z CD8+ CAR T cells, T cells exposed to MSLN antigen in vivo had lower levels of cytolytic function (FIG. 3A) (preinfusion cell lysis, 20.5%; tumor-infiltrating T-cell lysis, 13.1%; splenic T-cell lysis, 8.7%). In contrast, MBBz CAR T cells retained cytolytic function (preinfusion cell lysis, 18.3%; tumor-infiltrating T-cell lysis, 37.2%; splenic T-cell lysis, 22.2%). Sorted CD4+ CAR T cells demonstrated a similar pattern of results.

Cytokine levels were also measured upon ex vivo stimulation of tumor-infiltrating and splenic CAR T cells, and a decrease in Th1 cytokine secretion was observed for CD4+ M28z CAR T cells exposed in vivo to MSLN+ antigen. CD4+ MBBz CAR T cells also demonstrated a decrease in Th1 cytokine secretion, although these cells were better able to retain cytokine secretion when compared with M28z CAR T cells (FIG. 3B). CD8+ T cell supernatants contained significantly lower levels of cytokines, compared with CD4+ T cell supernatants (a finding previously observed Adusumilli et al., *Science Translational Medicine* 6(261):261ra151 (2014)). CD8+ T cells also had a decreased ability to secrete cytokines upon in vivo antigen exposure; CD8+ MBBz CAR T cells preferentially retained their ability to secrete IFN-γ. The mRNA levels of T cells harvested from tumor and spleen on day 3 after administration were assessed, and it was found that the in vivo expression levels of GzB, IL-2, and IFN-γ were mostly greater for CD4+ and CD8+ MBBz CAR T cells than for M28z CAR T cells, with the exception of IL-2 expression in the CD8+ subset (FIG. 3C).

These results demonstrate that mesothelin CAR T cells become exhausted following in vivo antigen exposure.

8.4. MBBz CAR T Cells Show Delayed Exhaustion In Vivo

Having demonstrated inhibition of both the cytolytic function and effector cytokine secretion in costimulated CAR T cells exposed to antigen in vivo, it was reasoned that repeated antigen stimulation may, similar to models of chronic infection, play a role in T-cell inhibition and that differing abilities to retain function upon repeated antigen encounter might explain enhanced efficacy of MBBz CAR T cells. Therefore, Mz, M28z, and MBBz CAR T cells were tested for their ability to withstand repeated antigen encounter in an in vitro model system, wherein cells were assessed for proliferation, cytolytic function, and cytokine secretion upon MSLN+ antigen stimulation every 7 days. M28z and MBBz CAR T cells had similar abilities to expand upon serial MSLN+ stimulation, expanding to levels 14-fold greater than those of Mz CAR T cells; they lost the ability to expand following the third stimulation (FIG. 4A). Both MBBz and M28z CAR T cells lost cytolytic function upon repeated antigen stimulation, although MBBz CAR T cells were better able to retain lytic function. Whereas lysis was equal among the three T-cell groups at the first stimulation, by the third stimulation, M28z lytic function was inhibited to a more pronounced level, such that MBBz CAR T cells had enhanced tumor lysis at multiple E:T ratios (FIG. 4B, right). Lytic function (as assessed by a degranulation assay measuring CD107a expression) at the third stimulation correlated with the results of chromium-release assays (FIG. 4C).

Next, Th1 cytokine secretion was measured. Similar levels between M28z and MBBz CAR T cells were noted at the first stimulation, as well as a successive decrease with each stimulation. As with cytotoxicity, MBBz CAR T cells preferentially retained cytokine secretion; cytokine concentrations decreased >30-fold for M28z and only around 2-fold for MBBz CAR T cells, when levels at the first and second stimulations were compared (FIG. 4D). The differences in cytokine production were confirmed by measuring intracellular levels of cytokines at the second stimulation. Reverse-transcriptase PCR analysis of CAR T cells at the time of antigen stimulation revealed that MBBz CAR T cells expressed markers that correlate with lower levels of exhaustion and inhibition, compared with M28z CAR T cells; MBBz CAR T cells expressed higher levels of Tbet and Eomesodermin and lower levels of PD1 and FoxP3 (FIG. 5). The in vivo function of persisting CAR T cells that had already been exposed to tumor antigen was tested. Although quantitative persistence is equal between M28z and MBBz CAR T cells, it was thought that MBBz CAR T cells would demonstrate enhanced function upon tumor rechallenge. Mice with established MSLN+ pleural tumors were administered intrapleural M28z or MBBz CAR T cells (at a dose of $1\times10^5$, E:T ratio 1:3000) to eradicate pleural tumor (FIG. 4E). Twenty days after the initial T-cell injection, tumor rechallenge was performed by injecting MSLN+ tumor cells ($1\times10^6$) into the pleural cavity of survivors; tumor burden was monitored using BLI. Persisting MBBz CAR T cells were better able to control tumor burden (4 of 4 MBBz-treated mice had a BLI signal at baseline levels vs. 2 of 4 M28z-treated mice) (FIG. 4E).

These results demonstrate that MBBz CAR T cells show delayed exhaustion in vivo.

8.5. Tumor Cell PD-L1 Inhibits Mesothelin CAR T-Cell Effector Functions

Having established that CAR T cells are inhibited by the in vivo tumor environment and that MBBz CAR T cells are better able to overcome this inhibition, at least in part because of their ability to retain function upon repeated antigen encounter (see above), it was next sought to assess the role that inhibitory receptor and ligand pathways play in the model. Tumor-infiltrating T cells, in M28z-treated mice with tumor progression, were stained for the expression of well-known pathways of inhibition. High levels of expression of PD-1, Tim-3, and LAG-3 were found (FIG. 6A). Tumor-infiltrating MBBz CAR T cells harvested 6 days after administration demonstrated upregulation of inhibitory receptors as well, although they expressed significantly lower levels of PD-1 receptor at both the protein and the mRNA level (FIG. 6B-D). CD4+ T cells expressed higher levels of PD-1, compared with CD8+ T cells. It was also observed that a significant fraction of both M28z and MBBz CAR T cells coexpressed PD-1 and LAG-3 or PD-1 and Tim-3, suggesting that multiple inhibitory pathways could be functioning simultaneously (FIG. 7). Next, tumor-expressed ligands were assessed: PD-L1 and PD-L2 (ligands for PD-1), galectin-9 (ligand for Tim-3), and MHC class II (ligand for LAG-3). Only PD-1 ligands were expressed on pleural tumor cells harvested after intrapleural administration of M28z CAR T cells (FIG. 6E). As reported elsewhere (McGray et al., *Mol. Ther.* 22(1):206-218 (2014); Spranger et al., *Science Translational Medicine* 5(200):200ra116 (2013)), coculture of tumor cells with IFN-γ and TNF-α (at concentrations similar to those secreted by T cells in FIGS. 1 and 4) resulted in a similar level of upregulation of PD-L1 and PD-L2 expression on tumor cells (FIG. 6F), reflecting an adaptation of tumor cells to resist immune attack ("adaptive immunoresistance"). The unique presence of expression of both PD-1 receptor and ligand in vivo suggests that this pathway may play a significant inhibitory role.

As some studies have suggested that costimulation may be sufficient to overcome inhibition by PD-1 (Carter et al., *Eur. J. Immunol.* 32(3):634-643 (2002); Freeman et al., *J. Exp. Med.* 192(7):1027-1034 (2000); Koehler et al., *Cancer Res.* 67(5):2265-2273 (2007)), it was next assessed whether overexpressed PD-L1 can inhibit CAR T-cell function in an in vitro model of PD-L1-mediated immuno inhibition (using 3T3 mouse fibroblasts transduced with either MSLN alone (MSLN+) or both MSLN and PD-L1 (MSLN+PD-L1+)) (FIG. 8A). In both M28z and MBBz CAR T cells, PD-L1 overexpression resulted in decreased accumulation upon successive stimulation (FIG. 8B) and Th1 effector cytokine secretion (FIG. 8D). Although tumor-cell lysis was not inhibited upon initial stimulation, chromium release assay performed with 3T3s as targets following two stimulations against MSTO MSLN+ tumor cells demonstrates decreased lytic function in both M28z and MBBz CAR T cells, a higher extent of decrease in M28z CAR T cells (FIG. 8C). This result may be due to the differential upregulation of PD-1 on M28z and MBBz CAR T cells following exposure to MSTO MSLN+ tumor cells.

These results demonstrate that tumor cell PD-L1 inhibits mesothelin CAR T-cell effector functions.

8.6. Cell Intrinsic PD-1 Resistance Rescues M28z CAR T-Cell Function In Vivo

The above results indicate that the PD-1 pathway is a functioning mechanism of tumor-mediated immuno inhibition and that PD-1 upregulation following repeated antigen stimulation decreases CAR T-cell efficacy. Therefore, checkpoint blockade was combined with CD28 costimulatory signaling. Since the goal was to provide CAR T-cell-specific checkpoint blockade that was not reliant on repeated dosing of systemically administered antibodies, the studies were focused on genetically engineered methods of overcoming immuno inhibition. A PD-1 dominant negative receptor (DNR) was constructed that contained the extracellular ligand binding domain of the receptor fused to a CD8 transmembrane domain. Since the PD-1 DNR lacks any signaling domain, it was thought that sufficiently overexpressed receptor would enhance T-cell efficacy by saturating PD-1 ligands and thereby blocking signaling through the endogenous PD-1 receptor. M28z CAR T cells were cotransduced with either the PD-1 DNR linked by a P2A element to an mCherry reporter (PD-1 DNR) or an empty vector containing only the reporter (EV) (FIG. 9A). M28z CAR T cells cotransduced with the PD-1 DNR had slight but statistically significant advantages in proliferative ability (FIG. 9B), enhanced cytotoxicity (FIG. 9C) at multiple E:T ratios, as well as augmented levels of IL-2 and IFN-γ secretion (FIG. 9D).

Next, it was assessed whether intrapleural administration of M28z CAR T cells cotransduced with a genetically engineered PD-1 resistance would provide an in vivo advantage. Mice with established pleural MSLN+-expressing tumors were administered a single intrapleural dose of $5\times10^4$ CAR+ M28z EV or M28z PD-1 DNR T cells, and treatment response was monitored by tumor burden measurements (using serial BLI) and median survival. Mice treated with M28z PD-1 DNR T cells had significantly enhanced tumor burden control and prolonged median survival (FIG. 9E); however, only some mice (7/16, 44%) had long-term tumor-free survival, suggesting that there are redundant mechanisms of immuno inhibition that must be overcome. A cohort of the mice (M28z PD-1 DNR) in this experiment survived beyond 450 days in spite of repeated tumor rechallenge, demonstrating the "functional persistence" of CAR T cells transduced with PD-1 DNR. These results demonstrate that, with an injection of 50,000 CAR T cells, not only was a large tumor burden eradicated but tumor relapse was prevented in spite of multiple tumor rechallenge over more than 15 months.

To investigate an alternative genetic strategy for overcoming PD-1-mediated immuno inhibition, M28z CAR T cells were cotransduced with vectors expressing PD-1-targeting shRNAs (FIG. 10A), which generated >60% PD-1 receptor knockdown at the protein level (FIG. 10B). In M28z CAR T cells, cotransduction with PD-1 shRNAs enhanced proliferative function upon MSLN+ antigen stimulation (FIG. 10C), augmented cytotoxicity (FIG. 10D), and enhanced cytokine secretion upon stimulation with either mesothelioma cells or MSLN+ PDL1+ 3T3 mouse fibroblasts (FIG. 10E), compared with cotransduction with an shRNA targeting a non-mammalian gene (M28z KanR). M28z PD-1 shRNA-transduced T cells did not achieve greater in vivo tumor rejection efficacy than M28z KanR T cells, but it is noteworthy that the level of knockdown was significantly lower in vivo than in vitro. Thus, the PD1 DNR proved to be the more effective strategy in vivo than the RNA interference approach.

These results demonstrate that cell intrinsic PD-1 resistance rescues M28z CAR T-cell function in vivo.

8.7 PD-1 DNR Binds Efficiently to Both PD-L1 and PD-L2

To test the binding of PD-1 DNR to the ligands PD-L1 and PD-L2, T cells labeled with mCherry and transduced with PD-1 DNR were exposed to plates coated with PD-L1 fused to an Fc ("PD-L1 Fc"), PD-L2 fused to an Fc ("PD-L2 Fc"), or control isotype Fc ("iso Fc"). Human T cells were transduced with an mCherry construct to label the T cells with mCherry essentially as described in section 7.6. The PD-L1 Fc fusion, PD-L2 Fc fusion and control Fc were purchased commercially.

Plates coated with PD-L1 Fc fusion protein, PD-L2 Fc protein, or control isotype Fc were exposed to mCherry labeled T cells alone, mCherry labeled T cells in the presence of a PD-1 antibody, mCherry labeled T cells transduced with PD-1 DNR, and mCherry labeled T cells transduced with PD-1 DNR in the presence of PD-1 antibody.

As shown in FIG. 11, compared to control T cells with mCherry and without PD-1 DNR transduction, T cells transduced with PD-1 DNR bound to both PD-L1 and PD-L2 efficiently. These results demonstrate that the PD-1 DNR binds to both PD-L1 and PD-L2. Since some tumor cells express either PD-L1 or PD-L2, and since some immune cells (T cells and non-T cells such as macrophages, etc.) express either PD-L1 or PD-L2, it is significant that the PD-1 DNR binds to both PD-L1 and PD-L2. Thus, the T cells transduced with PD-1 DNR can neutralize both PD-L1 and PD-L2.

8.8 Addition of Intracellular 4-1BB Signaling to PD-1 DNR Improves CAR T Cell Efficiency A PD-1 DNR, which inhibits PD-L1- or PD-L2-mediated inhibition of T cell activation, can be converted into a positive co-stimulatory signal. Human T cells were transduced with a mesothelin-specific (MSLN-specific) CAR having CD28 and CD3zeta domains (M28z) (see also description of m28z above in section 7.2). To counteract PD-1/PD-L1 inhibition, cell-intrinsic genetic-engineering strategies were evaluated by cotranducing M28z CAR T cells with a PD-1 dominant negative receptor (PD-1 DNR) fused to a transmembrane domain fused to a 4-1BB intracellular signaling domain, also referred to as a switch receptor.

FIG. 12A shows a schematic diagram illustrating co-expression of a CAR and a PD-1 DNR. The lower portion of FIG. 12A represents a T cell expressing a CAR that binds to an antigen on a target cell, exemplified in FIG. 12A as a tumor cell expressing the tumor cell antigen mesothelin (MSLN). Binding of the T cell expressing a tumor cell antigen-specific CAR to a tumor cell expressing the tumor cell antigen results in activation of the T cell. Co-expression of the PD-1 DNR inhibits the immune checkpoint inhibitor pathway mediated by the binding of PD-L1 or PD-L2 to wild type PD-1. FIG. 12B shows a schematic diagram illustrating co-expression of a CAR and a PD-1 DNR, where the PD-1 DNR has been converted into a costimulatory construct by fusing a costimulatory molecule, exemplified as 4-1 BB, to a transmembrane domain fused to the ligand binding domain of PD-1. Such a construct is an example of a construct referred to herein as a switch receptor (see Liu et al., *Cancer Res.* 76:1578-1590 (2016)). The 4-1BB domain acts as a second costimulatory signal for T cell activation.

Human T cells were transduced with M28z CAR, both M28z CAR and PD-1 DNR, or both M28z CAR and a PD-1/4-1BB switch receptor construct. Transduced cells were antigen stimulated and analyzed for T cell accumulation in culture. As shown in FIG. 12C, M28z CAR T cell accumulation was increased at day 7, and the accumulation was enhanced when the T cells expressing M28z CAR were cotransduced with PD-1 DNR or a PD-1/4-1BB switch receptor construct.

FIG. 12D shows cytokine secretion of interferon gamma (IFN-γ), interleukin 2 (IL-2), tumor necrosis factor alpha (TNF-α) and granulocyte-macrophage colony-stimulating factor (GM-CSF) in human T cells transduced with M28z CAR, both M28z CAR and PD-1 DNR, or both M28z CAR and a PD-1/4-1BB switch receptor construct. Cytokine secretion assays were performed essentially as described above in section 7.1. As shown in FIG. 12D, secretion of IFN-γ, IL-2, TNF-α and GM-CSF was enhanced in cells expressing M28z CAR and a PD-1/4-1BB switch receptor construct relative to the cytokine secretion observed in cells expressing M28z CAR or cells coexpressing M28z CAR and PD-1 DNR. These results demonstrate that PD-L1 (or PD-L2) inhibition can be converted into a positive costimulatory signal by cotransducing in T cells a PD-1/4-1BB switch receptor construct with M28z CAR, resulting in enhanced cytokine secretion and T-cell accumulation.

8.9. Overview and Discussion of Experimental Results

As described above, CAR T-cell therapy and PD-1 checkpoint blockade have been demonstrated to be a rational combination in a solid tumor model. In vitro and ex vivo stimulation assays were performed to assess the impact of PD-1/PD-L1 inhibition on mesothelin CAR T-cell function. To directly counteract PD-1-mediated inhibition, retroviral vectors were used to combine CAR-mediated costimulation with a PD-1 DNR. Optimal signaling provided by this combinatorial strategy (costimulation and checkpoint blockade) enhanced T-cell function in the presence of tumor-encoded PD-L1 expression, resulting in long-term tumor-free survival following a single low dose of CAR T cells. These studies are relevant to the clinical practice of adoptive T-cell therapy and are immediately translational for the following reasons: (1) the costimulatory signaling domains tested—CD28 and 4-1BB—are the two costimulatory domains used in ongoing clinical trials (NCT02414269, NCT02159716, NCT01583686), (2) the models of pleural mesothelioma recapitulate human disease and uses large, clinically relevant tumor burdens that elucidate the relevance of T-cell exhaustion (Adusumilli et al., *Science Translational Medicine* 6(261):261ra151 (2014); Servais et al., *Clin. Cancer Res.* 18(9):2478-2489 (2012); Servais et al., in *Current Protocols in Pharmacology*, Enna, ed., Chapter 14 (Unit14 21), John Wiley & Sons (2011); Servais et al., *PLoS One* 6(10):e26722 (2011)), and (3) the strategy of potentiating CAR T cells by genetically encoded checkpoint blockade uses human sequences that can be readily applied in the clinic (Adusumilli et al., *Science Translational Medicine* 6(261):261ra151 (2014); Feng et al., *Mol. Cancer Ther.* 8(5):1113-1118 (2009)).

The relatively higher expression of PD-1 in M28z CAR T cells led to the focus on CD28-stimulated CAR T cells. On the basis of this analysis, genetic strategies were pursued for counteracting PD-1 inhibitory signaling, such as generating a PD-1 dominant negative receptor (PD-1 DNR) and shRNAs targeting PD-1. When expressed at sufficient levels, the PD-1 DNR competes with the endogenous PD-1 receptor for binding PD-1 ligands (PD-L1 and PD-L2). CD28-costimulated T cells cotransduced with PD-1 DNR demonstrated enhanced in vitro T-cell functions and in vivo T-cell efficacy, suggesting PD-1 signaling as a significant mechanism by which tumor cells evade CAR T cells in the tumor model. Although only in vitro efficacy was demonstrated for PD-1-targeting shRNAs, the absence of in vivo efficacy is likely related to saturation of shRNA machinery by the high volume of PD-1 transcripts induced following multiple in vivo antigen encounters, a conclusion supported by the finding that PD-1 knockdown was significantly lower in vivo than in vitro. The findings described above point to the therapeutic usefulness of adoptively transferred T cells that are genetically engineered to resist tumor-mediated immune inhibition. A DNR that targets TGF-β has been validated in preclinical models and is currently being tested in clinical trials (Foster et al., *J. Immunother.* 31(5):500-505 (2008); Bollard et al., *Blood* 99(9):3179-3187 (2002)).

Whereas others have combined T-cell therapy with PD-1-blocking antibodies either in vivo or in vitro, the addition of a genetic strategy for coinhibitory blockade described in the experiments above overcomes several major obstacles limiting antibody therapy, including (1) the reliance on repeated administrations of antibodies and (2) the incidence of immune-related adverse events. T-cell therapy, then, has advantages over antibody therapy because it can establish long-term engraftment of T cells programmed for resistance to inhibition after a single dose and because it provides blockade of inhibitory pathways that is limited to a tumor-targeted T-cell repertoire, which may limit the autoimmunity that results from a more broadly applied antibody checkpoint blockade. Furthermore, it is possible that perhaps PD-L1 blocking antibodies can further prolong the efficacy of M28z and M28z PD-1 DNR CAR T cells.

The studies described above have identified one of the inhibitory mechanisms responsible for CAR T-cell and highlighted differences in the ability of costimulatory strategies to withstand immuno inhibition. Other inhibitory pathways may also function to potentially limit T-cell function. That a proportion of mice treated with PD-1 DNR-cotransduced M28z CAR T cells died of tumor progression suggests the action of other inhibitory mechanisms. Furthermore, the literature on chronic infection suggests the existence of other mechanisms of inhibition, both cell intrinsic and cell extrinsic, which are being assessed in tumor-targeted T-cell therapies (Moon et al., *Clin. Cancer Res.* 20(16):4262-4273 (2014); Riese et al., *Cancer Res.* 73(12):3566-3577 (2013)). Additional studies on inhibitory signaling can use an immunocompetent model that includes elements such as myeloid-derived suppressor cells and endogenous T cells, which have been shown to play important roles in tumor immune evasion.

The results described above have established the importance of tumor-mediated inhibition of CAR T-cell effector functions. By performing a comprehensive analysis of T-cell effector functions, it has been established that even costimulated CAR T cells, although they demonstrate enhanced persistence, are subject to inhibition upon repeated antigen encounter, both in vitro and within the tumor microenvironment. The results described demonstrate that CAR T-cell therapy can be used to counteract inhibitory signaling and provides the flexibility to engineer signaling domains that provide optimal costimulation and directly counteract inhibitory signals such as PD-1. Furthermore, in ongoing CAR T-cell therapy clinical trials in patients who show T-cell infiltration but a limited clinical response, combining PD-1/PD-L1 blockade following CAR T-cell therapy can be utilized to improve the efficacy of CAR T-cell therapy. The knowledge acquired from the clinical trials and the strategies presented herein are highly valuable to improve immunotherapy methods using CAR T cells, which is particularly use for therapy of solid tumors. Thus, the results described above exemplify methods that can be applied in a clinical setting to improve the efficacy of CAR T-cell therapy.

As described above, low-level tumor infiltration was modeled, and it was found that CAR T cells can be susceptible to tumor cell-mediated immune-inhibition, resulting in impaired T-cell function and diminished tumor rejection. T cells engineered to resist PD-1 signaling displayed enhanced anti-tumor potency. Following a single low-dose CAR T-cell therapy of advanced tumors, it was observed that, in response to CAR T-cell secreted cytokines, tumor cells upregulate PD-L1 leading to CAR T-cell inhibition and tumor relapse. To directly overcome the PD-L1-mediated immunosuppression, a PD-1 dominant negative receptor (PD-1 DNR) lacking the intracellular inhibitory signaling domain was designed. The cotransduction of PD-1 DNR with a CAR enhanced CAR T-cell function, resulting in a long-term cancer free survival following a single low-dose of CAR T cells. The coexpression of an immune checkpoint pathway receptor DNR with a CAR is immediately translatable to the clinic since a DNR can be added to any CAR without inhibiting CAR function or adding toxicity. Without being bound by a particular theory, it is believed that the DNR simply binds (consumes) negative signal induced by its corresponding ligand (for example, PD-L1 in the case of PD-1) and avoids downstream signaling.

The effectiveness of an immune cell expressing a CAR and a dominant negative form of an immune checkpoint inhibitor can also be enhanced by expression of a switch receptor, in which an intracellular co-stimulatory signaling domain is fused to a transmembrane domain fused to the extracellular ligand binding domain of an immune checkpoint inhibitor, such as PD-1. The results described above show that expression of a PD-1 extracellular domain fused to a transmembrane domain fused to the cytoplasmic domain of 4-1BB increased cytokine production and increased accumulation of CAR T cells. Expression of a switch receptor in an immune cell expressing a CAR can improve the efficacy of the immune cell for immunotherapy. Alternatively, a switch receptor can be expressed in a cell without a CAR. In both cases, the switch receptor functions as a dominant negative. Immune cells expressing a CAR and a switch receptor can be administered, concurrently or sequentially, with immune cells expressing a dominant negative form of an immune checkpoint inhibitor (that does not contain the co-stimulatory signaling domain, and thus is not a switch receptor), or with cells co-expressing a CAR and a dominant negative form of an immune checkpoint inhibitor (that does not contain the co-stimulatory signaling domain, and thus is not a switch receptor), to enhance the effectiveness of immunotherapy using such immune cells.

9. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of treating a viral infection in a subject in need thereof, comprising administering to the subject a therapeutically effective amount of a cell that is immunostimulatory cell or precursor cell thereof, which immunostimulatory cell or precursor cell recombinantly expresses:
 (a) a chimeric antigen receptor (CAR), and
 (b) a dominant negative form of programmed cell death protein 1 (PD-1), wherein the CAR binds to a viral antigen,
 wherein the viral antigen is an antigen associated with the viral infection.

2. The method of claim 1, wherein the cell is derived from a human, and the subject is a human.

3. The method of claim 1, wherein the cell is a precursor cell of an immunostimulatory cell, and the precursor cell is a hematopoietic stem or hematopoietic progenitor cell.

4. The method of claim 1, wherein the cell is an immunostimulatory cell, and the immunostimulatory cell is a T cell.

5. The method of claim 1, wherein the cell is an immunostimulatory cell, and the immunostimulatory cell is a cytotoxic T lymphocyte (CTL).

6. The method of claim 1, wherein the cell is an immunostimulatory cell, and the immunostimulatory cell is a Natural Killer (NK) cell.

7. The method of claim 1, wherein the viral antigen is of a virus that is a human pathogen.

8. The method of claim 1, wherein the viral antigen is selected from the group consisting of a human immunodeficiency virus (HIV) antigen, a hepatitis B virus (HBV) antigen, a hepatitis C virus (HCV) antigen, a herpes simplex virus (HSV) antigen, a varicella zoster virus (VZV) antigen, an adenovirus antigen, a cytomegalovirus (CMV) antigen, and an Epstein-Barr virus (EBV) antigen.

9. The method of claim 1, wherein the cell further recombinantly expresses a suicide gene.

10. The method of claim 9, wherein the suicide gene comprises inducible Caspase 9.

11. The method of claim 1, wherein the dominant negative form of PD-1 comprises (a) at least a portion of an extracellular domain of PD-1, (b) a transmembrane domain from a heterologous polypeptide, and (c) lacks some portion or all of a signaling domain.

12. The method of claim 11, wherein the heterologous polypeptide is CD8.

13. A method of treating a viral infection in a subject in need thereof, comprising administering to the subject a pharmaceutical composition comprising
 (a) a therapeutically effective amount of a cell that is an immunostimulatory cell or precursor cell thereof, which immunostimulatory cell or precursor cell recombinantly expresses:

(i) a chimeric antigen receptor (CAR), and
(ii) a dominant negative form of programmed cell death protein 1 (PD-1), wherein the CAR binds to a viral antigen; and
(b) a pharmaceutically acceptable carrier,
wherein the viral antigen is an antigen associated with the viral infection.

14. The method of claim 13, wherein the cell is derived from a human, and the subject is a human.

15. A method of treating a viral infection in a subject in need thereof, comprising administering to the subject a therapeutically effective amount of a T cell that recognizes and is sensitized to a viral antigen, which T cell recombinantly expresses a dominant negative form of programmed cell death protein 1 (PD-1),
wherein the viral antigen is an antigen associated with the viral infection.

16. The method of claim 15, wherein the cell is derived from a human and the subject is human.

17. The method of claim 15, wherein the therapeutically effective amount of the T cell is present in a pharmaceutical composition, which pharmaceutical composition further comprises a pharmaceutically acceptable carrier.

18. The method of claim 15, wherein the T cell is immunostimulatory.

19. The method of claim 15, wherein the T cell is CD4$^+$ or CD8$^+$.

20. The method of claim 15, wherein the viral antigen is of a virus that is a human pathogen.

21. The method of claim 15, wherein the viral antigen is selected from the group consisting of a human immunodeficiency virus (HIV) antigen, a hepatitis B virus (HBV) antigen, a hepatitis C virus (HCV) antigen, a herpes simplex virus (HSV) antigen, a varicella zoster virus (VZV) antigen, an adenovirus antigen, a cytomegalovirus (CMV) antigen, and an Epstein-Barr virus (EBV) antigen.

22. The method of claim 15, wherein the dominant negative form of PD-1 comprises (a) at least a portion of an extracellular domain of PD-1, (b) a transmembrane domain from a heterologous polypeptide, and (c) lacks some portion or all of a signaling domain.

23. The method of claim 22, wherein the heterologous polypeptide is CD8.

24. A method of treating an infection caused by a pathogen in a subject in need thereof, comprising administering to the subject a therapeutically effective amount of a cell that is an immunostimulatory cell or precursor cell thereof, which immunostimulatory cell or precursor cell recombinantly expresses:
(a) a chimeric antigen receptor (CAR), and
(b) a dominant negative form of programmed cell death protein 1 (PD-1), wherein the CAR binds to an antigen of a pathogen,
wherein the antigen of the pathogen to which the CAR binds is an antigen of the pathogen causing the infection.

25. The method of claim 24, wherein the cell is derived from a human and the subject is human.

26. The method of claim 24, wherein the therapeutically effective amount of the cell is present in a pharmaceutical composition, which pharmaceutical composition further comprises a pharmaceutically acceptable carrier.

27. The method of claim 24, wherein the cell is a precursor cell of an immunostimulatory cell, and the precursor cell is a hematopoietic stem or hematopoietic progenitor cell.

28. The method of claim 24, wherein the cell is an immunostimulatory cell, and the immunostimulatory cell is a T cell.

29. The method of claim 24, wherein the cell is an immunostimulatory cell, and the immunostimulatory cell is a cytotoxic T lymphocyte (CTL).

30. The method of claim 24, wherein the cell is an immunostimulatory cell, and the immunostimulatory cell is a Natural Killer (NK) cell.

31. The method of claim 24, wherein the pathogen is a human pathogen.

32. The method of claim 24, wherein the pathogen is selected from the group consisting of a bacterium, a fungus, and a protozoan.

33. The method of claim 24, wherein the dominant negative form of PD-1 comprises (a) at least a portion of an extracellular domain of PD-1, (b) a transmembrane domain from a heterologous polypeptide, and (c) lacks some portion or all of a signaling domain.

34. The method of claim 33, wherein the heterologous polypeptide is CD8.

35. A method of treating an infection caused by a pathogen in a subject in need thereof, comprising administering to the subject a therapeutically effective amount of a T cell that recognizes and is sensitized to an antigen of a pathogen, which T cell recombinantly expresses a dominant negative form of programmed cell death protein 1 (PD-1), wherein the antigen of the pathogen to which the T cell is sensitized is an antigen of the pathogen causing the infection.

36. The method of claim 35, wherein the cell is derived from a human and the subject is human.

37. The method of claim 35, wherein the therapeutically effective amount of the T cell is present in a pharmaceutical composition, which pharmaceutical composition further comprises a pharmaceutically acceptable carrier.

38. The method of claim 35, wherein the T cell is immunostimulatory.

39. The method of claim 35, wherein the T cell is CD4$^+$ or CD8$^+$.

40. The method of claim 35, wherein the pathogen is a human pathogen.

41. The method of claim 35, wherein the pathogen is selected from the group consisting of a bacterium, a fungus, and a protozoan.

42. The method of claim 35, wherein the dominant negative form of PD-1 comprises (a) at least a portion of an extracellular domain of PD-1, (b) a transmembrane domain from a heterologous polypeptide, and (c) lacks some portion or all of a signaling domain.

43. The method of claim 42, wherein the heterologous polypeptide is CD8.

* * * * *

UNITED STATES PATENT AND TRADEMARK OFFICE
CERTIFICATE OF CORRECTION

PATENT NO. : 11,738,048 B2
APPLICATION NO. : 16/329142
DATED : August 29, 2023
INVENTOR(S) : Prasad S. Adusumilli It is certified that error appears in the above-identified patent and that said Letters Patent is hereby corrected as shown below:

In the Claims

In Column 123, Line 43, Claim 1, insert --an-- between "that is" and "immunostimulatory cell";
In Column 123, Line 44, Claim 1, insert --a-- before "precursor cell thereof";
In Column 123, Line 56, Claim 3, insert --cell-- between "stem" and "or";
In Column 124, Line 55, Claim 11, insert --and-- before "(b)";
In Column 124, Line 56, Claim 11, delete "(c)" between "and" and "lacks";
In Column 124, Line 65, Claim 13, insert --a-- before "precursor cell thereof";
In Column 125, Line 19, Claim 16, insert --a-- between "is" and "human";
In Column 125, Line 39, Claim 22, insert --and-- before "(b)";
In Column 125, Line 40, Claim 22, delete "(c)" between "and" and "lacks";
In Column 125, Line 47, Claim 24, insert --a-- before "precursor cell thereof";
In Column 125, Line 58, Claim 25, insert --a-- between "is" and "human";
In Column 126, Line 5, Claim 27, insert --cell-- between "stem" and "or";
In Column 126, Line 24, Claim 33, insert --and-- before "(b)";
In Column 126, Line 25, Claim 33, delete "(c)" between "and" and "lacks";
In Column 126, Line 39, Claim 36, insert --a-- between "is" and "human";
In Column 126, Line 55, Claim 42, insert --and-- before "(b)";
In Column 126, Line 56, Claim 42, delete "(c)" between "and" and "lacks".

Signed and Sealed this
Twenty-fourth Day of October, 2023

Katherine Kelly Vidal
*Director of the United States Patent and Trademark Office*